United States Patent
Altmann et al.

(10) Patent No.: US 8,569,317 B2
(45) Date of Patent: *Oct. 29, 2013

(54) ARYL-QUINAZOLINE/ARYL-2AMINO-PHENYL METHANONE DERIVATIVES

(75) Inventors: Eva Altmann, Basel (CH); Rene Beerli, Basel (CH); Marc Gerspacher, Basel (CH); Johanne Renaud, Basel (CH); Sven Weiler, Basel (CH); Leo Widler, Basel (CH)

(73) Assignee: Novartis AG, Basel (CH)

( * ) Notice: Subject to any disclaimer, the term of this patent is extended or adjusted under 35 U.S.C. 154(b) by 971 days.

This patent is subject to a terminal disclaimer.

(21) Appl. No.: 12/579,735

(22) Filed: Oct. 15, 2009

(65) Prior Publication Data

US 2010/0063075 A1    Mar. 11, 2010

Related U.S. Application Data

(63) Continuation of application No. 10/540,359, filed as application No. PCT/EP03/14741 on Dec. 22, 2003, now Pat. No. 7,696,216.

(30) Foreign Application Priority Data

Dec. 23, 2002    (GB) .................................. 0230015.0

(51) Int. Cl.
- *A01N 43/54* (2006.01)
- *A61K 31/517* (2006.01)
- *C07D 239/72* (2006.01)
- *C07D 401/00* (2006.01)

(52) U.S. Cl.
USPC .................. 514/266.31; 514/266.21; 544/284; 544/286

(58) Field of Classification Search
USPC .................. 514/266.31, 266.21; 544/284, 286
See application file for complete search history.

(56) References Cited

U.S. PATENT DOCUMENTS

| | | |
|---|---|---|
| 3,305,553 A | 2/1967 | Hoefle et al. |
| 3,793,324 A | 2/1974 | Denzer |
| 3,812,257 A | 5/1974 | Yamamoto et al. |
| 3,910,911 A | 10/1975 | Ishizumi et al. |
| 3,923,003 A | 12/1975 | Carden |
| 3,925,548 A | 12/1975 | Oh |
| 3,926,993 A | 12/1975 | Ishizumi et al. |
| 3,953,446 A | 4/1976 | Ishizumi et al. |
| 4,067,868 A | 1/1978 | Ishizumi et al. |
| 4,171,441 A | 10/1979 | Smith |
| 4,202,974 A | 5/1980 | Yamamoto et al. |
| 4,236,006 A | 11/1980 | Gamboni et al. |
| 4,387,223 A | 6/1983 | Yamamoto et al. |
| 5,773,663 A | 6/1998 | Curtze et al. |
| 5,856,503 A | 1/1999 | Aebi et al. |
| 6,008,230 A | 12/1999 | Oku et al. |
| 6,031,803 A | 2/2000 | Kubota et al. |
| 6,211,244 B1 | 4/2001 | Van Wagenen et al. |
| 7,696,216 B2 * | 4/2010 | Altmann et al. .......... 514/266.31 |
| 2004/0180912 A1 | 9/2004 | Beerli et al. |

FOREIGN PATENT DOCUMENTS

| | | |
|---|---|---|
| CA | 1046063 A1 | 1/1979 |
| CH | 612186 A5 | 7/1979 |
| EP | 0634169 B1 | 1/2000 |
| EP | 1052254 A1 | 11/2000 |
| GB | 1248428 A | 10/1971 |
| GB | 1313789 A | 4/1973 |
| GB | 1353789 A | 5/1974 |
| GB | 1195066 A | 6/1979 |
| GB | 1181570 A | 7/2000 |
| WO | 02/43374 A1 | 7/2000 |
| WO | 02/24683 A1 | 3/2002 |
| WO | 02/102782 A2 | 12/2002 |

OTHER PUBLICATIONS

Russell R.K. at al., "Synthesis and renal vasodilator activity of substituted [4-alkyl(aryl)quinazolin-2-one-1-yl]alkanoic acids" European Journal of Medicinal Chemistry vol. 27, No. 3, 1992, pp. 277-284, XP002935850.

Database CAPLUS, 1980:121782, Chemical Abstract, XP 002280288.

Naruhito et al., "Studies on Metal Complex Formation in Solution. I. Cryptotanshinone-FeCl3 Complex" Chemical & Pharmaceutical Bulletin, vol. 25, No. 11, 1977, pp. 3018-3022.

Database CAPLUS, 1982:503745, Chemical Abstract, XP 002280289.

(Continued)

*Primary Examiner* — Paul V. Ward
(74) *Attorney, Agent, or Firm* — John B. Alexander

(57) ABSTRACT

A compound of formula (1): wherein R1, R2, R3 and Y are as defined herein, or a pharmaceutically-acceptable and -cleavable ester, or acid addition salt thereof, useful for promoting the release of parathyroid hormone, e.g. for preventing or treating bone conditions which are associated with increased calcium depletion or resorption or in which stimulation of bone formation and calcium fixation in the bone is desirable.

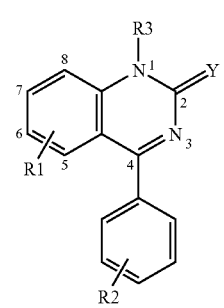

(I)

3 Claims, No Drawings

(56) References Cited

OTHER PUBLICATIONS

Jaeda et al., "Synthesis of Some Novel 2(1H)-Quinazolinones and 2-Thioxo Analogues from Newly Synthesised 1-Azyl-3-alkoxyphehylureas and Thioureas" Journal of chemical technology and biotechnology, vol. 58, No. 4. 1993, pp. 391-394.

Database CAPLUS, 1981 461773, Chemical Abstract XP 002280291.

Berger et al., "3-Bromo-6-methylamino-2'-methoxybenzophenone" Acta Crystallogr. Sect. C: Cryst. truct Commun, vol. 50, 1994, pp. 773-775.

Chemical Abstract 108:112476, (1988).

Chemical Abstract 86:87535, (1988).

Chemical Abstract 79:66369, (1998).

Merck Index 11th edition(1989), No. 4120 "Flupro-quazone".

* cited by examiner

ARYL-QUINAZOLINE/ARYL-2AMINO-PHENYL METHANONE DERIVATIVES

This invention relates to 4-aryl-2(1H)-quinazolinone derivatives and aryl-(2-amino-phenyl)-methanone derivatives and to pharmaceutical uses thereof.

4-Aryl-2(1H)-quinazolinone derivatives and 2-substituted-4-aryl-quinazoline derivatives have been described together with their use as promoters of PTH (Parathyroid hormone) release in our co-pending international patent application WO 02/102782.

We have now synthesised additional new 4-aryl-2(1H)-quinazolinone derivatives and aryl-(2-amino-phenyl)-methanone derivatives which have activity as promoters of PTH release.

Accordingly the invention provides a compound of formula I

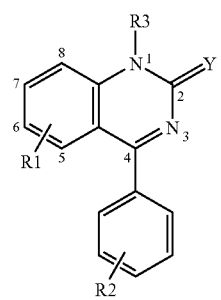

wherein Y is O or S;

R1 represents from 1 to 3 substituents independently selected from OH, SH, halo, $NO_2$, optionally substituted (lower allyl, lower alkoxy, lower alkenyl, lower alkenyloxy, lower alkynyl, lower alkynyloxy, lower alkanoyl, cycloalkyl, lower alkylsulphone, lower alkylsulphoxide or amino);

R2 represents from 1 to 3 substituents selected from halo, optionally substituted (lower alkyl, lower alkenyl, cycloalkyl or lower alkoxy);

R3 is

A) lower alkyl optionally substituted by 1 to 3 substituents selected from cycloalkyl, lower alkylene, lower alkyl, Br, F, $CF_3$, CN, COOH, lower alkyl-carboxylate, OH, lower alkoxy or —$O_x$—$(CH_2)_y$—$SO_z$-lower alkyl, wherein x is 0 or 1, y is 0, 1 or 2 and z is 0, 1 or 2; or B) Benzyl which is
   a. mono- or di-(preferably mono-) substituted by —$O_x$—$(CH_2)_y$—$SO_z$-lower alkyl or —$O_x$—(CR, R')$_y$—COO—R", wherein x, y and z are as defined above and R, R' or R" is H or lower alkyl (preferably x=0, y=1, R,R' and R"=H),
   b. substituted by 1 or 2 substituents selected from morpholino-lower alkoxy, aryl-lower alkoxy, optionally N-lower alkyl substituted arylamino-lower alkoxy,
   c. substituted at the 2-position by lower alkoxy-, hydroxy-lower alkoxy- or lower alkoxy-lower alkoxy,
   d. substituted on the —$CH_2$— group thereof; or C) optionally substituted (aryl-$C_2$-$C_8$-alkyl, aryl-$C_2$-$C_8$-alkenyl, heteroarylmethyl or 4-heteroarylbenzyl); or when R1 is 2 substituents one of which is OH, preferably at the 6-position, and the other of which is optionally substituted (lower alkyl, cycloalkyl-lower-alkyl or lower alkenyl), preferably at the 5-position, R3 is H or optionally substituted (lower alkyl, aryl, aryl-lower alkyl, arylcycloalkyl, cycloalkyl-lower alkyl, cycloalkenyl-lower alkyl, hetereoaryl-lower alkyl, hetereoaryl, or carbonyl lower alkyl); or when R1 is 2-propynyloxy and R2 is isopropyl, R3 is also benzyl which is substituted by 1 to 3 substituents selected from lower alkyl, lower alkoxy, halo, halo-lower alkyl, e.g. $CF_3$; or when R1 is 2-propynyloxy and R2 is isopropyl, R3 is also benzyl which is substituted by OH and a second and optionally third substituent selected from lower alkyl, lower alkoxy, halo, —O—CH(H or lower alkyl)-COO(H or lower alkyl); or when R1 is 2-propynyloxy and R2 is cyclopropyl, R3 is also optionally substituted lower allyl or benzyl (preferably R3 is also benzyl which is substituted by 1 to 3 substituents selected from lower alkyl, lower alkoxy, halo, —O—CH(H or lower alkyl)-COO(H or lower alkyl)); or when Y is S and R1 is as defined above but not methoxy, R3 is also optionally substituted benzyl; or a compound selected from 4-(4-isopropyl-phenyl)-1-(3,4-diamino-benzyl)-6-prop-2-ynyloxy-1H-quinazolin-2-one, 1-(2,6-dichloro-benzyl)-4-(4-isopropyl-phenyl)-6-prop-2-ynyloxy-1H-quinazolin-2-one, 1-benzyl-4-(4-isopropyl-phenyl)-6-prop-2-ynyloxy-1H-quinazoline-2-thione; 1-(3,5 di-tert-butyl-4-hydroxy-benzyl)-4-(4-isopropyl-phenyl)-6-prop-2-ynyloxy-1H-quinazolin-2-one, or 1-[3-(2-hydroxy-ethoxy)-benzyl]-4-(4-isopropyl-phenyl)-6-prop-2-ynyloxy-1H-quinazoline-2-thione; or a pharmaceutically-acceptable and -cleavable ester, or acid addition salt thereof; and provided that when Y is O and R3 is lower alkyl or cycloalkyl, R3 is not isopropyl or cyclopentyl; or provided the compound of formula I is not 4-(4-isopropyl-phenyl)-6-methoxy-1-pyridin-3-ylmethyl-1.H.-quinazolin-2-one, 4-(4-isopropyl-phenyl)-6-methoxy-1-pyridin-2-ylmethyl-1.H.-quinazolin-2-one, 1-(6-chloro-pyridin-3-ylmethyl)-4-(4-isopropyl-phenyl)-6-methoxy-1.H.-quinazolin-2-one, 4-(4-isopropyl-phenyl)-6-methoxy-1-(5-nitro-furan-2-ylmethyl)-1.H.-quinazolin-2-one or 1-[2-(1.H.-indol-2-yl)-ethyl]-4-(4-isopropyl-phenyl)-6-methoxy-1.H.-quinazolin-2-one, 4-(4-isopropyl-phenyl)-6-methoxy-1-phenethyl-1H-quinazolin-2-one, 1-(2-hydroxy-2-phenyl-ethyl)-4-(4-isopropyl-phenyl)-6-prop-2-ynyloxy-1H-quinazolin-2-one, methanesulfonic acid 2-[4-(4-isopropyl-phenyl)-2-oxo-6-prop-2-ynyloxy-2H-quinazolin-1-ylmethyl]-phenyl ester, or acetic acid 2-[4-(4-isopropyl-phenyl)-2-oxo-6-prop-2-ynyloxy-2H-quinazolin-1-yl]-1-phenyl-ethyl ester, 5-allyl-6-hydroxy-1-isopropyl-4-(4-isopropyl-phenyl)-1.H.-quinazolin-2-one, 1-cyclopropylmethyl-4-(o-tolyl)-6-nitro-2(1H)-quinazolinone, 1-ethyl-4-(o-tolyl)-6-chloro-2(1H)-quinazolinone, 1-cyclopropylmethyl-4-(o-tolyl)-6-chloro-2(1H)-quinazolinone, 1-cyclopropylmethyl-4-(o-fluorophenyl)-6-chloro-2(1H)-quinazolinone, 1-cyclopropylmethyl-4-(m-chlorophenyl)-6-chloro-2(1H)-quinazolinone, 1-cyclopropylmethyl-4-(o-chlorophenyl)-6-nitro-2(1H)-quinazolinone.

Above and elsewhere in the present description the following terms have the following meanings: Halo or halogen denote I, Br, Cl or F. The term "lower" referred to above and hereinafter in connection with organic radicals or compounds respectively defines such as branched or unbranched with up to and including 7, preferably up to and including 4 and advantageously one or two carbon atoms. A lower alkyl group is branched or unbranched and contains 1 to 7 carbon atoms, preferably 1-4 carbon atoms. Lower alkyl represents; for example, methyl, ethyl, propyl, butyl, isopropyl isobutyl, or tertiary butyl. Halo-substituted lower alkyl is $C_1$-$C_7$lower allyl substituted by up to 6 halo atoms. A lower alkoxy group is branched or unbranched and contains 1 to 7 carbon atoms, preferably 1-4 carbon atoms. Lower alkoxy represents for example methoxy, ethoxy, propoxy, butoxy, isopropoxy, isobutoxy or tertiary butoxy. A lower alkene, alkenyl or alkenyloxy group is branched or unbranched and contains 2 to 7 carbon atoms, preferably 1-4 carbon atoms and contains at least one carbon-carbon double bond. Lower alkene lower alkenyl or lower alkenyloxy represents for example vinyl, prop-1-enyl, allyl, butenyl, isopropenyl or isobutenyl and the oxy equivalents thereof. A lower alkyne, alkynyl or alkynyloxy group is branched or unbranched and contains 2 to 7 carbon atoms, preferably 1-4 carbon atoms and contains at least one carbon-carbon triple bond. Lower alkyne or alkynyl represents for example ethynyl, prop-1-ynyl, propargyl, butynyl, isopropynyl or isobutynyl and the oxy equivalents thereof (In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.). Aryl represents carbocyclic or heterocyclic aryl. Carbocyclic aryl represents monocyclic, bicyclic or tricyclic aryl, for example phenyl or phenyl mono-, di- or trisubstituted by one, two or three radicals selected from lower alkyl, lower alkoxy, aryl, hydroxy, halogen, cyano, trifluoromethyl, lower alkylenedioxy and oxy-$C_2$-$C_3$-alkylene; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as carbocyclic aryl is naphthyl, phenyl or phenyl mono-, di- or trisubstituted by lower alkoxy, phenyl, halogen, lower alkyl or trifluoromethyl, especially phenyl or phenyl mono- or disubstituted by lower alkoxy, halogen or trifluoromethyl, and in particular phenyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, benzothiadiazolyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted as defined above.

Preferably, heterocyclic aryl is pyridyl, pyrimidyl, indolyl, quinoxalinyl, quinolinyl, benzothiadiazolyl, pyrrolyl, thiazolyl, isoxazolyl, triazolyl, tetrazolyl, pyrazolyl, imidazolyl, thienyl, or any said radical substituted, especially mono- or di-substituted as defined above.

Cycloalkyl represents a saturated cyclic hydrocarbon optionally substituted by lower alkyl which contains 3 to 10 ring carbons and is advantageously cyclopropyl, cyclobutyl, cyclopentyl, cyclohexyl, cycloheptyl or cyclooctyl optionally substituted by lower alkyl.

R1 may represent from 1 to 3 substituents; though more preferably represent 1 or 2 substituents. The R1 substituents may be present at any of positions 5, 6, 7 or 8; for instance, at positions 5, 6 or 7, e.g. when R1 represent 2 substituents these may be present at the 5 and 6 or 6 and 7 positions. Preferably one of the R1 substituents is at the 6 position. R1 as optionally substituted (lower alkyl, lower alkoxy, lower alkenyl, lower alkenyloxy, lower alkynyl, lower alkynyloxy, lower alkanoyl or amino) may be substituted by 1 or 2 substituents independently selected from halo, e.g. Cl, lower alkyl, e.g. ethyl or methyl, lower alkenyl, lower alkynyl, cycloalkyl, e.g. $C_3$-$C_6$ cycloalkyl, or cyano.

In a particular embodiment R1 is 2 substituents one of which is OH, preferably at the 6-position, and the other of which is optionally substituted (lower alkyl, cycloalkyl lower alkyl or lower alkenyl), e.g. ethyl, propyl, cyclopropylmethyl or allyl, preferably at the 5-position.

Particularly preferred significances for R1 are: propargyloxy, hydroxy, methoxy, ethoxy, allyloxy, 2-chloroethoxy, isopropoxy, n-propoxy, cyclopropylmethoxy, 3-chloropropoxy, 2-methyl-allyloxy, n-butoxy, allyl, amino, acetonitrileoxy, methylamino, dimethylamino, propargylamino, or allylamino; in particular, e.g. as hereinafter described in the Examples.

R2 represents 1, 2 or 3; for instance, 1 substituent, in the 2-position or 3-position or more preferably in the 4-position, selected from halo, optionally substituted (lower alkyl or amino) in which lower alkyl is preferably unsubstituted, e.g. branched lower alkyl, and amino is preferably mono- or di-substituted by lower alkyl.

Preferred significances for R2 include: methyl, ethyl, isopropyl, t-butyl, cyclopropyl or chloro. Most preferably R2 is isopropyl in the 4-position.

R3 as alkyl substituted by —$O_x$—$(CH_2)_y$—$SO_z$-lower allyl, may be substituted by —$SO_z$-lower alkyl, e.g. —S-lower alkyl.

R3 as benzyl which is mono- or di- (preferably mono-) substituted by —$O_x$—$(CH_2)_y$—$SO_z$-lower alkyl, may be benzyl mono-substituted by —$SO_z$-lower alkyl, e.g. —S(O)—$CH_3$ or —S($O_2$)—$CH_3$.

R3 as benzyl may be substituted on the —$CH_2$— group thereof, by 1 or 2 substituents independently selected from halogen, OH, lower alkyl, e.g. methyl, or lower alkoxy, e.g. methoxy.

R3 as optionally substituted (aryl-$C_2$-$C_8$-alkyl, aryl-$C_2$-$C_8$-alkenyl, heteroarylmethyl or 4-heteroarylbenzyl) may be substituted by up to 8, typically up to 5, usually 1, 2 or 3 substituents, independently selected from halo, nitro, cyano, amino, OH, SH, lower alkyl, lower alkoxy, lower thioalkoxy, lower alkoxycarbonyl, lower alkylsulphonyl, lower alkoxysulphonyl, lower alkylcarbonyloxy, trifluoromethyl, optionally halo-substituted aryl, optionally oxo-substituted pyrrolidinyl or —X-A-Z, wherein
—X— is —CO—O—, —O—, —$CH_2$—O—, —CO—NR5-, —NR5-, —$CH_2$—NR5-, —CO—$CH_2$—, —S—, —S(O)—, —S($O_2$)—, —$CH_2$—S—, $CH_2$S(O)—, —$CH_2$S($O_2$)—, —SO—NR5-, —$SO_2$—NR5-, —NR5-CO—, NR5S(O)—, NR5S($O_2$)— or —O—CO—, where R5 is H or optionally substituted (lower alkyl, lower alkenyl, lower alkoxy-lower alkyl, aryl lower alkyl or optionally mono- or di-lower alkyl-substituted amino lower allyl), -A- is $C_1$-$C_{10}$ alkyl, preferably $C_3$-$C_8$ alkyl optionally interrupted by one or more, e.g. up to 4, preferably 1, 2 or 3, of —O—, —S— or —NR5-, or HO-(lower alkoxy)$_p$-, e.g. HO(ethoxy)$_p$, or lower alkoxy-(lower alkoxy)$_p$-, e.g. methoxy-(ethoxy)$_p$, where p is an integer from 1 up to and including 10, preferably from 1 up to and including 4, and Z is H, halo, hydroxy, lower alkoxy, lower alkoxy-lower alkyl, —NR5R5', —N⁺R5R5'R5'', —COOH, imidazolyl, optionally R5 substituted -piperazinyl, —CH(COOH)₂, —SO₃⁻, —NR5-(CH₂)ₙ—CH₂—NR5R5', —NR5-(CH₂)ₙ—CH₂—OR5, morpholino or tetrahydropyranyl, where R5, R5' and R5'' are independently H or optionally substituted (lower alkyl, lower alkoxy-lower alkyl or aryl lower alkyl, e.g. indolylethyl), or R5, R5' or R5'' may be linked together in an optionally substituted N-heterocyclic ring containing from 3 to 8 ring atoms one or more of which may comprise a further heteroatom selected from O, S or —NR5-, wherein R5 is as defined above.

R3 as optionally substituted (aryl-$C_2$-$C_8$-alkyl) may be carbocyclic aryl-$C_2$-$C_8$-alkyl, e.g. phenyl-$C_2$-$C_8$-alkyl, or hetrocyclic aryl-$C_2$-$C_8$-alkyl, e.g. pyridyl-$C_2$-$C_8$-alkyl, all optionally substituted.

R3 as optionally substituted (aryl-$C_2$-$C_8$-alkyl) may be arylethyl, aryl propyl, arylbutyl etc, e.g. phenylethyl or pyridylethyl, all optionally substituted.

R3 as optionally substituted (aryl-$C_2$-$C_8$-alkenyl) may be carbocyclic aryl-$C_2$-$C_8$-alkenyl, e.g. phenyl-$C_2$-$C_8$-alkenyl, or heterocyclic aryl-$C_2$-$C_8$-alkenyl, e.g. pyridyl-$C_2$-$C_8$-alkenyl, all optionally substituted.

R3 as optionally substituted (aryl-$C_2$-$C_8$-alkenyl) may be arylvinyl, arylpropenyl, arylbutenyl etc, e.g. styryl or pyridylvinyl, all optionally substituted.

R3 as optionally substituted (aryl-$C_2$-$C_8$-alkyl and aryl-$C_2$-$C_8$-alkenyl) may be substituted on the aryl ring preferably by 1, 2 or 3 substituents independently selected from halogen, nitro, cyano, amino, OH, SH, lower alkyl, lower alkoxy, lower alkyl-SO$_z$—(CH₂)$_y$—O$_x$—, wherein x is 0 or 1, y is 0, 1 or 2 and z is 0, 1 or 2, or —X-A-Z, HO-(lower alkoxy)$_p$- or lower alkoxy-(lower alkoxy)$_p$ as defined above.

R3 as optionally substituted (aryl-$C_2$-$C_8$-alkyl and aryl-$C_2$-$C_8$-alkenyl) is optionally substituted on the $C_2$-$C_8$-alkyl or on the $C_2$-$C_8$-alkenyl by 1 to 6, preferably 1, 2 or 3 substituents independently selected from halogen, nitro, cyano, amino, OH, SH, lower alkyl, lower alkoxy, lower alkyl-SO$_z$—(CH₂)$_y$—O$_x$—, wherein x is 0 or 1, y is 0, 1 or 2 and z is 0, 1 or 2, or —X-A-Z, HO-(lower alkoxy)$_p$- or lower alkoxy-(lower alkoxy)$_p$ as defined above. For example, when $C_2$-$C_8$-alkyl is ethyl, it may be substituted, e.g. at the 2-position, preferably by 1 or 2 substituents independently selected from halogen, OH, lower alkyl, e.g. methyl, or lower alkoxy, e.g. methoxy.

R3 as heteroarylmethyl is preferably pyridinylmethyl, e.g. pyridin-2-ylmethyl, pyridin-3-ylmethyl or pyridin-4-ylmethyl, imidazolylmethyl, e.g. imidazol-4-ylmethyl, quinoxalinylmethyl, e.g. quinoxalin-6-ylmethyl, triphenylmethyl, e.g. thiophen-2-ylmethyl, pyrazolylmethyl, e.g. pyrazol-3-ylmethyl, pyrimidinylmethyl, e.g. pyrimidin-5-ylmethyl, indolylmethyl, or furanylmethyl, e.g. furan-2-ylmethyl.

R3 as heteroarylmethyl is optionally substituted on the heteroaryl ring preferably by 1, 2 or 3 substituents independently selected from halogen, nitro, cyano, amino (optionally substituted by lower alkyl), OH, SH, lower alkyl (optionally substituted by halogen, nitro, amino, OH or SH), lower alkoxy, lower thioalkoxy, lower alkoxy-lower alkoxy, hydroxy-lower alkoxy-lower alkoxy or aryl, or —X-A-Z, HO-(lower alkoxy)$_p$- or lower alkoxy-(lower alkoxy)$_p$ as defined above.

R3 as 4-heteroarylbenzyl may comprise 4-pyrazinylbenzyl, e.g. 4-pyrazin-2-ylbenzyl, or 4-triazolylbenzyl, e.g. 4-(1,2,3)triazol-2-ylbenzyl.

Accordingly in particular embodiments the invention provides a compound of formula I' wherein Y is O or S;
R1 and R2 are as defined above for formula I;
R3' is
A) lower alkyl substituted by 1 to 3 substituents independently selected from —S-lower alkyl, lower alkylene, cycloalkyl, Br, F or CF₃; or
B) benzyl which is
  a. mono- or di- (preferably mono-) substituted by —O$_x$—(CH₂)$_y$—SO$_z$-lower alkyl, wherein x is 0 or 1, y is 0, 1 or 2 and z is 0, 1 or 2,
  b. substituted by 1 or 2 substituents selected from morpholino-lower alkoxy, aryl-lower alkoxy, optionally N-lower alkyl substituted arylamino-alkoxy,
  c. substituted at the 2-position by lower alkoxy-, hydroxy-lower alkoxy- or lower alkoxy-lower alkoxy, or
C) optionally substituted (arylvinyl, arylethyl, heteroarylmethyl or 4-heteroarylbenzyl); or
  when R1 is 2 substituents one of which is OH, preferably at the 6-position, and the other of which is optionally substituted (lower alkyl or lower alkenyl), preferably at the 5-position, R3' is H or optionally substituted (lower alkyl, aryl, aryl-lower alkyl, arylcycloalkyl, cycloalkyl-lower alkyl, cycloalkenyl-lower alkyl, hetereoaryl-lower alkyl, hetereoaryl, or carbonyl lower alkyl); or
  when R1 is 2-propynyl and R2 is isopropyl, R3' is also benzyl which is substituted by 1 to 3 substituents selected from lower alkyl, lower alkoxy, halo, halo-lower alkyl, e.g. CF₃, —O—CH(H or lower alkyl)-COO(H or lower alkyl); or
  when R1 is 2-propynyl and R2 is isopropyl, R3' is also benzyl which is substituted by OH and a second and optionally third substituent selected from lower alkyl, lower alkoxy, halo, —O—CH(H or lower alkyl)-COO(H or lower alkyl); or
  when R1 is 2-propynyl and R2 is cyclopropyl, R3' is also optionally substituted benzyl (preferably R3 is also benzyl which is substituted by 1 to 3 substituents selected from lower alkyl, lower alkoxy, halo, —O—CH(H or lower alkyl)-COO(H or lower alkyl)); or
  when X is S and R1 is as defined above but not methoxy, R3' is also optionally substituted benzyl; or
  a compound selected from 4-(4-isopropyl-phenyl)-1-(3,4-diamino-benzyl)-6-prop-2-ynyloxy-1H-quinazolin-2-one, 1-(2,6-dichloro-benzyl)-4-(4-isopropyl-phenyl)-6-prop-2-ynyloxy-1H-quinazolin-2-one, 1-benzyl-4-(4-isopropyl-phenyl)-6-prop-2-ynyloxy-1H-quinazoline-2-thione; 1-(3di-tert-butyl-4-hydroxy-benzyl)-4-(4-isopropyl-phenyl)-6-prop-2-ynyloxy-1H-quinazolin-2-one, or 1-[3-(2-hydroxy-ethoxy)-benzyl]-4-(4-isopropyl-phenyl)-6-prop-2-ynyloxy-1H-quinazoline-2-thione; or a pharmaceutically-acceptable and -cleavable ester, or acid addition salt thereof; and provided that when Y is O and R3' is lower alkyl or cycloalkyl, R3' is not isopropyl or cyclopentyl; or provided the compound of formula I' is not 4-(4isopropyl-phenyl)-6-methoxy-1-pyridin-3-ylmethyl-1.H.-quinazolin-2-one, 4-(4-isopropyl-phenyl)-6-methoxy-1-pyridin-2-ylmethyl-1.H.-quinazolin-2-one, 1-(6-chloro-pyridin-3-ylmethyl)-4-(4-isopropyl-phenyl)-6-methoxy-1.H.-quinazolin-2-one, 4-(4-isopropyl-phenyl)-6-methoxy-1-(5-nitro-furan-2-ylmethyl)-1.H.-quinazolin-2-one or 1-[2-(1.H.-indol-2-yl)-ethyl]-4-(4-isopropyl-phenyl)-6-methoxy-1.H.-quinazolin-2-one, 4-(4-isopropyl-phenyl)-6-methoxy-1-phenethyl-1H-quinazolin-2-one, 1-(2hydroxy-2-phenyl-ethyl)-4-(4-isopropyl-phenyl)-6-prop-2-ynyloxy-1H-quinazolin-2-one, methanesulfonic acid 2-[4-(4-isopropyl-phenyl)-2-oxo-6-prop-2-ynyloxy-2H-quinazolin-1-ylmethyl]-phenyl ester, or acetic acid 2-[4-(4-isopropyl-phenyl)-2-oxo-6-prop-2-ynyloxy-2H-quinazolin-1-yl]-1-phenyl-ethyl ester, 5-allyl-6-hydroxy-1-isopropyl-4-(4-isopropyl-phenyl)-1.H.-quinazolin-2-one, 1-cyclopropylmethyl-4-(o-tolyl)-6-nitro-2(1H)-quinazolinone, 1-Ethyl-4-(o-tolyl)-6-chloro-2(1H)-quinazolinone, 1-cyclopropylmethyl-4-(o-tolyl)-6-chloro-2(1H)-quinazolinone, 1-cyclopropylmethyl-4-(o-fluorophenyl)-6-chloro-2 (1H)-quinazolinone, 1-cyclopropylmethyl-4-(m-chlorophenyl)-6-chloro-2(1H)-quinazolinone, 1-cyclopropylmethyl-4-(o-chlorophenyl)-6-nitro-2(1H)-quinazolinone.

Accordingly in particular embodiments the invention further provides a compound of formula I"

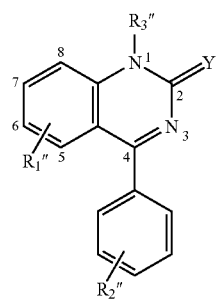

wherein Y is O or S;

R1" is 2 substituents one of which is OH, preferably at the 6-position, and the other of which is optionally substituted (lower alkyl or lower alkenyl), preferably at the 5-position; or R1" is 2-propynyloxy, preferably at the 6-position;

R2'" is isopropyl, tert. butyl or cyclopropyl;

R3" is benzyl which is substituted by 1 to 3 substituents selected from lower alkyl, lower alkoxy, halo, halo-lower alkyl, e.g. CF$_3$, —CH(H or lower alkyl)-COO(H or lower alkyl); —COO(H or lower alkyl); or R3" is benzyl which is substituted by OH and a second and optionally third substituent selected from lower alkyl, lower alkoxy, halo, —CH(H or lower alkyl)-COO(H or lower alkyl); or when R1" is 2-propynyl and R2" is cyclopropyl, R3" is benzyl which is substituted by 1 to 3 substituents selected from lower alkyl, lower alkoxy, halo, —CH(H or lower alkyl)-COO(H or lower alkyl)); or when X is S and R1" is as defined above but not methoxy, R3" is also optionally substituted benzyl; or a pharmaceutically-acceptable and -cleavable ester, or acid addition salt thereof.

Moreover, further embodiments of the invention are provided as a compound of formula I'"

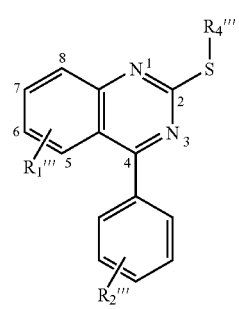

wherein R1'" is 1 to 2 substituents selected from lower alkoxy, lower alkenoxy, lower alknoxy, lower alkyl, lower alkenyl, lower alkinyl, OH or halo (preferably R1'" is propynyloxy, preferably at the 6 position);

R2'" is 1 to 3 substituents selected from halo, lower alkyl or lower alkoxy, provided one substituent is isopropyl, tert. butyl or cyclopropyl;

R4'" is optionally substituted (aryl-lower alkyl, aryl, hetereoaryl, hetereoaryl-lower alkyl, lower alkyl, cycloalkyl, cycloalkyl-lower alkyl, lower alkenyl, lower alkynyl); or a pharmaceutically-acceptable and -cleavable ester, or acid addition salt thereof;

provided that the compound of formula I'" is not 4-(4-isopropyl-phenyl)-2-isopropylsulfanyl-6,7-dimethyoxy-quinazoline.

As hereinafter described compounds of formula I may be prepared by cyclisation of a compound of formula II

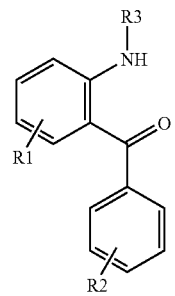

wherein R1, R2 and R3 are as defined above. Compounds of formula II have activity as promoters of PTH release and are included within the present invention, e.g. for use as PTH release promoters.

As hereinafter described compounds of formula I' may be prepared by cyclisation of a compound of formula II'

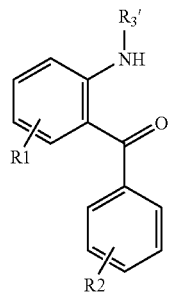

wherein R1, R2 and R3' are as defined above. Compounds of formula II' have activity as promoters of PTH release and are included within the present invention, e.g. for use as PTH release promoters.

As hereinafter described compounds of formula I" may be prepared by cyclisation of a compound of formula II"

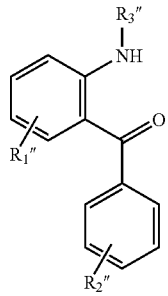

wherein R1", R2" and R3" are as defined above. Compounds of formula II" have activity as promoters of PTH release and are included within the present invention, e.g. for use as PTH release promoters.

As hereinafter described compounds of formula I'" may be prepared by reaction of a compound of formula I'" a

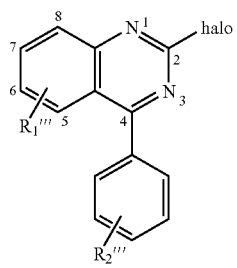

wherein R1'" and R3'" are as defined above, with HS—R4'", wherein R4'" is as defined above.

Alternatively, the compounds of formula I'" may be prepared by reaction of formula II'"b

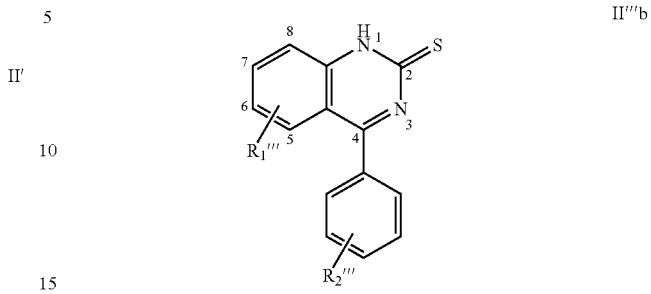

wherein R1'" and R2'" are as defined above, with Halo-R4'", wherein R4'" is as defined above.

Compounds of formula I'"a or compounds of formula II'"b have activity as promoters of PTH release and are included within the present invention, e.g. for use as PTH release promoters.

Accordingly in a further aspect the invention provides a compound of formula II

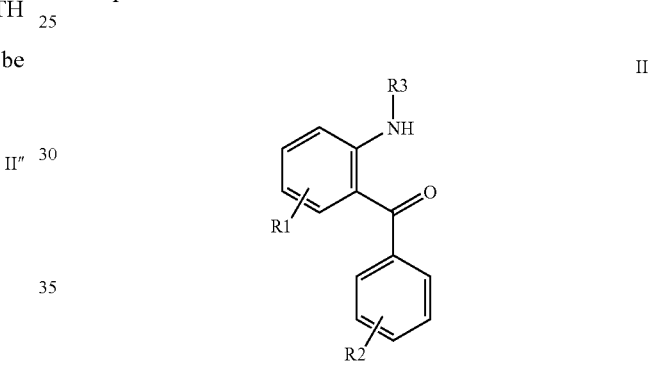

wherein R1, R2 and R3 are as defined above;

provided that the compound of formula II is not {2-[2-(3,5-dimethoxy-phenyl)-2-methyl-propylamino]-4,5-dimethoxy-phenyl}-(4-isopropyl-phenyl)-methanone, (4-isopropyl-phenyl)-{5-methoxy-2-[(pyridin-3-ylmethyl)-amino]-phenyl}-methanone, (4-isopropyl-phenyl)-{5-methoxy-2-[(pyridin-2-ylmethyl)-amino]-phenyl}-methanone; or a compound selected from {2-[2-(2-hydroxy-ethoxy)-benzylamino]-5-prop-2-ynyloxy-phenyl}-(4-isopropyl-phenyl)-methanone or {2-[(2,3-dimethoxy-quinoxalin-6-ylmethyl)-amino]-5-prop-2-ynyloxy-phenyl}-(4-isopropyl-phenyl)-methanone;

or a pharmaceutically-acceptable and -cleavable ester, or acid addition salt thereof.

Preferred significances for R1, R2 and R3 in formula II are as described above for R1, R2 and R3 in formula I.

Particular significances for R3 in formula II include:

Optionally substituted aryl-$C_2$-$C_8$-alkyl; for instance, optionally substituted phenylethyl, e.g. optionally mono- or di-lower alkoxy substituted phenylethyl, in which the ethyl is optionally mono- or di-substituted (e.g. at the 2-position) by halogen, OH, lower alkyl (e.g. methyl) or lower alkoxy (e.g. methoxy);

Optionally substituted heteroarylmethyl; for instance, optionally substituted pyridinylmethyl or quinoxalinylmethyl, e.g. optionally mono- or di-disubstituted by halogen, OH, lower alkyl (e.g. methyl), lower alkoxy (e.g. methoxy), hydroxy-lower alkoxy, (e.g. hydroxy-ethoxy) or lower alkoxy-lower alkoxy (e.g. methoxy-ethoxy); and Benzyl which is substituted at the 2-position by lower alkoxy-, hydroxy-lower alkoxy- or lower alkoxy-lower alkoxy, e.g 2-(2-hydroxy-ethoxy)-benzyl.

Accordingly in particular embodiments the invention provides a compound of formula II'

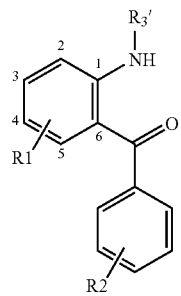

II' wherein R1 and R2 are as defined above for formula I;

R'$_3$ is as defined above for formula I' provided that the compound of formula II' is not {2-[2-(3,5-dimethoxy-phenyl)-2-methyl-propylamino]-4,5-diethoxy-phenyl}-(4-isopropyl-phenyl)-methanone, (4-isopropyl-phenyl)-{5-methoxy-2-[(pyridin-3-ylmethyl)-amino]-phenyl}-methanone, (4-isopropyl-phenyl)-{5-methoxy-2-[(pyridin-2-ylmethyl)-amino]-phenyl}-methanone; or a compound selected from {2-[2-(2-hydroxy-ethoxy)-benzylamino]-5-prop-2-ynyloxy-phenyl}-(4-isopropyl-phenyl)-methanone or {2-[(2,3-dimethoxy-quinoxalin-6-ylmethyl)-amino]-5-prop-2-ynyloxy-phenyl}-(4-isopropyl-phenyl)-methanone;

or a pharmaceutically-acceptable and -cleavable ester, or acid addition salt thereof.

The substituents and optional substituents on R3' are as described above for the optional substituents on R3, including the preferred significances thereof.

In particular the invention includes the compounds of formula I and formula II as hereinafter described in the Examples, or pharmaceutically-acceptable and -cleavable esters, or acid addition salts thereof.

The compounds of formula I and II, and salts and esters thereof, in particular as identified in the Examples are hereinafter referred to as Agents of the Invention.

The Agents of the Invention which comprise free hydroxyl groups may be also used in the form of pharmaceutically acceptable, physiologically cleavable esters, and as such and where novel are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an azyl-carboxylic acid.

Agents of the Invention may also exist in the form of pharmaceutically acceptable salts, and as such and where novel are included within the scope of the invention.

Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, trifluoroacetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclo-hexylsulfamic acid; also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

Agents of the Invention of formula I and II may be prepared as follows:

Agents of the Invention of Formula I

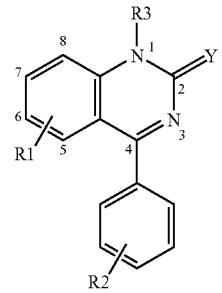

I wherein R1, R2 and R3 are as defined above may be prepared by cyclising a compound of formula II

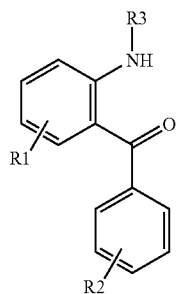

II with a condensation reagent such as chlorosulfonyl isocyanate (ClSO$_2$NCO), sodium cyanate, benzoyl isothiocyanate in THF, followed by treatment with K$_2$CO$_3$/methanol or sodium thiocyanate and acetic acid, and thereafter, if required converting the R1, R2 or R3 residues into an alternative R1, R2 or R3 residues to give alternative compound of formula II. For example, in the cyclisation reaction the benzophenone of formula II in solution is treated with a solution of sodium cyanate, e.g. in acetic acid at room temperature.

Benzophenone Compounds of Formula II May be Prepared by Treatment of the Corresponding Amine of Formula X

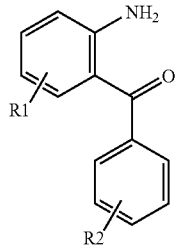

X with the corresponding halide, e.g. bromide, R3Br and a suitable base such as K₂CO₃. In particular, compounds of formula X where R1 is OH in 6 position and R1 is also 2-propenyl, cyclopropyl-methyl or propyl may be prepared as e.g. described in Example for compound 5-allyl-1-benzyl-6-hydroxy-4-(4-isopropyl-phenyl)-1H-quinazolin-2-one and following.

Alternatively, compounds of formula II may be prepared by reductive amination of the corresponding aldehyde with the amine X, using Ti (Oi-pr)₄ or molecular sieves as dehydrating agent and NaBH(OAc)₃ or NaCNBH₃ as the reducing agent. The amine X is obtainable from the corresponding nitro derivative (see below compound of formula XI) by reduction, e.g. with iron in acetic acid.

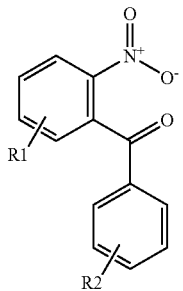

XI wherein R2 is as previously defined and R1 is an activating group.

The compound of formula XI may in turn be obtained by the oxidation, e.g. with Jones reagent, of the corresponding alcohol which may in turn be obtained by coupling an organometallic compound derived from the corresponding bromide of formula XIII and aldehyde of formulae XII respectively; for instance as described in the Examples

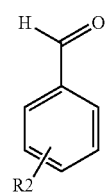

XII

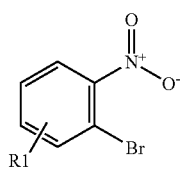

XIII

In a further alternative, compounds of formula II, in particular where R3 is substituted pyridyl-methyl, may be prepared by reacting the corresponding alcohol, R3-OH, e.g. pyridyl-methyl-hydroxide, with the corresponding amine of formula X, e.g. in the presence of Hünig's base and mesyl chloride; for instance as hereinafter described in the Examples.

In a yet further alternative Agents of the Invention of formula II, in which R3 is optionally substituted aryl-lower alkyl may be prepared by alkylation of an Agent of the Invention of formula XX

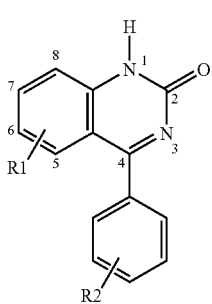

XX at the 1-position with the corresponding optionally substituted aryl-lower alkylhalide; for instance, in the presence of e.g. LiHMDS and NaI, in solution, e.g. THF/DMF, with mild heating.

Alternatively Compounds of Formula XXII

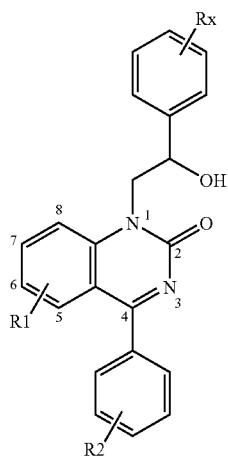

XXII wherein Rx is halo, lower alkyl or lower alkoxy;
may be prepared by reacting a compound of formula XX with the corresponding oxirane of formula XXI

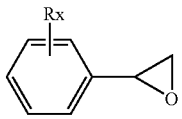

XXI

Where Rx is the optional substitution on the phenyl ring; for instance in the presence of benzyltriethylammonium chloride and potassium carbonate, e.g. as hereinafter described in the Examples. Corresponding compounds of formula II in which R3 is optionally substituted styryl may be prepared by treatment of a compound of formula XXII with a reagent such as trifluoromethanesulphonic anhydride.

The compound of formula XX may be prepared from the corresponding compound of formula II in which R3 is H by treatment with a condensation reagent such as sodium cyanate.

Agents of the Invention of formula II may be prepared as intermediates in the preparation of Agents of the Invention of formula I, e.g. as described above, or as hereinafter described in the Examples.

Accordingly the Invention includes processes for the preparation of Agents of the Invention of formula I

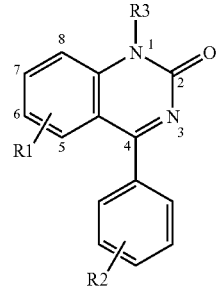
I wherein the symbols are as defined above comprising a) cyclising a compound of formula II

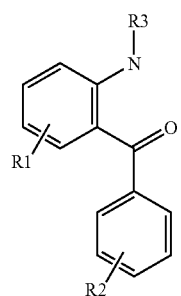
II with a condensation reagent such as chlorosulfonyl isocyanate (ClSO$_2$NCO) or sodium cyanate or sodium thiocyanate; or b) for an Agent of the Invention of formula I, in which R3 is optionally substituted aryl-lower alkyl, alkylation of a compound of formula XX

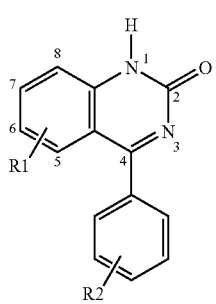
XX at the 1-position with the corresponding optionally substituted aryl-lower alkylhalide; and thereafter, if required converting the R1, R2 or R3 residues into alternative R1, R2 or R3 residues to give an alternative compound of formula I.

The preparation of Agents of the Invention of formula II as described above is also included within the invention.

Accordingly in a further aspect the invention provides processes for the preparation of Agents of the Invention of formula II

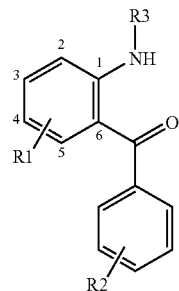
II wherein R1, R2 and R3 are as defined above comprising alkylation of the corresponding aminobenzophenone compound of formula X

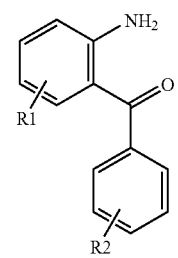
X wherein R1 and R2 are as defined above, and thereafter, if required, converting R1, R2 or R3 residues into alternative R1, R2 or R3 residues to give an alternative compound of formula II.

The invention is described by way of illustration only in the following non-limiting Examples which relate to the preparation of compounds of the invention of formulae I and II.

EXAMPLES

Example 1

1-(2,3-Dimethoxy-quinoxalin-6-ylmethyl)-4-(4-isopropyl-phenyl)-6-prop-2-ynyloxy-1H-quinazolin-2-one

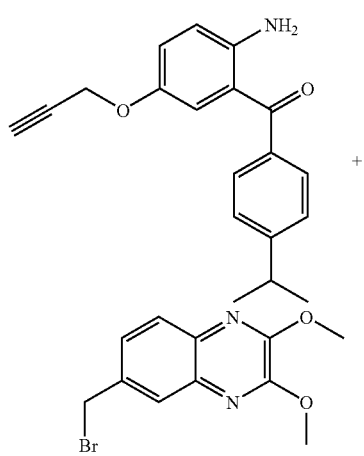

-continued

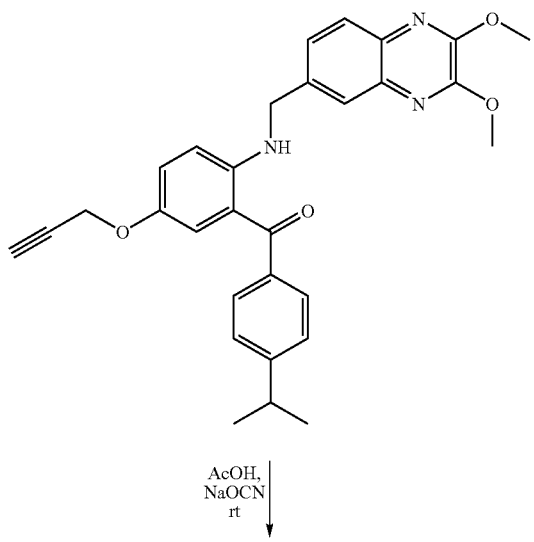

AcOH,
NaOCN
rt

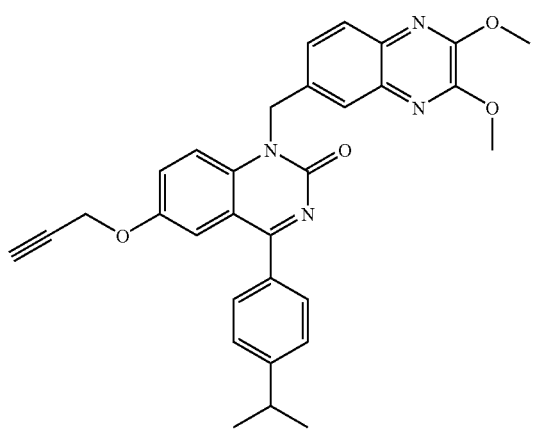

A. Synthesis of {2-[(2,3-dimethoxy-quinoxalin-6-ylmethyl)-amino]-5-prop-2-ynyloxy-phenyl}-(4isopropyl-phenyl)-methanone

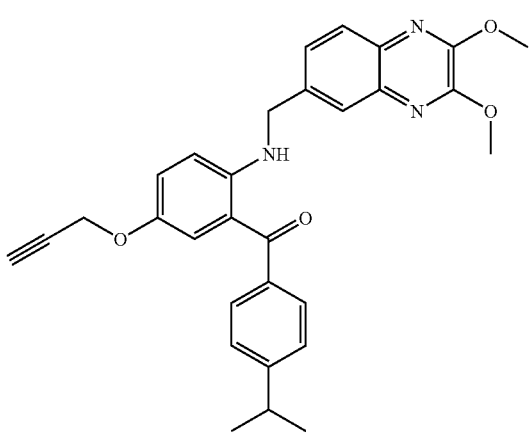 [SMILES: C#CCOc1ccc(NCc2ccc3nc(OC)c(OC)nc3c2)c(C(=O)c2ccc(C(C)C)cc2)c1]

To a solution of 82 mg (0.280 mmol) (2-amino-5-propargyloxy-phenyl)-(4-isopropyl-phenyl)-methanone in 3 ml dioxane is added 193 mg (1.40 mmol) potassium carbonate and 119 mg (0.419 mmol) 6-Bromomethyl-2,3-dimethoxy-quinoxaline. The mixture is stirred at 80° C. for two days, diluted with water and extracted with $CH_2Cl_2$. Purification of the crude product by chromatography (ethyl acetate/hexanes 1:1) affords a yellow oil.

$^1$H NMR (300 MHz, $CDCl_3$): 7.04-7.60 (m, 10H), 4.94 (s, 2H), 4.52 (d, 2H), 4.26 (s, 3H), 4.08 (s, 3H), 2.96 (hept, 1H), 2.48 (t, 1H), 1.28 (d, 6H).

MS: 496 $(M+1)^+$

B. Synthesis of 1-(2,3-dimethoxy-quinoxalin-6-ylmethyl)-4-(4-isopropyl-phenyl)-6-prop-2-ynyloxy-1H-quinazolin-2-one

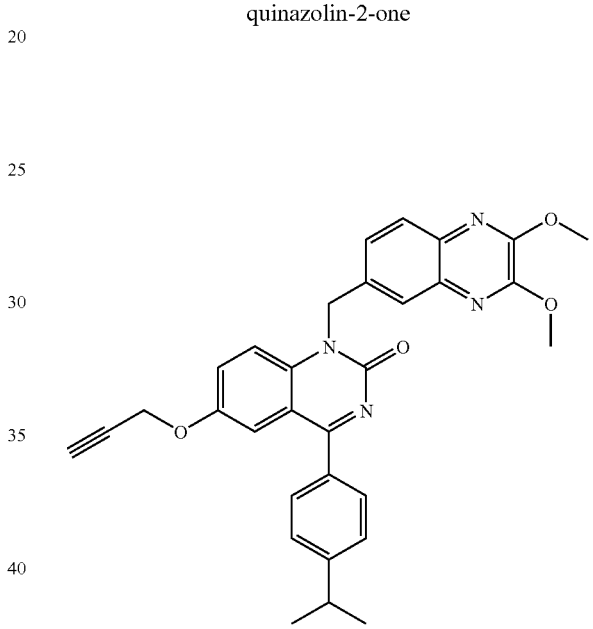

To a solution of 52 mg (0.105 mmol) {2-[(2,3-dimethoxy-quinoxalin-6-ylmethyl)-amino]-5-prop-2-ynyloxy-phenyl}-(4isopropyl-phenyl)-methanone in 1 ml acetic acid is added 14 mg (0.210 mmol) sodium cyanate. After stirring for 2 h the solvent is removed in vacuo and the residue is partitioned between $CH_2Cl_2$ and water. The organic layer is extracted with 2 M sodium hydroxide and evaporated. Purification of the crude product by flash-chromatography (ethyl acetate/hexanes 9:1) affords a yellow oil.

$^1$H NMR (300 MHz, $CDCl_3$): 7.78 (d, 2H), 7.70 (d, 1H), 7.48 (d, 1H), 7.14-7.51 (m, 6H), 6.10 (s, 2H), 4.62 (d, 2H), 4.24 (s, 3H), 4.18 (s, 3H), 3.01 (hept, 1H), 2.52 (m, 1H), 1.32 (d, 6H).

MS: 521 $(M+1)^+$

The (2-amino-5-propargyloxy-phenyl)-(4isopropyl-phenyl)-methanone building block is prepared as follows:

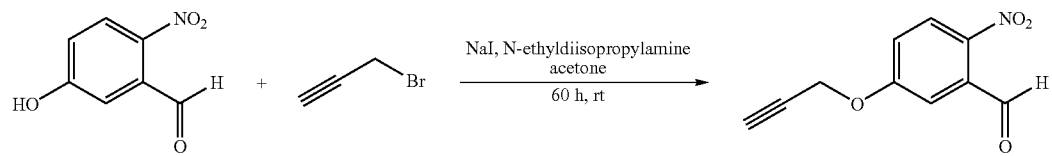
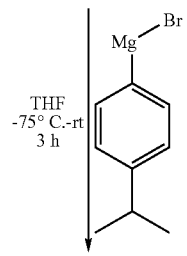
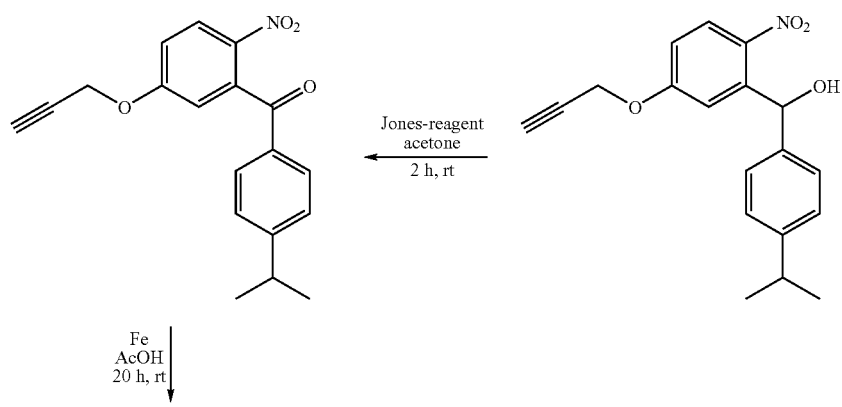
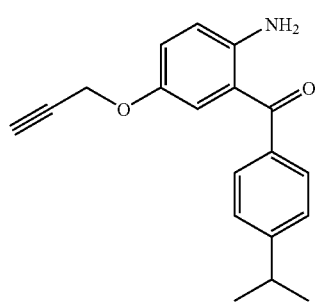

A. Synthesis of 2-nitro-5-propargyloxy-benzaldehyde

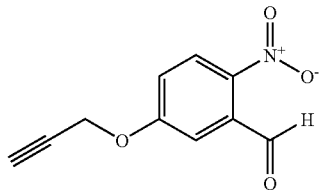

A mixture of 25 g (150 mmol) 5-hydroxy-2-nitro-benzaldehyde, 44.9 g (299 mmol) sodium iodide, 44.5 g propargyl bromide (80% in toluene), 42 ml N-ethyl-diisopropy-lamine and 400 ml acetone is stirred at rt for 6 d. The reaction mixture is filtered, concentrated, taken up in 1M aqueous hydrochloric acid and extracted with ethyl acetate to yield 2-nitro-5-propargyloxy-benzaldehyde.

$^1$H NMR (300 MHz, CDCl$_3$): 10.49 (s, 1H), 8.19 (d, 1H), 7.43 (s, 1H), 7.25 (d, 2H), 4.85 (s, 2H), 2.60 (s, 1H).

B. Synthesis of (4-isopropyl-phenyl)-(2-nitro-5-propargyloxy-phenyl)-methanol

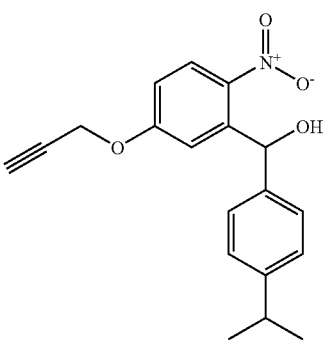 [SMILES: C#CCOc1ccc([N+](=O)[O-])c(C(O)c2ccc(C(C)C)cc2)c1]

To a solution of 30.7 g (150 mmol) 2-nitro-5-propargyloxy-benzaldehyde in 200 ml THF are added at −75° C. during 40 min 200 ml (175 mmol) of a 0.88 M solution of 4-isopropyl magnesium bromide in THF. After stirring for 1 h at −75° C. saturated aqueous ammonium chloride solution is added and the reaction mixture is extracted with portions of ethyl acetate. Evaporation of the organic phases yields (4-isopropyl-phenyl)-(2-nitro-5-propargyloxy-phenyl)-methanol.

$^1$H NMR (300 MHz, CDCl$_3$): 8.09 (d, 1H), 7.45 (d, 1H), 7.26 (d, 2H), 7.19 (d, 2H), 6.98 (dd, 1H), 6.52 (broad, 1H), 4.80 (d, 2H), 2.88 (hept, 1H), 2.71 (broad, 1H), 2.56 (t, 1H), 1.23 (d, 6H).

MS: 308 (100) (M-OH)$^+$, 294 (50)

C. Synthesis of (4-isopropyl-phenyl)-(2-nitro-5-propargyloxy-phenyl)-methanone

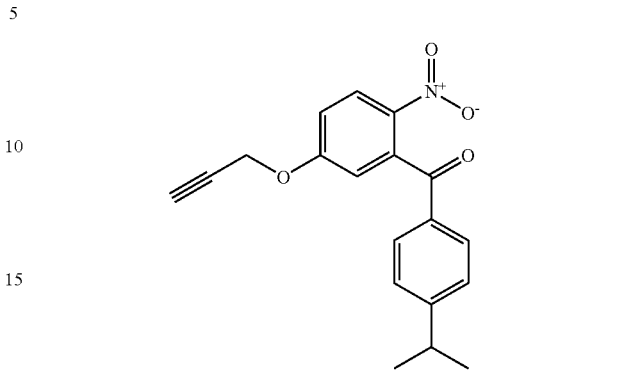

To an ice cold solution of (4-isopropyl-phenyl)-(2-nitro-5-propargyloxy-phenyl)-methanol in 200 ml acetone are added dropwise 60 ml Jones reagent. After stirring for 2 h at rt the reaction is quenched by the addition of isopropanol and sodium bisulphite solution (40%). Extraction with dichloromethane affords (4-isopropyl-phenyl)-(2-nitro-5-propargyloxy-phenyl)-methanone.

$^1$H NMR (300 MHz, CDCl$_3$): 8.27 (d, 1H), 7.70 (d, 2H), 7.30 (d, 2H), 7.18 (dd, 1H), 6.97 (d, 1H), 4.81 (d, 2H), 2.96 (hept, 1H), 2.59 (t, 1H), 1.27 (d, 6H).

D. Synthesis of (2-amino-5-propargyloxy-phenyl)-(4-isopropyl-phenyl)-methanone

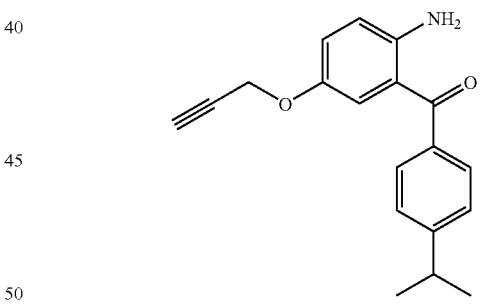

To a solution of 10.59 g (30.7 mmol) (4-isopropyl-phenyl)-(2-nitro-5-propargyloxy-phenyl)-methanone in 250 ml acetic acid are added 13.6 g (246 mmol) iron powder. After stirring for 20 h at rt the reaction mixture is basified by the addition of 2M sodium hydroxide solution, filtered and extracted with dichloromethane. Aider purification by chromatography using hexanes/ethyl acetate (7:3) as eluent (2-amino-5-propargyloxy-phenyl)-(4-isopropyl-phenyl)-methanone is obtained.

$^1$H NMR (300 MHz, CDCl$_3$): 7.64 (d, 2H), 7.30 (d, 2H), 7.12 (s, 1H), 7.05 (d, 1H), 6.72 (d, 1H), 5.71 (broad, 2H), 4.64 (s, 2H), 2.98 (hept, 1H), 2.48 (s, 1H), 1.30 (d, 6H).

MS: 294 (M+1)$^+$

The (2-amino-4,5-dimethoxy-phenyl)-(4-isopropyl-phenyl)-methanone building block is synthesised following the procedure outlined immediately above.

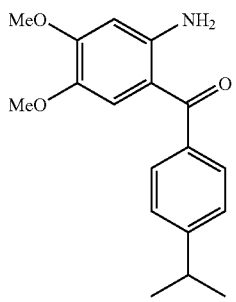 [SMILES: COc1cc(N)c(C(=O)c2ccc(C(C)C)cc2)cc1OC]

Example 2

4-(4-Isopropyl-phenyl)-1-(3-methane-sulphonyl-benzyl)-5-propargyloxy-phenyl-methanone

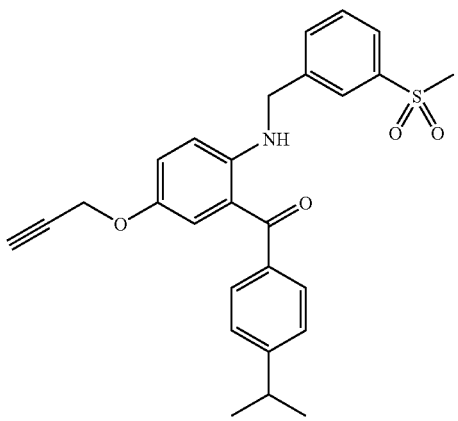 [SMILES: C#CCOc1ccc(NCc2cccc(S(C)(=O)=O)c2)c(C(=O)c2ccc(C(C)C)cc2)c1]

A mixture of 100 mg (0.34 mmol) (2-amino-5-propargyloxy-phenyl)-(4-isopropyl-phenyl)-methanone, 80 mg (0.58 mmol) $K_2CO_3$ and 77 mg (0.375 mmol) 1-chloro-methyl-3-methanesulphonyl-benzene in 1 ml dimethylformamide is stirred at 80° C. for 6 h and at 100° C. for 3 h. Then the reaction mixture is poured onto water and extracted with ethyl acetate. The combined organic layers are washed with water and brine, dried over $MgSO_4$, filtered and concentrated in vacuo. The residue is purified by flash-chromatography on silica gel (hexane:EtOAc=2:1) to afford the title compound as a yellow foam.

$^1$H-NMR (300 MHz, DMSO): 8.34 (t, 1H), 7.90 (s, 1H), 7.80 (d, 1H), 7.67 (d, 1H), 7.60-7.56 (m, 3H), 7.39 (m, 2H), 7.09 (dd, 1H), 7.01 (d, 1H), 6.70 (d, 1H), 4.61-4.53 (m, 4H), 3.54 (m, 1H), 3.19 (s, 3H), 2.96 (m, 1H), 1.25 (d, 6H).

MS: 462 (M+1)$^+$

The starting materials may be prepared as follows:

A. Synthesis of 1-chloromethyl-3-methanesulphonyl-benzene

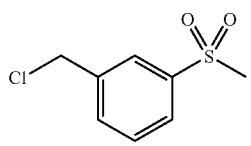

0.267 ml (3.45 mmol) methanesulphonyl-chloride is added to o a solution of 584 mg (3.14 mmol) (3-methanesulphonyl-phenyl)-methanol and 0.66 ml (4.71 mmol) triethylamine in 6 ml dichloromethane. This reaction mixture is stirred at room temperature for 1 h and at 50° C. for additional 3 h. The reaction mixture is then poured into water and extracted twice with dichloromethane. The combined organic layers are washed with water and brine, dried, filtered and concentrated in vacuo to afford the title compound, which is used in the next step without further purification.

$^1$H-NMR (300 MHz, DMSO): 7.98 (broad s, 1H), 7.86 (d, 1H), 7.77 (d, 2H), 7.64 (t, 1H), 4.86 (s, 2H), 3.21 (s, 3H).

B. Synthesis of (3-methanesulphonyl-phenyl)-methanol

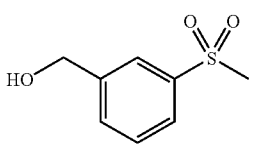

$NaBH_4$ is added to a solution of 750 mg (4.08 mmol) 3-methanesulphonyl-benzaldehyde in 20 ml ethanol (see P. L. Ornstein, T. J. Bleisch, M. B. Arnold, R. A. Wright, B. G. Johnson, J. P. Tizzano, D. R. Helton, M. J. Kallman, D. D. Schoepp, M. Herin, *J. Med. Chem.* 1998, 41(3), 358-378 or B. Eistert, W. Schade, H. Selzer, Ber. 1964, 97(5), 1470-81). The reaction mixture is stirred at room temperature for 1 h. The reaction mixture is poured into water and extracted three times with ethyl acetate. The combined organic layers are washed with water and brine, dried, filtered and concentrated in vacuo to afford the title compound, used in the next step without further purification.

¹H-NMR (300 MHz, DMSO): 7.85 (broad s, 1H), 7.78 (d, 1H), 7.62 (d, 2H), 7.59 (t, 1H), 5.45 (t, 3H), 4.58 (d, 2H), 3.19 (s, 3H).

Example 3

4-(4-Isopropyl-phenyl)-1-(3-methane-sulphonyl-benzyl)-6-propargyloxy-1H-quinazoline-2-one

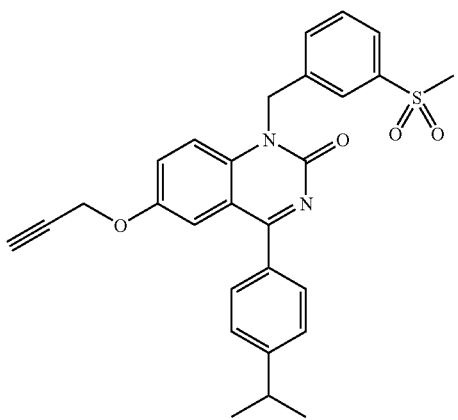 [SMILES: C#CCOc1ccc2c(c1)c(-c1ccc(C(C)C)cc1)nc(=O)n2Cc1cccc(S(C)(=O)=O)c1]

A mixture of 97 mg (0.21 mmol) 4-(4-isopropyl-phenyl)-1-(3-methane-sulphonyl-benzyl)-5-propargyloxy-phenyl-methanone and 17 mg (0.25 mmol) sodium cyanate in 3 ml acetic acid is stirred at room temperature for 72 h. Then the reaction mixture is poured into water and extracted with ethyl acetate. The combined organic layers are washed with water and brine, dried over MgSO₄, filtered and concentrated in vacuo. The residue is purified by flash-chromatography on silica gel (hexane:EtOAc 1:3) to afford the title compound as a yellow foam.

¹H-NMR (300 MHz, DMSO): 7.95 (s, 1H), 7.81 (d, 1H), 7.70 (d, 2H), 7.61-7.50 (m, 2H), 7.47 (m, 2H), 7.45 (d, 2H), 7.38 (m, 1H), 5.59 (broad s, 2H), 4.78 (d, 2H), 3.64 (m, 1H), 3.20 (s, 3H), 3.00 (m, 1H), 1.25 (d, 6H).

MS: 487 (M+1)⁺

Example 4

4-(4-Isopropyl-phenyl)-1-[3-(2-methanesulphinyl-ethoxy)-benzyl]-6-prop-2-ynyloxy-1H-quinazolin-2-one

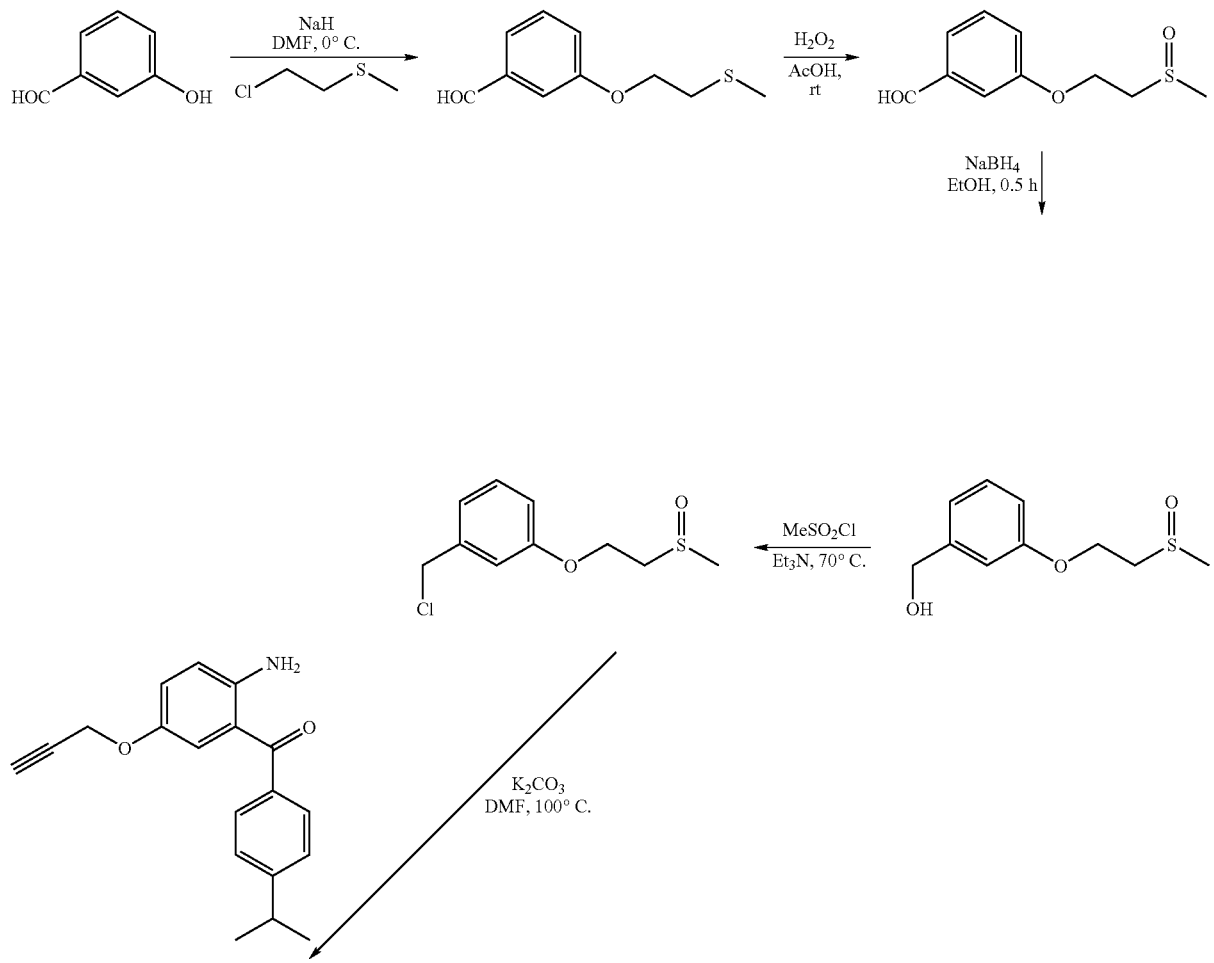

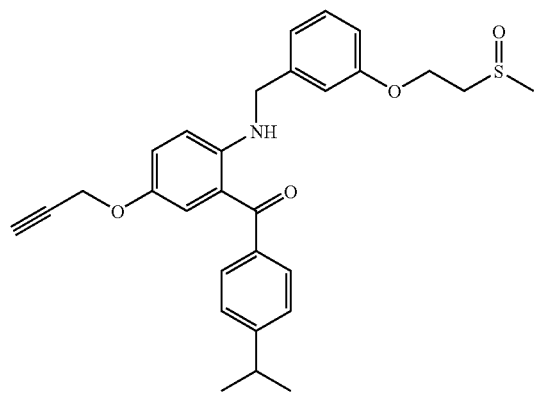

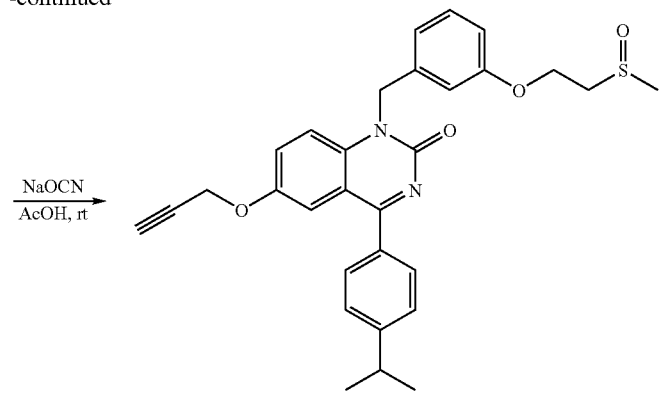

A. Synthesis of 3-(2-methylsulphanyl-ethoxy)-benzaldehyde

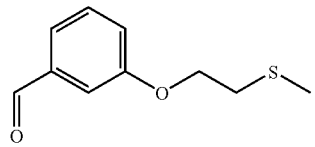

NaH (1.3 g, 54 mmol) is added to a solution of 5.0 g (41 mmol) 3-hydroxybenzaldehyde in 30 ml DMF at 0° C. After stirring for 1 h 4.44 ml (45 mmol) 2-chloroethyl methyl sulphide is added. The reaction mixture is warmed to room temperature and stirring is continued for 16 h. Then the reaction mixture is poured onto water and extracted with ethyl acetate. The combined organic layers are washed with water and brine, dried over MgSO$_4$, filtered and concentrated in vacuo. The residue is purified by flash-chromatography on silica gel (hexane/EtOAc=3:1) to afford the title compound as a colorless oil.

$^1$H-NMR (300 MHz, DMSO-d$_6$): 9.94 (s, 1H), 7.51 (m, 1H), 7.50 (s, 1H), 7.41 (bs, 1H), 7.27 (m, 1H), 4.20 (t, 2H), 2.85 (t, 2H), 2.18 (s, 3H).

B. Synthesis of 3-(2-methanesulphinyl-ethoxy)-benzaldehyde

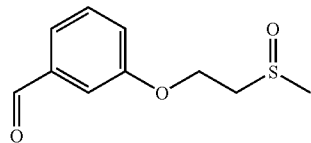

A solution of 1.6 g (8.15 mmol) 3-(2-methylsulphanyl-ethoxy)-benzaldehyde and 1 ml (9.78 mmol) hydrogen peroxide solution in 30 ml acetic acid is stirred for 2 h at room temperature. Then the reaction mixture is poured onto 4N NaOH and extracted with ethyl acetate. The combined organic layers are washed with sodium bisulphite solution, water and brine, dried over MgSO$_4$, filtered and concentrated in vacuo to afford the title compound as a colorless solid, sufficiently pure for the next step.

$^1$H-NMR (300 MHz, DMSO-d$_6$): 9.96 (s, 1H), 7.52 (m, 1H), 7.51 (s, 1H), 7.46 (bs, 1H), 7.30 (m, 1H), 4.40 (m, 2H), 3.26 and 3.08 (m, 2H), 2.62 (s, 3H).
MS: 213 (M+1)$^+$

C. Synthesis of [3-(2-methanesulphinyl-ethoxy)-phenyl]-methanol

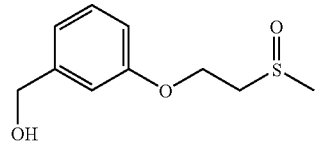

To a solution of 1.1 g (5.18 mmol) 3-(2-methanesulphinyl-ethoxy)-benzaldehyde in 20 ml ethanol (anhydrous) is added NaBH$_4$ (0.215 g, 5.7 mmol). The reaction mixture is stirred at room temperature for 0.5 h. Then it is poured onto water and extracted with ethyl acetate. The combined organic layers are washed with water and brine, dried over MgSO$_4$, filtered and concentrated in vacuo to afford the title compound as a colorless oil that is of sufficient purity for the next step.

$^1$H-NMR (300 MHz, DMSO-d$_6$): 7.20 (t, 1H), 6.90 (bs, 1H), 6.88 (d, 1H), 6.80 (d, 1H), 5.18 (t, 1H), 4.45 (d, 2H), 4.30 (m, 2H), 3.25 and 3.04 (m, 2H), 2.61 (s, 3H).

D. Synthesis of 1-chloromethyl-3-(2-methanesulphinyl-ethoxy)-benzene

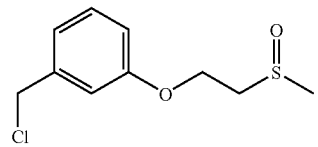

To a solution of 0.7 g (3.27 mmol) and 1.7 ml triethylamine in 30 ml dichloromethane MeSO$_2$Cl (0.315 ml, 4 mmol) is added at 0° C. The reaction mixture is stirred at 0° C. for 1 h and at room temperature for 70 h. After that the reaction mixture is poured onto water and extracted with ethyl acetate. The combined organic layers are washed with water and brine, dried over MgSO$_4$, filtered and concentrated in vacuo. The residue is purified by flash-chromatography on silica gel (dichloromethane/MeOH=9:1) to afford the title compound as a colorless oil.

¹H-NMR (300 MHz, DMSO-d₆): 7.28 (t, 1H), 7.04 (bs, 1H), 7.02 (d, 1H), 6.94 (d, 1H), 4.71 (s, 2H), 4.32 (m, 2H), 3.26 and 3.04 (m, 2H), 2.62 (s, 3H)

MS: 233 (M+1)⁺

E. Synthesis of (4-isopropyl-phenyl)-{2-[3-(2-methanesulphinyl-ethoxy)-benzylamino]-5-prop-2-ynyloxy-phenyl}-methanone

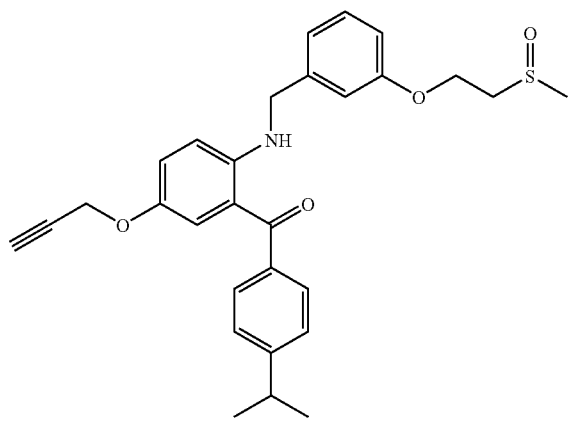 [SMILES: C#CCOc1ccc(NCc2cccc(OCCS(C)=O)c2)c(C(=O)c2ccc(C(C)C)cc2)c1]

The title compound is prepared from 2-amino-5-propargyloxy-phenyl)-(4-isopropyl-phenyl)-methanone and 1-chloromethyl-3-(2-methanesulphinyl-ethoxy)-benzene as described for the preparation of example 2.

¹H-NMR (300 MHz, DMSO-d₆): 8.32 (t, 1H), 7.56 (d, 2H), 7.38 (d, 2H), 7.24 (t, 1H), 7.10 (dd, 1H), 7.00 (bs, 1H), 6.95 (m, 2H), 6.86 (dd, 1H), 6.74 (d, 1H), 4.57 (s, 2H), 4.42 (d, 2H), 4.28 (m, 2H), 3.55 (m, 1H), 3.24-3.00 (m, 2H), 3.00 (m, 1H), 2.60 (s, 3H), 1.24 (d, 6H).

MS: 490 (M+1)⁺

F. Synthesis of 4-(4-Isopropyl-phenyl)-1-[3-(2-methanesulphinyl-ethoxy)-benzyl]-6-prop-2-ynyloxy-1H-quinazoline-2-one

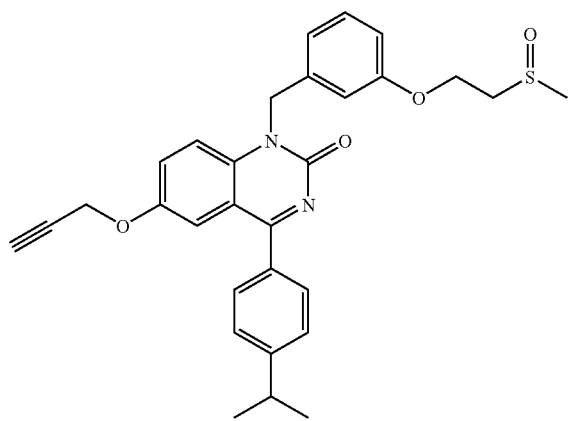 [SMILES: C#CCOc1ccc2c(c1)c(-c1ccc(C(C)C)cc1)nc(=O)n2Cc1cccc(OCCS(C)=O)c1]

The title compound (yellow oil) is prepared from (4-isopropyl-phenyl)-{2-[3-(2-methanesulphinyl-ethoxy)-benzylamino]-5-prop-2-ynyloxy-phenyl}-methanone and sodium cyanate as described for the preparation of example 3.

¹H-NMR (300 MHz, DMSO-d₆): 7.72 (d, 2H), 7.48 (d, 2H), 7.46 (s, 2H), 7.35 (bs, 1H), 7.24 (t, 1H), 6.94 (bs, 1H), 6.87 (dd, 1H), 6.81 (d, 1H), 5.46 (bs, 2H), 4.79 (s, 2H), 4.30 (m, 2H), 3.67 (m, 1H), 3.24-3.00 (m, 2H), 3.02 (m, 1H), 2.61 (s, 3H), 1.29 (d, 6H).

MS: 515 (M+1)⁺

Example 5

4-(4-Isopropyl-phenyl)-1-[3-(2-methanesulphonyl-ethoxy)-benzyl]-6-prop-2-ynyloxy-1H-quinazoline-2-one

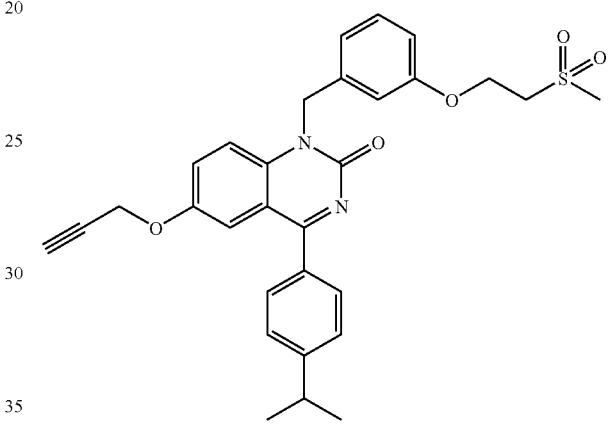

¹H-NMR (300 MHz, DMSO-d₆): 7.66 (d, 2H), 7.46 (d, 2H), 7.44 (s, 2H), 7.30 (bs, 1H), 7.20 (t, 1H), 6.95 (bs, 1H), 6.87 (m, 1H), 6.76 (d, 1H), 5.42 (s, 2H), 4.75 (s, 2H), 4.27 (t, 2H), 3.63 (m, 1H), 3.56 (t, 2H), 3.02 (s, 3H), 3.00 (m, 1H), 1.24 (d, 6H).

MS: 531 (M+1)⁺

1-Chloromethyl-3-(2-methanesulphonyl-ethoxy)-benzene can be prepared from 3-(2-methanesulphonyl-ethoxy)-benzaldehyde as described for the preparation of 1-chloromethyl-3-(2-methanesulphinyl-ethoxy)-benzene (example 4B)

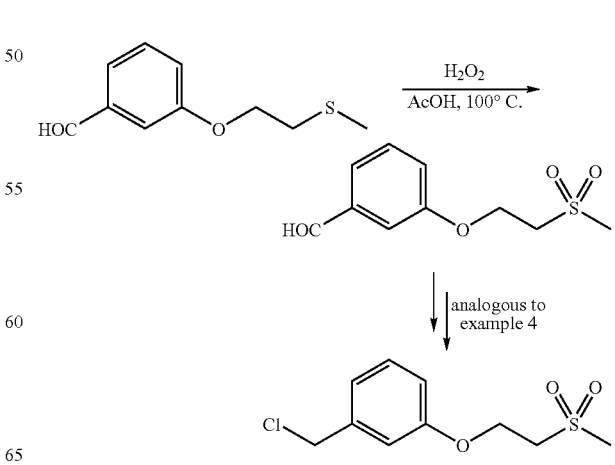

A solution of 2.0 g (10.2 mmol) 3-(2-methylsulphanyl-ethoxy)-benzaldehyde and 2.3 ml (22.4 mmol) hydrogen peroxide solution in 10 ml acetic acid is stirred for 2 h at 100° C. Then the reaction mixture is poured onto 2N NaOH and extracted with ethyl acetate. The combined organic layers are washed with sodium bisulphite solution, water and brine, dried over MgSO$_4$, filtered and concentrated in vacuo. The residue is purified by flash-chromatography on silica gel (hexane/EtOAc=3:1) to afford the title compound as a white crystalline compound.

$^1$H-NMR (300 MHz, DMSO-d$_6$): 9.96 (s, 1H), 7.54 (2d, 2H), 7.46 (bs, 1H), 7.32 (m, 1H), 4.42 (t, 2H), 3.63 (t, 2H), 3.06 (s, 3H)

MS: 229 (M+1)$^+$

Example 6

4-(4-Isopropyl-phenyl)-1-[2-(2-methoxy-ethyl)-2H-tetrazol-5-ylmethyl]-6-prop-2-ynyloxy-1H-quinazolin-2-thione

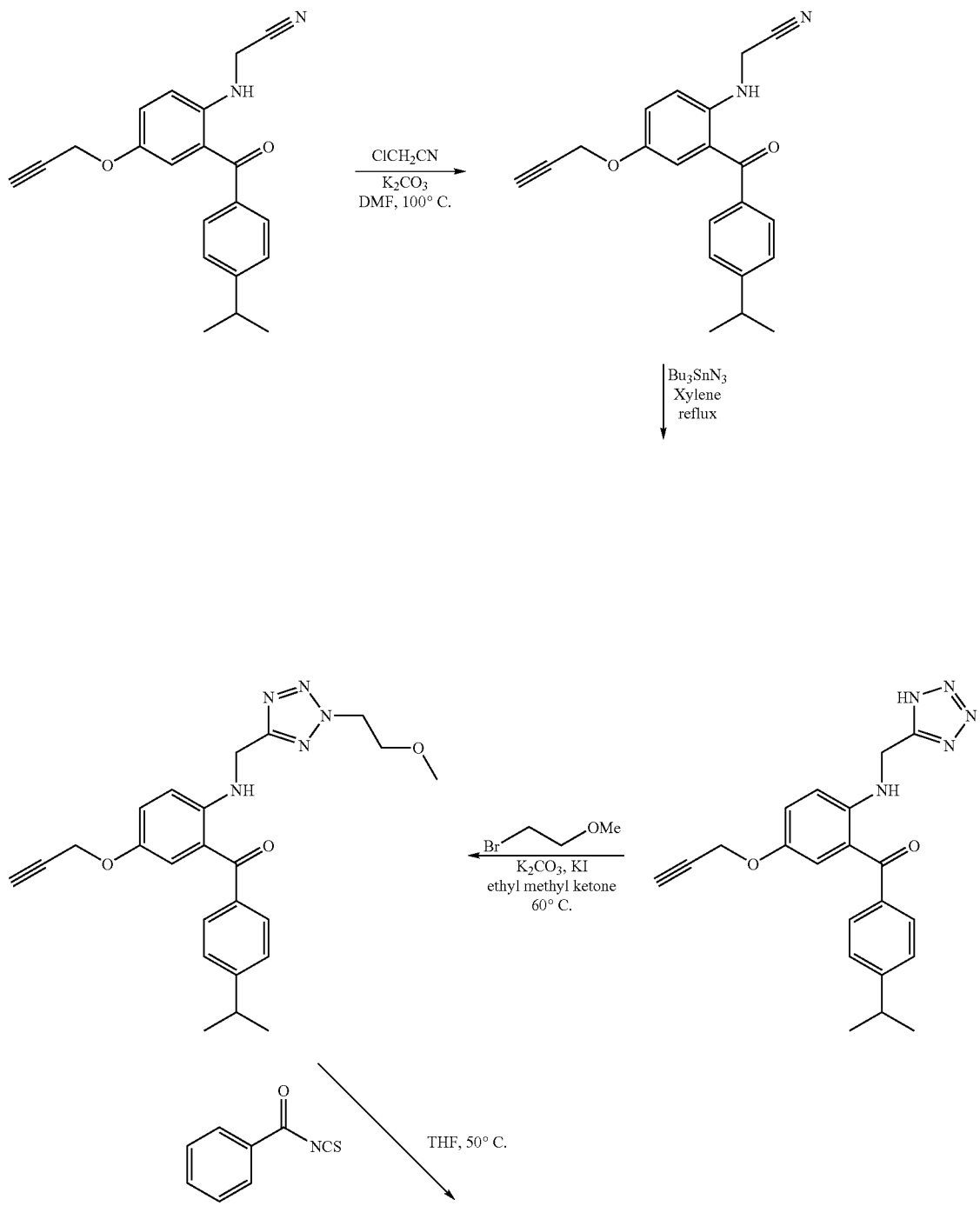

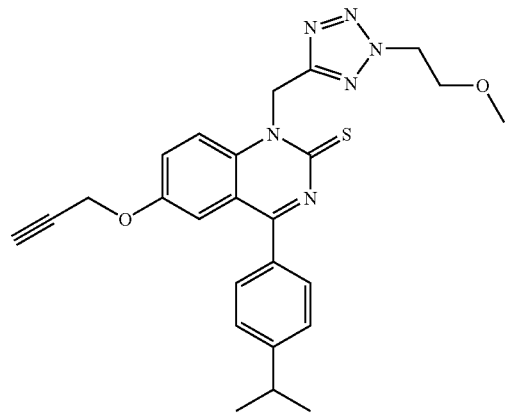

A. Synthesis of [2-(4-isopropyl-benzoyl)-4-prop-2-ynyloxy-phenylamino]-acetonitrile

B. Synthesis of (4-isopropyl-phenyl)-{5-prop-2-ynyloxy-2-[(1H-tetrazol-5-ylmethyl)-amino]-phenyl}-methanone

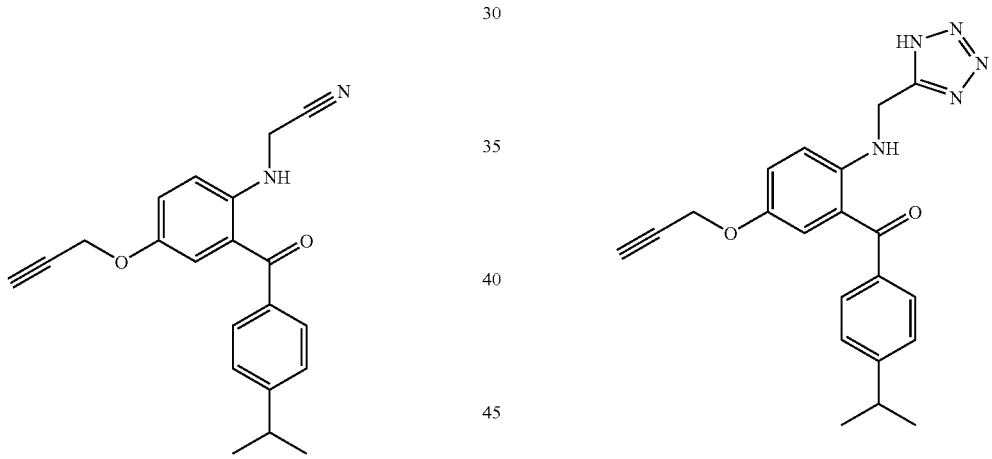

A mixture of 2.0 g (6.83 mmol) 2-amino-5-propargyloxyphenyl)-(4-isopropyl-phenyl)-methanone, 0.516 g (7.5 mmol) chloroacetonitrile and 1.6 g $K_2CO_3$ in 20 ml DMF is heated to 100° C. and stirred at this temperature for 20 h. The reaction mixture is cooled to room temperature and poured onto water and extracted with ethyl acetate. The combined organic layers are washed with water and brine, dried over $MgSO_4$, filtered and concentrated in vacuo. The residue is purified by flash-chromatography on silica gel (hexane/EtOAc=3:1) to afford 1.26 g of the title compound as a yellow crystalline solid.

$^1$H-NMR (300 MHz, DMSO-$d_6$): 7.60 (m, 1H), 7.60 (d, 2H), 7.40 (d, 2H), 7.28 (dd, 1H), 7.04 (bs, 1H), 6.96 (d, 1H), 4.67 (s, 2H), 4.42 (d, 2H), 3.59 (s, 1H), 2.98 (m, 1H), 1.25 (d, 6H).

MS: 333 (M+1)$^+$

A solution of 0.82 g (2.47 mmol) [2-(4-isopropyl-benzoyl)-4-prop-2-ynyloxy-phenyl-amino]-acetonitrile and 0.8 ml (3.31 mmol) $Bu_3SnN_3$ in 20 ml m-xylene is stirred at reflux temperature for 5 h. Then the reaction mixture is cooled to room temperature and 15 ml 2N KOH and 2 ml MeOH are added. This mixture is stirred vigorously for 15 min. After that the phases are separated and to the water layer 4 N HCl is added until a pH ~1 is reached. The aqueous layer is extracted with dichloromethane/isopropanol=3:1. The combined organic layers are washed with water and brine, dried over $MgSO_4$, filtered and concentrated in vacuo. The resulting solid is suspended in diethyl ether, stirred for 0.5 h, filtered and dried to afford 0.89 g of the title compound as yellow crystals.

$^1$H-NMR (300 MHz, DMSO-$d_6$): 8.22 (t, 1H), 7.59 (d, 2H), 7.40 (d, 2H), 7.14 (dd, 1H), 7.04 (bs, 1H), 6.72 (d, 1H), 4.81 (d, 2H), 4.61 (s, 2H), 3.59 (s, 1H), 2.98 (m, 1H), 1.25 (d, 6H).

MS: 376 (M+1)$^+$

C. Synthesis of (4-isopropyl-phenyl)-(2-{[2-(2-methoxy-ethyl)-2H-tetrazol-5-ylmethyl]-amino}-5-prop-2-ynyloxy-phenyl)-methanone

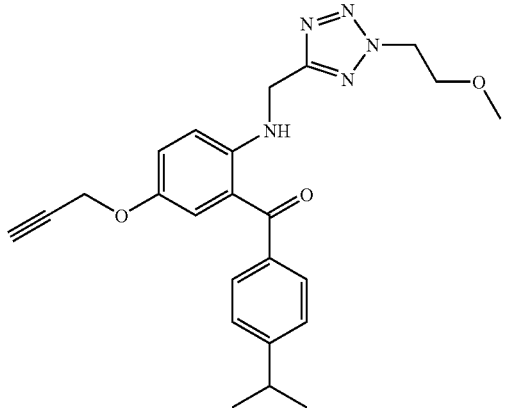 [SMILES: C#CCOc1ccc(NCc2nnn(CCOC)n2)c(C(=O)c2ccc(C(C)C)cc2)c1]

A mixture of 1.04 g (2.77 mmol) (4-isopropyl-phenyl)-{5-prop-2-ynyloxy-2-[(1H-tetrazol-5-ylmethyl)-amino]-phenyl}-methanone, 0.85 g K₂CO₃, 0.25 g KI and 0.41 g (2.95 mmol) chloroacetonitrile and 40 ml ethyl methyl ketone is stirred at 60° C. for 20 h. The reaction mixture is cooled to room temperature and poured onto water and extracted with ethyl acetate. The combined organic layers are washed with water and brine, dried over MgSO₄, filtered and concentrated in vacuo. The residue is purified by flash-chromatography on silica gel (hexane/EtOAc=2:1) to afford 0.65 g of (4-isopropyl-phenyl)-(2-{[2-(2-methoxy-ethyl)-2H-tetrazol-5-ylmethyl]-amino}-5-prop-2-ynyloxy-phenyl)-methanone (yellow oil, title compound) and 0.3 g of (4-isopropyl-phenyl)-(2-{[1-(2-methoxy-ethyl)-1H-tetrazol-5-ylmethyl]-amino}-5-prop-2-ynyloxy-phenyl)-methanone (yellow oil).

¹H-NMR (300 MHz, DMSO-d₆): 8.32 (t, 1H), 7.56 (d, 2H), 7.38 (d, 2H), 7.18 (dd, 1H), 7.02 (bs, 1H), 6.92 (d, 1H), 4.78 (t, 2H), 4.72 (d, 2H), 4.60 (s, 2H), 3.80 (t, 2H), 3.55 (s, 1H), 3.18 (s, 3H), 2.96 (m, 1H), 1.24 (d, 6H).
MS: 434 (M+1)⁺

D. Synthesis of 4-(4-isopropyl-phenyl)-1-[2-(2-methoxy-ethyl)-2H-tetrazol-5-ylmethyl]-6-prop-2-ynyloxy-1H-quinazolin-2-thione

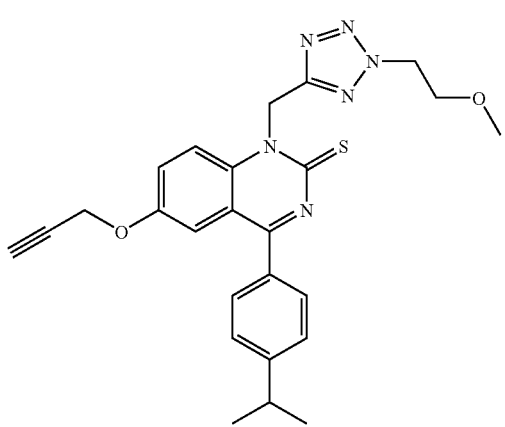 [SMILES: C#CCOc1ccc2c(c1)c(-c1ccc(C(C)C)cc1)nc(=S)n2Cc1nnn(CCOC)n1]

The title compound (red foam) is prepared from (4-isopropyl-phenyl)-(2-{[2-(2-methoxy-ethyl)-2H-tetrazol-5-ylmethyl]-amino}-5-prop-2-ynyloxy-phenyl)-methanone and benzoylisothiocyanate as described for the preparation of example 111.

¹H-NMR (300 MHz, DMSO-d₆): 7.74 (d, 2H), 7.73 (d, 1H), 7.60 (dd, 1H), 7.48 (d, 2H), 7.41 (m, 1H), 6.40 (bs, 2H), 4.88 (bs, 2H), 4.77 (t, 2H), 3.76 (t, 2H), 3.74 (m, 1H), 3.16 (s, 3H), 3.00 (m 1H), 1.28 (d, 6H).
MS: 475 (M+1)⁺

The compounds of the following examples are prepared by analogy:

Example 7

4-(4-Isopropyl-phenyl)-1-(3-methane-sulphonyl-benzyl)-5-propargyloxy-phenyl-methanone

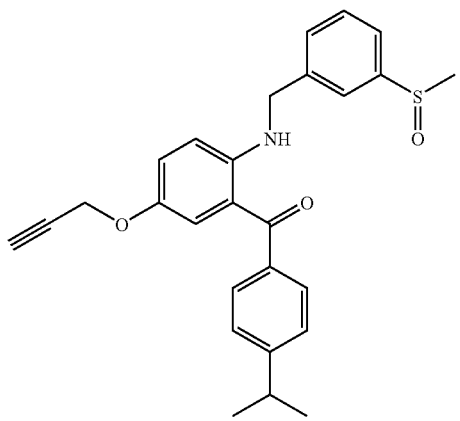 [SMILES: C#CCOc1ccc(NCc2cccc(S(C)=O)c2)c(C(=O)c2ccc(C(C)C)cc2)c1]

The title compound can be prepared using the synthesis methodology as described using 1-chloromethyl-3-methane-sulphinyl-benzene (see S. A. Laufer, G. K. Wagner *J. Med. Chem.* 2002, 45(13), 2733-40).
MS: 446 (M+1)⁺

Example 8

4-(4-Isopropyl-phenyl)-1-(3-methane-sulphinyl-benzyl)-6-propargyloxy-1H-quinazoline-2-one

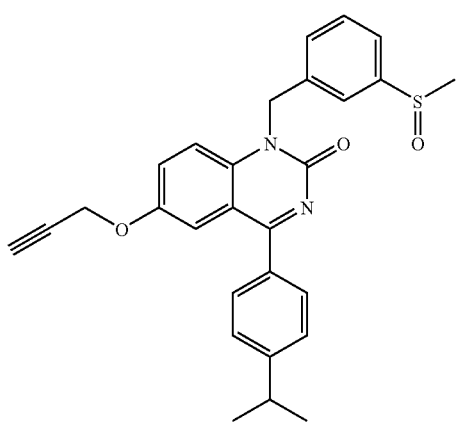 [SMILES: C#CCOc1ccc2c(c1)c(-c1ccc(C(C)C)cc1)nc(=O)n2Cc1cccc(S(C)=O)c1]

¹H-NMR (300 MHz, DMSO): 7.70 (d, 2H), 7.66 (s, 1H), 7.58-7.44 (m, 6H), 7.39 (broad s, 1H), 7.35 (broad s, 1H), 5.59 (broad s, 2H), 4.78 (d, 2H), 3.67 (m, 1H), 3.02 (m, 1H), 2.72 (s, 3H), 1.28 (d, 6H).
MS: 471 (M+1)⁺

Example 9

4-(4-Isopropyl-phenyl)-6-prop-2-ynyloxy-1-pyridin-2-ylmethyl-1H-quinazolin-2-one

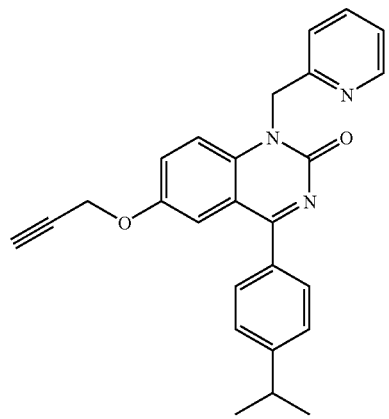 [SMILES: C#CCOc1ccc2c(c1)c(-c1ccc(C(C)C)cc1)nc(=O)n2Cc1ccccn1]

$^1$H NMR (300 MHz, CDCl$_3$): 8.58 (d, 1H), 7.76 (d, 2H), 7.20-7.70 (m, 8H), 5.68 (s, 2H), 4.64 (d, 2H), 3.02 (hept, 1H), 2.54 (t, 1H), 1.32 (d, 6H).

MS: 410 (M+1)$^+$

Example 10

4-(4-Isopropyl-phenyl)-6-prop-2-ynyloxy-1-(4-[1,2,3]triazol-2-yl-benzyl)-1H-quinazolin-2-one

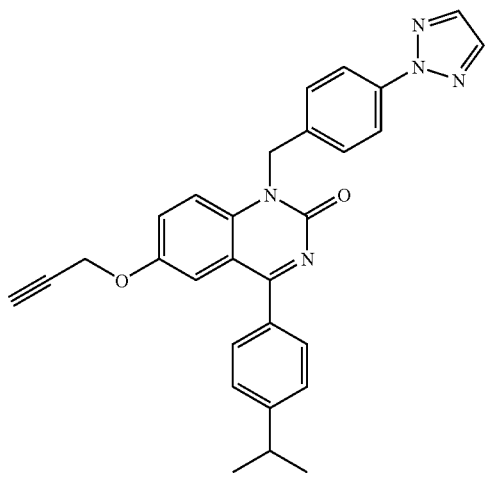 [SMILES: C#CCOc1ccc2c(c1)c(-c1ccc(C(C)C)cc1)nc(=O)n2Cc1ccc(-n2nccn2)cc1]

$^1$H NMR (300 MHz, CDCl$_3$): 8.04 (d, 2H), 7.72-7.80 (m, 3H), 7.20-7.52 (m, 8H), 5.60 (s, 2H), 4.64 (d, 2H), 3.02 (hept, 1H), 2.55 (m, 1H), 1.33 (d, 6H).

MS: 476 (M+1)$^+$

Example 11

1-(3-Bromo-propyl)-4-(4-isopropyl-phenyl)-6-prop-2-ynyloxy-1H-quinazolin-2-one

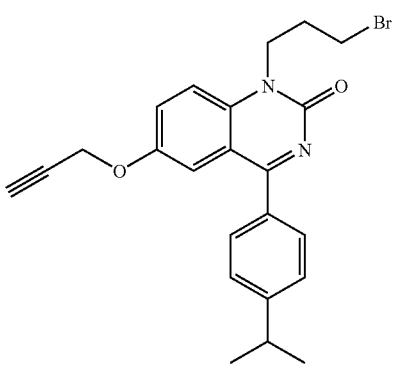 [SMILES: C#CCOc1ccc2c(c1)c(-c1ccc(C(C)C)cc1)nc(=O)n2CCCBr]

$^1$H NMR (300 MHz, CDCl$_3$): 7.69 (d, 2H), 7.46-7.53 (m, 3H), 7.37 (d, 2H), 4.63 (d, 2H), 4.42 (m, 2H), 3.58 (t, 2H), 2.99 (hept, 1H), 2.58 (m, 1H), 2.38 (m, 2H), 1.30 (d, 6H).

MS: 441 (M+1)$^+$

Example 12

4-(4-Isopropyl-phenyl)-6-prop-2-ynyloxy-1-pyridin-3-ylmethyl-1H-quinazolin-2-one

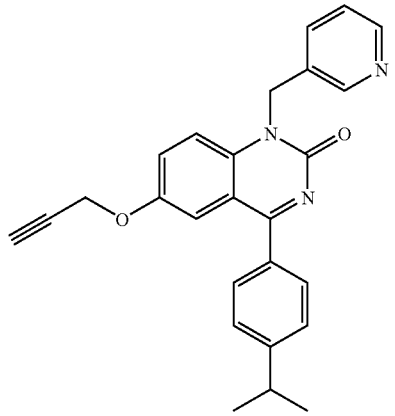 [SMILES: C#CCOc1ccc2c(c1)c(-c1ccc(C(C)C)cc1)nc(=O)n2Cc1cccnc1]

$^1$H NMR (300 MHz, CDCl$_3$): 8.78 (s, 1H), 8.58 (d, 1H), 7.90 (d, 1H), 7.74 (d, 2H), 7.54 (d, 1H), 7.26-7.44 (m, 5H), 5.60 (s, 2H), 4.64 (d, 2H), 3.01 (hept, 1H), 2.56 (t, 1H), 1.32 (d, 6H).

MS: 410 (M+1)$^+$

Example 13

1-[2-(2-Hydroxy-ethoxy)-benzyl]-4-(4-isopropyl-phenyl)-6-prop-2-ynyloxy-1H-quinazolin-2-one

A. Synthesis of {2-[2-(2-Hydroxy-ethoxy)-benzylamino]-5-prop-2-ynyloxy-phenyl}-(4-isopropyl-phenyl)-methanone

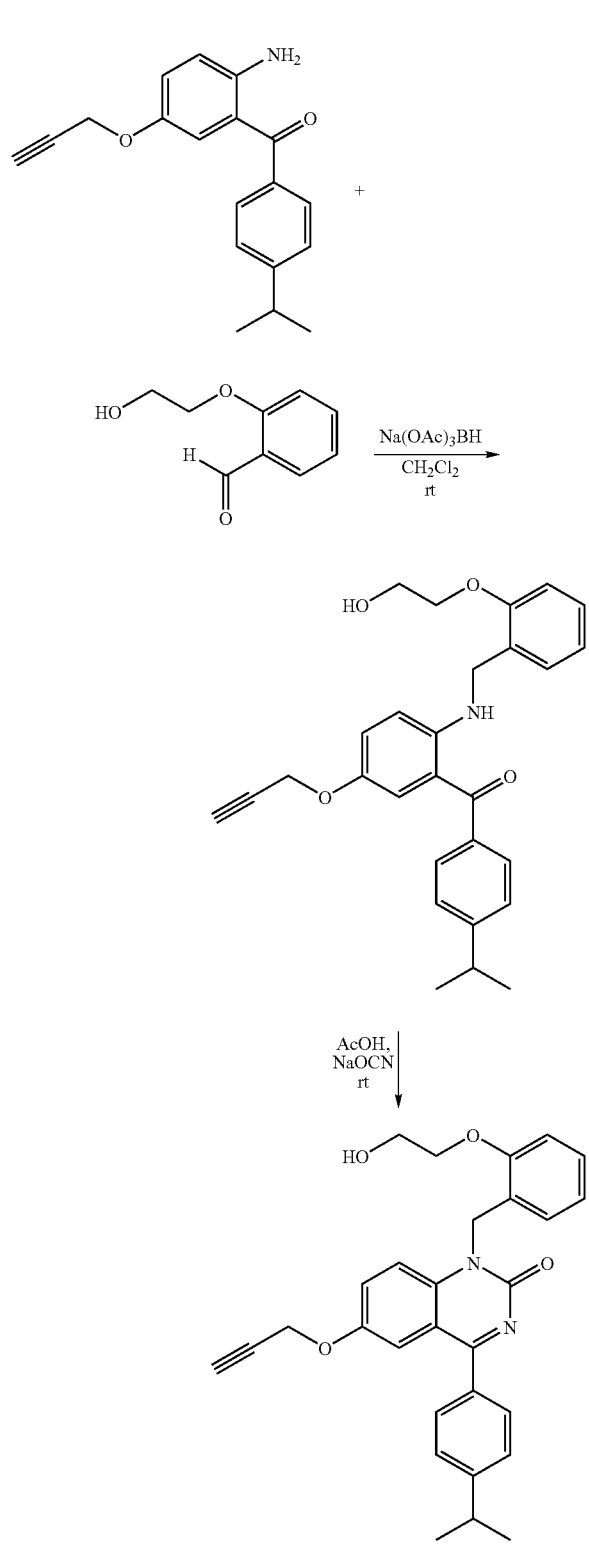

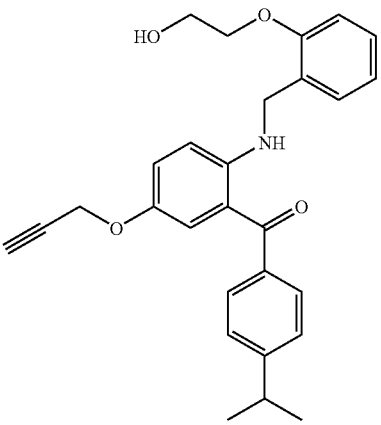 [SMILES: C#CCOc1ccc(NCc2ccccc2OCCO)c(C(=O)c2ccc(C(C)C)cc2)c1]

To a solution of 100 mg (0.341 mmol) (2-amino-5-propargyloxy-phenyl)-(4-isopropyl-phenyl)-methanone in 1.5 ml CH$_2$Cl$_2$ is added 61 mg (0.36 mmol) 2-(2-hydroxyethoxy) benzaldehyde and 84 mg (0.38 mmol) sodium triacetoxyborohydride. The mixture is stirred at r.t. for two days, diluted with water and extracted with CH$_2$Cl$_2$. Purification of the crude product by chromatography (ethyl acetate/hexanes 1:1) affords a yellow solid.

$^1$H NMR (300 MHz, CD$_3$OD): 7.56 (d, 2H), 7.34 (d, 2H), 7.16-7.30 (m, 2H), 7.06-7.12 (m, 2H), 6.84-7.00 (m, 3H), 4.50-4.54 (m, 4H), 4.12 (t, 2H), 3.96 (t, 2H), 3.00 (hept, 1H), 2.92 (t, 1H), 1.32 (d, 6H).

MS: 444 (M+1)$^+$

B. Synthesis of 1-[2-(2-Hydroxy-ethoxy)-benzyl]-4-(4-isopropyl-phenyl)-6-prop-2-ynyloxy-1H-quinazolin-2-one

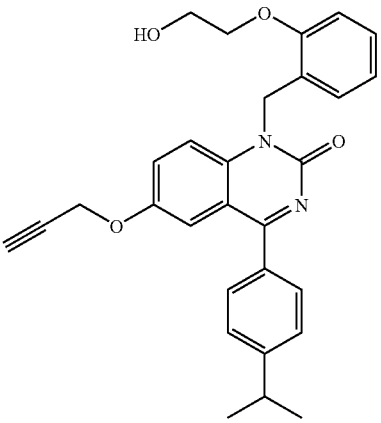 [SMILES: C#CCOc1ccc2c(c1)c(-c1ccc(C(C)C)cc1)nc(=O)n2Cc1ccccc1OCCO]

To a solution of 85 mg (0.192 mmol) {2-[2-(2-Hydroxy-ethoxy)-benzylamino]-5-prop-2-ynyloxy-phenyl}-(4-isopropyl-phenyl)-methanone in 2 ml acetic acid is added 25 mg (0.383 mmol) sodium cyanate. After stirring for 2 h the solvent is removed in vacuo and the residue is partitioned between CH$_2$Cl$_2$ and water. The organic layer is extracted with 2 M sodium hydroxide solution. After evaporation of the organic phase the product is obtained as a yellow oil.

$^1$H NMR (300 MHz, CDCl$_3$): 7.76 (d, 2H), 7.20-7.56 (m, 6H), 6.94 (t, 1H), 6.86 (d, 1H), 5.62 (s, 2H), 4.04 (t, 2H), 3.94 (t, 2H), 3.02 (hept, 1H), 2.56 (m, 1H), 1.32 (d, 6H).

MS: 469 (M+1)$^+$

Example 14

1-[3-(2-Hydroxy-ethoxy)-thiophen-2-ylmethyl]-4-(4-isopropyl-phenyl)-6-prop-2-ynyloxy-1H-quinazolin-2-one

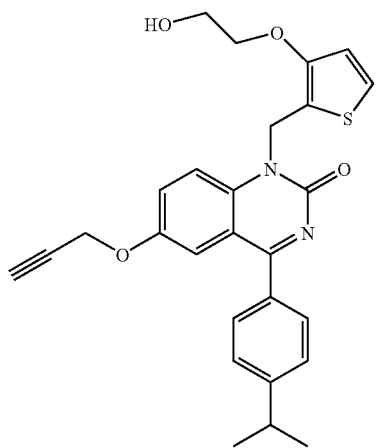

$^1$H-NMR (300 MHz, CDCl$_3$): 7.64-7.84 (m, 3H), 7.22-7.50 (m, 4H), 7.12 (d, 1H), 6.76 (d, 1H), 5.58 (s, 2H), 4.62 (d, 2H), 4.20 (t, 2H), 3.96 (t, 2H), 3.42 (broad s, 1H), 3.00 (hept, 1H), 2.54 (t, 1H), 1.30 (d, 6H).

MS: 475 (M+1)$^+$

The starting material may be prepared as follows:

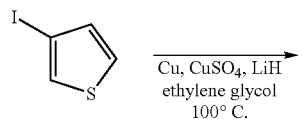

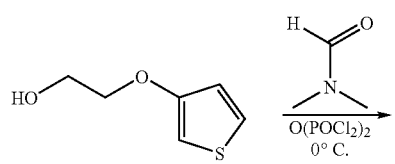

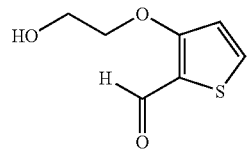

A. Synthesis of 2-(thiophen-3-yloxy)-ethanol

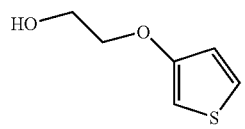

To a solution of 1.0 g (4.76 mmol) 3-iodothiophene in 5 ml ethylene glycol is added 109 mg (1.71 mmol) copper powder, 114 mg (0.714 mmol) copper(II)sulphate and 151 mg (19.0 mmol) lithium hydride. The reaction mixture is heated overnight in a sealed flask at 100° C. The reaction mixture is filtered through Celite and evaporated. The resulting oil is then filtered through a 50 g silica pad and eluted with ethyl acetate/hexanes (7:3) to give after evaporation 750 mg of an orange liquid, which is used without purification directly in the next reaction.

HPLC-MS: t=1.31 min. ((M+1)$^+$=145)

B. Synthesis of 3-(2-hydroxy-ethoxy)-thiophene-2-carboxaldehyde

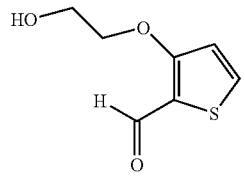 [SMILES: O=Cc1sccc1OCCO]

The crude material (750 mg) obtained in the reaction above is added dropwise at 0° C. to a mixture of 1.15 ml (8.32 mmol) diphosphoryl chloride and 1 ml (13 mmol) DMF. The reaction mixture is stirred for two hours at room temperature. 50 ml of cold 2N NaHCO$_3$ solution are added and the resulting mixture is extracted with dichloromethane, dried, filtered through Celite and evaporated in vacuo. Flash-chromatography (hexanes/ethyl acetate) gives a yellow oil, which is used without further purification in the reductive amination reaction.

Example 15

1-(3-Chloro-4-hydroxy-5-methoxy-benzyl)-4-(4-isopropyl-phenyl)-6-prop-2-ynyloxy-1H-quinazolin-2-one

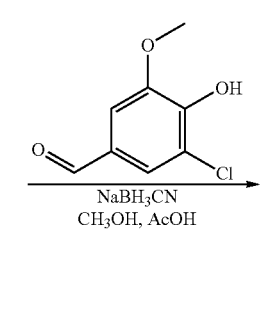

-continued

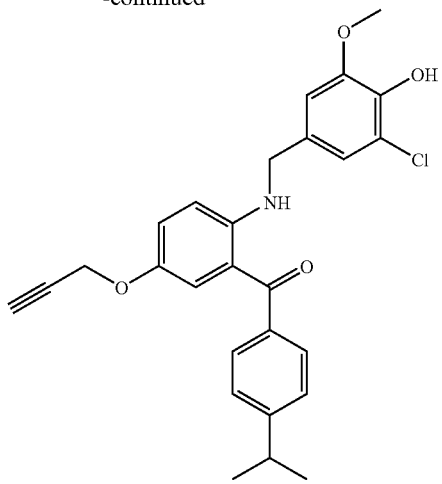

A. Synthesis of [2-(3-chloro-4-hydroxy-5-methoxy-benzylamino)-5-prop-2-ynyloxy-phenyl]-(4-isopropyl-phenyl)-methanone

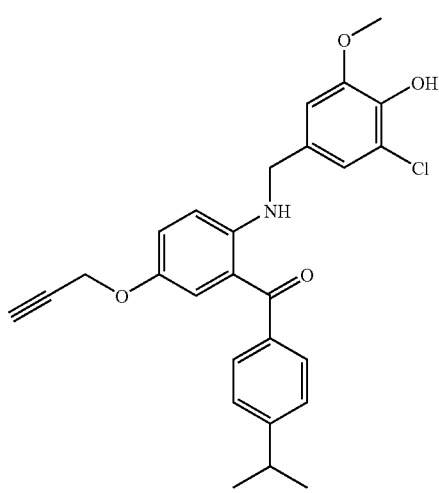 [SMILES: C#CCOc1ccc(NCc2cc(Cl)c(O)c(OC)c2)c(C(=O)c2ccc(C(C)C)cc2)c1]

To a stirred mixture of 146.7 mg (0.5 mmol) of (2-amino-5-prop-2-ynyloxy-phenyl)-4-isopropyl-phenyl)-methanone and 28.6 μl (0.5 mmol) of acetic acid in 1.5 ml of methanol is added 93.3 mg (0.5 mmol) of 5-chlorovanillin followed by 31.4 mg (0.5 mmol) of sodium cyanoborohydride. After stirring for 40 h at r.t., the reaction is quenched with 1N HCl and subsequently made alkaline with 1N aqueous NaOH solution. Methanol is removed in vacuo, the residue diluted with water and extracted twice with ethyl acetate. The combined organic layers are dried (Na$_2$SO$_4$) and evaporated. Flash chromatography of the residue (SiO$_2$, hexane/ethyl acetate) affords the title compound as a yellow solid.

$^1$H-NMR (400 MHz, DMSO-d6): 9.28 (s, 1H), 8.20 (t, 1H), 7.57 (d, 2H), 7.40 (d, 2H), 7.13 (dd, 1H), 7.02 (d, 1H), 6.95 (d, 1H), 6.90 (d, 1H), 6.76 (d, 1H), 4.59 (d, 2H), 4.34 (d, 2H), 3.77 (s, 3H), 3.54 (t, 1H), 2.97 (m, 1H), 1.24 (d, 6H).

MS: 464 (M+1)$^+$

B. Synthesis of 1-(3-chloro-4-hydroxy-5-methoxy-benzyl)-4-(4-isopropyl-phenyl)-6-prop-2-ynyloxy-1H-quinazolin-2-one

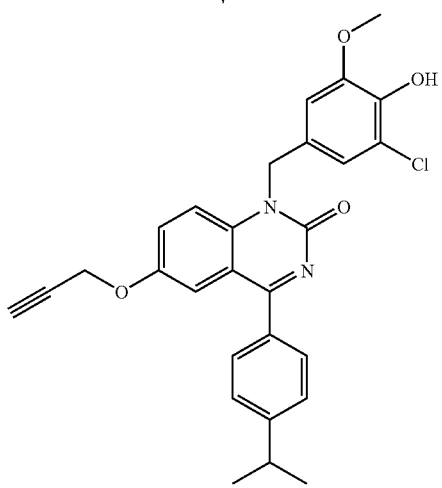

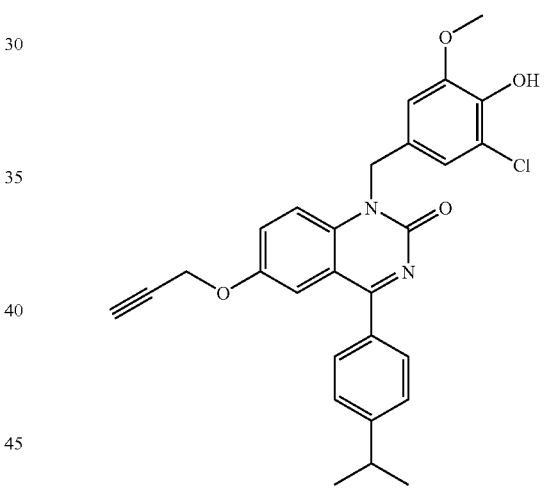

To a mixture of 43.1 mg (0.093 mmol) of [2-(3-Chloro-4-hydroxy-5-methoxy-benzyl-amino)-5-prop-2-ynyloxy-phenyl]-(4-isopropyl-phenyl)-methanone in 1 ml of acetic acid is added 12.1 mg (0.186 mmol) of sodium cyanate. After stirring for 12 h at r.t. the solvent is removed in vacuo and the residue partitioned between saturated NaHCO$_3$ solution and ethyl acetate. The organic layer is separated and the aqueous phase extracted twice with ethyl acetate. The combined organic extracts are dried (Na$_2$SO$_4$) and evaporated in vacuo. Flash chromatography (SiO2, hexane/ethyl acetate) affords the title compound as an amorphous yellow solid.

$^1$H NMR (400 MHz, DMSO-d6): 9.41 (s, 1H), 7.73 (d, 2H), 7.48-7.58 (m, 4H), 7.36 (d, 1H), 7.07 (d, 1H), 6.84 (d, 1H), 5.39 (broad s, 2H), 4.81 (d, 2H), 3.81 (s, 3H), 3.68 (t, 1H), 3.03 (m, 1H), 1.29 (d, 6H).

MS: 489 (M+1)$^+$

The compounds of the following examples are prepared in an analogous manner.

Example 16

1-(2-Ethoxy-benzyl)-4-(4-isopropyl-phenyl)-6-prop-2-ynyloxy-1H-quinazolin-2-one

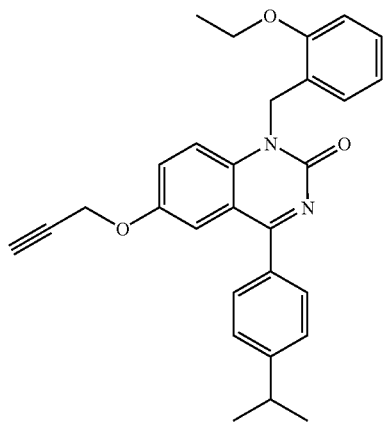 [SMILES: C#CCOc1ccc2c(c1)c(-c1ccc(C(C)C)cc1)nc(=O)n2Cc1ccccc1OCC]

$^1$H NMR (400 MHz, DMSO-d6): 7.73 (d, 2H), 7.46-7.50 (m, 3H), 7.37 (d, 1H), 7.30 (d, 1H), 7.23 (dt, 1H), 7.06 (d, 1H), 6.76-6.83 (m, 2H), 5.39 (broad s, 2H), 4.79 (d, 2H), 4.16 (q, 2H), 3.67 (t, 1H), 3.03 (m, 1H), 1.41 (t, 3H), 1.29 (d, 6H).

MS: 453 (M+1)$^+$

Example 17

1-(3-Ethoxy-benzyl)-4-(4-isopropyl-phenyl)-6-prop-2-ynyloxy-1H-quinazolin-2-one

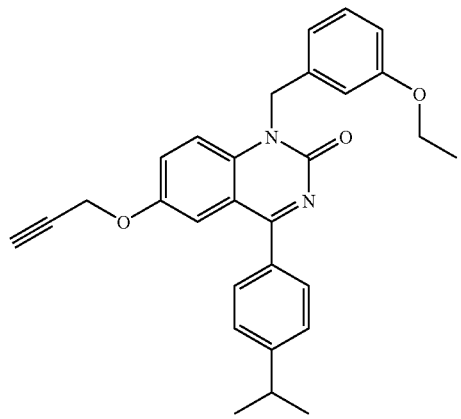 [SMILES: C#CCOc1ccc2c(c1)c(-c1ccc(C(C)C)cc1)nc(=O)n2Cc1cccc(OCC)c1]

$^1$H NMR (400 MHz, DMSO-d6): 7.72 (d, 2H), 7.46-7.50 (m, 4H), 7.36 (d, 1H), 7.22 (t, 1H), 6.86 (m, 1H), 6.79-6.81 (m, 2H), 5.45 (broad s, 2H), 4.78 (d, 2H), 3.97 (q, 2H), 3.66 (t, 1H), 3.02 (m, 1H), 1.26-1.30 (m, 9H).

MS: 453 (M+1)$^+$

Example 18

1-(2-Hydroxy-6-methoxy-benzyl)-4-(4-isopropyl-phenyl)-6-prop-2-ynyloxy-1H-quinazolin-2-one

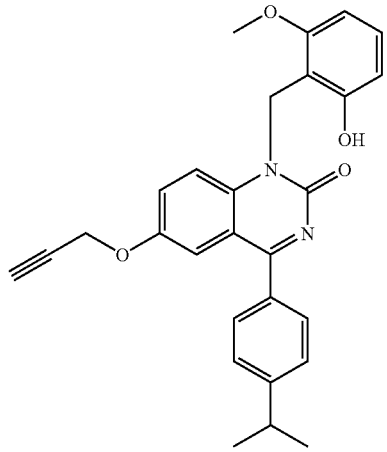 [SMILES: C#CCOc1ccc2c(c1)c(-c1ccc(C(C)C)cc1)nc(=O)n2Cc1c(O)cccc1OC]

$^1$H NMR (400 MHz, DMSO-d6): 9.90 (s, 1H), 7.67 (d, 2H), 7.61 (d, 1H), 7.40-7.47 (m, 3H), 7.27 (d, 1H), 7.03 (t, 1H), 6.43 (d, 2H), 5.44 (s, 2H), 4.75 (d, 2H), 3.65 (s, 3H), 3.63 (t, 1H), 3.00 (m, 1H), 1.27 (d, 6H).

MS: 455 (M+1)$^+$

Example 19

1-(3-Ethoxy-4-methoxy-benzyl)-4-(4-isopropyl-phenyl)-6-prop-2-ynyloxy-1H-quinazolin-2-one

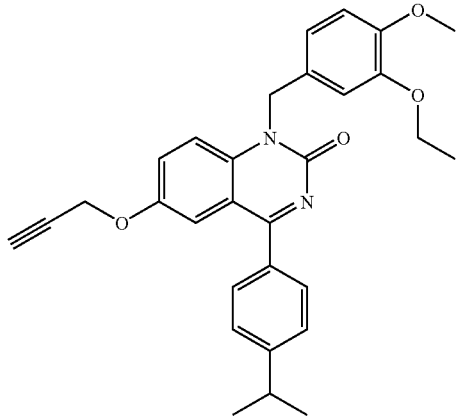 [SMILES: C#CCOc1ccc2c(c1)c(-c1ccc(C(C)C)cc1)nc(=O)n2Cc1ccc(OC)c(OCC)c1]

$^1$H NMR (400 MHz, DMSO-d6): 7.71 (d, 2H), 7.47-7.55 (m, 4H), 7.35 (d, 1H), 7.05 (s, 1H), 6.86 (d, 1H), 6.73-6.76 (m, 1H), 5.41 (broad s, 2H), 4.79 (d, 2H), 3.97 (q, 2H), 3.69 (s, 3H), 3.66 (m, 1H), 3.02 (m, 1H), 1.26-1.32 (m, 9H).

MS: 483 (M+1)$^+$

Example 20

1-(1H-Indol-4-ylmethyl)-4-(4-isopropyl-phenyl)-6-prop-2-ynyloxy-1H-quinazolin-2-one

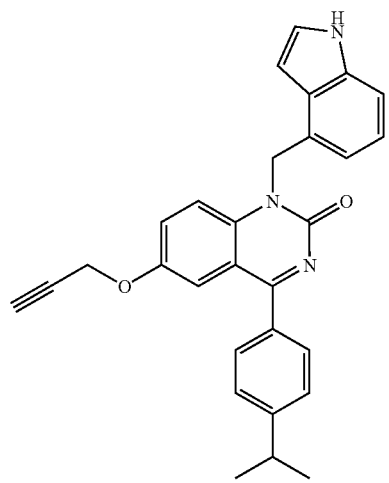 [SMILES: C#CCOc1ccc2c(c1)c(-c1ccc(C(C)C)cc1)nc(=O)n2Cc1cccc2[nH]ccc12]

$^1$H NMR (400 MHz, DMSO-d6): 11.10 (s, 1H), 7.74 (d, 2H), 7.49 (d, 2H), 7.29-7.42 (m, 5H), 6.96 (t, 1H), 6.64 (m, 1H), 6.59 (d, 1H), 5.74 (broad s, 2H), 4.76 (d, 2H), 3.65 (t, 1H), 3.03 (m, 1H), 1.29 (d, 6H).
MS: 448 (M+1)$^+$

Example 21

1-(4Hydroxy-3-methoxy-benzyl)-4-(4-isopropyl-phenyl)-6-prop-2-ynyloxy-1H-quinazolin-2-one

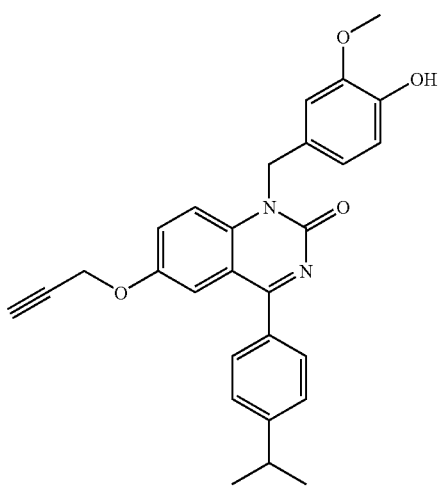 [SMILES: C#CCOc1ccc2c(c1)c(-c1ccc(C(C)C)cc1)nc(=O)n2Cc1ccc(O)c(OC)c1]

$^1$H NMR (400 MHz, DMSO-d6): 7.70 (d, 2H), 7.56 (d, 1H), 7.45-7.49 (m, 3H), 7.34 (d, 1H), 7.03 (d, 1H), 6.61-6.69 (m, 2H), 5.37 (broad s, 2H), 4.78 (d, 2H), 3.73 (s, 3H), 3.66 (t, 1H), 3.01 (m, 1H), 1.28 (d, 6H).
MS: 455 (M+1)$^+$

Example 22

1-(2-Hydroxy-4-methoxy-benzyl)-4-(4-isopropyl-phenyl)-6-prop-2-ynyloxy-1H-quinazolin-2-one

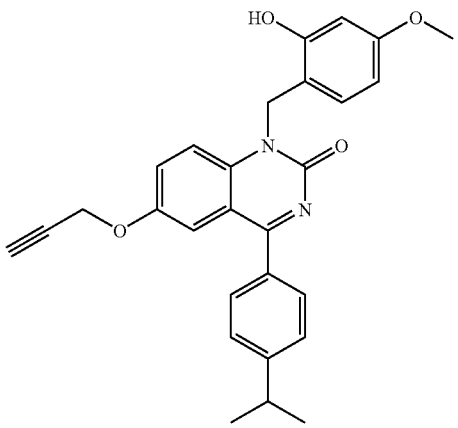 [SMILES: C#CCOc1ccc2c(c1)c(-c1ccc(C(C)C)cc1)nc(=O)n2Cc1ccc(OC)cc1O]

$^1$H NMR (400 MHz, DMSO-d6): 10.05 (broad s, 1H), 7.70 (d, 2H), 7.40-7.50 (m, 4H), 7.35 (d, 1H), 6.76 (d, 1H), 6.46 (d, 1H), 6.28 (dd, 1H), 5.29 (broad s, 2H), 4.78 (d, 2H), 3.66 (m, 1H), 3.64 (s, 3H), 3.02 (m, 1H), 1.28 (d, 6H).
MS: 455 (M+1)$^+$

Example 23

2-Hydroxy-5-[4-(4-isopropyl-phenyl)-2-oxo-6-prop-2-ynyloxy-2H-quinazolin-1-ylmethyl]-benzoic acid methyl ester

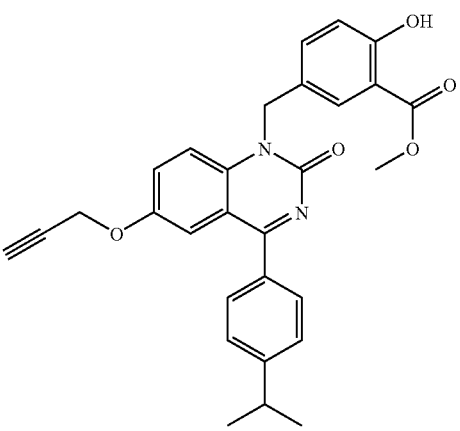 [SMILES: C#CCOc1ccc2c(c1)c(-c1ccc(C(C)C)cc1)nc(=O)n2Cc1ccc(O)c(C(=O)OC)c1]

$^1$H NMR (400 MHz, DMSO-d6): 10.44 (s, 1H), 7.82 (d, 1H), 7.71 (d, 2H), 7.47-7.56 (m, 5H), 7.35 (d, 1H), 6.95 (d, 1H), 5.44 (broad s, 2H), 4.78 (d, 2H), 3.86 (s, 3H), 3.66 (t, 1H), 3.02 (m, 1H), 1.28 (d, 6H).
MS: 483 (M+1)$^+$

Example 24

1-(3-Chloro-4-hydroxy-benzyl)-4-(4-isopropyl-phenyl)-6-prop-2-ynyloxy-1H-quinazolin-2-one

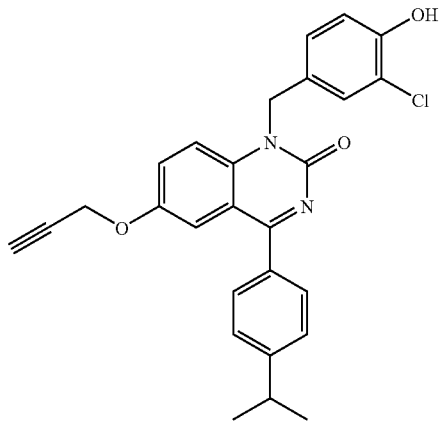 [SMILES: C#CCOc1ccc2c(c1)c(-c1ccc(C(C)C)cc1)nc(=O)n2Cc1ccc(O)c(Cl)c1]

$^1$H NMR (400 MHz, DMSO-d6): 10.15 (s, 1H), 7.70 (d, 2H), 7.46-7.54 (m, 4H), 7.35 (m, 2H), 7.09 (dd, 1H), 6.90 (d, 1H), 5.37 (broad s, 2H), 4.78 (d, 2H), 3.66 (t, 1H), 3.02 (m, 1H), 1.28 (d, 6H).

MS: 459 (M+1)$^+$

Example 25

1-(2-Chloro-benzyl)-4-(4-isopropyl-phenyl)-6-prop-2-ynyloxy-1H-quinazolin-2-one

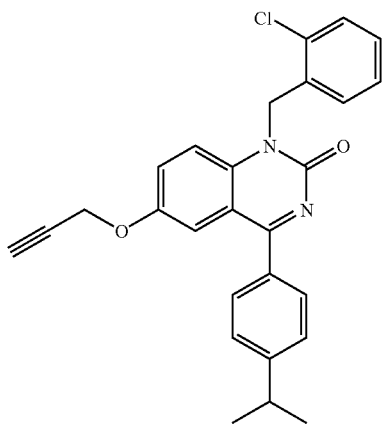 [SMILES: C#CCOc1ccc2c(c1)c(-c1ccc(C(C)C)cc1)nc(=O)n2Cc1ccccc1Cl]

$^1$H NMR (400 MHz, DMSO-d6): 7.74 (d, 2H), 7.56 (dd, 1H), 7.47-7.51 (m, 3H), 7.40 (d, 1H), 7.32 (dt, 1H), 7.25 (d, 1H), 7.21 (dt, 1H), 6.81 (dd, 1H), 5.48 (broad s, 2H), 4.80 (d, 2H), 3.69 (t, 1H), 3.03 (m, 1H), 1.29 (d, 6H).

MS: 443 (M+1)$^+$

Example 26

1-(4-Hydroxy-3,5-dimethoxy-benzyl)-4-(4-isopropyl-phenyl)-6-prop-2-ynyloxy-1H-quinazolin-2-one

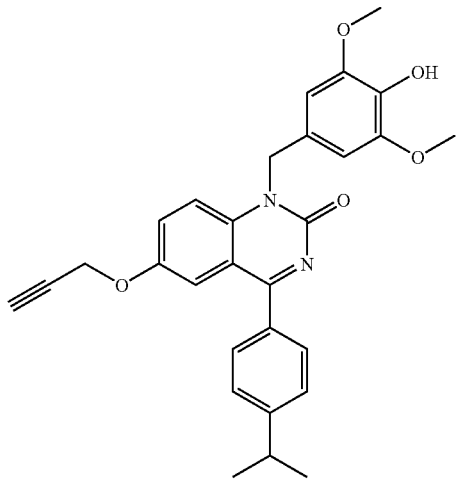

$^1$H NMR (400 MHz, DMSO-d6): 8.34 (s, 1H), 7.71 (d, 2H), 7.59 (d, 1H), 7.46-7.50 (m, 3H), 7.35 (d, 1H), 6.66 (s, 2H), 5.37 (broad s, 2H), 4.78 (d, 2H), 3.68 (s, 6H), 3.66 (t, 1H), 3.01 (m, 1H), 1.28 (d, 6H).

MS: 485 (M+1)$^+$

Example 27

1-(2,5-Dimethoxy-benzyl)-4-(4-isopropyl-phenyl)-6-prop-2-ynyloxy-1H-quinazolin-2-one

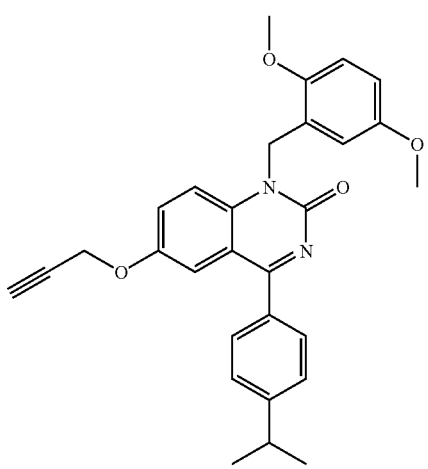 [SMILES: C#CCOc1ccc2c(c1)c(-c1ccc(C(C)C)cc1)nc(=O)n2Cc1cc(OC)ccc1OC]

$^1$H NMR (400 MHz, DMSO-d6): 7.72 (d, 2H), 7.46-7.49 (m, 3H), 7.37 (d, 1H), 7.28 (d, 1H), 7.02 (d, 1H), 6.83 (dd, 1H), 6.29 (d, 1H), 5.35 (broad s, 2H), 4.78 (d, 2H), 3.87 (s, 3H), 3.67 (t, 1H), 3.56 (s, 3H), 3.02 (m, 1H), 1.28 (d, 6H).

MS: 469 (M+1)$^+$

Example 28

4-[4-(4-Isopropyl-phenyl)-2-oxo-6-prop-2-ynyloxy-2H-quinazolin-1-ylmethyl]-1H-indole-2-carboxylic acid amide

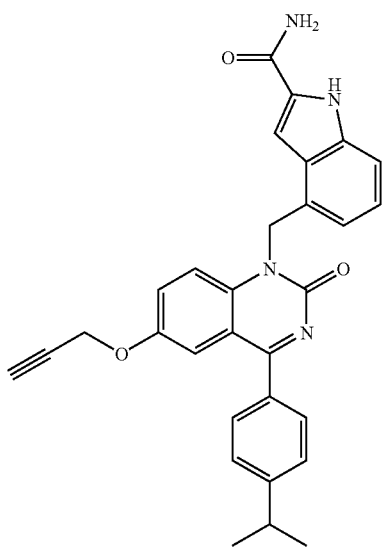 [SMILES: C#CCOc1ccc2c(c1)c(-c1ccc(C(C)C)cc1)nc(=O)n2Cc1cccc2[nH]c(C(N)=O)cc12]

$^1$H NMR (400 MHz, DMSO-d6): 11.50 (s, 1H), 8.03 (broad s, 1H), 7.75 (d, 2H), 7.50 (d, 2H), 7.38-7.44 (m, 4H), 7.26-7.32 (m, 2H), 7.04 (t, 1H), 6.47 (d, 2H), 5.72 (broad s, 2H), 4.78 (d, 2H), 3.67 (t, 1H), 3.03 (m, 1H), 1.29 (d, 6H).

MS: 491 (M+1)$^+$

Example 29

1-(2-Ethyl-butyl)-4-(4-isopropyl-phenyl)-6-prop-2-ynyloxy-1H-quinazolin-2-one

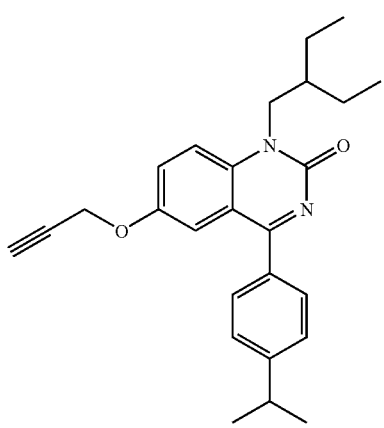 [SMILES: C#CCOc1ccc2c(c1)c(-c1ccc(C(C)C)cc1)nc(=O)n2CC(CC)CC]

$^1$H NMR (400 MHz, DMSO-d6): 7.68 (d, 2H), 7.55-7.60 (m, 2H), 7.46 (d, 2H), 7.34 (d, 1H), 4.80 (d, 2H), 4.20 (d, 2H), 3.69 (t, 1H), 3.01 (m, 1H), 1.85 (m, 1H), 1.30-1.38 (m, 4H), 1.28 (d, 6H), 0.87 (t, 6H).

MS: 403 (M+1)$^+$

Example 30

{3-[4-(4-Isopropyl-phenyl)-2-oxo-6-prop-2-ynyloxy-2H-quinazolin-1-ylmethyl]-phenoxy}-acetic acid

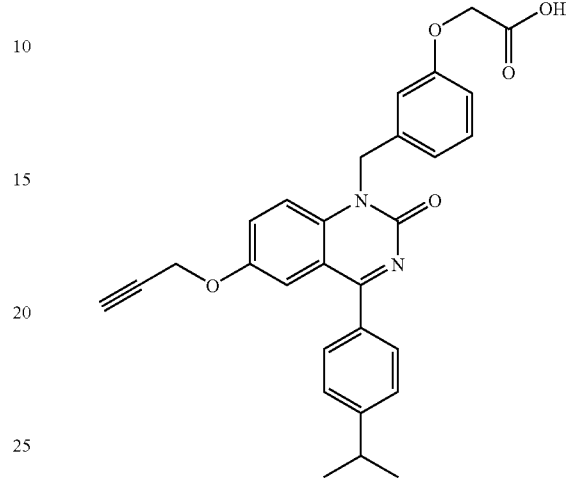

$^1$H NMR (400 MHz, DMSO-d6): 7.71 (d, 2H), 7.45-7.48 (m, 4H), 7.35 (d, 1H), 7.17 (m, 1H), 6.81 (broad s, 1H), 6.69-6.76 (m, 2H), 5.43 (broad s, 2H), 4.77 (d, 2H), 4.30 (s, 2H), 3.65 (t, 1H), 3.01 (m, 1H), 1.28 (d, 6H).

MS: 483 (M+1)$^+$

Example 31

1-(2,3-Dimethoxy-benzyl)-4-(4-isopropyl-phenyl)-6-prop-2-ynyloxy-1H-quinazolin-2-one

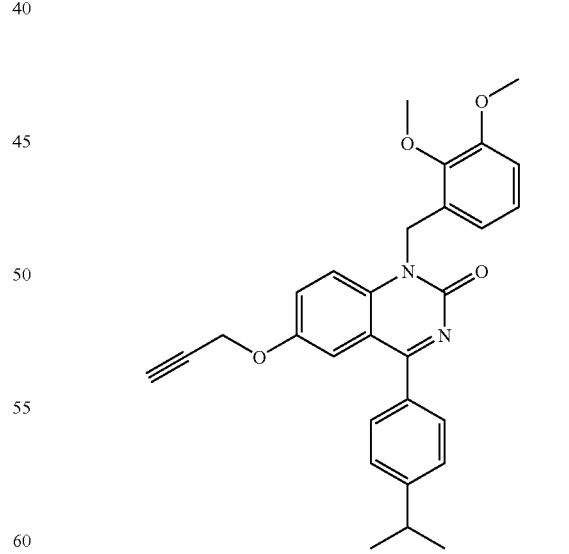

$^1$H NMR (400 MHz, DMSO-d6): 7.72 (d, 2H), 7.47-7.50 (m, 3H), 7.32-7.37 (m, 2H), 6.91-6.98 (m, 2H), 6.41 (dd, 1H), 5.45 (broad s, 2H), 4.78 (d, 2H), 3.87 (s, 3H), 3.82 (s, 3H), 3.67 (t, 1H), 3.02 (m, 1H), 1.28 (d, 6H).

MS: 469 (M+1)$^+$

Example 32

1-(2,3-Dihydro-benzo[1,4]dioxin-6-ylmethyl)-4-(4-isopropyl-phenyl)-6-prop-2-ynyloxy-1H-quinazolin-2-one

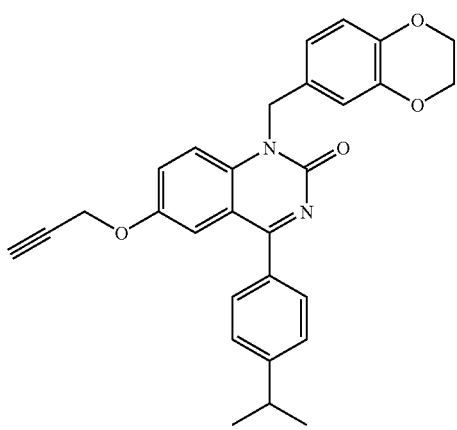 [SMILES: C#CCOc1ccc2c(c1)c(-c1ccc(C(C)C)cc1)nc(=O)n2Cc1ccc2c(c1)OCCO2]

$^1$H NMR (400 MHz, DMSO-d6): 7.70 (d, 2H), 7.46-7.51 (m, 4H), 7.35 (d, 1H), 6.77-6.82 (m, 3H), 5.37 (broad s, 2H), 4.18 (s, 4H), 3.66 (t, 1H), 3.01 (m, 1H), 1.28 (d, 6H).

MS: 467 (M+1)$^+$

Example 33

4-(4-Isopropyl-phenyl)-1-(4-oxo-4H-chromen-3-ylmethyl)-6-prop-2-ynyloxy-1H-quinazolin-2-one

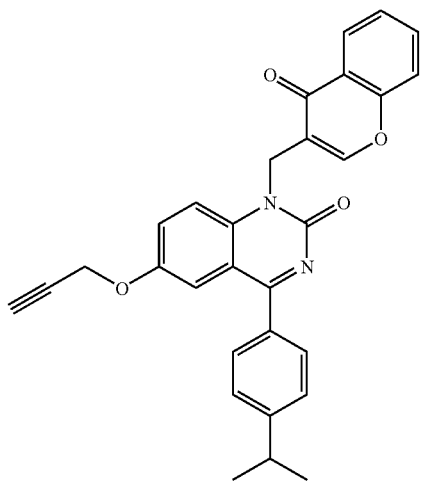 [SMILES: C#CCOc1ccc2c(c1)c(-c1ccc(C(C)C)cc1)nc(=O)n2Cc1coc2ccccc2c1=O]

$^1$H NMR (400 MHz, DMSO-d6): 8.23 (s, 1H), 8.13 (dd, 1H), 7.82 (dt, 1H), 7.70 (d, 2H), 7.62-7.65 (m, 2H), 7.47-7.54 (m, 4H), 7.35 (d, 1H), 5.25 (s, 2H), 4.80 (d, 2H), 3.67 (m, 1H), 3.02 (m, 1H), 1.28 (d, 6H).

MS: 477 (M+1)$^+$

Example 34

4-(4-Isopropyl-phenyl)-1-(2-methyl-butyl)-6-prop-2-ynyloxy-1H-quinazolin-2-one

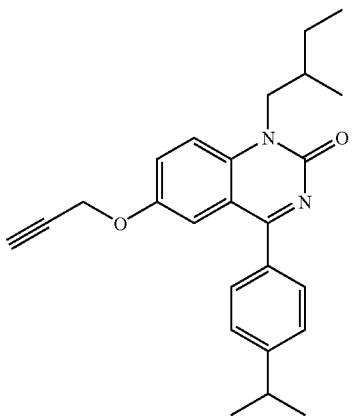 [SMILES: C#CCOc1ccc2c(c1)c(-c1ccc(C(C)C)cc1)nc(=O)n2CC(C)CC]

$^1$H NMR (400 MHz, DMSO-d6): 7.62-7.68 (m, 3H), 7.53 (dd, 1H), 7.46 (d, 2H), 7.33 (d, 1H), 4.80 (d, 2H), 4.14 (m, 2H), 3.68 (t, 1H), 3.00 (m, 1H), 1.92-2.01 (m, 1H), 1.37-1.45 (m, 1H), 1.27 (d, 6H), 1.18-1.26 (m, 1H), 0.88 (m, 6H).

MS: 389 (M+1)$^+$

Example 35

1-(2,6-Dichloro-benzyl)-4-(4-isopropyl-phenyl)-6-prop-2-ynyloxy-1H-quinazolin-2-one

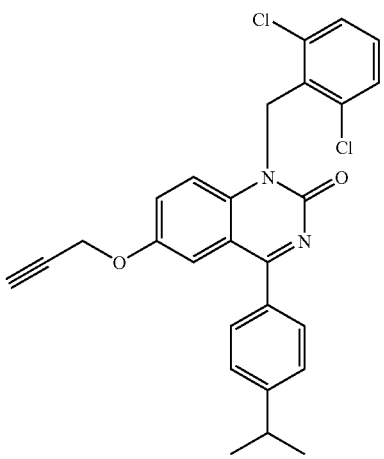 [SMILES: C#CCOc1ccc2c(c1)c(-c1ccc(C(C)C)cc1)nc(=O)n2Cc1c(Cl)cccc1Cl]

$^1$H NMR (300 MHz, CDCl$_3$): 7.78 (d, 2H), 7.44 (d, 1H), 7.38 (d, 2H), 7.15-7.40 (m, 5H), 5.90 (s, 2H), 4.62 (d, 2H), 3.01 (hept, 1H), 2.55 (m, 1H), 1.31 (d, 6H).

MS: 477 (M+1)$^+$

Example 36

1-(2,3-Dichloro-benzyl)-4-(4-isopropyl-phenyl)-6-prop-2-ynyloxy-1H-quinazolin-2-one

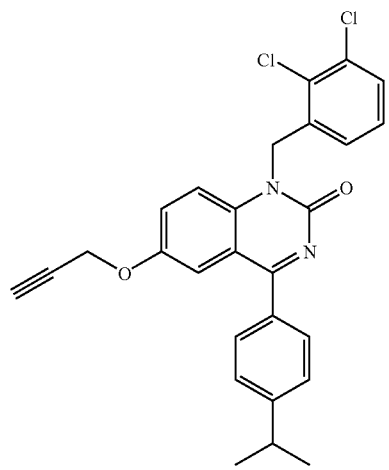 [SMILES: C#CCOc1ccc2c(c1)c(-c1ccc(C(C)C)cc1)nc(=O)n2Cc1cccc(Cl)c1Cl]

$^1$H NMR (400 MHz, DMSO-d6): 7.74 (d, 2H), 7.57-7.60 (m, 1H), 7.46-7.51 (m, 3H), 7.40 (d, 1H), 7.31 (d, 1H), 7.23 (t, 1H), 6.76 (d, 1H), 5.49 (s, 2H), 4.80 (d, 2H), 3.69 (t, 1H), 3.03 (m, 1H), 1.29 (d, 6H).

MS: 477/479 (M+1)$^+$

Example 37

4-(4-Isopropyl-phenyl)-6-prop-2-ynyloxy-1-(3-trifluoromethyl-benzyl)-1H-quinazolin-2-one

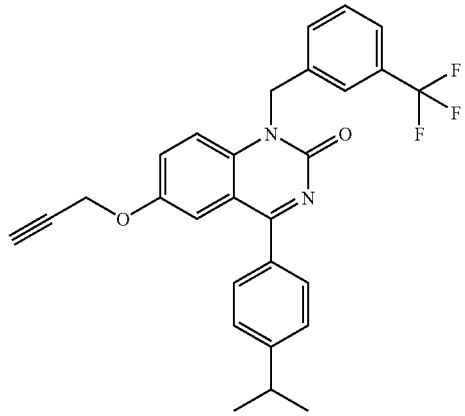 [SMILES: C#CCOc1ccc2c(c1)c(-c1ccc(C(C)C)cc1)nc(=O)n2Cc1cccc(C(F)(F)F)c1]

$^1$H NMR (400 MHz, DMSO-d6): 7.78 (s, 1H), 7.72 (d, 2), 7.64 (m, 1H), 7.47-7.58 (m, 6H), 7.38 (d, 1H), 5.58 (s, 2H), 4.79 (d, 2H), 3.67 (t, 1H), 3.02 (m, 1H), 1.28 (d, 6H).

MS: 477 (M+1)$^+$

Example 38

4-(4-Isopropyl-phenyl)-6-prop-2-ynyloxy-1-(4-trifluoromethyl-benzyl)-1H-quinazolin-2-one

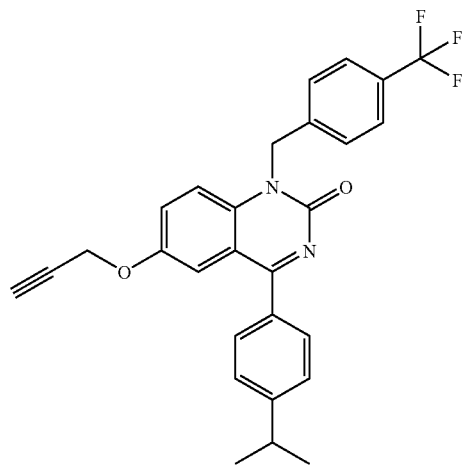 [SMILES: C#CCOc1ccc2c(c1)c(-c1ccc(C(C)C)cc1)nc(=O)n2Cc1ccc(C(F)(F)F)cc1]

$^1$H NMR (400 MHz, DMSO-d6): 7.71 (m, 4H), 7.43-7.51 (m, 6H), 7.37 (d, 1H), 5.59 (broad s, 2H), 4.79 (d, 2H), 3.67 (t, 1H), 3.02 (m, 1H), 1.28 (d, 6H).

MS: 477 (M+1)$^+$

Example 39

1-(3-Ethoxy-4-hydroxy-benzyl)-4-(4-isopropyl-phenyl)-6-prop-2-ynyloxy-1H-quinazolin-2-one

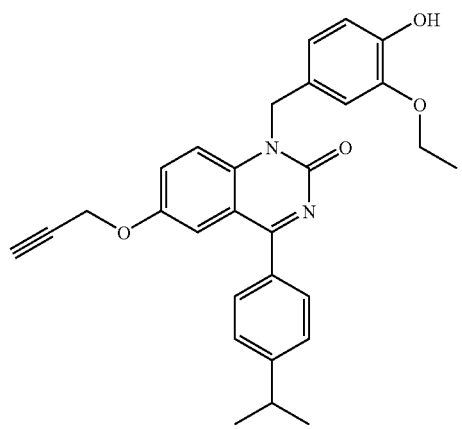 [SMILES: C#CCOc1ccc2c(c1)c(-c1ccc(C(C)C)cc1)nc(=O)n2Cc1ccc(O)c(OCC)c1]

$^1$H NMR (400 MHz, DMSO-d6): 8.86 (s, 1H), 7.70 (d, 2H), 7.46-7.55 (m, 4H), 7.33 (d, 1H), 7.00 (s, 1H), 6.63-6.70 (m, 2H), 5.36 (broad s, 2H), 4.78 (d, 2H), 3.97 (q, 2H), 3.65 (t, 1H), 3.02 (m, 1H), 1.29 (t, 3H), 1.28 (d, 6H).

MS: 469 (M+1)$^+$

Example 40

4-(4-Isopropyl-phenyl)-1-(3-phenyl-butyl)-6-prop-2-ynyloxy-1H-quinazolin-2-one

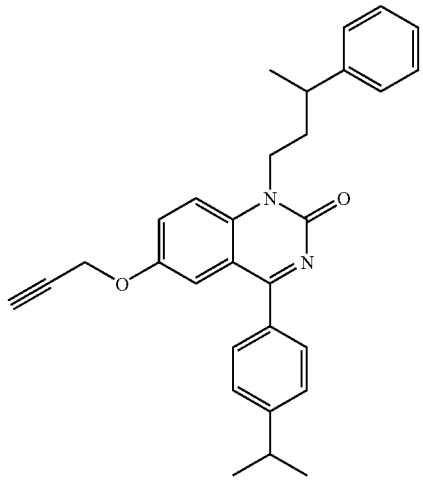 [SMILES: C#CCOc1ccc2c(c1)c(-c1ccc(C(C)C)cc1)nc(=O)n2CCC(C)c1ccccc1]

¹H NMR (400 MHz, DMSO-d6): 7.63 (d, 2H), 7.50 (dd, 1H), 7.45 (d, 2H), 7.37 (d, 1H), 7.28-7.32 (m, 5H), 7.17-7.21 (m, 1H), 4.79 (d, 2H), 4.12-4.21 (m, 1H), 3.97-4.04 (m, 1H), 3.68 (t, 1H), 2.91-3.03 (m, 2H), 1.86-2.01 (m, 2H), 1.27 (m, 9H).

MS: 451 (M+1)+

Example 41

1-(3,4-Diethoxy-benzyl)-4-(4-isopropyl-phenyl)-6-prop-2-ynyloxy-1H-quinazolin-2-one

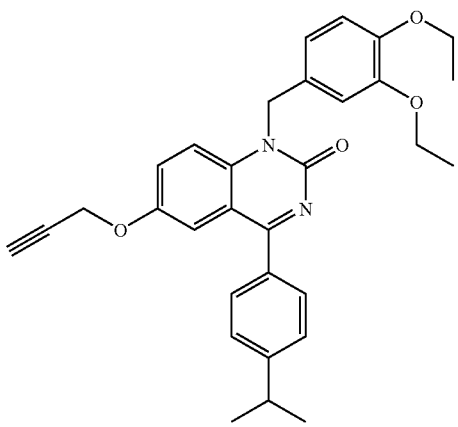 [SMILES: C#CCOc1ccc2c(c1)c(-c1ccc(C(C)C)cc1)nc(=O)n2Cc1ccc(OCC)c(OCC)c1]

¹H NMR (400 MHz, DMSO-d6): 7.70 (d, 2H), 7.46-7.54 (m, 4H), 7.33 (d, 1H), 7.04 (d, 1H), 6.84 (d, 1H), 6.71 (dd, 1H), 5.39 (broad s, 2H), 4.78 (d, 2H), 3.91-4.00 (m, 4H), 3.65 (t, 1H), 3.01 (m, 1H), 1.25-1.30 (m, 12H).

MS: 497 (M+1)+

Example 42

1-(3-Fluoro-4-methoxy-benzyl)-4-(4-isopropyl-phenyl)-6-prop-2-ynyloxy-1H-quinazolin-2-one

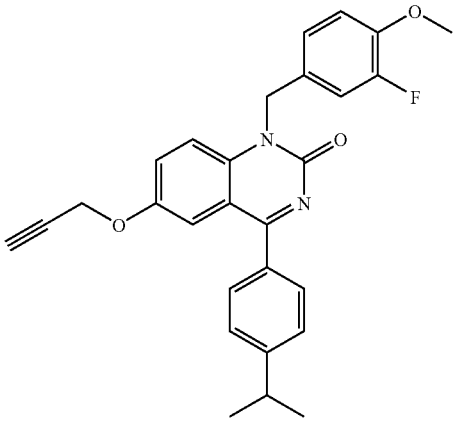 [SMILES: C#CCOc1ccc2c(c1)c(-c1ccc(C(C)C)cc1)nc(=O)n2Cc1ccc(OC)c(F)c1]

¹H NMR (400 MHz, DMSO-d6): 7.71 (d, 2H), 7.47-7.53 (m, 4H), 7.35 (d, 1H), 7.24 (dd, 1H), 7.06-7.13 (m, 2H), 5.42 (broad s, 2H), 4.78 (d, 2H), 3.78 (s, 3H), 3.67 (t, 1H), 3.02 (m, 1H), 1.28 (d, 6H).

MS: 457 (M+1)+

Example 43

{4-[4-(4-Isopropyl-phenyl)-2-oxo-6-prop-2-ynyloxy-2H-quinazolin-1-ylmethyl]-phenoxy}-acetic acid

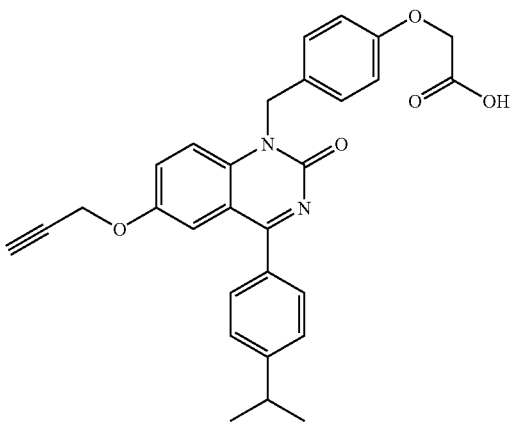 [SMILES: C#CCOc1ccc2c(c1)c(-c1ccc(C(C)C)cc1)nc(=O)n2Cc1ccc(OCC(=O)O)cc1]

¹H NMR (400 MHz, DMSO-d6): 7.69 (d, 2H), 7.45-7.52 (m, 4H), 7.32 (d, 1H), 7.20 (d, 2H), 6.79 (d, 2H), 5.40 (broad s, 2H), 4.77 (d, 2H), 4.33 (s, 2H), 3.65 (t, 1H), 3.01 (m, 1H), 1.28 (d, 6H).

MS: 483 (M+1)+

Example 44

4-(4-Isopropyl-phenyl)-1-(4-methoxy-2,3-dimethyl-benzyl)-6-prop-2-ynyloxy-1H-quinazolin-2-one

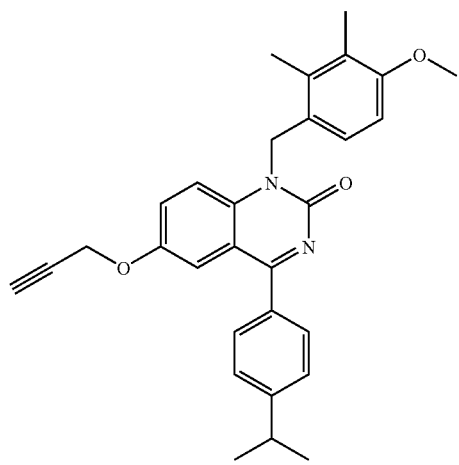 [SMILES: C#CCOc1ccc2c(c1)c(-c1ccc(C(C)C)cc1)nc(=O)n2Cc1ccc(OC)c(C)c1C]

$^1$H NMR (400 MHz, DMSO-d6): 7.74 (d, 2H), 7.49 (d, 2H), 7.44 (dd, 1H), 7.38 (d, 1H), 7.21 (d, 1H), 6.63 (d, 1H), 6.32 (d, 1H), 5.37 (broad s, 2H), 4.79 (d, 2H), 3.69 (t, 1H), 3.67 (s, 3H), 3.03 (m, 1H), 2.32 (s, 3H), 2.15 (s, 3H), 1.29 (d, 6H).

MS: 467 (M+1)$^+$

Example 45

1-(4-Benzyloxy-benzyl)-4-(4-isopropyl-phenyl)-6-prop-2-ynyloxy-1H-quinazolin-2-one

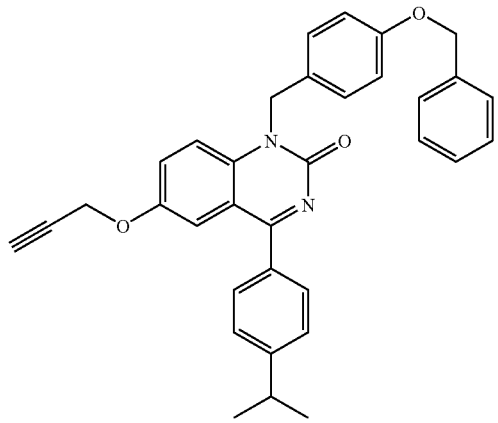 [SMILES: C#CCOc1ccc2c(c1)c(-c1ccc(C(C)C)cc1)nc(=O)n2Cc1ccc(OCc2ccccc2)cc1]

$^1$H NMR (400 MHz, DMSO-d6): 7.71 (d, 2H), 7.47-7.53 (m, 4H), 7.24-7.53 (m, 8H), 6.97 (d, 2H), 5.43 (broad s, 2H), 5.05 (s, 2H), 4.78 (d, 2H), 3.67 (t, 1H), 3.02 (m, 1H), 1.28 (d, 6H).

MS: 515 (M+1)$^+$

Example 46

1-(3-Hydroxy-6-methyl-pyridin-2-ylmethyl)-4-(4-isopropyl-phenyl)-6-prop-2-ynyloxy-1H-quinazolin-2-one

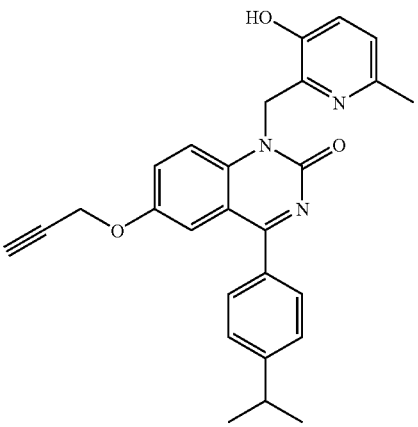 [SMILES: C#CCOc1ccc2c(c1)c(-c1ccc(C(C)C)cc1)nc(=O)n2Cc1nc(C)ccc1O]

$^1$H NMR (400 MHz, DMSO-d6): 10.06 (s, 1H), 7.71 (d, 2H), 7.44-7.49 (m, 4H), 7.35 (d, 1H), 7.12 (d, 1H), 6.96 (d, 1H), 5.46 (broad s, 2H), 4.79 (d, 2H), 3.67 (t, 1H), 3.02 (m, 1H), 2.14 (s, 3H), 1.28 (d, 6H).

MS: 440 (M+1)$^+$

Example 47

{2-[4-(4-Isopropyl-phenyl)-2-oxo-6-prop-2-ynyloxy-2H-quinazolin-1-ylmethyl]-6-methoxy-phenoxy}-acetic acid

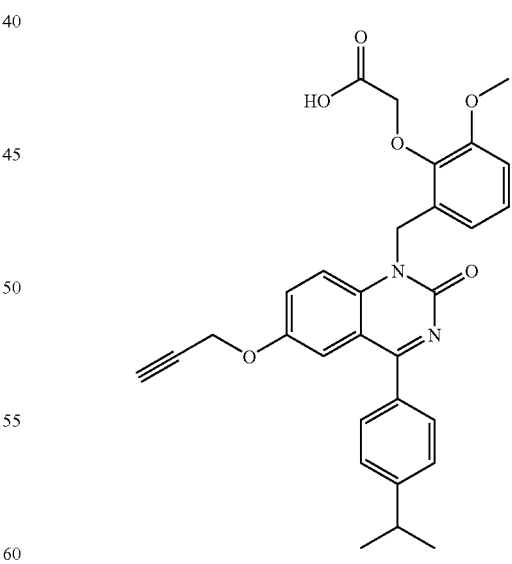

$^1$H NMR (400 MHz, DMSO-d6): 7.71 (d, 2H), 7.62 (d, 1H), 7.48 (d, 2H), 7.43 (dd, 1H), 7.33 (d, 1H), 6.92 (dd, 1H), 6.84 (t, 1H), 6.22 (d, 1H), 5.68 (broad s, 2H), 4.78 (d, 2H), 4.68 (s, 2H), 3.81 (s, 3H), 3.66 (t, 1H), 3.02 (m, 1H), 1.28 (d, 6H).

MS: 513 (M+1)$^+$

Example 48

4-(4-Isopropyl-phenyl)-1-(3-methoxy-benzyl)-6-propargyloxy-1H-quinazolin-2-one

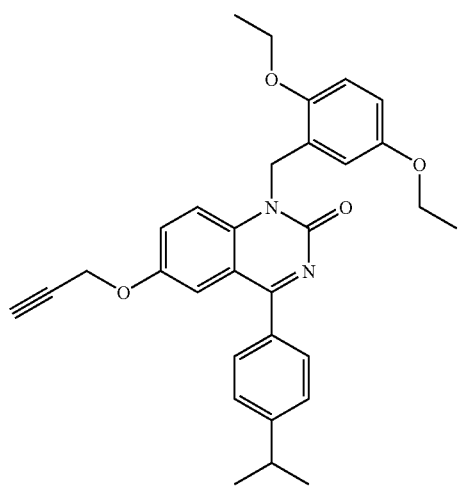 [SMILES: C#CCOc1ccc2c(c1)c(-c1ccc(C(C)C)cc1)nc(=O)n2Cc1cc(OCC)ccc1OCC]

¹H-NMR (300 MHz, CDCl₃): 7.75 (d, 2H), 7.49 (d, 1H), 7.39 (d, 2H), 7.20-7.34 (m, 3H), 6.76-6.92 (m, 3H), 5.53 (broad, 2H), 4.64 (d, 2H), 3.77 (s, 3H), 3.02 (hept, 1H), 2.55 (t, 1H), 1.33 (d, 6H).

MS: 439 (M+1)⁺

Example 49

4-(4-Isopropyl-phenyl)-1-(3,4-dimethoxy-benzyl)-6-propargyloxy-1H-quinazolin-2-one

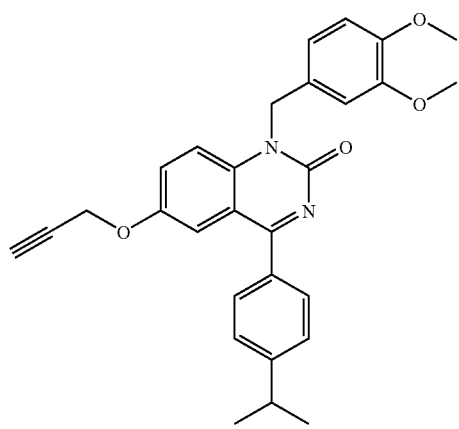

m.p. 97° C.

¹H-NMR (300 MHz, CDCl₃): 7.75 (d, 2H), 7.49 (dd, 1H), 7.38 (d, 2H), 7.32-7.36 (m, 2H), 6.96 (d, 1H), 6.87 (dd, 1H), 6.79 (d, 1H), 5.48 (broad, 2H), 4.64 (d, 2H), 3.85 (s, 3H), 3.84 (s, 3H), 3.02 (hept, 1H), 2.65 (t, 1H), 1.32 (d, 6H).

MS: 469 (M+1)⁺

Example 50

4-(4-Isopropyl-phenyl)-1-(4-methoxy-benzyl)-6-propargyloxy-1H-quinazolin-2-one

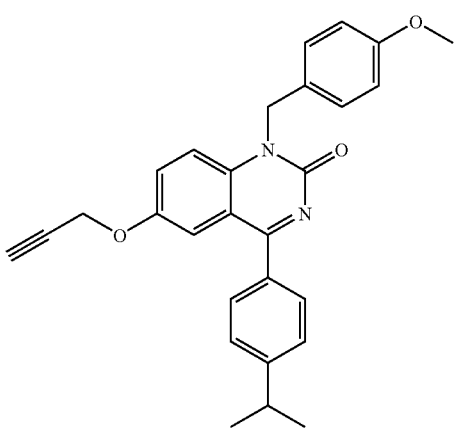

¹H-NMR (300 MHz, CDCl₃): 7.74 (d, 2H), 7.48 (broad s, 1H), 7.38 (d, 2H), 7.24-7.34 (m, 4H), 6.85 (d, 2H), 5.49 (broad, 2H), 4.64 (d, 2H), 3.77 (s, 3H), 3.02 (hept, 1H), 2.55 (t, 1H), 1.32 (d, 6H).

MS: 439 (M+1)⁺

Example 51

4-(4-Isopropyl-phenyl)-1-(3,5-dimethoxy-benzyl)-6-propargyloxy-1H-quinazolin-2-one

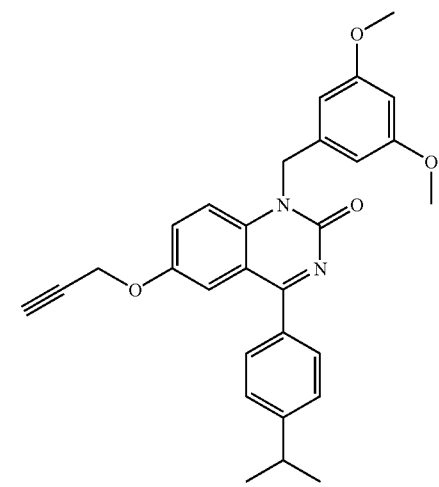 [SMILES: C#CCOc1ccc2c(c1)c(-c1ccc(C(C)C)cc1)nc(=O)n2Cc1cc(OC)cc(OC)c1]

¹H-NMR (300 MHz, CDCl₃): 7.75 (d, 2H), 7.48 (d, 1H), 7.38 (d, 2H), 7.31 (d, 1H), 7.29 (s, 1H), 6.46 (d, 2H), 6.35 (t, 1H), 5.48 (broad, 2H), 4.65 (d, 2H), 3.75 (s, 6H), 3.02 (hept, 1H), 2.55 (t, 1H), 1.33 (d, 6H).

MS: 469 (M+1)⁺

Example 52

4-(4-Isopropyl-phenyl)-1-(3,5-dimethoxy-benzyl)-6-propargyloxy-1H-quinazolin-2-one

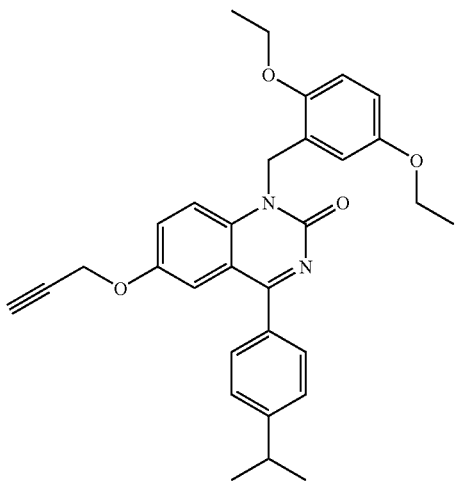 [SMILES: C#CCOc1ccc2c(c1)c(-c1ccc(C(C)C)cc1)nc(=O)n2Cc1cc(OCC)ccc1OCC]

m.p. 77-78° C.
$^1$H-NMR (300 MHz, CDCl$_3$): 7.76 (d, 2H), 7.47 (d, 1H), 7.38 (d, 2H), 7.28-7.32 (m, 2H), 6.83 (d, 1H), 6.72 (dd, 1H), 6.65 (d, 1H), 5.54 (broad, 2H), 4.64 (d, 2H), 4.12 (q, 2H), 3.85 (q, 2H), 3.02 (hept, 1H), 2.54 (t, 1H), 1.49 (t, 3H), 1.33 (d, 6H), 1.28 (t, 3H).
MS: 497 (M+1)$^+$

Example 53

4-(4-Isopropyl-phenyl)-1-(4-ethoxy-2-hydroxy-benzyl)-6-propargyloxy-1H-quinazolin-2-one

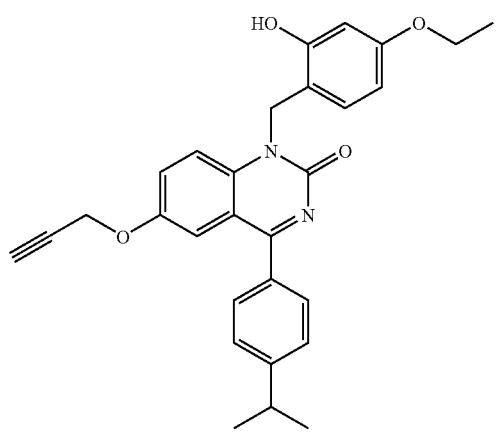 [SMILES: C#CCOc1ccc2c(c1)c(-c1ccc(C(C)C)cc1)nc(=O)n2Cc1ccc(OCC)cc1O]

m.p. 186-187° C.
$^1$H-NMR (300 MHz, CDCl$_3$): 10.13 (broad, OH), 7.88 (d, 1H), 7.71 (d, 2H), 7.54 (s, 1H), 7.52 (d, 1H), 7.34-7.40 (m, 3H), 6.51 (d, 1H), 6.42 (dd, 1H), 5.41 (broad, 2H), 4.68 (d, 2H), 3.98 (q, 2H), 3.01 (hept, 1H), 2.56 (t, 1H), 1.38 (t, 3H), 1.32 (d, 6H).
MS: 469 (M+1)$^+$

Example 54

4-(4-Isopropyl-phenyl)-1-(2,4-diethoxy-benzyl)-6-propargyloxy-1H-quinazolin-2-one

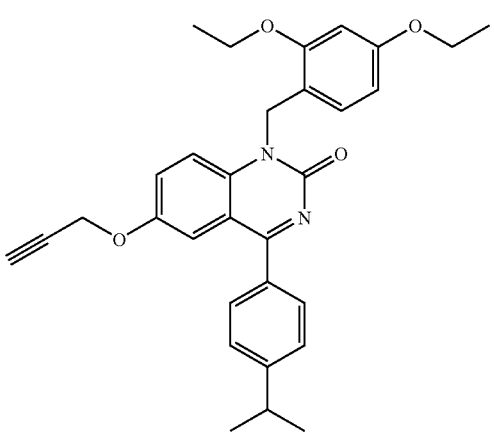 [SMILES: C#CCOc1ccc2c(c1)c(-c1ccc(C(C)C)cc1)nc(=O)n2Cc1ccc(OCC)cc1OCC]

$^1$H-NMR (300 MHz, CDCl$_3$): 7.74 (d, 2H), 7.46 (d, 1H), 7.38 (d, 1H), 7.37 (d, 2H), 7.29 (dd, 1H), 7.00 (d, 1H), 6.47 (d, 1H), 6.34 (dd, 1H), 5.49 (broad, 2H), 4.64 (d, 2H), 4.13 (q, 2H), 3.96 (q, 2H), 3.01 (hept, 1H), 2.54 (t, 1H), 1.51 (t, 3H), 1.38 (t, 3H), 1.32 (d, 6H).
MS: 497(M+1)$^+$

Example 55

4-(4-Isopropyl-phenyl)-1-(2,4-diethoxy-benzyl)-6-propargyloxy-1H-quinazolin-2-one

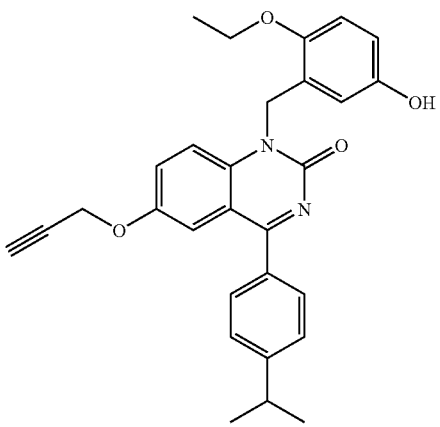 [SMILES: C#CCOc1ccc2c(c1)c(-c1ccc(C(C)C)cc1)nc(=O)n2Cc1cc(O)ccc1OCC]

m.p. 199-201° C.
$^1$H-NMR (300 MHz, CDCl$_3$): 9.15 (broad, OH), 7.85 (d, H), 7.71 (d, 2H), 7.49-7.56 (m, 3H), 7.38 (d, 2H), 7.01 (d, 1H), 6.90 (d, 1H), 6.79 (dd, 1H), 5.44 (broad, 2H), 4.68 (d, 2H), 3.97 (q, 2H), 3.02 (hept, 1H), 2.57 (t, 1H), 1.39 (t, 3H), 1.32 (d, 6H).
MS: 469 (M+1)$^+$

Example 56

4-(4-Isopropyl-phenyl)-1-(2-methoxy-benzyl)-6-prop-2-ynyloxy-1H-quinazolin-2-one

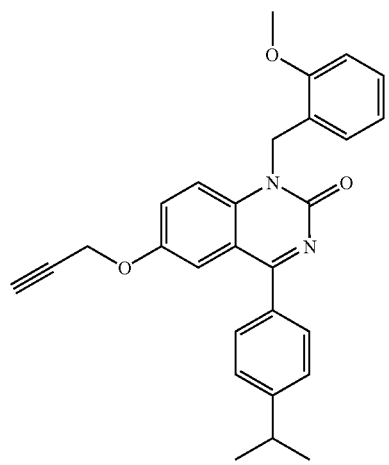 [SMILES: C#CCOc1ccc2c(c1)c(-c1ccc(C(C)C)cc1)nc(=O)n2Cc1ccccc1OC]

¹H NMR (300 MHz, CDCl₃): 7.76 (d, 2H), 7.48 (d, 1H), 7.38 (d, 2H), 7.18-7.32 (m, 3H), 6.76-7.02 (m, 3H), 5.56 (s, 2H), 4.62 (d, 2H), 3.96 (s, 3H), 3.02 (hept, 1H), 2.56 (t, 1H), 1.32 (d, 6H).

MS: 439 (M+1)⁺

Example 57

4-(4-Isopropyl-phenyl)-1-(4-ethoxy-benzyl)-6-propargyloxy-1H-quinazolin-2-one

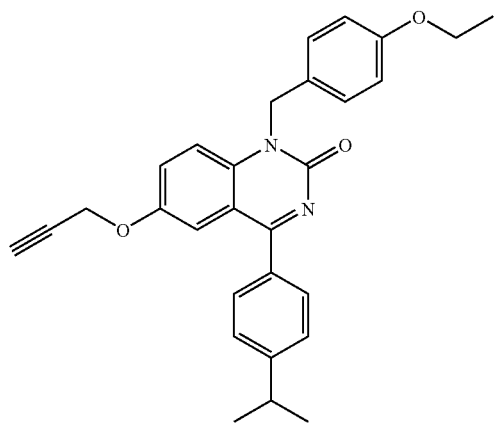 [SMILES: C#CCOc1ccc2c(c1)c(-c1ccc(C(C)C)cc1)nc(=O)n2Cc1ccc(OCC)cc1]

m.p. 181-183° C.

¹H-NMR (300 MHz, CDCl₃): 7.73 (d, 2H), 7.47 (s, 1H), 7.37 (d, 2H), 7.30 (s, 2H), 7.22-7.28 (m, 2H), 6.83 (d, 2H), 5.47 (broad, 2H), 4.63 (d, 2H), 3.98 (q, 2H), 3.01 (hept, 1H), 2.53 (broad, 1H), 1.38 (t, 3H), 1.31 (d, 6H).

MS: 453 (M+1)⁺

Example 58

4-(4-Isopropyl-phenyl)-1-(3-isopropoxy-benzyl)-6-propargyloxy-1H-quinazolin-2-one

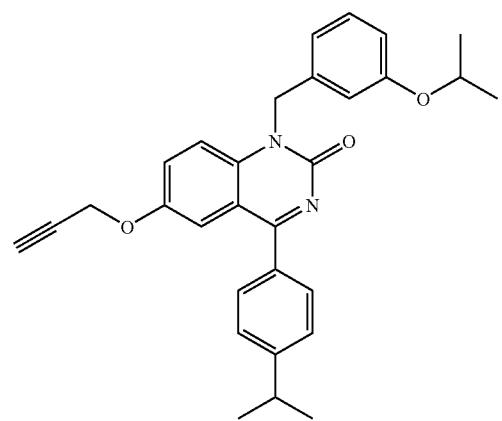 [SMILES: C#CCOc1ccc2c(c1)c(-c1ccc(C(C)C)cc1)nc(=O)n2Cc1cccc(OC(C)C)c1]

m.p. 69° C.

¹H-NMR (300 MHz, CDCl₃): 7.74 (d, 2H), 7.48 (d, 1H), 7.37 (d, 2H), 7.28 (td, 1H), 7.25 (d, 1H), 7.19 (d, 1H), 6.74-6.88 (m, 3H), 5.50 (broad, 2H), 4.63 (d, 2H), 4.50 (hept, 1H), 3.01 (hept, 1H), 2.54 (t, 1H), 1.32 (d, 6H), 1.29 (d, 6H).

MS: 467 (M+1)⁺

Example 59

4-(4-Isopropyl-phenyl)-1-(2,4-diethoxy-benzyl)-6-propargyloxy-1H-quinazolin-2-one

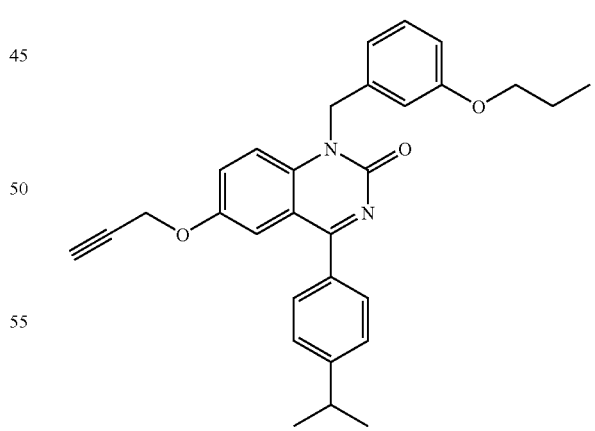

¹H-NMR (300 MHz, CDCl₃): 7.74 (d, 2H), 7.48 (d, 1H), 7.37 (d, 2H), 7.26-7.33 (m, 2H), 7.20 (d, 1H), 6.83-6.90 (m, 2H), 6.75-6.80 (m, 1H), 5.51 (broad, 2H), 4.63 (d, 2H), 3.87 (t, 2H), 3.01 (hept, 1H), 2.54 (t, 1H), 1.76 (hex, 2H), 1.32 (d, 6H), 1.00 (t, 3H).

MS: 467 (M+1)⁺

Example 60

1-(4-Bromo-3-methoxy-benzyl)-4-(4-isopropyl-phenyl)-6-propargyloxy-1H-quinazolin-2-one

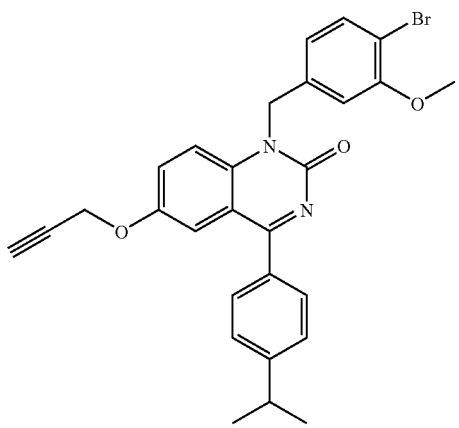 [SMILES: C#CCOc1ccc2c(c1)c(-c1ccc(C(C)C)cc1)nc(=O)n2Cc1ccc(Br)c(OC)c1]

m.p. 72-74° C.

$^1$H-NMR (300 MHz, CDCl$_3$): 7.76 (d, 2H), 7.48-7.54 (m, 2H), 7.38 (d, 2H), 7.32 (dd, 1H), 7.04 (d, 1H), 6.68 (dd, 1H), 6.47 (d, 1H), 5.53 (broad s, 2H), 4.65 (d, 2H), 3.64 (s, 3H), 3.02 (hept, 1H), 2.55 (t, 1H), 1.32 (d, 6H).

MS: 517/519 (M+1)$^+$

Example 61

4-(4-Isopropyl-phenyl)-1-(3-hydroxy-4-methoxy-benzyl)-6-propargyloxy-1H-quinazolin-2-one

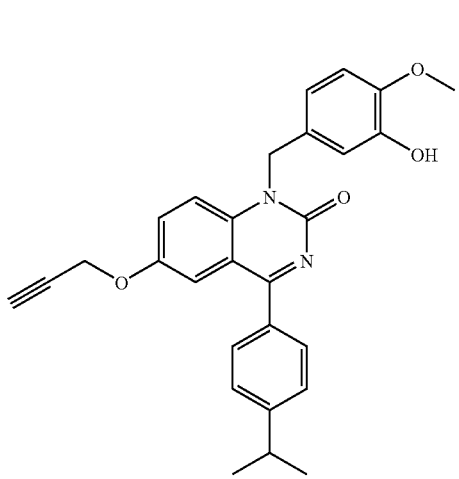 [SMILES: C#CCOc1ccc2c(c1)c(-c1ccc(C(C)C)cc1)nc(=O)n2Cc1ccc(OC)c(O)c1]

m.p. 112° C.

$^1$H-NMR (300 MHz, CDCl$_3$): 7.73 (d, 2H), 7.47 (d, 1H), 7.37 (d, 2H), 7.25-7.33 (m, 2H), 6.88 (d, 1H), 6.82 (dd, 1H), 6.77 (d, 1H), 5.60 (s, OH), 5.45 (broad s, 2H), 4.63 (d, 2H), 3.85 (s, 3H), 3.01 (hept, 1H), 2.54 (t, 1H), 1.32 (d, 6H).

MS: 455 (M+1)$^+$

Example 62

4-(4-Isopropyl-phenyl)-1-(2-methoxymethoxy-benzyl)-6-prop-2-ynyloxy-1H-quinazolin-2-one

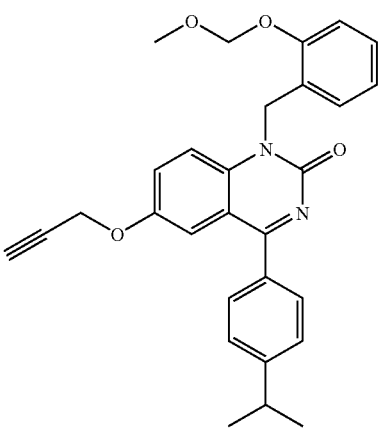

$^1$H NMR (300 MHz, CDCl$_3$): 7.76 (d, 2H), 7.48 (d, 1H), 7.38 (d, 2H), 7.10-7.32 (m, 4H), 7.02 (d, 1H), 6.86 (t, 1H), 5.58 (s, 2H), 5.34 (s, 2H), 4.62 (d, 2H), 3.58 (s, 3H), 3.02 (hept, 1H), 2.56 (t, 1H), 1.32 (d, 6H).

MS: 469 (M+1)$^+$

Example 63

1-(4-Bromo-3-ethoxy-benzyl)-4-(4-isopropyl-phenyl)-6-propargyloxy-1H-quinazolin-2-one

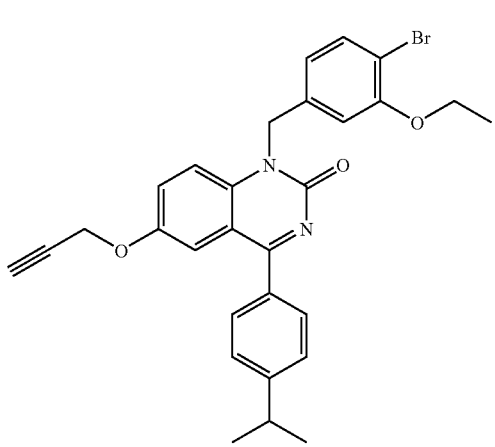 [SMILES: C#CCOc1ccc2c(c1)c(-c1ccc(C(C)C)cc1)nc(=O)n2Cc1ccc(Br)c(OCC)c1]

m.p. 144-146° C.

$^1$H-NMR (300 MHz, CDCl$_3$): 7.77 (d, 2H), 7.50 (s, 1H), 7.49 (d, 1H), 7.39 (d, 2H), 7.32 (dd, 1H), 7.04 (d, 1H), 6.67 (dd, 1H), 6.48 (d, 1H), 5.53 (broad s, 2H), 4.65 (d, 2H), 3.84 (q, 2H), 3.02 (hept, 1H), 2.55 (t, 1H), 1.32 (d, 6H), 1.28 (t, 3H).

MS: 532 (M+1)$^+$

Example 64

1-(4-Chloro-4-methoxy-benzyl)-4-(4-isopropyl-phenyl)-6-propargyloxy-1H-quinazolin-2-one

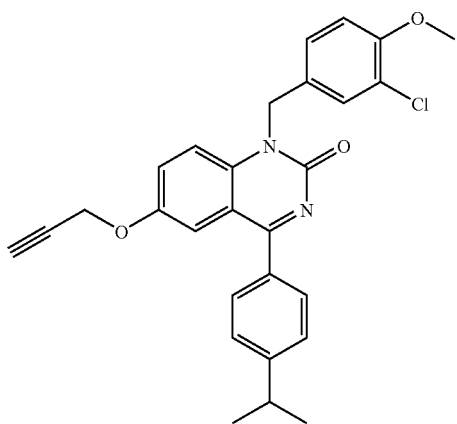 [SMILES: C#CCOc1ccc2c(c1)c(-c1ccc(C(C)C)cc1)nc(=O)n2Cc1ccc(OC)c(Cl)c1]

m.p. 159-161° C.

$^{1}$H-NMR (300 MHz, CDCl$_3$): 7.74 (d, 2H), 7.48 (d, 1H), 7.30-7.40 (m, 4H), 7.17-7.28 (m, 2H), 6.86 (d, 1H), 5.45 (broad s, 2H), 4.64 (d, 2H), 3.86 (s, 3H), 3.01 (hept, 1H), 2.54 (t, 1H), 1.31 (d, 6H).

MS: 487 (M+1)$^+$

Example 65

1-(3-Chloro-4-methoxy-benzyl)-4-(4-isopropyl-phenyl)-6-propargyloxy-1H-quinazolin-2-one

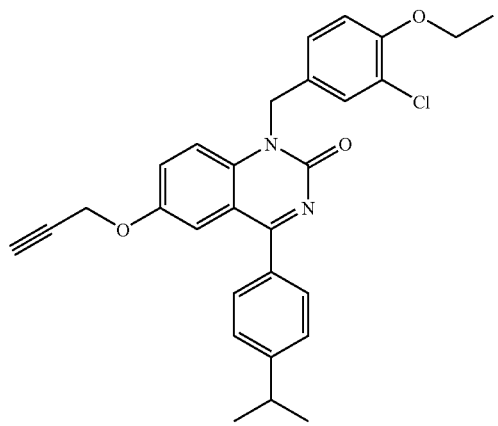 [SMILES: C#CCOc1ccc2c(c1)c(-c1ccc(C(C)C)cc1)nc(=O)n2Cc1ccc(OCC)c(Cl)c1]

m.p. 147-149° C.

$^{1}$H-NMR (300 MHz, CDCl$_3$): 7.74 (d, 2H), 7.49 (d, 1H), 7.39 (s, 1H), 7.37 (d, 2H), 7.30-7.36 (m, 2H), 7.22-7.26 (m, 1H), 7.17 (dd, 1H), 6.85 (d, 1H), 5.44 (broad s, 2H), 4.64 (d, 2H), 4.07 (q, 2H), 3.01 (hept, 1H), 2.55 (t, 1H), 1.44 (t, 3H), 1.32 (d, 6H).

MS: 473 (M+1)$^+$

Example 66

1-(3-Chloro-4,5-dimethoxy-benzyl)-4-(4-isopropyl-phenyl)-6-propargyloxy-1H-quinazolin-2-one

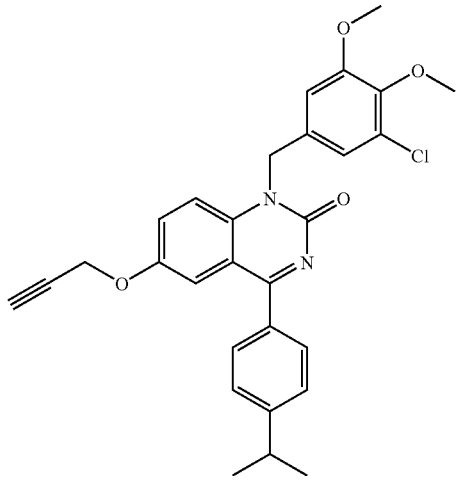 [SMILES: C#CCOc1ccc2c(c1)c(-c1ccc(C(C)C)cc1)nc(=O)n2Cc1cc(Cl)c(OC)c(OC)c1]

m.p. 80° C.

$^{1}$H-NMR (300 MHz, CDCl$_3$): 7.74 (d, 2H), 7.51 (d, 1H), 7.33-7.41 (m, 3H), 7.28 (s, 1H), 6.88 (dd, 2H), 5.43 (broad s, 2H), 4.65 (d, 2H), 3.82 (s, 3H), 3.81 (s, 3H), 3.01 (hept, 1H), 2.55 (t, 1H), 1.32 (d, 6H).

MS: 503, 505 (M+1)$^+$

Example 67

1-(4-Chloro-3-methoxy-benzyl)-4-(4-isopropyl-phenyl)-6-propargyloxy-1H-quinazolin-2-one

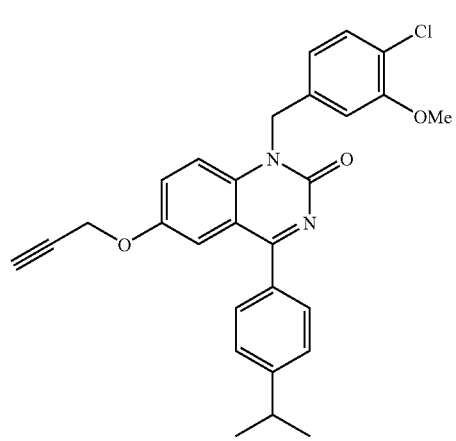 [SMILES: C#CCOc1ccc2c(c1)c(-c1ccc(C(C)C)cc1)nc(=O)n2Cc1ccc(Cl)c(OC)c1]

m.p. 133-135° C.

$^{1}$H NMR (300 MHz, CDCl$_3$): 7.74 (d, 2H), 7.50 (d, 1H), 7.33 (d, 2H), 7.22-7.36 (m, 3H), 6.97 (d, 1H), 6.83 (dd, 1H), 5.49 (broad s, 2H), 4.64 (d, 2H), 3.85 (s, 3H), 3.01 (hept, 1H), 2.54 (t, 1H), 1.32 (d, 6H).

MS: 473 (M+1)$^+$

Example 68

1-(3-Fluoro-benzyl)-4-(4-isopropyl-phenyl)-6-propargyloxy-1H-quinazolin-2-one

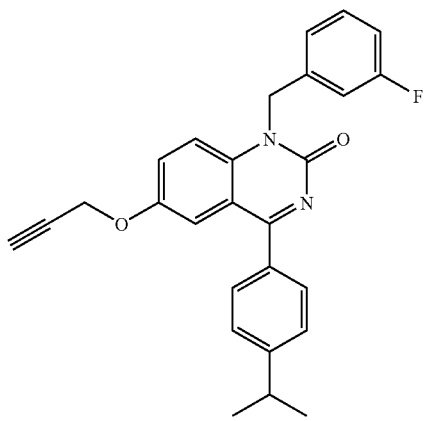 [SMILES: C#CCOc1ccc2c(c1)c(-c1ccc(C(C)C)cc1)nc(=O)n2Cc1cccc(F)c1]

m.p. 72-73° C.

¹H NMR (300 MHz, CDCl₃): 7.74 (d, 2H), 7.50 (d, 1H), 7.37 (d, 2H), 7.30 (td, 2H), 7.18 (d, 1H), 7.08 (d, 1H), 6.90-7.02 (m, 2H), 5.53 (broad s, 2H), 4.63 (d, 2H), 3.01 (hept, 1H), 2.54 (t, 1H), 1.31 (d, 6H).

MS: 427 (M+1)⁺

Example 69

1-(3,4-Difluoro-benzyl)-4-(4-isopropyl-phenyl)-6-propargyloxy-1H-quinazolin-2-one

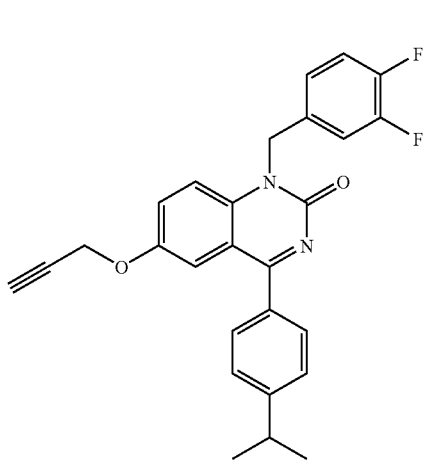 [SMILES: C#CCOc1ccc2c(c1)c(-c1ccc(C(C)C)cc1)nc(=O)n2Cc1ccc(F)c(F)c1]

m.p. 84° C.

¹H NMR (300 MHz, CDCl₃): 7.74 (d, 2H), 7.51 (d, 1H), 7.38 (d, 2H), 7.33 (dd, 1H), 7.02-7.22 (m, 4H), 5.48 (broad s, 2H), 4.64 (d, 2H), 3.01 (hept, 1H), 2.55 (t, 1H), 1.31 (d, 6H).

MS: 445 (M+1)⁺

Example 70

1-(4-Chloro-benzyl)-4-(4-isopropyl-phenyl)-6-propargyloxy-1H-quinazolin-2-one

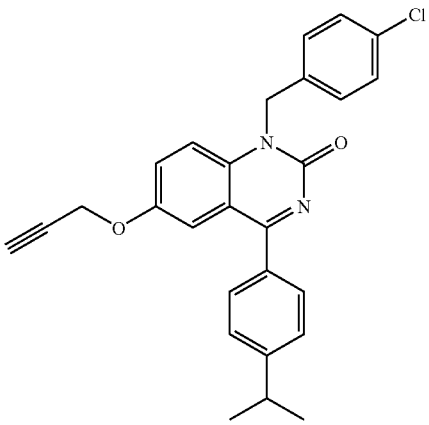 [SMILES: C#CCOc1ccc2c(c1)c(-c1ccc(C(C)C)cc1)nc(=O)n2Cc1ccc(Cl)cc1]

¹H NMR (300 MHz, CDCl₃): 7.74 (d, 2H), 7.51 (d, 1H), 7.38 (d, 2H), 7.33 (dd, 1H), 7.02-7.22 (m, 4H), 5.48 (broad s, 2H), 4.64 (d, 2H), 3.01 (hept, 1H), 2.55 (t, 1H), 1.31 (d, 6H).

MS: 443, 445 (M+1)⁺

Example 71

1-(4-Fluoro-benzyl)-4-(4-isopropyl-phenyl)-6-propargyloxy-1H-quinazolin-2-one

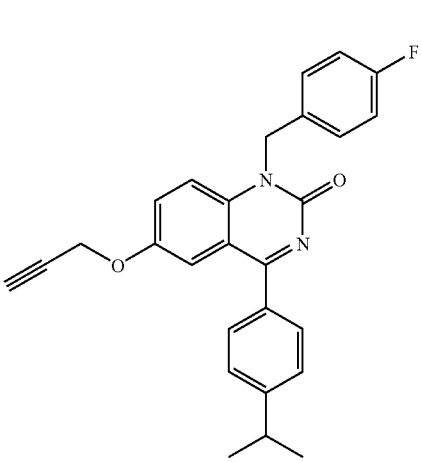 [SMILES: C#CCOc1ccc2c(c1)c(-c1ccc(C(C)C)cc1)nc(=O)n2Cc1ccc(F)cc1]

m.p. 71-73° C.

¹H NMR (300 MHz, CDCl₃): 7.73 (d, 2H), 7.48 (d, 1H), 7.37 (d, 2H), 7.20-7.34 (m, 4H), 7.00 (t, 2H), 5.50 (broad s, 2H), 4.63 (d, 2H), 3.01 (hept, 1H), 2.54 (broad t, 1H), 1.31 (d, 6H).

MS: 427 (M+1)⁺

Example 72

1-(3-chloro-benzyl)-4-(4-isopropyl-phenyl)-6-propargyloxy-1H-quinazolin-2-one

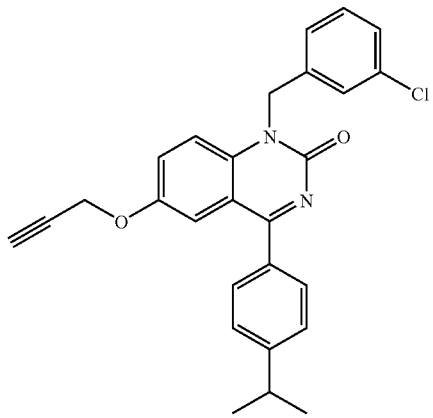

m.p. 110-112° C.

$^1$H NMR (300 MHz, CDCl$_3$): 7.75 (d, 2H), 7.50 (d, 1H), 7.38 (d, 2H), 7.21-7.35 (m, 4H), 7.18 (d, 2H), 5.51 (broad s, 2H), 4.64 (d, 2H), 3.01 (hept, 1H), 2.54 (broad t, 1H), 1.32 (d, 6H).

MS: 443, 445 (M+1)$^+$

Example 73

1-(3-Bromo-4-hydroxy-5-methoxy-benzyl)-4-(4-isopropyl-phenyl)-6-propargyloxy-1H-quinazolin-2-one

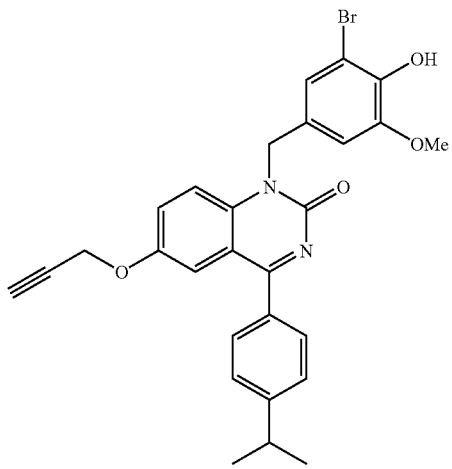 [SMILES: C#CCOc1ccc2c(c1)c(-c1ccc(C(C)C)cc1)nc(=O)n2Cc1cc(Br)c(O)c(OC)c1]

m.p. 175-177° C.

$^1$H NMR (300 MHz, CDCl$_3$): 7.74 (d, 2H), 7.50 (d, 1H), 7.37 (d, 2H), 7.32 (t, 2H), 7.07 (broad d, 1H), 6.89 (broad d, 1H), 5.42 (broad s, 2H), 4.65 (d, 2H), 3.85 (s, 3H), 3.01 (hept, 1H), 2.55 (broad t, 1H), 1.31 (d, 6H).

MS: 533, 535 (M+1)$^+$

Example 74

1-(3-Bromo-4-hydroxy-5-methoxy-benzyl)-4-(4-isopropyl-phenyl)-6-propargyloxy-1H-quinazolin-2-one

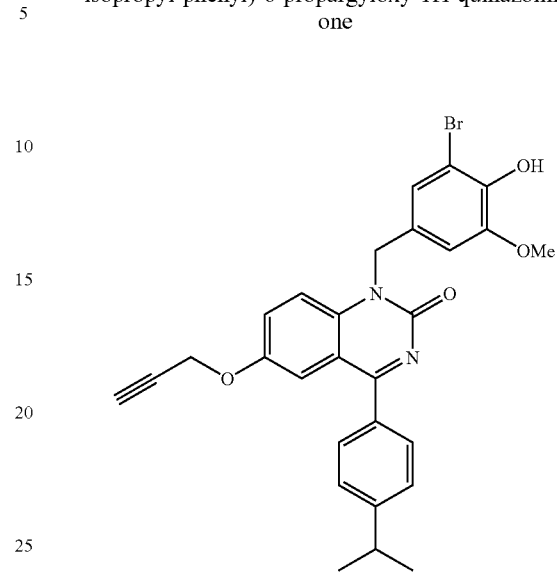

m.p. 175-177° C.

$^1$H NMR (300 MHz, CDCl$_3$): 7.74 (d, 2H), 7.50 (d, 1H), 7.37 (d, 2H), 7.32 (t, 2H), 7.07 (broad d, 1H), 6.89 (broad d, 1H), 5.42 (broad s, 2H), 4.65 (d, 2H), 3.85 (s, 3H), 3.01 (hept, 1H), 2.55 (broad t, 1H), 1.31 (d, 6H).

MS: 533, 535 (M+1)$^+$

Example 75

1-(4-Bromo-4-hydroxy-5-methoxy-benzyl)-4-(4-isopropyl-phenyl)-6-propargyloxy-1H-quinazolin-2-one

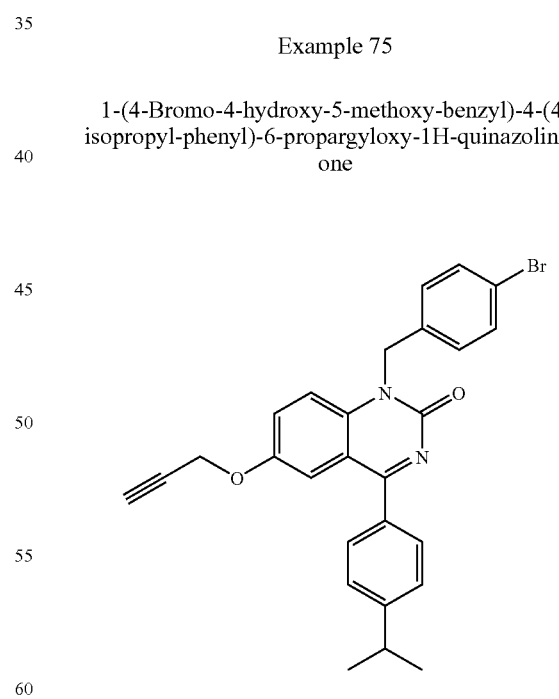

m.p. 122-123° C.

$^1$H NMR (300 MHz, CDCl$_3$): 7.74 (d, 2H), 7.50 (d, 1H), 7.45 (d, 2H), 7.38 (d, 2H), 7.32 (dd, 1H), 7.16-7.22 (m, 3H), 5.49 (broad s, 2H), 4.64 (d, 2H), 3.02 (hept, 1H), 2.55 (broad t, 1H), 1.32 (d, 6H).

MS: 487, 489 (M+1)$^+$

Example 76

1-(3-Bromo-benzyl)-4-(4-isopropyl-phenyl)-6-propargyloxy-1H-quinazolin-2-one

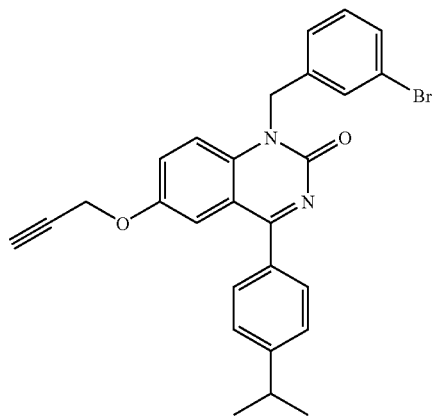 [SMILES: C#CCOc1ccc2c(c1)c(-c1ccc(C(C)C)cc1)nc(=O)n2Cc1cccc(Br)c1]

m.p. 144-146° C.

$^1$H NMR (300 MHz, CDCl$_3$): 7.75 (d, 2H), 7.51 (d, 1H), 7.46 (broad s, 1H), 7.28-7.41 (m, 4H), 7.14-7.25 (m, 3H), 5.51 (broad s, 2H), 4.65 (d, 2H), 3.02 (hept, 1H), 2.56 (broad t, 1H), 1.32 (d, 6H).

MS: 487, 489 (M+1)$^+$

Example 77

1-(3-Bromo-4,5-dimethoxy-benzyl)-4-(4-isopropyl-phenyl)-6-propargyloxy-1H-quinazolin-2-one

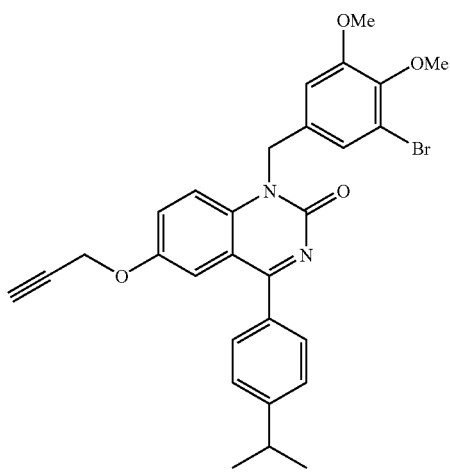 [SMILES: C#CCOc1ccc2c(c1)c(-c1ccc(C(C)C)cc1)nc(=O)n2Cc1cc(Br)c(OC)c(OC)c1]

m.p. 132-142° C.

$^1$H NMR (300 MHz, CDCl$_3$): 7.80 (d, 2H), 7.56 (d, 1H), 7.43 (d, 2H), 7.41 (d, 1H), 7.32 (d, 1H), 7.12 (br d, 1H), 5.48 (broad s, 2H), 4.70 (d, 2H), 3.86 (s, 6H), 3.06 (hept, 1H), 2.60 (broad t, 1H), 1.36 (d, 6H).

MS: 546, 548 (M+1)$^+$

Example 78

1-(3,4-Dibromo-benzyl)-4-(4-isopropyl-phenyl)-6-propargyloxy-1H-quinazolin-2-one

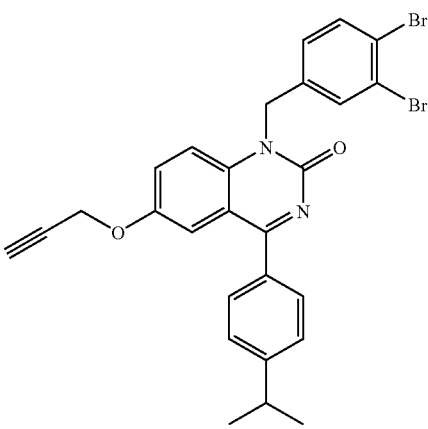 [SMILES: C#CCOc1ccc2c(c1)c(-c1ccc(C(C)C)cc1)nc(=O)n2Cc1ccc(Br)c(Br)c1]

m.p. 86-88° C.

$^1$H NMR (300 MHz, CDCl$_3$): 7.75 (d, 2H), 7.50-7.61 (m, 3H), 7.32-7.42 (m, 3H), 7.10-7.19 (m, 2H), 5.46 (broad s, 2H), 4.66 (broad s, 2H), 3.02 (hept, 1H), 2.55 (broad, 1H), 1.32 (d, 6H).

MS: 565, 567, 569 (M+1)$^+$ (Br$_2$-isotope pattern)

Example 79

1-(3,4-Dichloro-benzyl)-4-(4-isopropyl-phenyl)-6-propargyloxy-1H-quinazolin-2-one

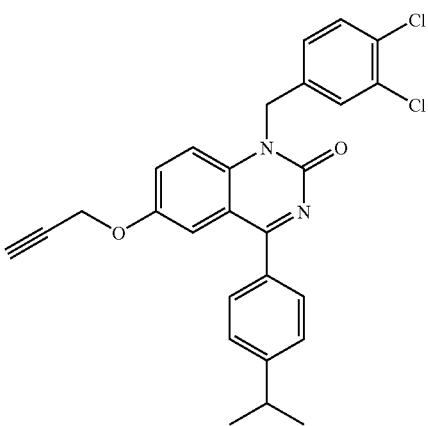 [SMILES: C#CCOc1ccc2c(c1)c(-c1ccc(C(C)C)cc1)nc(=O)n2Cc1ccc(Cl)c(Cl)c1]

m.p. 73-74° C.

$^1$H NMR (300 MHz, CDCl$_3$): 7.75 (d, 2H), 7.52 (d, 1H), 7.31-7.44 (m, 5H), 7.16 (d, 2H), 5.48 (broad s, 2H), 4.65 (broad d, 2H), 3.02 (hept, 1H), 2.55 (broad, 1H), 1.32 (d, 6H).

MS: 477, 479, 481 (M+1)$^+$ (Cl$_2$-isotope pattern)

Example 80

1-(4-Methyl-benzyl)-4-(4-isopropyl-phenyl)-6-propargyloxy-1H-quinazolin-2-one

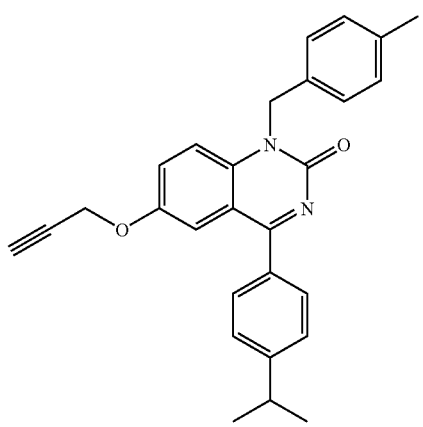 [SMILES: C#CCOc1ccc2c(c1)c(-c1ccc(C(C)C)cc1)nc(=O)n2Cc1ccc(C)cc1]

m.p. 92-93° C.

$^1$H NMR (300 MHz, CDCl$_3$): 7.74 (d, 2H), 7.47 (s, 1H), 7.37 (d, 2H), 7.29 (s, 2H), 7.21 (d, 2H), 7.12 (d, 2H), 5.51 (broad s, 2H), 4.63 (broad d, 2H), 3.01 (hept, 1H), 2.55 (broad, 1H), 2.31 (s, 3H), 1.32 (d, 6H).

MS: 423 (M+1)$^+$

Example 81

1-(3-Methyl-benzyl)-4-(4-isopropyl-phenyl)-6-propargyloxy-1H-quinazolin-2-one

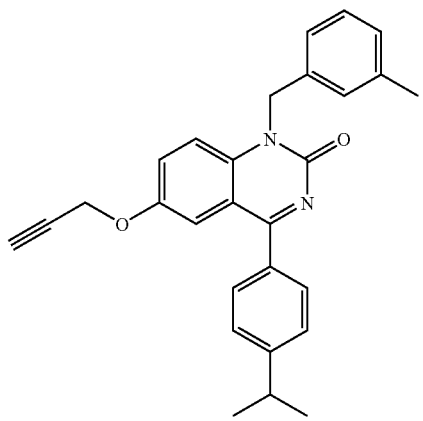 [SMILES: C#CCOc1ccc2c(c1)c(-c1ccc(C(C)C)cc1)nc(=O)n2Cc1cccc(C)c1]

m.p. 115-116° C.

$^1$H NMR (300 MHz, CDCl$_3$): 7.75 (d, 2H), 7.48 (d, 1H), 7.38 (d, 2H), 7.27-7.34 (m, 2H), 7.20 (t, 1H), 7.03-7.14 (m, 3H), 5.51 (broad s, 2H), 4.64 (d, 2H), 3.02 (hept, 1H), 2.54 (broad, 1H), 2.31 (s, 3H), 1.32 (d, 6H).

MS: 423 (M+1)$^+$

Example 82

1-(4-Ethyl-benzyl)-4-(4-isopropyl-phenyl)-6-propargyloxy-1H-quinazolin-2-one

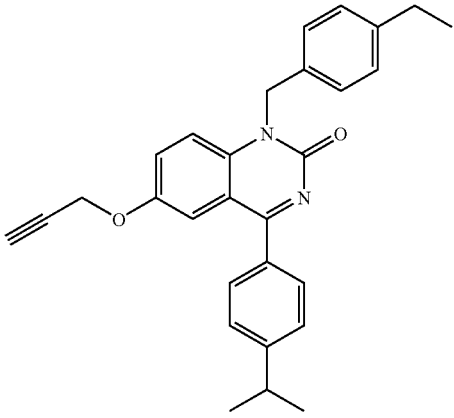 [SMILES: C#CCOc1ccc2c(c1)c(-c1ccc(C(C)C)cc1)nc(=O)n2Cc1ccc(CC)cc1]

m.p. 75-76° C.

$^1$H NMR (300 MHz, CDCl$_3$): 7.74 (d, 2H), 7.48 (s, 1H), 7.38 (d, 2H), 7.30 (s, 2H), 7.23 (d, 2H), 7.14 (d, 2H), 5.52 (broad s, 2H), 4.63 (d, 2H), 3.02 (hept, 1H), 2.61 (q, 2H), 2.54 (broad t, 1H), 1.32 (d, 6H), 1.20 (t, 3H).

MS: 437 (M+1)$^+$

Example 83

1-(3,4-Dimethyl-benzyl)-4-(4-isopropyl-phenyl)-6-propargyloxy-1H-quinazolin-2-one

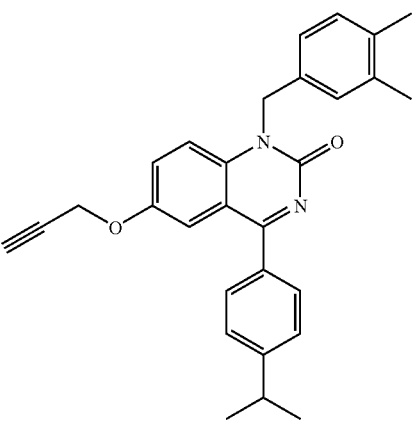 [SMILES: C#CCOc1ccc2c(c1)c(-c1ccc(C(C)C)cc1)nc(=O)n2Cc1ccc(C)c(C)c1]

m.p. 143-144° C.

$^1$H NMR (300 MHz, CDCl$_3$): 7.74 (d, 2H), 7.47 (s, 1H), 7.38 (d, 2H), 7.31 (broad d, 2H), 7.02-7.12 (m, 3H), 5.48 (broad s, 2H), 4.63 (d, 2H), 3.01 (hept, 1H), 2.54 (broad t, 1H), 2.21 (s, 6H), 1.32 (d, 6H).

MS: 437 (M+1)$^+$

Example 84

1-Cyclopropylmethyl-4-(4-isopropyl-phenyl)-6-propargyloxy-1H-quinazolin-2-one

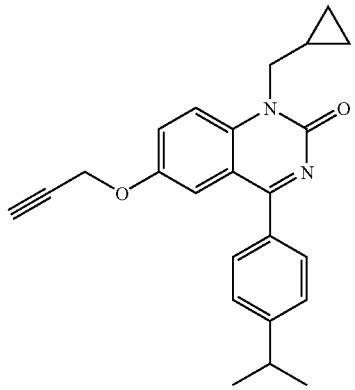 [SMILES: C#CCOc1ccc2c(c1)c(-c1ccc(C(C)C)cc1)nc(=O)n2CC1CC1]

$^1$H-NMR (300 MHz, CDCl$_3$): 7.70 (d, 2H), 7.43-7.50 (m, 3H), 7.38 (d, 2H), 7.35 (d, 2H), 4.67 (d, 2H), 4.26 (d, 2H), 3.00 (hept, 1H), 2.55 (t, 1H), 1.30 (d, 6H), 0.52-0.67 (m, 4H).
MS: 373 (M+1)$^+$

Example 85

1-(2-Bromo-thiazol-5-ylmethyl)-4-(4-isopropyl-phenyl)-6-prop-2-ynyloxy-1H-quinazolin-2-one

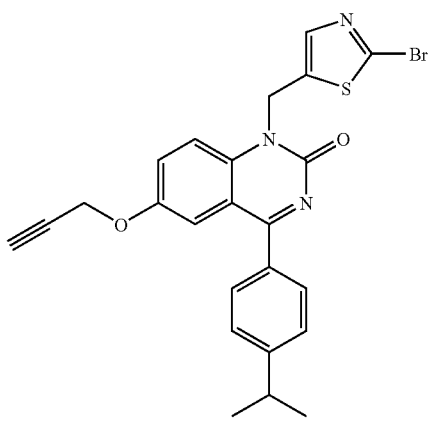 [SMILES: C#CCOc1ccc2c(c1)c(-c1ccc(C(C)C)cc1)nc(=O)n2Cc1cnc(Br)s1]

$^1$H-NMR (300 MHz, CDCl$_3$): 7.66-7.72 (m, 3H), 7.32-7.52 (m, 5H), 5.54 (s, 2H), 4.66 (d, 2H), 2.98 (hept, 1H), 2.54 (t, 1H), 1.32 (d, 6H).
MS: 496 (M+1)$^+$

Example 86

1-(4,5-Dichloro-thiophen-2-ylmethyl)-4-(4-isopropyl-phenyl)-6-prop-2-ynyloxy-1H-quinazolin-2-one

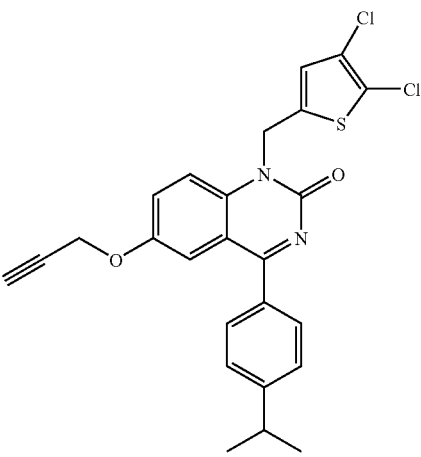 [SMILES: C#CCOc1ccc2c(c1)c(-c1ccc(C(C)C)cc1)nc(=O)n2Cc1cc(Cl)c(Cl)s1]

$^1$H-NMR (300 MHz, CDCl$_3$): 7.76 (d, 2H), 7.36-7.54 (m, 5H), 6.96 (s, 1H), 5.48 (s, 2H), 4.62 (d, 2H), 3.02 (hept, 1H), 2.58 (t, 1H), 1.32 (d, 6H).
MS: 483 (M+1)$^+$

Example 87

4-(4-Isopropyl-phenyl)-1-(5-methyl-thiophen-2-ylmethyl)-6-prop-2-ynyloxy-1H-quinazolin-2-one

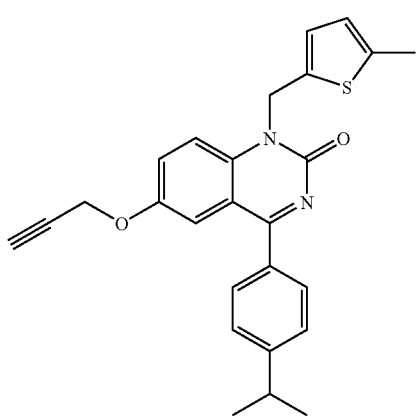 [SMILES: C#CCOc1ccc2c(c1)c(-c1ccc(C(C)C)cc1)nc(=O)n2Cc1ccc(C)s1]

$^1$H-NMR (300 MHz, CDCl$_3$): 7.72 (d, 2H), 7.30-7.60 (m, 5H), 6.96 (d, 1H), 6.58 (d, 1H), 5.54 (s, 2H), 4.64 (d, 2H), 3.02 (hept, 1H), 2.54 (t, 1H), 2.42 (s, 3H), 1.30 (d, 6H).
MS: 429 (M+1)$^+$

Example 88

4-(4-Isopropyl-phenyl)-6-prop-2-ynyloxy-1-quinolin-2-ylmethyl-1H-quinazolin-2-one

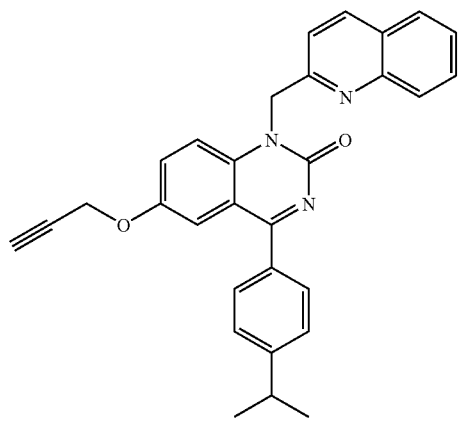 [SMILES: C#CCOc1ccc2c(c1)c(-c1ccc(C(C)C)cc1)nc(=O)n2Cc1ccc2ccccc2n1]

$^1$H-NMR (300 MHz, CDCl$_3$): 8.16 (d, 2H), 7.62-7.82 (m, 5H), 7.56 (d, 2H), 7.26-52 (d, 4H), 5.92 (s, 2H), 4.62 (d, 2H), 3.02 (hept, 1H), 2.52 (t, 1H), 1.32 (d, 6H).

MS: 460 (M+1)$^+$

Example 89

4-(4-Isopropyl-phenyl)-6-prop-2-ynyloxy-1-[2-(2,6,6-trimethyl-cyclohex-1-enyl)-ethyl]-1H-quinazolin-2-one

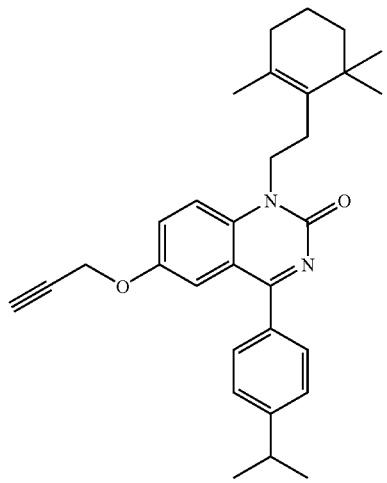 [SMILES: C#CCOc1ccc2c(c1)c(-c1ccc(C(C)C)cc1)nc(=O)n2CCC1=C(C)CCCC1(C)C]

$^1$H-NMR (300 MHz, CDCl$_3$): 7.72 (d, 2H), 7.42-7.50 (m, 3H), 7.42 (d, 2H), 4.68 (d, 2H), 4.26 (t, 2H), 3.02 (hept, 1H), 2.56 (t, 1H), 2.50 (t, 2H), 1.98 (t, 2H), 1.93 (s, 3H), 1.62 (d, 2H), 1.48 (d, 2H), 1.32 (d, 6H), 1.16 (s, 3H).

MS: 469 (M+1)$^+$

Example 90

4-Ethyl-4-{[2-(4-isopropyl-benzoyl)-4-prop-2-ynyloxy-phenylamino]-methyl}-hexanoic acid

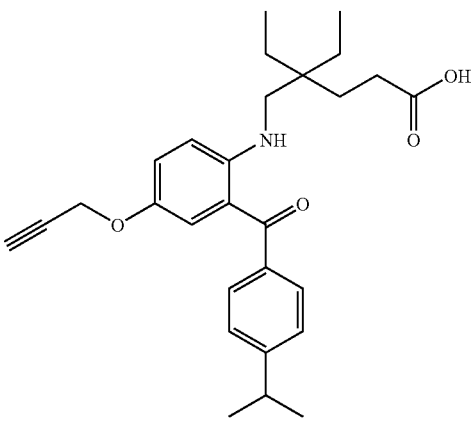 [SMILES: C#CCOc1ccc(NCC(CC)(CC)CCC(=O)O)c(C(=O)c2ccc(C(C)C)cc2)c1]

$^1$H-NMR (300 MHz, CDCl$_3$): 7.62 (d, 2H), 7.36-7.82 (m, 5H), 4.58 (d, 2H), 2.84-3.08 (m, 3H), 2.48 (t, 1H), 2.32 (m, 2H), 1.74 (m, 2H), 1.42 (m, 4H), 1.32 (d, 6H), 0.82 (m, 6H).

MS: 450 (M+1)$^+$

Example 91

4-(4-Isopropyl-phenyl)-6-propargyloxy-1-(3,3,3-trifluoro-propyl)-1H-quinazolin-2-one

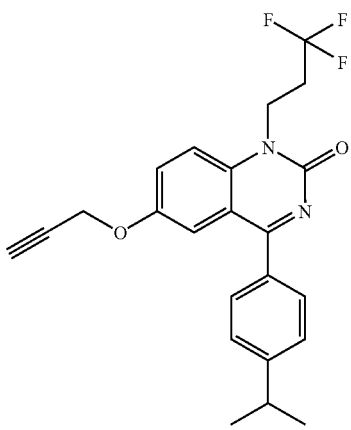 [SMILES: C#CCOc1ccc2c(c1)c(-c1ccc(C(C)C)cc1)nc(=O)n2CCC(F)(F)F]

$^1$H-NMR (300 MHz, CDCl$_3$): 7.69 (d, 2H), 7.51 (s, 1H), 7.49 (dd, 1H), 7.37 (d, 2H), 7.33 (d, 1H), 4.68 (d, 2H), 4.47-4.56 (m, 2H), 3.01 (hept, 1H), 2.60-2.78 (m, 2H), 2.57 (t, 1H), 1.31 (d, 6H).

MS: 415 (M+1)$^+$

Example 92

1-(3,3-Dimethyl-butyl)-4-(4-Isopropyl-phenyl)-6-propargyloxy-1H-quinazolin-2-one

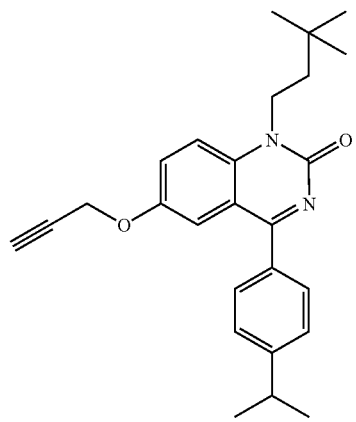 [SMILES: C#CCOc1ccc2c(c1)c(-c1ccc(C(C)C)cc1)nc(=O)n2CCC(C)(C)C]

$^1$H-NMR (300 MHz, CDCl$_3$): 7.68 (d, 2H), 7.42-7.48 (m, 2H), 7.35 (d, 2H), 7.32 (d, 1H), 4.66 (d, 2H), 4.25-4.35 (m, 2H), 3.00 (hept, 1H), 2.56 (t, 1H), 1.66-1.74 (m, 2H), 1.31 (d, 6H), 1.10 (s, 9H). m.p. 69° C.
MS: 403 (M+1)$^+$

Example 93

1-(2,2-Dimethyl-pent-4-enyl)-4-(4-isopropyl-phenyl)-6-prop-2-ynyloxy-1H-quinazolin-2-one

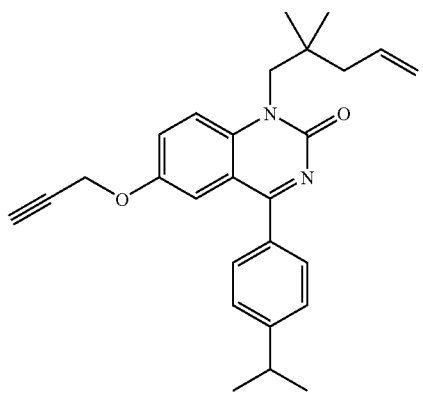 [SMILES: C#CCOc1ccc2c(c1)c(-c1ccc(C(C)C)cc1)nc(=O)n2CC(C)(C)CC=C]

$^1$H NMR (300 MHz, CDCl$_3$): 7.78 (d, 2H), 7.36-7.52 (m, 5H), 5.90 (m, 1H), 5.12 (m, 2H), 4.68 (d, 2H), 4.32 (broad s, 2H), 3.02 (hept, 1H), 2.58 (m, 1H), 2.18 (d, 2H), 1.32 (d, 6H), 1.02 (s, 6H).
MS: 415 (M+1)$^+$

Example 94

1-(3,5-Dimethyl-1-phenyl-1H-pyrazol-4-ylmethyl)-4-(4-isopropyl-phenyl)-6-prop-2-ynyloxy-1H-quinazolin-2-one

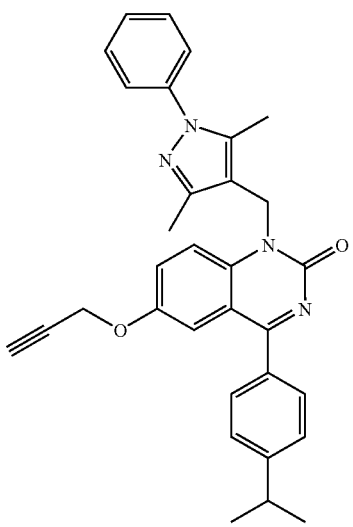 [SMILES: C#CCOc1ccc2c(c1)c(-c1ccc(C(C)C)cc1)nc(=O)n2Cc1c(C)nn(-c2ccccc2)c1C]

$^1$H NMR (300 MHz, CDCl$_3$): 7.78 (d, 2H), 7.52 (d, 1H), 7.26-7.50 (m, 9H), 5.48 (s, 2H), 4.66 (d, 2H), 3.02 (hept, 1H), 2.56 (m, 1H), 2.32 (s, 3H), 2.22 (s, 3H), 1.32 (d, 6H).
MS: 503 (M+1)$^+$

Example 95

1-(5-Bromo-thiophen-2-ylmethyl)-4-(4-isopropyl-phenyl)-6-prop-2-ynyloxy-1H-quinazolin-2-one

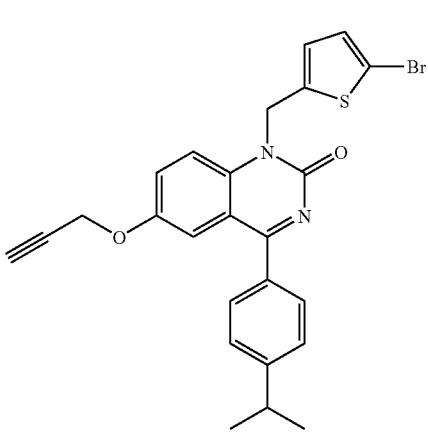 [SMILES: C#CCOc1ccc2c(c1)c(-c1ccc(C(C)C)cc1)nc(=O)n2Cc1ccc(Br)s1]

$^1$H NMR (300 MHz, CDCl$_3$): 7.68 (d, 2H), 7.31-7.50 (m, 5H), 7.34 (d, 2H), 6.94 (d, 1H), 6.88 (d, 1H), 5.52 (s, 2H), 4.64 (d, 2H), 3.00 (hept, 1H), 2.56 (m, 1H), 1.30 (d, 6H).
MS: 495 (M+1)$^+$

Example 96

1-(5-Hydroxymethyl-furan-2-ylmethyl)-4-(4-isopropyl-phenyl)-6-prop-2-ynyloxy-1H-quinazolin-2-one

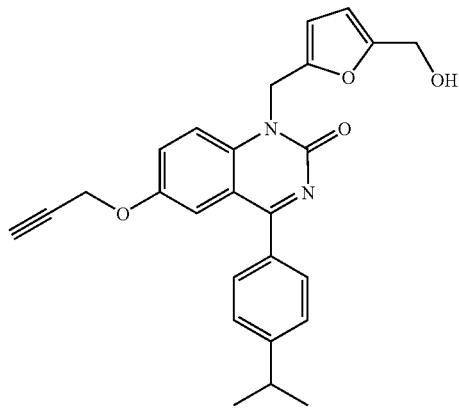 [SMILES: C#CCOc1ccc2c(c1)c(-c1ccc(C(C)C)cc1)nc(=O)n2Cc1ccc(CO)o1]

¹H NMR (300 MHz, CDCl₃): 7.70 (d, 2H), 7.62 (d, 1H), 7.42-7.52 (m, 2H), 7.38 (d 2H), 6.38 (d, 1H), 6.22 (d, 1H), 6.96 (dd, 1H), 5.48 (s, 2H), 4.52-4.70 (m, 4H), 3.02 (hept, 1H), 2.58 (t, 1H), 1.32 (d, 6H).

MS: 429 (M+1)⁺

Example 97

1-(2-Butyl-5-chloro-1H-imidazol-4-ylmethyl)-4-(4-isopropyl-phenyl)-6-prop-2-ynyloxy-1H-quinazolin-2-one

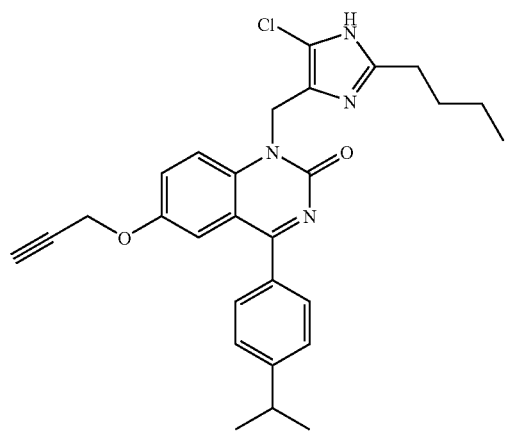 [SMILES: C#CCOc1ccc2c(c1)c(-c1ccc(C(C)C)cc1)nc(=O)n2Cc1nc(CCCC)[nH]c1Cl]

¹H NMR (300 MHz, CDCl₃): 7.72 (d, 1H), 7.46-7.60 (m, 3H), 7.38 (d, 2H), 5.36 (s, 2H), 4.66 (d, 2H), 3.00 (hept, 1H), 2.70 (m, 2H), 2.56 (t, 1H), 1.66 (m, 2H), 1.30 (d, 6H), 0.86 (t, 3H).

MS: 489 (M+1)⁺

Example 98

4-(4-Isopropyl-phenyl)-1-(6-methoxy-pyridin-3-ylmethyl)-6-prop-2-ynyloxy-1H-quinazolin-2-one

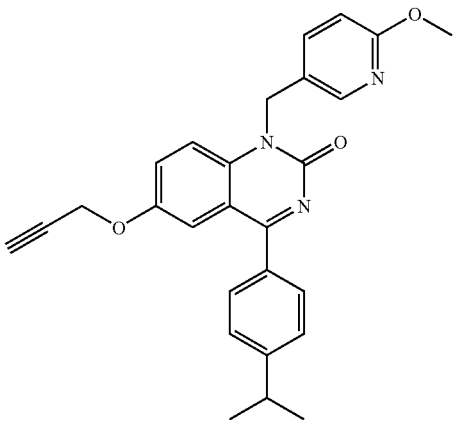 [SMILES: C#CCOc1ccc2c(c1)c(-c1ccc(C(C)C)cc1)nc(=O)n2Cc1ccc(OC)nc1]

¹H NMR (300 MHz, CDCl₃): 8.22 (m, 1H), 7.64-7.78 (m, 3H), 7.50 (d, 1H), 7.30-7.42 (m, 4H), 6.72 (d, 1H), 5.48 (s, 2H), 4.66 (d, 2H), 3.94 (s, 3H), 3.02 (hept, 1H), 2.56 (t 1H), 1.32 (d, 6H).

MS: 440 (M+)⁺

Example 99

7-[4-(4-Isopropyl-phenyl)-2-oxo-6-prop-2-ynyloxy-2H-quinazolin-1-ylmethyl]-1H-indole-2-carbonitrile

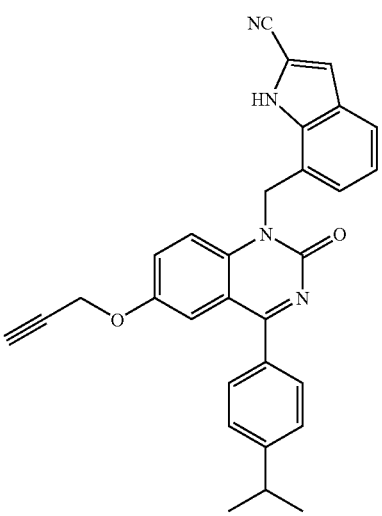

¹H NMR (300 MHz, CDCl₃): 11.52 (s, 1H), 7.92 (d, 1H), 7.74 (d, 2H), 7.64 (t, 2H), 7.46-7.54 (m, 2H), 7.38 (d, 2H), 7.12-7.26 (m, 2H), 6.76 (broad s, 2H), 4.64 (d, 2H), 3.02 (hept, 1H), 2.56 (t 1H), 1.32 (d, 6H).

MS: 473 (M+1)⁺

Example 100

1-(2,4-Diamino-pyrimidin-5-ylmethyl)-4-(4-isopropyl-phenyl)-6-prop-2-ynyloxy-1H-quinazolin-2-one

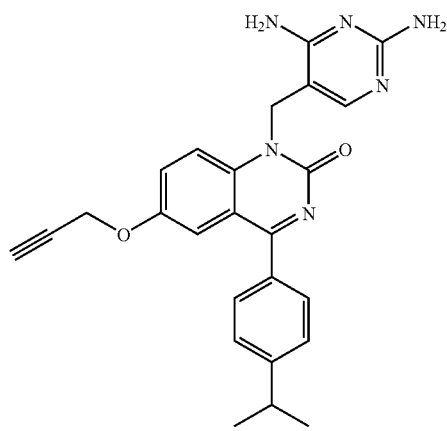 [SMILES: C#CCOc1ccc2c(c1)c(-c1ccc(C(C)C)cc1)nc(=O)n2Cc1cnc(N)nc1N]

¹H NMR (300 MHz, CD₃OD): 7.40-7.80 (m, 8H), 5.36 (s, 2H), 4.74 (d, 2H), 2.98-3.12 (m, 2H), 1.32 (d, 6H).
MS: 441 (M+1)⁺

Example 101

1-(6-Hydroxymethyl-pyridin-2-ylmethyl)-4-(4-isopropyl-phenyl)-6-prop-2-ynyloxy-1H-quinazolin-2-one

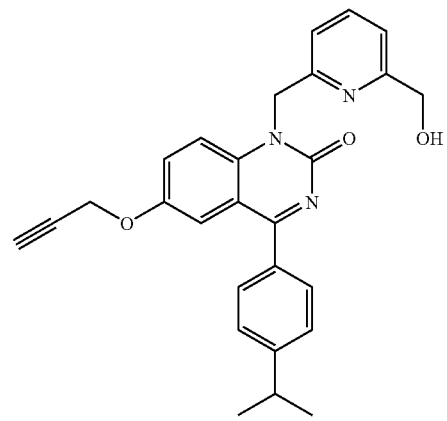 [SMILES: C#CCOc1ccc2c(c1)c(-c1ccc(C(C)C)cc1)nc(=O)n2Cc1cccc(CO)n1]

¹H NMR (300 MHz, CDCl₃): 7.76 (d, 2H), 7.64 (t, 1H), 7.20-7.52 (m, 6H), 7.16 (d, 1H), 5.64 (s, 2H), 4.76 (s, 2H), 4.64 (d, 2H), 3.02 (hept, 1H), 2.56 (t, 1H), 1.32 (d, 6H).
MS: 440 (M+1)

Example 102

1-(3,5-Di-tert-butyl-4-hydroxy-benzyl)-4-(4-isopropyl-phenyl)-6-prop-2-ynyloxy-1H-quinazolin-2-one

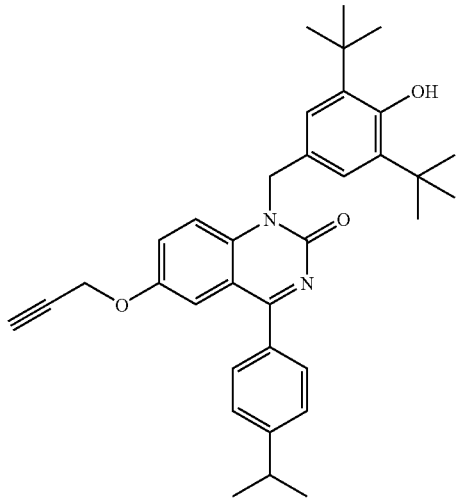 [SMILES: C#CCOc1ccc2c(c1)c(-c1ccc(C(C)C)cc1)nc(=O)n2Cc1cc(C(C)(C)C)c(O)c(C(C)(C)C)c1]

¹H NMR (300 MHz, CDCl₃): 7.76 (d, 2H), 7.30-7.52 (m, 5H), 7.16 (s, 2H), 5.44 (s, 2H), 4.66 (s, 2H), 3.02 (hept, 1H), 2.56 (t, 1H), 1.30 (d, 6H).
MS: 537 (M+1)⁺

Example 103

4-[4-(4-Isopropyl-phenyl)-2-oxo-6-prop-2-ynyloxy-2H-quinazolin-1-ylmethyl]-2,2-dimethyl-oxazolidine-3-carboxylic acid tert-butyl ester

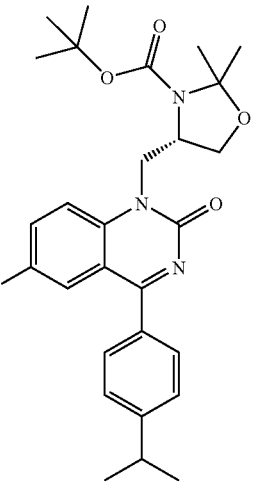

¹H NMR (300 MHz, CDCl₃): 8.20 (d, 1H), 7.70 (d, 2H), 7.30-7.58 (m, 4H), 4.94 (dd, 1H), 4.66 (d, 2H), 4.31 (d, 2H), 4.20 (m, 1H), 3.84 (dd, 1H), 3.00 (hept, 1H), 2.56 (t, 1H), 1.40-1.64 (m, 15H), 1.32 (d, 6H).
MS: 532 (M+1)⁺

Example 104

4-(4-Isopropyl-phenyl)-1-(4-methylamino-2-methyl-sulphanyl-pyrimidin-5-ylmethyl)-6-prop-2-ynyloxy-1H-quinazolin-2-one

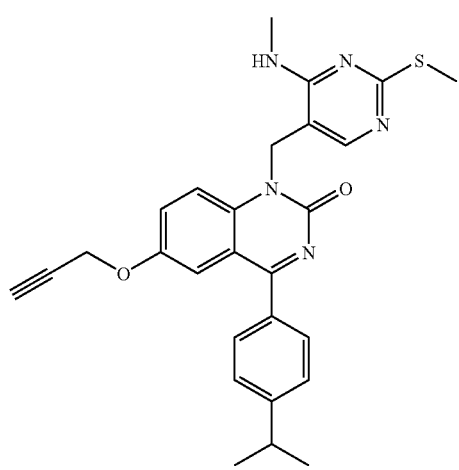 [SMILES: C#CCOc1ccc2c(c1)c(-c1ccc(C(C)C)cc1)nc(=O)n2Cc1cnc(SC)nc1NC]

$^1$H NMR (300 MHz, CDCl$_3$): 8.18 (s, 1H), 7.86 (d, 1H), 7.72 (d, 2H), 7.64 (d, 1H), 7.52 (d, 1H), 7.44 (dd, 1H), 7.38 (d, 2H), 5.34 (broad s, 2H), 4.64 (d, 2H), 3.02 (hept, 1H), 2.96 (d, 3H), 2.58 (t, 1H), 2.50 (s, 3H), 1.32 (d, 6H).

MS: 486 (M+1)$^+$

Example 105

4-(4-Isopropyl-phenyl)-1-{4-[2-(methyl-pyridin-2-yl-amino)-ethoxy]-benzyl}-6-prop-2-ynyloxy-1H-quinazolin-2-one

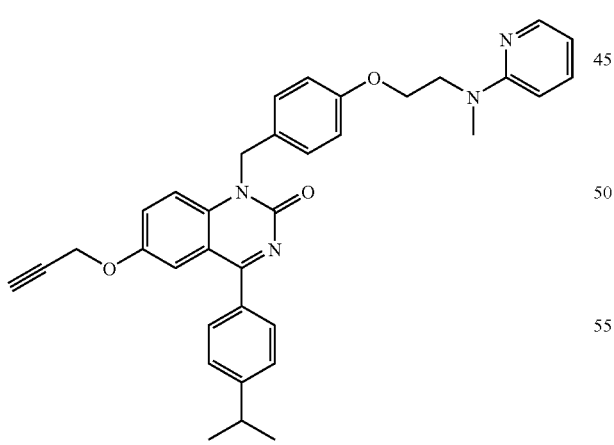

$^1$H NMR (300 MHz, CDCl$_3$): 8.12 (dd, 1H), 7.74 (d, 2H), 7.20-7.50 (m, 7H), 6.84 (d, 2H), 6.46-6.56 (m, 2H), 5.46 (broad s, 2H), 4.64 (d, 2H), 4.36 (t, 2H), 3.92 (t, 2H), 3.12 (s, 3H), 3.02 (hept, 1H), 2.54 (t, 1H), 1.40-1.64 (m, 15H), 1.32 (d, 6H).

MS: 559 (M+1)$^+$

Example 106

4-(4-Isopropyl-phenyl)-1-(2-methyl-hex-4-enyl)-6-prop-2-ynyloxy-1H-quinazolin-2-one

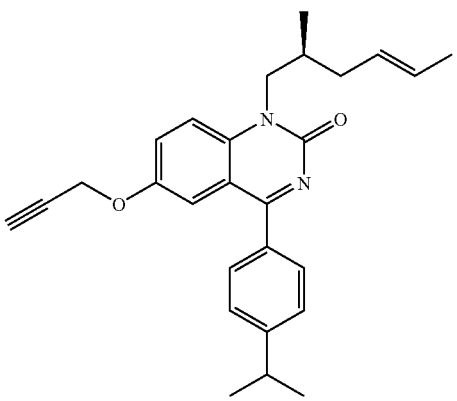 [SMILES: C#CCOc1ccc2c(c1)c(-c1ccc(C(C)C)cc1)nc(=O)n2C[C@@H](C)C/C=C/C]

$^1$H NMR (300 MHz, CDCl$_3$): 7.72 (d, 2H), 7.30-7.52 (m, 5H), 5.42 (m, 2H), 4.64 (d, 2H), 4.24 (m, 2H), 3.00 (hept, 1H), 2.58 (t, 1H), 2.00-2.22 (m, 3H), 1.62 (d, 3H), 1.30 (d, 6H), 0.98 (d, 3H).

MS: 415 (M+1)$^+$

Example 107

4-(4-Isopropyl-phenyl)-6-prop-2-ynyloxy-1-(4-pyrazin-2-yl-benzyl)-1H-quinazolin-2-one

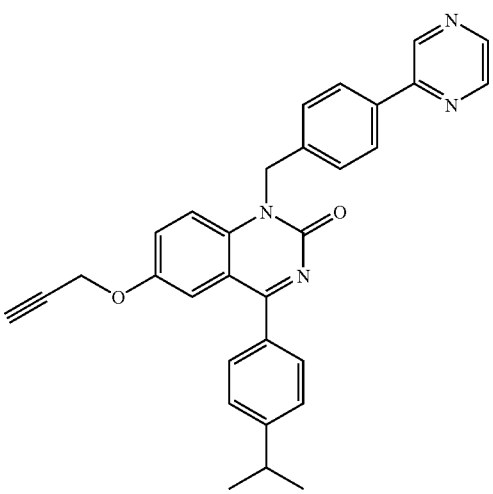 [SMILES: C#CCOc1ccc2c(c1)c(-c1ccc(C(C)C)cc1)nc(=O)n2Cc1ccc(-c2cnccn2)cc1]

$^1$H NMR (300 MHz, CDCl$_3$): 8.88 (s, 1H), 8.60 (d, 1H), 8.46 (d, 1H), 7.88 (d, 2H), 7.76 (d, 2H), 7.20-7.58 (m, 6H), 5.62 (broad s, 2H), 4.64 (d, 2H), 3.02 (hept, 1H), 2.56 (t, 1H), 1.32 (d, 6H).

MS: 487 (M+1)$^+$

Example 108

4-(4-Isopropyl-phenyl)-1-(3-methylsulphanyl-propyl)-6-prop-2-ynyloxy-1H-quinazolin-2-one

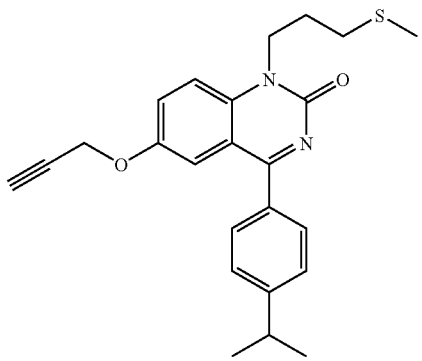 [SMILES: C#CCOc1ccc2c(c1)c(-c1ccc(C(C)C)cc1)nc(=O)n2CCCSC]

$^1$H NMR (300 MHz, CDCl$_3$): 7.72 (d, 2H), 7.48-7.52 (m, 3H), 7.38 (d, 2H), 4.69 (d, 2H), 4.43 (dd, 2H), 3.58 (t, 2H), 3.03 (hept, 1H), 2.71 (m, 2H), 2.58 (m, 1H), 2.08-2.32 (m, 5H), 1.31 (d, 6H).
MS: 407 (M+1)$^+$

Example 109

4-(4-Isopropyl-phenyl)-6-prop-2-ynyloxy-1-thiophen-2-ylmethyl-1H-quinazolin-2-one

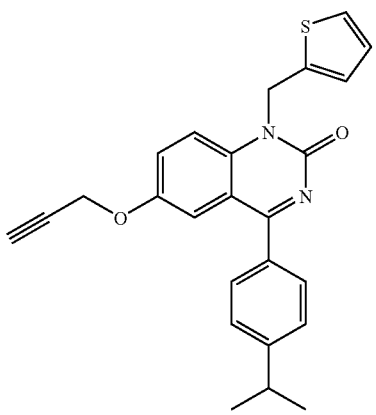 [SMILES: C#CCOc1ccc2c(c1)c(-c1ccc(C(C)C)cc1)nc(=O)n2Cc1cccs1]

$^1$H NMR (300 MHz, CDCl$_3$): 7.72 (d, 2H), 7.39-7.51 (m, 3H), 7.38 (d, 2H), 7.21 (dd, 1H), 7.18 (dd, 1H), 6.96 (dd, 1H), 5.65 (s, 2H), 4.66 (d, 2H), 3.00 (hept, 1H), 2.58 (t, 1H), 1.31 (d, 6H).
MS: 415 (M+1)$^+$

Example 110

1-Benzyl-4-(4-isopropyl-phenyl)-6-prop-2-ynyloxy-1H-quinazoline-2-thione

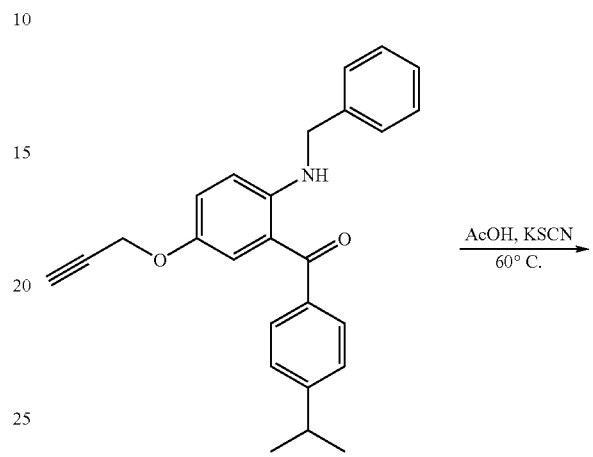

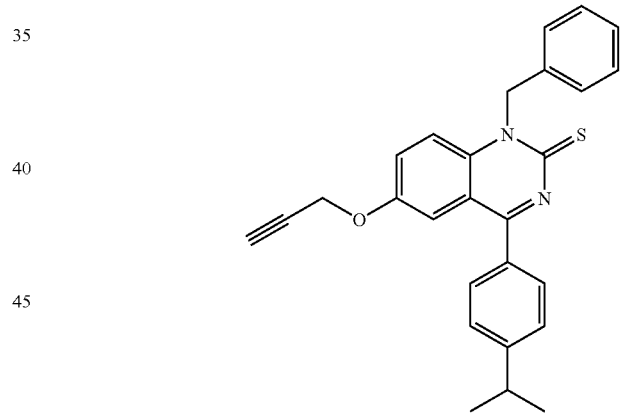

To a solution of 140 mg (0.365 mmol) (2-benzylamino-5-propargyloxy-phenyl)-(4-isopropyl-phenyl)-methanone in 5 ml acetic acid is added 68 mg (0.695 mmol) potassium thiocyanate. The reaction is stirred for two days at 60° C. The solvent is removed and the residue is extracted with water/dichloromethane. After evaporation of the organic phase the crude product is purified by flash-chromatography (MeOH/CH$_2$Cl$_2$, 1:9) to give 25 mg (16%) of a yellow oil.

$^1$H NMR (300 MHz, CDCl$_3$): 7.82 (d, 2H), 7.52 (s, 1H), 7.20-7.43 (m, 9H), 6.22 (broad s, 2H), 4.64 (d, 2H), 3.02 (hept, 1H), 2.56 (t, 1H), 1.32 (d, 6H).
MS: 425 (M+1)$^+$

Example 111

4-(4-Isopropyl-phenyl)-1-(3-methane-sulphonyl-benzyl)-6-propargyloxy-1H-quinazoline-2-thione

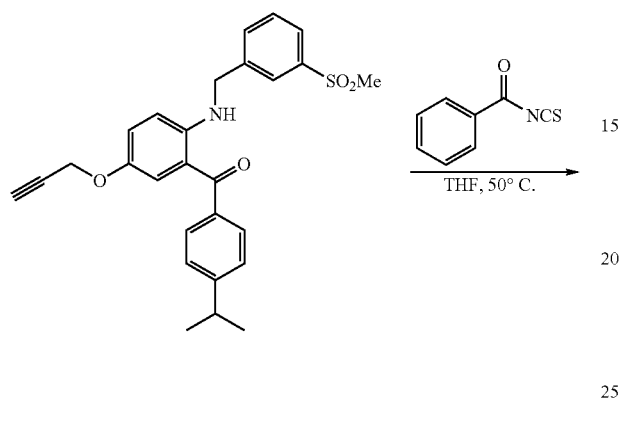

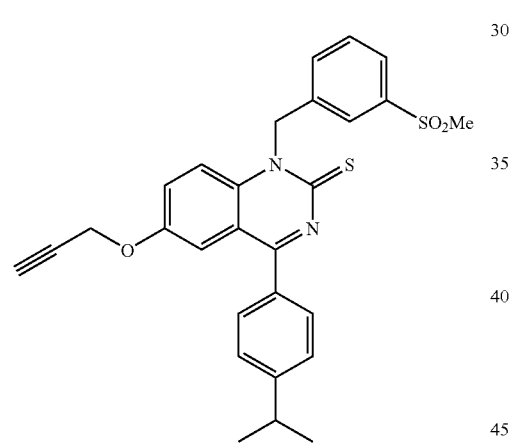

A solution of 1.87 g (4.06 mmol) 4-(4-isopropyl-phenyl)-1-(3-methane-sulphonyl-benzyl)-5-propargyloxy-phenyl-methanone (example 2) and 0.72 g (4.42 mmol) benzoyl-isothiocyanate in 9 ml THF is stirred at 50° C. for 2 h. Then the reaction mixture is cooled to room temperature and $K_2CO_3$ (1.2 g suspended in 17 ml MeOH) is added and stirring is continued for 20 h. After that the reaction mixture is poured onto water and extracted with ethyl acetate. The combined organic layers are washed with water and brine, dried over $MgSO_4$, filtered and concentrated in vacuo. The residue is purified by flash-chromatography on silica gel (hexane/EtOAc=1:1) to afford the title compound as a dark yellow foam.

$^1$H-NMR (300 MHz, DMSO-d$_6$): 7.88 (s, 1H), 7.78 (d, 1H), 7.75 (d, 2H), 7.58-7.38 (m, 7H), 4.80 (s, 2H), 3.48 (m, 1H), 3.18 (s, 3H), 2.99 (m, 1H), 1.22 (d, 6H).

MS: 503 (M+1)$^+$

The compounds of the following examples are prepared by analogy:

Example 112

4-(4-Isopropyl-phenyl)-6-prop-2-ynyloxy-1-thiophen-2-ylmethyl-1H quinazoline-2-thione

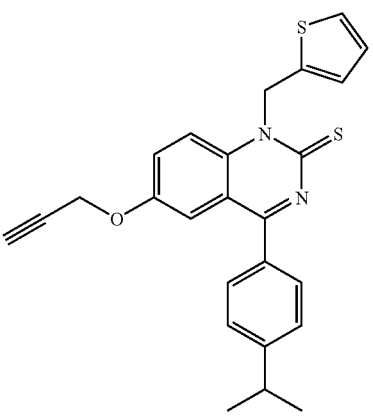 [SMILES: C#CCOc1ccc2c(c1)c(-c1ccc(C(C)C)cc1)nc(=S)n2Cc1cccs1]

$^1$H NMR (300 MHz, CDCl$_3$): 7.76 (d, 2H), 7.64 (d, 1H), 7.50 (d, 1H), 7.44 (dd, 1H), 7.38 (d, 2H), 7.12-7.30 (m, 2H), 6.88 (m, 1H), 6.32 (broad s, 2H), 4.68 (d, 2H), 3.02 (hept, 1H), 2.58 (t, 1H), 1.32 (d, 6H).

MS: 431 (M+1)$^+$

Example 113

1-[3-(2-Hydroxy-ethoxy)-benzyl]-4-(4-isopropyl-phenyl)-6-prop-2-ynyloxy-1H-quinazoline-2-thione

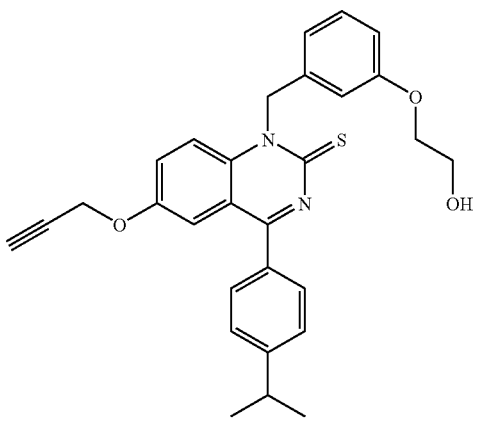 [SMILES: C#CCOc1ccc2c(c1)c(-c1ccc(C(C)C)cc1)nc(=S)n2Cc1cccc(OCCO)c1]

$^1$H-NMR (300 MHz, CDCl$_3$): 7.82 (d, 2H), 7.52 (m, 1H), 7.20-7.42 (m, 5H), 6.76-6.94 (m, 3H), 6.18 (broad s, 2H), 4.66 (d, 2H), 4.03 (t, 2H), 3.92 (t, 2H), 3.00 (hept, 1H), 2.56 (t, 1H), 1.30 (d, 6H).

MS: 485 (M+1)$^+$

Example 114

1-Benzyl-4-(4-isopropyl-phenyl)-6-methoxy-1H-quinazoline-2-thione

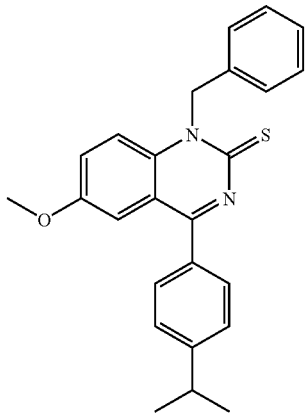 [SMILES: COc1ccc2c(c1)c(-c1ccc(C(C)C)cc1)nc(=S)n2Cc1ccccc1]

$^1$H NMR (300 MHz, CDCl$_3$): 7.76 (d, 2H), 7.39-7.23 (m, 10H), 6.21 (s, broad, 1H), 3.76 (s, 3H), 3.00 (hept, 1H), 1.30 (d, 6H).
MS: 401 (M+1)$^+$

Example 115

4-(4-Isopropyl-phenyl)-1-[2-(2-methoxy-ethoxy)-pyridin-3-ylmethyl]-6-propargyloxy-1H-quinazolin-2-thione

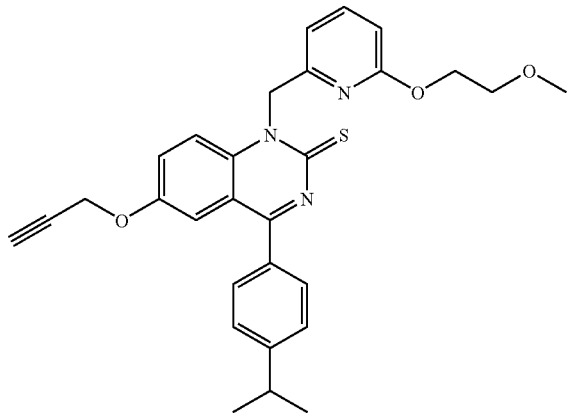 [SMILES: C#CCOc1ccc2c(c1)c(-c1ccc(C(C)C)cc1)nc(=S)n2Cc1cccc(OCCOC)n1]

$^1$H-NMR (300 MHz, CDCl$_3$): 7.76 (d, 2H), 7.44-7.55 (m, 3H), 7.32-7.38 (m, 3H), 6.91 (d, 1H), 6.68 (d, 1H), 4.66 (d, 2H), 4.35-4.40 (m, 2H), 3.64-3.69 (m, 2H), 3.40 (s, 3H), 2.99 (hept, 1H), 2.55 (t, 1H), 1.30 (d, 6H).
MS: 500 (M+1)$^+$

Example 116

4-(4-Isopropyl-phenyl)-1-[2-(2-methoxy-ethoxy)-pyridin-3-ylmethyl]-6-propargyloxy-1H-quinazolin-2-thione

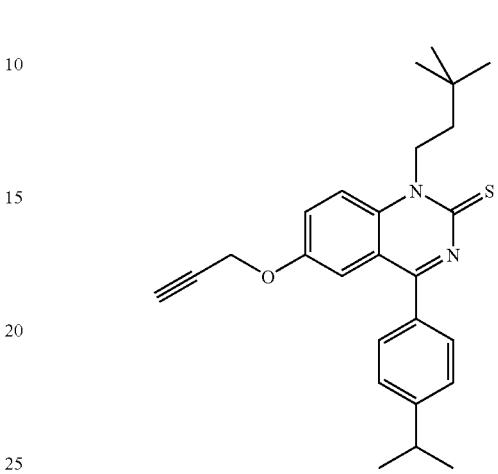

m.p. 174-175° C.
$^1$H-NMR (300 MHz, CDCl$_3$): 7.72 (d, 2H), 7.42-7.52 (m, 3H), 7.33 (d, 2H), 4.69 (d, 2H), 2.99 (hept, 1H), 2.57 (t, 1H), 1.85 (very broad, 2H), 1.29 (d, 6H), 1.12 (s, 9H).
MS: 419 (M+1)$^+$

Example 117

1-Benzo[1,2,5]thiadiazol-5-ylmethyl-4-(4-isopropyl-phenyl)-6-propargyloxy-1H-quinazolin-2-thione

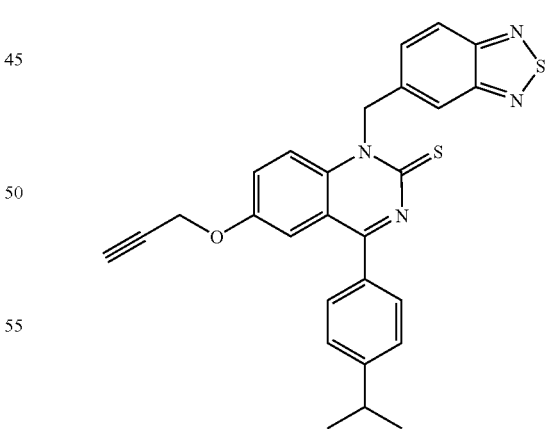

m.p. 102-106° C.
$^1$H-NMR (300 MHz, CDCl$_3$): 8.02 (d, 1H), 7.81 (d, 2H), 7.70 (broad s, 1H), 7.63 (dd, 1H), 7.55 (d, 1H), 7.39 (d, 2H), 7.26-7.35 (m, 2H), 4.66 (d, 2H), 3.02 (hept, 1H), 2.55 (t, 1H), 1.32 (d, 6H).
MS: 483 (M+1)$^+$

Example 118

Acetic acid 2-{3-[4-(4-isopropyl-phenyl)-6-prop-2-ynyloxy-2-thioxo-2H-quinazolin-1-ylmethyl]-phenoxy}-ethyl ester

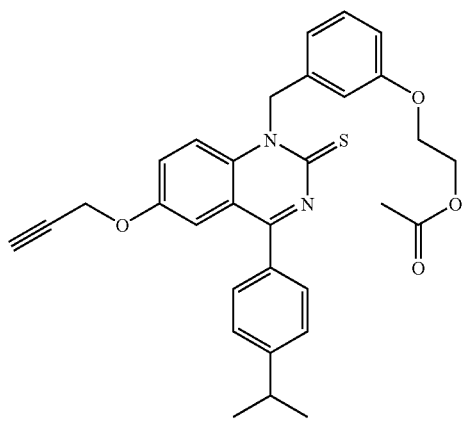 [SMILES: C#CCOc1ccc2c(c1)c(-c1ccc(C(C)C)cc1)nc(=S)n2Cc1cccc(OCCOC(C)=O)c1]

$^1$H-NMR (300 MHz, CDCl$_3$): 7.79 (d, 2H), 7.52 (m, 1H), 7.21-7.41 (m, 5H), 6.76-6.93 (m, 3H), 6.18 (bs, 2H), 4.66 (d, 2H), 4.37 (t, 2H), 4.12 (t, 2H), 3.04 (hept, 1H), 2.58 (t, 1H), 2.08 (s, 3H), 1.32 (d, 6H).
MS: 527 (M+1)$^+$

Example 119

1-(2,3-Dimethoxy-quinoxalin-6-ylmethyl)-4-(4-isopropyl-phenyl)-6-prop-2-ynyloxy-1H-quinazoline

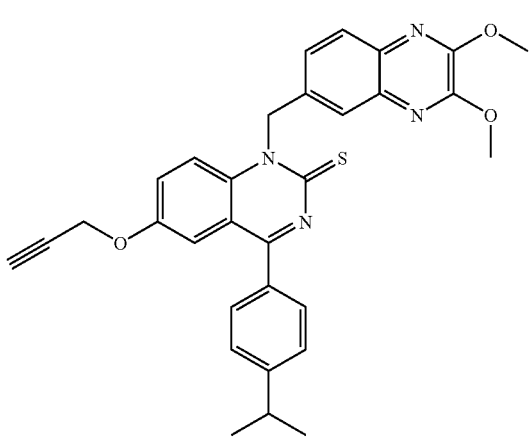

$^1$H-NMR (300 MHz, CDCl$_3$): 7.80 (d, 2H), 7.70 (d, 1H), 7.52 (d, 1H), 7.16-7.40 (m, 6H), 6.76 (bs, 2H), 4.64 (d, 2H), 4.22 (s, 3H), 4.18 (s, 3H), 3.00 (hept, 1H), 2.52 (t, 1H), 1.30 (d, 6H).
MS: 537 (M+1)$^+$

Example 120

1-[3-(2-Hydroxy-ethoxy)-thiophen-2-ylmethyl]-4-(4-isopropyl-phenyl)-6-prop-2-ynyloxy-1H-quinazoline-2-thione

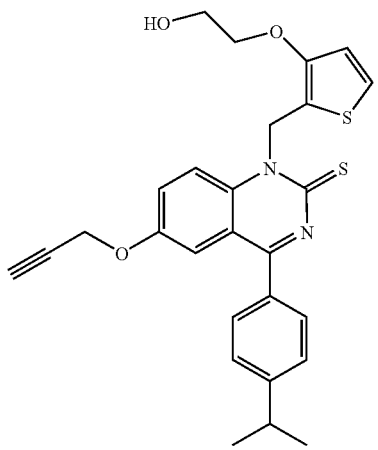 [SMILES: C#CCOc1ccc2c(c1)c(-c1ccc(C(C)C)cc1)nc(=S)n2Cc1sccc1OCCO]

$^1$H-NMR (300 MHz, CDCl$_3$): 8.02 (d, 1H), 7.76 (d, 2H), 7.42-7.52 (m, 3H), 7.38 (d, 2H), 7.16 (d, 1H), 6.80 (d, 1H), 6.22 (bs, 2H), 4.64 (d, 2H), 4.28 (t, 2H), 4.08 (m, 2H), 3.00 (hept, 1H), 2.56 (t, 1H), 1.30 (d, 6H).
MS: 491 (M+1)$^+$

Example 121

1-Isopropyl-4-(4-isopropyl-phenyl)-6-prop-2-ynyloxy-1H-quinazoline-2-thione

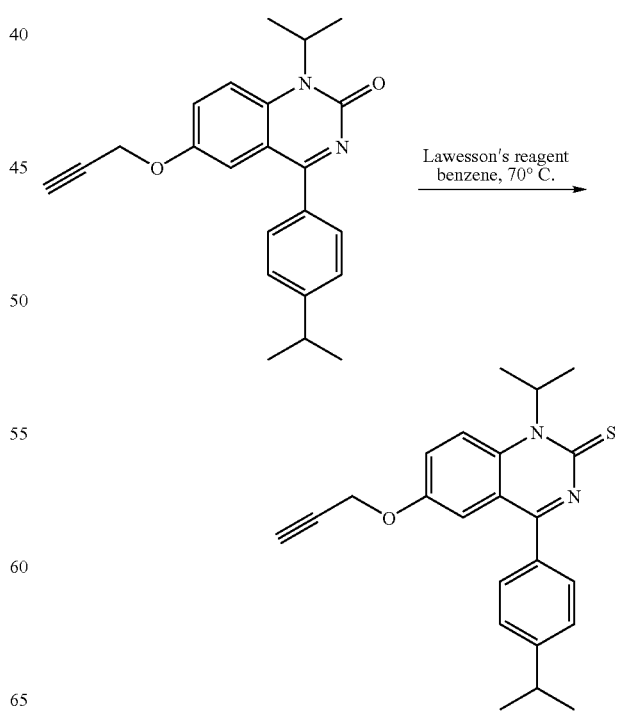

A suspension of 50 mg (0.139 mmol) 1-isopropyl-4-(4-isopropyl-phenyl)-6-prop-2-ynyloxy-1H-quinazoline-2-one and 56 mg (0.139 mmol) Lawesson's reagent in 2 ml benzene is heated to 70° C. overnight. The reaction mixture is extracted (water/di-chloromethane) and the organic layer is dried and evaporated.

Flash-chromatography (hexanes/ethyl acetate) yields the product as an orange oil.

$^1$H-NMR (300 MHz, CDCl$_3$): 7.78 (d, 2H), 7.46 (d, 1H), 7.42 (dd, 1H), 7.36 (d, 2H), 6.52 (hept, 1H), 4.72 (d, 2H), 3.02 (hept, 1H), 2.58 (t, 1H), 1.78 (d, 6H), 1.30 (d, 6H).
MS: 377 (M+1)$^+$ Example 122

1-Benzyl-4-(4-cyclopropyl-phenyl)-6-propargyloxy-1H-quinazolin-2-one

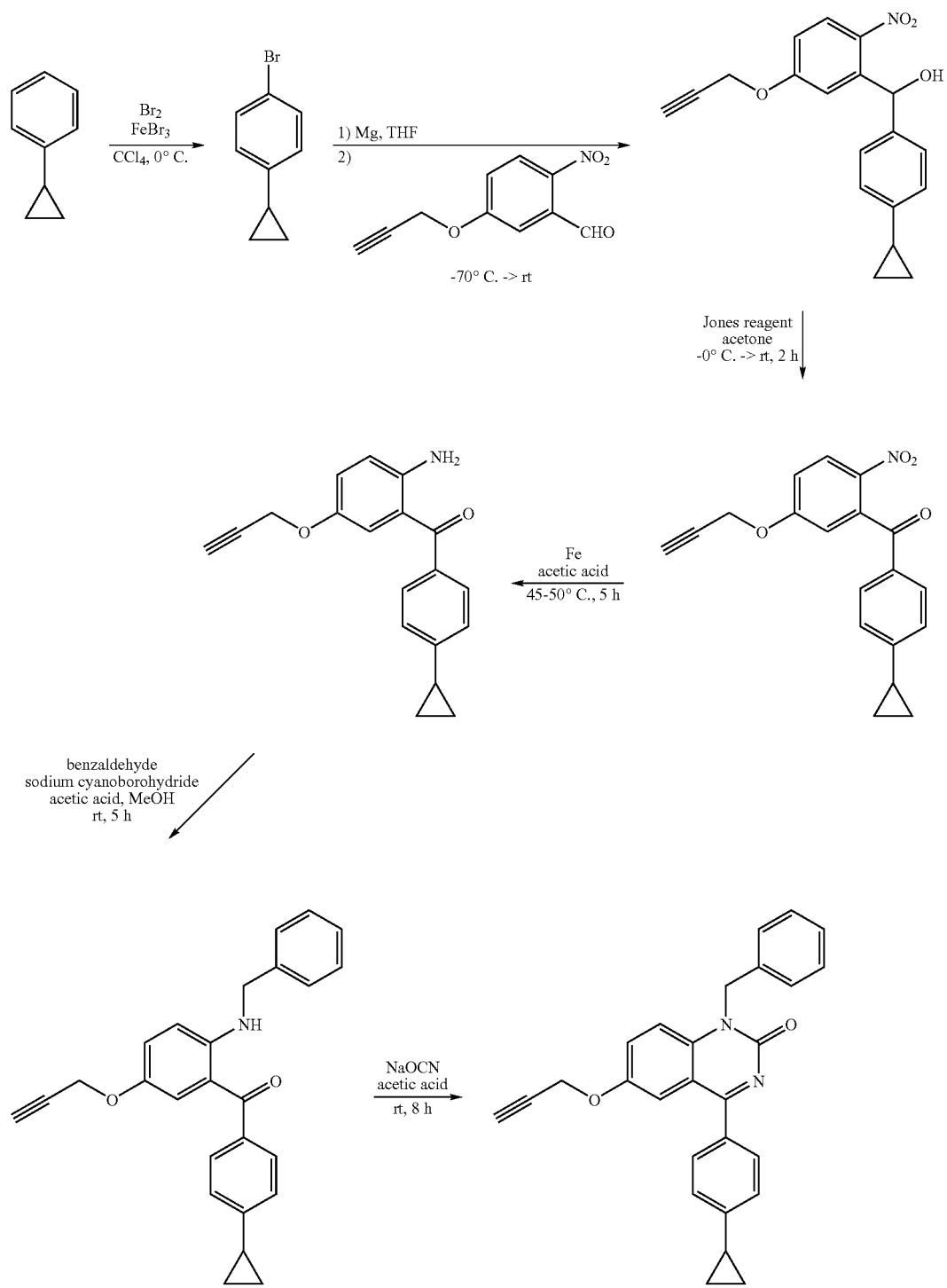

A. Synthesis of 1-bromo-4-cyclopropyl-benzene

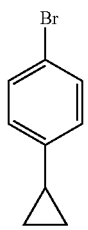

A solution of 5.0 g (42.3 mmol) cyclopropyl benzene and 300 mg of the catalyst iron(III) bromide in 30 ml carbon tetrachloride is cooled to 0° C. and treated dropwise with 6.76 g (42.3 mmol) bromine (diluted with an equal volume of CCl$_4$). The bromination is complete after ½ h. Extractive workup with dichloromethane and aqueous sodium thiosulphate solution affords a yellow oil, which is purified by flash chromatography (petroleum ether to yield a slightly yellow liquid.

$^1$H-NMR (300 MHz, CDCl$_3$): 7.35 (d, 2H), 6.93 (d, 2H), 1.80-1.90 (m, 1H), 0.94-1.01 (m, 2H), 0.63-0.70 (m, 2H).

B. Synthesis of (2-nitro-5-propargyloxyphenyl)-(4-cyclopropyl-phenyl)-methanol

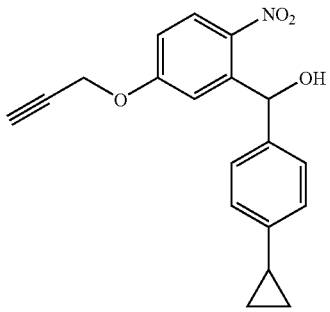 [SMILES: C#CCOc1ccc([N+](=O)[O-])c(C(O)c2ccc(C3CC3)cc2)c1]

A suspension of 407 mg (16.7 mmol) magnesium turnings in 5 ml anhydrous THF is treated with a solution of 1-bromo-4-cyclopropyl-benzene in 20 ml THF at such a rate to maintain gentle reflux. Stirring is continued for another ½ h after complete addition. The resulting Grignard reagent is then slowly added to a solution of 2-nitro-5-propargyloxy-benzaldehyde in 30 ml THF at −75° C. The reaction is kept between −75° C. and −65° C. throughout the addition, followed by slow warming to rt. The mixture is then poured into saturated aqueous ammonium chloride solution and extracted with diethyl ether. Purification of the crude product by flash chromatography (hexane/dichloromethane) yields a yellow brown oil.

$^1$H-NMR (300 MHz, CDCl$_3$): 8.06 (d, 1H), 7.41 (d, 1H), 7.21 (d, 2H), 7.01 (d, 2H), 6.97 (dd, 1H), 6.49 (d, 1H), 4.78 (d, 1H), 2.68 (d, OH), 2.55 (t, 1H), 1.82-1-92 (m, 1H), 0.91-0.99 (m, 2H), 0.64-0.70 (m, 2H).

C. Synthesis of (2-nitro-5-propargyloxyphenyl)-(4-cyclopropyl-phenyl)-methanone

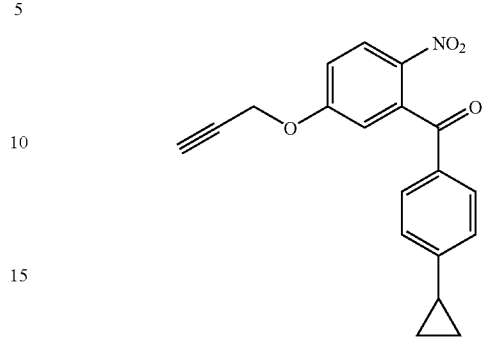

A solution of 2.8 g (8.66 mmol) of the alcohol prepared in step B in 20 ml acetone is treated dropwise with 4.3 ml 2.6 M Jones reagent. An exothermic reaction occurs and the mixture turns dark. After 2 h the chromium salts formed are separated and rinsed several times with dichloromethane. The combined organic phases are concentrated and the crude product obtained is purified by chromatography (hexane/dichloromethane) to yield white crystals.

m.p. 107° C.

$^1$H-NMR (300 MHz, CDCl$_3$): 8.24 (d, 1H), 7.64 (d, 2H), 7.16 (dd, 1H), 7.09 (d, 2H), 6.95 (d, 1H), 4.80 (d, 1H), 2.58 (t, 1H), 1.89-1-99 (m, 1H), 1.03-1.12 (m, 2H), 0.75-0.83 (m, 2H).

MS: 322 (M+1)$^+$

D. Synthesis of (2-amino-5-propargyloxyphenyl)-(4-cyclopropyl-phenyl)-methanone

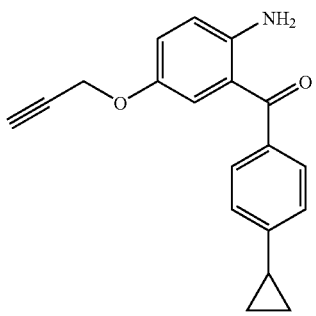 [SMILES: C#CCOc1ccc([N+](=O)[O-])c(C(=O)c2ccc(C3CC3)cc2)c1]

A solution of 2.2 g (6.85 mmol) of (2-nitro-5-propargyloxyphenyl)-(4-cyclopropyl-phenyl)-methanol (step C above) in 40 ml glacial acetic acid is heated to 50° C. and treated with 3.06 g (8 equiv.) of iron powder. After 5 h stirring at that temperature the reaction is complete. The green-grey suspension is cooled to rt, diluted by the addition of 500 ml water and 200 ml ethyl acetate and filtered through a pad of Celite. The layers are separated and the organic phase washed with water and sat. bicarbonate solution. The yellow and sticky crude product is purified by chromatography (dichloromethane/MeOH) to yield a viscous yellow oil.

¹H-NMR (300 MHz, CDCl₃): 8.60 (d, 2H), 7.07-7.14 (m, 3H), 7.04 (dd, 1H), 6.71 (d, 1H), 5.67 (broad, 2H), 4.53 (d, 2H), 2.48 (t, 1H), 1.91-1-2.01 (m, 1H), 1.02-1.11 (m, 2H), 0.76-0.83 (m, 2H).

MS: 292 (M+1)⁺

E. Synthesis of (2-benzylamino-5-propargyloxyphenyl)-(4-cyclopropyl-phenyl)-methanone

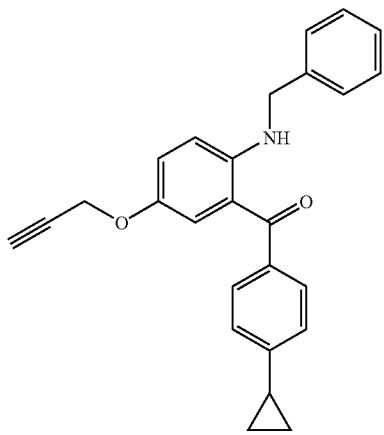 [SMILES: C#CCOc1ccc(NCc2ccccc2)c(C(=O)c2ccc(C3CC3)cc2)c1]

A mixture of 490 mg (1.68 mmol) of the aniline prepared in step D, 256 µl benzaldehyde and 150 µl AcOH in 5 ml MeOH is treated with 200 mg 95% sodium cyanoborohydride. Temperature is kept around rt by a cooling bath. After 5 hours the reaction mixture is distributed between water and ethyl acetate. The crude orange oil obtained after concentration i.V. is purified by chromatography (hexane/ethyl acetate) to yield a yellow solid. m.p. 116-118° C.

¹H-NMR (300 MHz, CDCl₃): 8.24 (d, 1H), 7.64 (d, 2H), 7.16 (dd, 1H), 7.09 (d, 2H), 6.95 (d, 1H), 4.80 (d, 1H), 2.58 (t, 1H), 1.89-1.99 (m, 1H), 1.03-1.10 (m, 2H), 0.76-0.83 (m, 2H).

MS: 382 (M+1)⁺

F. Synthesis of 1-Benzyl-4-(4-cyclopropyl-phenyl)-6-propargyloxy-1H-quinazolin-2-one

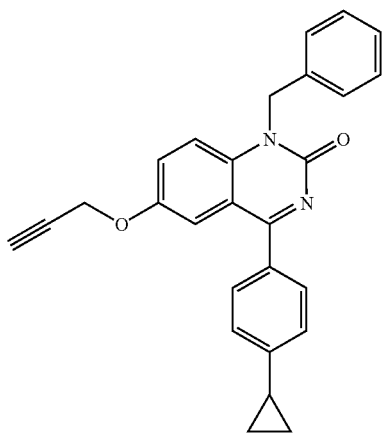 [SMILES: C#CCOc1ccc2c(c1)c(-c1ccc(C3CC3)cc1)nc(=O)n2Cc1ccccc1]

A solution of 460 mg (1.21 mmol) of (2-benzylamino-5-propargyloxyphenyl)-(4-cyclopropyl-phenyl)-methanone (step E) and 118 mg (1.81 mmol) sodium cyanate in 20 ml glacial acetic acid is stirred at rt for 8 h. Then the mixture is diluted with water and ethyl acetate. The layers are separated and the organic phase is washed with water and bicarbonate solution. Chromatography (dichloromethane/MeOH) of the crude product affords a yellow foam. m.p. 112-113° C.

¹H-NMR (300 MHz, CDCl₃): 7.72 (d, 2H), 7.46 (d, 1H), 7.18-7.35 (m, 9H), 5.56 (broad, 2H), 4.63 (d, 2H), 2.55 (t, 1H), 1.95-2.05 (m, 1H), 1.05-1.12 (m, 2H), 0.79-0.86 (m, 2H).

MS: 407 (M+1)⁺

The compounds of the following examples are prepared by analogy:

Example 123

4-(4-Cyclopropyl-phenyl)-1-(3,3-dimethyl-butyl)-6-propargyloxy-1H-quinazolin-2-one

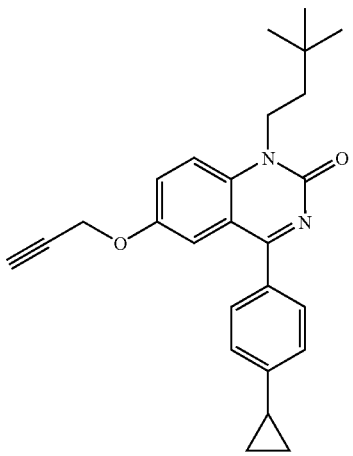 [SMILES: C#CCOc1ccc2c(c1)c(-c1ccc(C3CC3)cc1)nc(=O)n2CCC(C)(C)C]

m.p. 159-160° C.

¹H-NMR (300 MHz, CDCl₃): 7.65 (d, 2H), 7.41-7.47 (m, 2H), 7.31 (d, 1H), 7.18 (d, 2H), 4.66 (d, 2H), 4.26-4.34 (m, 2H), 2.56 (t, 1H), 1.92-2.04 (m, 1H), 1.65-1.75 (m, 2H), 1.10 (s, 9H), 1.02-1.08 (m, 2H), 0.76-0.83 (m, 2H).

MS: 401 (M+1)⁺

Example 124

4-(4-Cyclopropyl-phenyl)-1-(3-ethoxy-4-methoxy-benzyl)-6-propargyloxy-1H-quinazolin-2-one

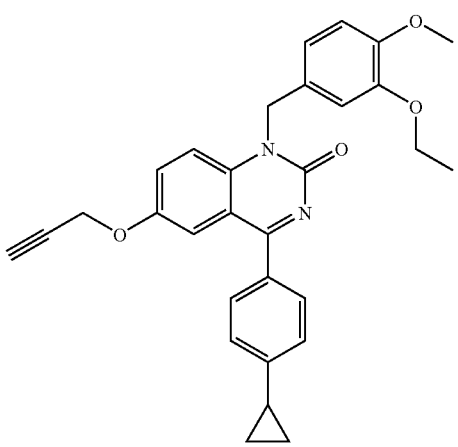 [SMILES: C#CCOc1ccc2c(c1)c(-c1ccc(C3CC3)cc1)nc(=O)n2Cc1ccc(OC)c(OCC)c1]

m.p. 66-68° C.

¹H-NMR (300 MHz, CDCl₃): 7.70 (d, 2H), 7.42-7.46 (m, 1H), 7.27-7.36 (m, 2H), 7.19 (d, 2H), 6.94 (d, 1H), 6.85 (dd, 1H), 6.78 (d, 1H), 5.45 (broad, 2H), 4.62 (d, 2H), 4.04 (q, 2H), 3.82 (s, 3H), 2.54 (t, 1H), 1.93-2.04 (m, 1H), 1.41 (t, 3H), 1.03-1.11 (m, 2H), 0.77-0.84 (m, 2H).

MS: 481 (M+1)⁺

Example 125

4-(4-Cyclopropyl-phenyl)-1-isopropyl-6-propargyloxy-1H-quinazolin-2-one

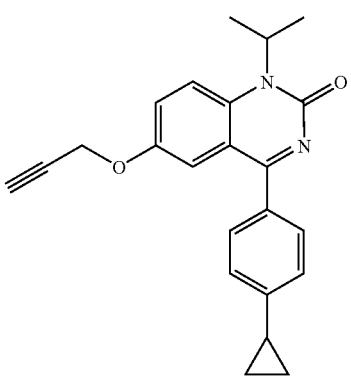 [SMILES: C#CCOc1ccc2c(c1)c(-c1ccc(C3CC3)cc1)nc(=O)n2C(C)C]

m.p. 124-125° C.

¹H-NMR (300 MHz, CDCl₃): 7.68 (d, 2H), 7.54 (d, 1H), 7.36-7.44 (m, 2H), 7.18 (d, 2H), 5.20 (broad hept, 1H), 4.66 (d, 2H), 2.56 (t, 1H), 1.93-2.04 (m, 1H), 1.69 (d, 6H), 1.03-1.11 (m, 2H), 0.77-0.83 (m, 2H).

MS: 359 (M+1)⁺

Example 126

1-Benzyl-4-(4-cyclopropyl-phenyl)-6-propargyloxy-1H-quinazolin-2-thione

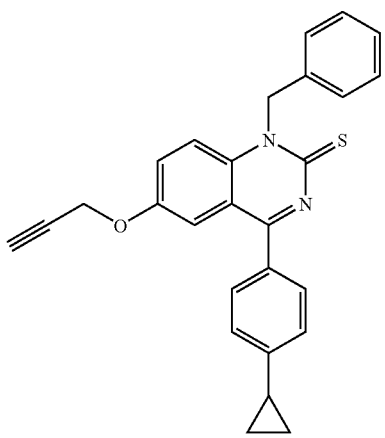 [SMILES: C#CCOc1ccc2c(c1)c(-c1ccc(C3CC3)cc1)nc(=S)n2Cc1ccccc1]

m.p. 104-106° C.

¹H-NMR (300 MHz, CDCl₃): 7.77 (d, 2H), 7.49 (t, 1H), 7.23-7.37 (m, 7H), 7.20 (d, 2H), 6.22 (broad, 2H), 4.66 (d, 2H), 2.57 (t, 1H), 1.94-2.05 (m, 1H), 1.05-1.13 (m, 2H), 0.78-0.85 (m, 2H).

MS: 423 (M+1)⁺

Example 127

2-{3-[4-(4-Isopropyl-phenyl)-2-oxo-6-propargyloxy-2H-quinazolin-1-ylmethyl]-peony}-butyric acid

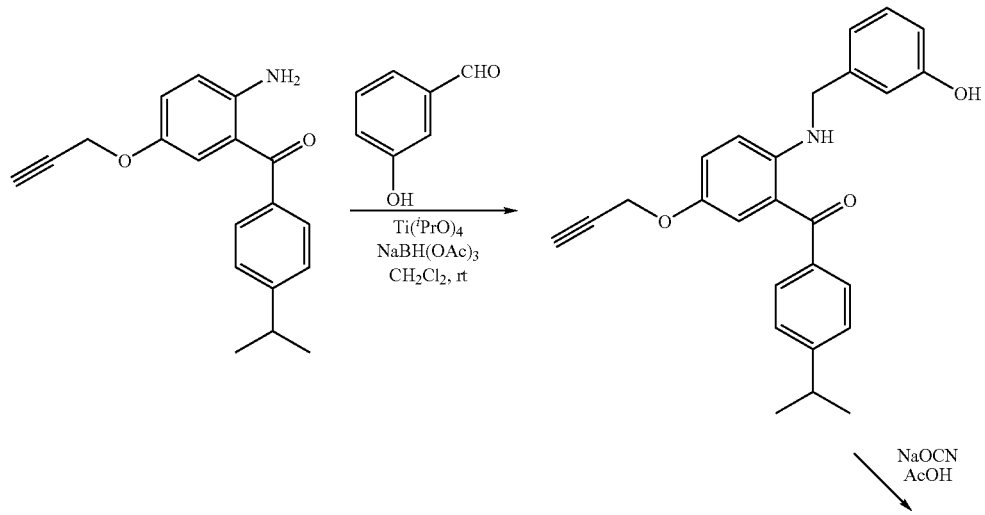

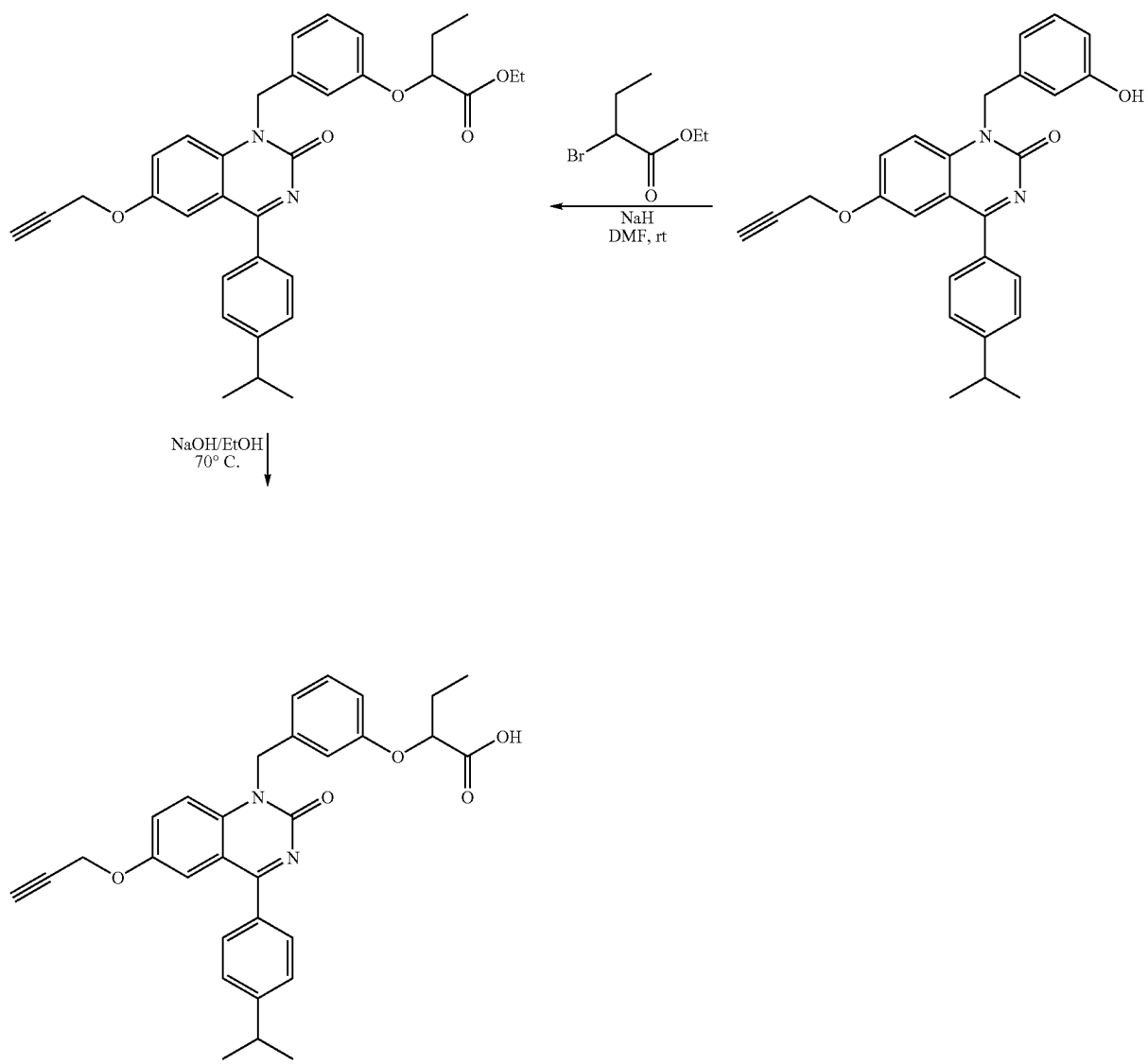

A. Synthesis of [2-(3-hydroxy-benzylamino)-5-propargyloxy-phenyl]-(4-isopropyl-penyl)-methanone

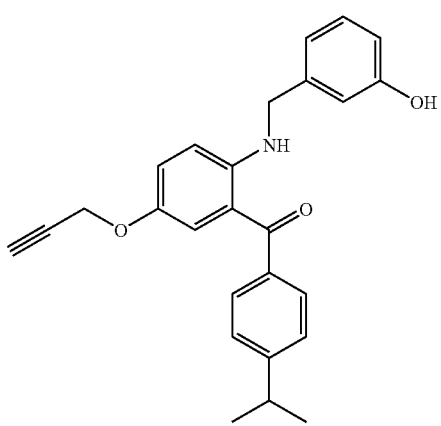 [SMILES: C#CCOc1ccc(NCc2cccc(O)c2)c(C(=O)c2ccc(C(C)C)cc2)c1]

To a solution of 267 mg (0.91 mmol) [2-(3-hydroxy-benzylamino)-5-propargyloxy-phenyl]-(4-isopropyl-phenyl)-methanone in 5 ml $CH_2Cl_2$ are added 122 mg (1.00 mmol) 3-hydroxy-benzaldehyd and 404 µl (1.37 mmol) tetra-isopropoxy-titanium. The deep red solution is stirred for 6 h at rt. Then 289 mg (1.37 mmol) sodium triacetoxyborohydride and 200 µl EtOH are added and stirring is continued overnight. The resulting yellow-orange suspension is distributed between water and $CH_2Cl_2$. Filtration of the organic layer through Hiflo is followed by washing with bicarbonate solution and concentrated i.V. The crude product is purified by chromatography (hexane/ethyl acetate) to yield a red oil.

$^1$H-NMR (300 MHz, $CDCl_3$): 8.57 (broad t, NH), 7.61 (d, 2H), 7.30 (d, 2H), 7.17-7.24 (m, 2H), 7.07 (dd, 1H), 6.94 (d, 1H), 6.84 (broad s, 1H), 6.72 (d, 1H), 6.65 (d, 1H), 4.78 (broad s, OH), 4.51-4.53 (m, 2H), 4.43 (d, 2H), 2.99 (hept, 1H), 2.47 (t, 1H), 1.39 (d, 6H).

MS: $(M+1)^+$

B. Synthesis of 1-(3-hydroxy-benzyl)-4-(4-isopropyl-phenyl)-6-propargyloxy-1H-quinazolin-2-one

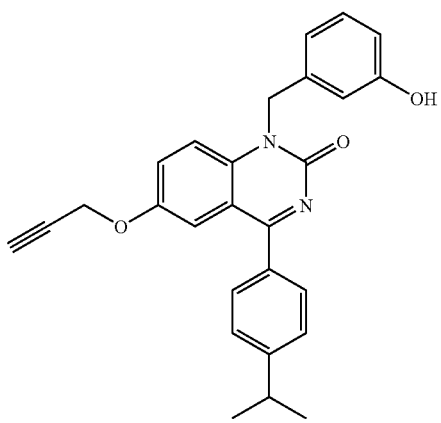 [SMILES: C#CCOc1ccc2c(c1)c(-c1ccc(C(C)C)cc1)nc(=O)n2Cc1cccc(O)c1]

A solution of 3.0 g (7.51 mmol) of the product prepared in step A in 45 ml AcOH is treated with 732 mg (11.3 mmol) sodium cyanate. The dark red solution is stirred for 2 h at rt. The resulting yellow-orange suspension is diluted with water and filtered. The orange product is washed well with water and diethyl ether to yield an orange solid. m.p. 230° C.

$^1$H-NMR (300 MHz, DMSO-$d_6$): 9.36 (broad, OH), 7.68 (d, 2H), 7.36-7.49 (m, 4H), 7.31-7.34 (m, 1H), 7.04-7.12 (m, 1H), 6.64 (dd, 2H), 6.58 (s, 1H), 5.39 (broad s, 2H), 4.76 (d, 2H), 3.65 (t, 1H), 2.99 (hept, 1H), 2.47 (t, 1H), 1.26 (d, 6H).
MS: 539 (M+1)$^+$ C. Synthesis of 2-{3-[4-(4-isopropyl-phenyl)-2-oxo-6-propargyloxy-2H-quinazolin-1-ylmethyl]-peony}-butyric acid ethyl ester

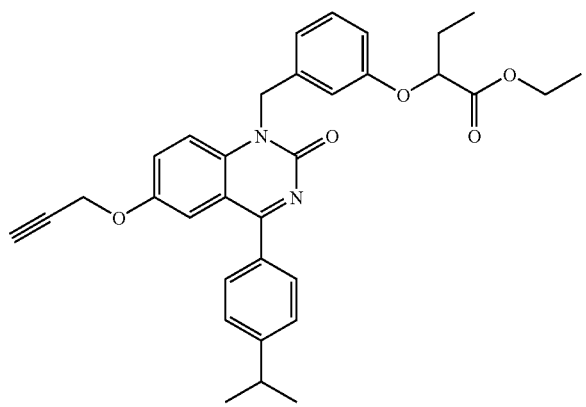 [SMILES: C#CCOc1ccc2c(c1)c(-c1ccc(C(C)C)cc1)nc(=O)n2Cc1cccc(OC(CC)C(=O)OCC)c1]

A suspension of 200 mg (0.47 mmol) of the phenol prepared in step B in 3 ml DMF is cooled with an ice/water bath and treated with 27 mg (0.61 mmol) sodium hydride. A yellow solution formed to which 83 µl (0.56 mmol) 2-bromo-butyric acid ethyl ester is added after 15 minutes. Rapid reaction sets in and after another 15 minutes the reaction mixture is hydrolyzed by the addition of 2 ml water and 5 ml ethyl acetate. Extractive work-up affords a yellow resin, which is chromatographed (hexane/ethyl acetate).

$^1$H-NMR (300 MHz, CDCl$_3$): 7.75 (d, 2H), 7.48 (d, 1H), 7.38 (d, 2H), 7.30 (dd, 1H), 7.22 (d, 1H), 7.19 (d, 1H), 6.91 (d, 1H), 6.85 (broad s, 1H), 6.72 (dd, 1H), 5.50 (broad, 2H), 4.63 (d, 2H), 4.51 (t, 1H), 4.14 (q, 2H), 3.02 (hept, 1H), 2.54 (t, 1H), 1.94 (quint, 2H), 1.32 (d, 6H), 1.20 (t, 3H), 1.05 (t, 3H).
MS: 539 (M+1)$^+$ D. Synthesis of 2-{3-[4-(4-Isopropyl-phenyl)-2-oxo-6-propargyloxy-2H-quinazolin-1-ylmethyl]-phenoxy}-butyric acid

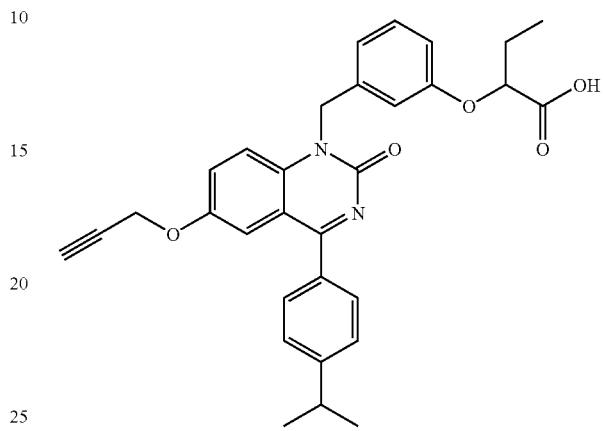

A solution of 140 mg (0.26 mmol) of the ester prepared in step D in 3 ml MeOH is treated with 2 ml 2N NaOH. After heating to 70° C. for 2 h, the reaction mixture is distributed between ethyl acetate and water. The aqueous phase is adjusted to pH 1 by the addition of 1 N HCl. The crude product is chromatographed (MeOH/CH$_2$Cl$_2$) to give the corresponding acid. m.p. 189° C. (dec.).

$^1$H-NMR (300 MHz, DMSO): 7.70 (d, 2H), 7.40-7.50 (m, 4H), 7.34 (d, 1H), 7.11 (t, 1H), 6.77 (broad s, 1H), 6.69 (t, 2H), 5.40 (broad, 2H), 4.76 (d, 2H), 4.29 (broad t, 1H), 3.65 (t, 2H), 3.01 (hept, 1H), 1.67-1.86 (m, 1H), 1.27 (d, 6H), 0.92 (t, 3H).
MS: 511 (M+1)$^+$ The compound of the following example is prepared by analogy:

Example 128

2-{3-[4-(4-Isopropyl-phenyl)-2-oxo-6-propargyloxy-2H-quinazolin-1-ylmethyl]-phenoxy}-2-methyl-propionic acid

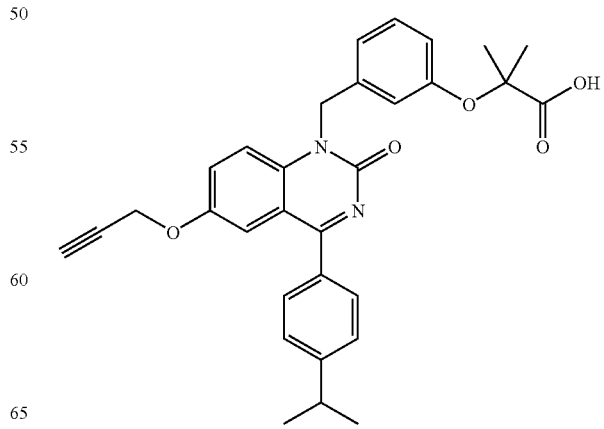

111

¹H-NMR (300 MHz, CDCl₃): 7.73 (d, 2H), 7.47 (d, 1H), 7.37 (d, 2H), 7.30 (dd, 1H), 7.22 (dd, 1H), 7.16 (d, 1H), 6.98 (d, 1H), 6.85 (broad s, 1H), 6.79 (d, 1H), 5.47 (broad, 2H), 4.63 (d, 2H), 3.00 (hept, 1H), 2.53 (broad t, 1H), 1.50 (s, 6H), 1.31 (d, 6H).
MS: 511 (M+1)⁺

112

Example 129

4-(4-Isopropyl-phenyl)-1-[2-(2-methoxy-ethoxy)-pyridin-3-ylmethyl]-6-prop-2-ynyloxy-1H-quinazolin-2-one

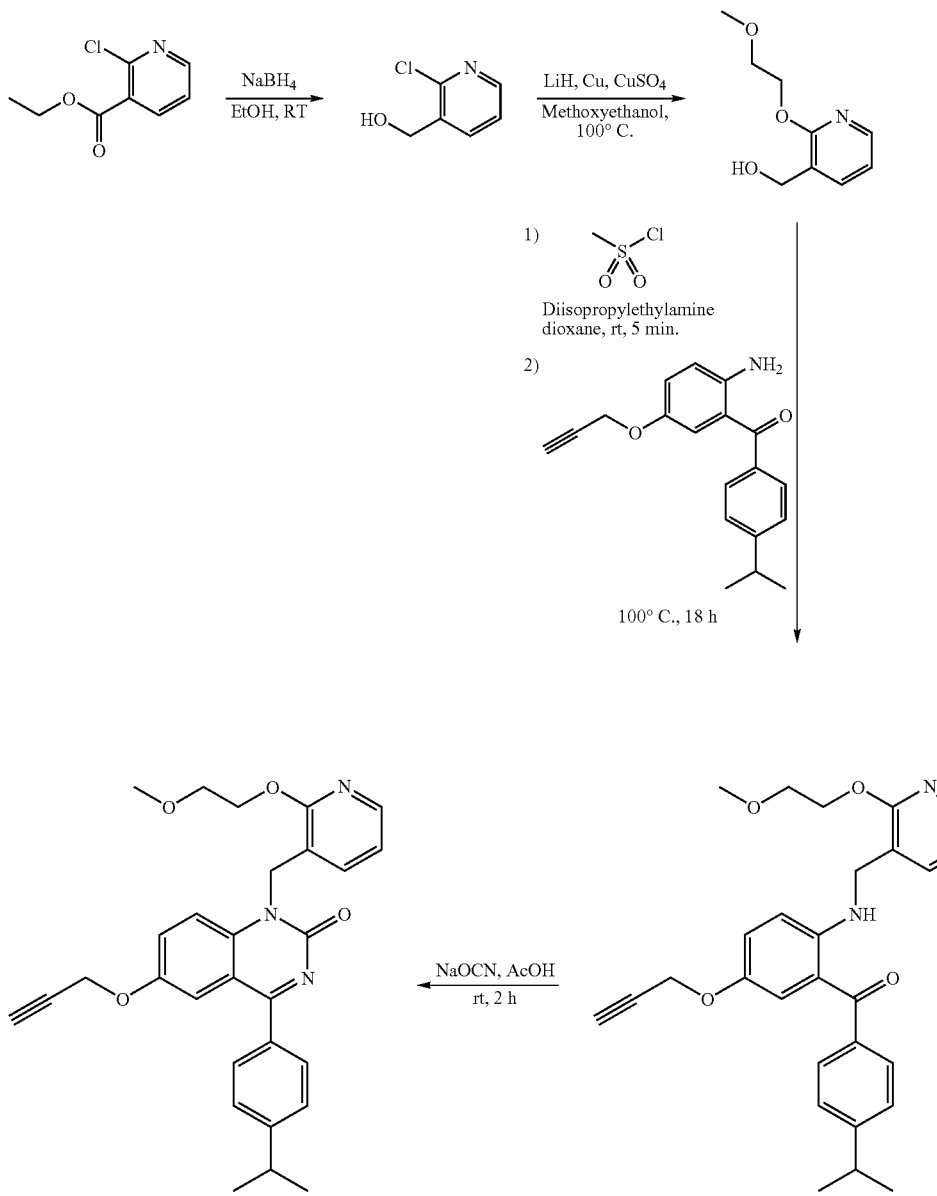

A. Synthesis of (2-chloro-pyridin-3-yl)-methanol

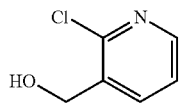

To a solution of ethyl 2-chloronicotinate (1 g, 5.39 mmol) in 10 ml EtOH at room temperature is added 2.04 g (53.9 mmol) NaBH₄ over 30 minutes in several portions. The solution is stirred for. The excess borohydride is quenched by the addition of methanol. The solvents are evaporated and the residue partitioned between dichloromethane and water. The aqueous Phase is extracted 3× with 10 ml of dichloromethane. The combined organic layers are washed with brine, dried with MgSO₄, filtered and evaporated in vacuo to yield a light yellow oil.

¹H-NMR (300 MHz, CDCl₃): 8.42 (d, 1H), 8.04 (d, 1H), 7.40 (m, 1H), 5.41 (s, 3H) 4.82 (s, 2H).

MS: 144 (M+1)⁺

B. Synthesis of [2-(2-methoxy-ethoxy)-pyridin-3-yl]-methanol

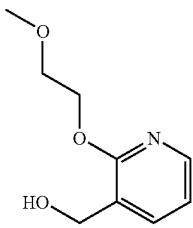

153 mg (19.2 mmol) LiH is added to 10 ml methoxyethanol and the mixture is stirred for 5 min until evolution of gas ceases. 690 mg (4.81 mmol) (2-Chloro-pyridin-3-yl)-methanol is added followed by 110 mg (1.73 mmol) Cu and 115 mg (0.721 mmol) CuSO₄ and the mixture is stirred at 100° C. After 2 days the reaction is cooled to r.t. and filtered with help of methanol. After evaporation ether is added to the residue and extracted twice with brine, then dried with Na₂SO₄, filtered and evaporated until constant weight is reached.

¹H-NMR (300 MHz, CDCl₃): 8.22 (m, 1H), 7.74 (d, 1H), 7.04 (m, 1H), 5.44 (s, 3H) 4.82 (d, 2H), 4.68 (m, 2H), 3.92 (m, 2H), 3.58 (s, 3H).

MS: 184 (M+1)⁺

C. Synthesis of (4-isopropyl-phenyl)-(2-{[2-(2-methoxy-ethoxy)-pyridin-3-ylmethyl]-amino}-5-prop-2-ynyloxy-phenyl)-methanone

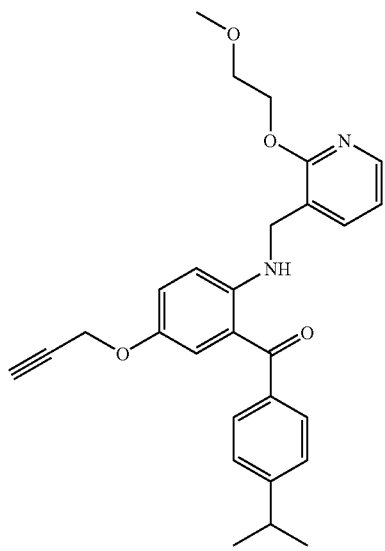 [SMILES: C#CCOc1ccc(NCc2cccnc2OCCOC)c(C(=O)c2ccc(C(C)C)cc2)c1]

To a solution of 400 mg (2.18 mmol) [2-(2-methoxy-ethoxy)-pyridin-3-yl]-methanol in 4 ml dioxane at r.t. is added 1.12 ml (6.55 mmol) Hünig's base followed by 170 μl (2.18 mmol) mesyl chloride and the mixture is stirred for 5 min. 641 mg (2.18 mmol) (2-amino-5-propargyloxy-phenyl)-(4-isopropyl-phenyl)-methanone is added to this mixture with the addition of 1 ml of dioxane. The reaction mixture is then heated to 100° C. and stirred overnight. The mixture is partitioned between ether/water and the organic layer is washed with brine, dried with Na₂SO₄, filtered and evaporated. Flash-chromatography (ethyl acetate/ether 1:1) yields a yellow oil ¹H NMR (300 MHz, CDCl₃): 8.04 (m, 1H), 7.56-7.64 (m, 3H), 7.30 (d, 2H), 7.20 (d, 1H), 7.08 (dd, 1H), 6.84 (dd, 1H), 6.70 (d, 1H), 4.58 (m, 2H), 4.46 (s, 2H), 3.80 (m, 2H), 3.44 (s, 3H), 2.98 (hept, 1H), 1.32 (d, 6H).

MS: 459 (M+1)⁺

D. Synthesis of 4-(4-isopropyl-phenyl)-1-[2-(2-methoxy-ethoxy)-pyridin-3-ylmethyl]-6-prop-2-ynyloxy-1H-quinazolin-2-one

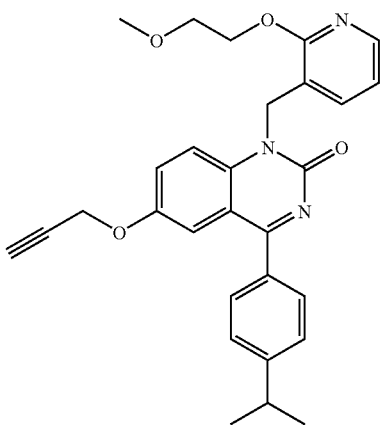 [SMILES: C#CCOc1ccc2c(c1)c(-c1ccc(C(C)C)cc1)nc(=O)n2Cc1cccnc1OCCOC]

To a solution of 200 mg (0.436 mmol) (4-Isopropyl-phenyl)-(2-{[2-(2-methoxy-ethoxy)-pyridin-3-ylmethyl]-amino}-5-prop-2-ynyloxy-phenyl)-methanone in 1.5 ml acetic acid is added 28 mg (0.436 mmol) sodium cyanate. After stirring for 2 h the solvent is removed in vacuo and the residue is partitioned between CH₂Cl₂ and water. The organic layer is dried and evaporated. Purification of the crude product by flash-chromatography (CH₂Cl₂/ether 3:7) affords a yellow oil.

¹H NMR (300 MHz, CDCl₃): 8.06 (d, 1H), 7.74 (d, 2H), 7.30-7.52 (m, 6H), 6.78 (dd, 1H), 5.64 (s, 2H), 4.62-4.66 (m, 4H), 3.84n(dd, 2H), 3.50 (s, 3H), 3.02 (hept, 1H), 2.56 (t, 1H), 1.32 (d, 6H).

MS: 484 (M+1)⁺

Example 130
Synthesis of 1-[6-(2-hydroxy-ethoxy)-pyridin-2-ylmethyl]-4-(4-isopropyl-phenyl)-6-propargyloxy-1H-quinazolin-2-one
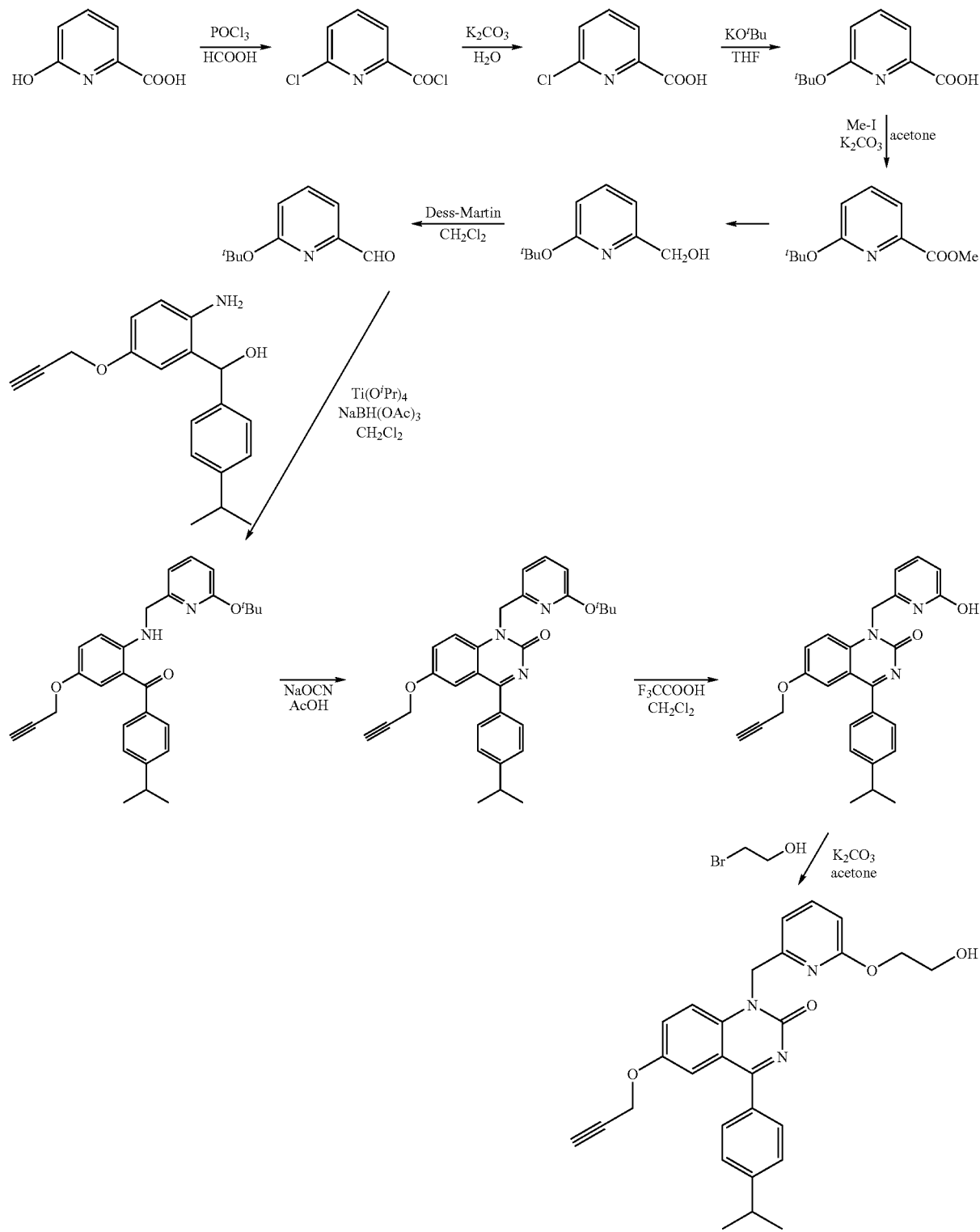

A. Synthesis of 6-chloro-pyridine-2-carboxylid acid

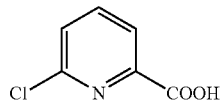

A suspension of 4.0 g (28.8 mmol) of 6-hydroxypicolinic acid, 6.0 ml phosphorus oxychloride and 20 g phosphorus pentachloride is slowly heated to 90° C. within 1.5 hours. Stirring is continued for another 12 h. After cooling to r.t. the mixture is quenched by careful addition of 1.4 ml formic acid. Concentration under HV affords 5.36 g of a dark solid which is subjected to hydrolysis in water (50 ml) in the presence of 5.56 g (40 mmol) potassium carbonate. Extractive work-up with petroleum ether/water and conc. i.v. results in a slightly yellow solid. m.p. 188-190° C.

$^1$H-NMR (300 MHz, CDCl$_3$): 8.17 (dd, 1H), 7.93 (t, 1H), 7.62 (dd, 1H).

MS: 158 (M+1)$^+$

B. Synthesis of 6-tert-butoxy-pyridine-2-carboxylic acid

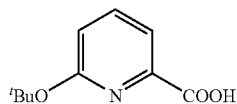

A solution of 2.70 g (17.1 mmol) of 6-chloro-pyridine-2-carboxylic acid in 200 ml THF is heated for 19 h to reflux. Then the mixture is poured into water and adjusted to neutral pH by the addition of citric acid. Extractive workup with ethyl acetate yields a slightly yellow solid.

$^1$H-NMR (300 MHz, CDCl$_3$): 7.72 (m, 2H), 6.94 (dd, 1H), 1.64 (s, 9H).

MS: 140 [(M+1)$^+$-butene]

C. Synthesis of 6-tert-butoxy-pyridine-2-carboxylic acid methyl ester

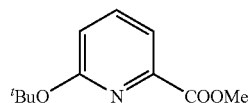 [SMILES: COC(=O)c1cccc(OC(C)(C)C)n1]

A yellow suspension of 2.60 g (13.3 mmol) of 2-tert-butoxy-pyridine-2-carboxylic acid and 2.8 g (20 mmol) potassium carbonate in 40 ml acetone is treated at r.t. with 2.64 g (18.6 mmol) of iodomethane. After stirring for 4 h at 40° C. the mixture is distributed between water and ethyl acetate. Concentration of the organic layer affords a yellow oil.

$^1$H-NMR (300 MHz, CDCl$_3$): 7.58-7.64 (m, 2H), 6.81 (dd, 1H), 3.94 (s, 3H), 1.64 (s, 9H).

MS: 154 [(M+1)$^+$-butene]

D. Synthesis of (6-tert-butoxy-pyridin-2-yl)-methanol

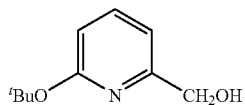

A solution of 2.32 g (11.1 mmol) of the ester from step C in 25 ml of ethanol is reduced by portion wise addition of 2.09 g (55.4 mmol) of sodium borohydride. HPLC analysis after stirring at r.t. for 12 hours shows complete reaction. The mixture is diluted with methanol and extracted with ethyl acetate/water to yield a yellow oil.

$^1$H-NMR (300 MHz, CDCl$_3$): 7.61 (dd, 1H), 6.74 (dd, 1H), 6.56 (dd, 1H), 4.65 (d, 2H), 3.42 (t, 1H), 1.60 (s, 9H).

E. Synthesis of 6-tert-butoxy-pyridin-2-carbaldehyd

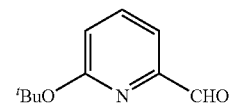

1.65 g (9.10 mmol) of the alcohol obtained in step D in 50 ml dichloromethane is oxidised with 3.86 g (9.10 mmol) of Dess-Martin periodinane. The reaction is complete after 12 h. The reaction mixture is extracted with ethyl acetate/aqueous sodium thiosulphate solution and the organic layer concentrated i.V. Flash-chromatography of the crude product petroleum ether/ethyl acetate) affords a yellow oil.

$^1$H-NMR (300 MHz, CDCl$_3$): 9.91 (s, 1H), 7.67 (t, 1H), 7.50 (dd, 1H), 6.86 (dd, 1H), 1.66 (s, 9H).

MS: 124 [(M+)$^+$-butene]

F. Synthesis of {2-[(6-tert-butoxy-pyridin-2-ylmethyl)-amino]-5-propargyloxy-phenyl}-(4-isopropyl-phenyl)-methanone

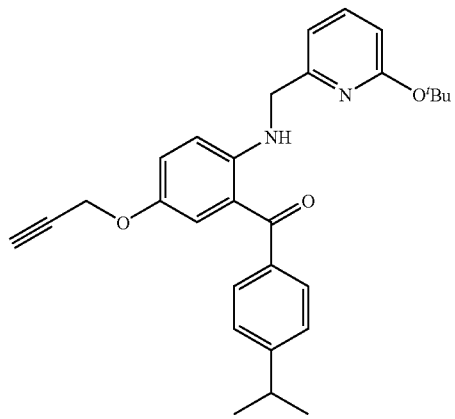 [SMILES: C#CCOc1ccc(NCc2cccc(OC(C)(C)C)n2)c(C(=O)c2ccc(C(C)C)cc2)c1]

A solution of 600 mg (2.05 mmol) of (2-amino-5-propargyloxy-phenyl)-4-isopropyl-phenyl)-methanone and 403 mg (2.25 mmol) of the aldehyde obtained in the step above in 18 ml dichloromethane is treated with 872 mg (3.07 mmol) of titanium(IV)isopropoxyde. The imine obtained after stirring overnight is reduced with 650 mg (3.07 mmol) of sodium triacetoxyborohydride in the presence of 2.4 ml of EtOH. The crude product after extractive workup with ethyl acetate/petroleum ether is purified by flash chromatography (ethyl acetate/petroleum ether) to yield a yellow oil.

$^1$H-NMR (300 MHz, CDCl$_3$): 7.61 (d, 2H), 7.46 (dd, 1H), 7.30 (d, 2H), 7.21 (d, 1H), 7.04-7.11 (m, 1H), 6.86 (d, 1H), 6.72 (d, 1H), 6.63 (d, 1H), 4.53 (d, 2H), 4.48 (d, 2H), 2.99 (hept, 1H), 2.48 (t, 1H), 1.60 (s, 9H), 1.34 (d, 6H).
MS: 457 (M+1)$^+$

G. Synthesis of 1-[(6-tert-butoxy-pyridin-2-ylmethyl)-4-(4-isopropyl-phenyl)-6-propargyloxy-1H-quinazolin-2-one

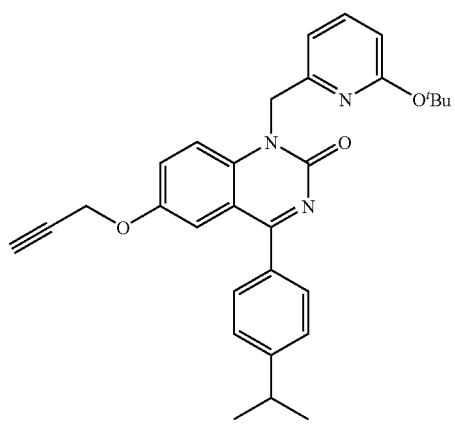 [SMILES: C#CCOc1ccc2c(c1)c(-c1ccc(C(C)C)cc1)nc(=O)n2Cc1cccc(OC(C)(C)C)n1]

A solution of 120 mg (0.26 mmol) of the starting material (step F) in 3 ml acetic acid is cyclised with 21 mg (0.315 mmol) sodium cyanate overnight to afford the quinazolinone after flash-chromatography (hexane/ethyl acetate). m.p. 62-65° C.

$^1$H-NMR (300 MHz, CDCl$_3$): 7.72 (d, 2H), 7.46-7.50 (m, 2H), 7.43 (d, 1H), 7.39 (d, 2H), 7.31 (dd, 1H), 6.90 (d, 1H), 6.52 (d, 1H), 5.56 (broad s, 2H), 3.03 (hept, 1H), 2.55 (t, 1H), 1.41 (s, 9H), 1.33 (d, 6H).
MS: 482 (M+1)$^+$

H. Synthesis of 1-[(6-tert-pyridin-2-ylmethyl)-4-(4-isopropyl-phenyl)-6-propargyloxy-1H-quinazolin-2-one

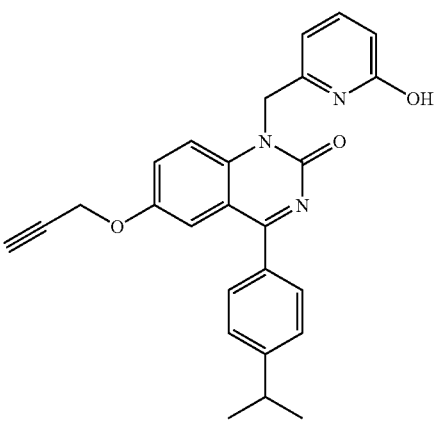 [SMILES: C#CCOc1ccc2c(c1)c(-c1ccc(C(C)C)cc1)nc(=O)n2Cc1cccc(O)n1]

A mixture of 60 mg (0.13 mmol) of the t-butyl ether (step G) in 6 ml dichloromethane is treated with 15 μl trifluoroacetic acid and stirred overnight at it. Extractive workup with aqueous sodium bicarbonate solution/dichloromethane yields a yellow solid. m.p. 219-222° C.

$^1$H-NMR (300 MHz, CDCl$_3$): 7.76 (d, 2H), 7.55 (d, 1H), 7.32-7.48 (m, 5H), 6.50 (d, 1H), 6.23 (d, 1H), 5.38 (broad s, 2H), 4.69 (d, 2H), 3.04 (hept, 1H), 2.58 (t, 1H), 1.34 (d, 6H).
MS: 426 (M+1)$^+$

I. Synthesis of Synthesis of 1-[6-(2-hydroxyethoxy)-pyridin-2-ylmethyl]-4-(4-isopropyl-phenyl)-6-propargyloxy-1H-quinazolin-2-one

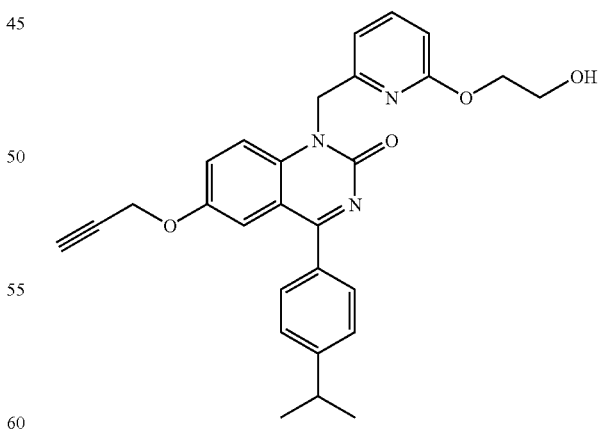

A suspension of 40 mg (0.094 mmol) of the pyridyl-alcohol obtained in step H, 16 mg (0.132 mmol) 2-bromoethanol and 19 mg (0.141 mmol) potassium carbonate in 4 ml acetone is stirred overnight at 70° C. The crude product obtained after extraction with ethyl acetate/water is purified by flash chromatography (hexane/ethyl acetate) to yield a yellow oil.

¹H-NMR (300 MHz, CDCl₃): 7.74 (d, 2H), 7.32-7.56 (m, 6H), 6.92 (d, 1H), 6.68 (d, 1H), 5.53 (broad s, 2H), 4.66 (d, 2H), 4.38-4.52 (m, 2H), 3.91 (broad, 2H), 3.02 (help, 1H), 2.75 (broad, OH), 2.56 (t, 1H), 1.33 (d, 6H).
MS: 470 (M+1)⁺

Example 131

1-[6-Chloro-pyridin-3-ylmethyl]-4-(4-isopropyl-phenyl)-6-propargyloxy-1H-quinazolin-2-one A. Synthesis of 2-bromomethyl-2-chloro-pyridine

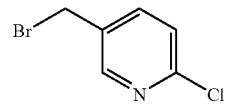

A solution of 1.28 g (10.0 mmol) 2-chloro-5-methyl-pyridine in 25 ml carbon tetra-chloride is treated with 1.79 g (10.0 mmol) of freshly recrystallised N-bromo-succinimid and 30 mg benzoyl peroxide. The mixture is heated to reflux for 17 h and filtered. The filtrate is washed with water and concentrated. Flash chromatography (hexane/ethyl acetate) results in a white low melting solid. m.p. 40-43° C.
MS: 210 (2), 208 (100), 206 (75) (chloro-bromo isotope pattern) (M+1)⁺

B. Synthesis of {2-[(6-chloro-pyridin-3-ylmethyl)-amino]-5-propargyloxy-phenyl}-(4-isopropyl-phenyl)-methanone

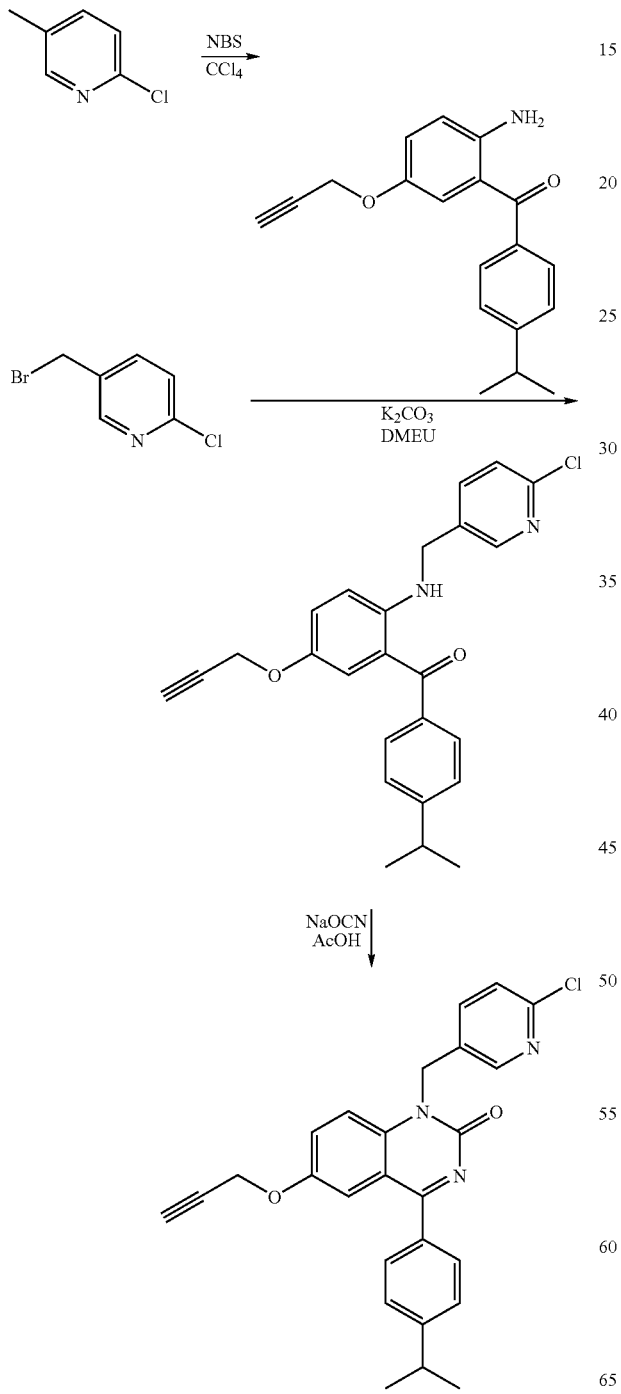

To a solution of 323 mg (1.10 mmol) of (2-amino-5-propargyloxy-phenyl)-4-isopropyl-phenyl)-methanone and 250 mg (1.21 mmol) of 2-bromomethyl-2-chloro-pyridine (step A) in 2 ml 1,3-dimethyl-2-imidazolidinone (DMEU) 213 mg (1.54 mmol) of potassium carbonate are added. The reaction is complete after stirring for 2 h at 60° C. The cooled yellow suspension is distributed between ethyl acetate and bicarbonate solution. Flash chromatography (hexane/ethyl acetate) affords a yellow solid. m.p. 96° C.
¹H-NMR (300 MHz, CDCl₃): 8.49 (t, 1H), 8.40 (d, 1H), 7.67 (dd, 1H), 7.61 (d, 2H), 7.31 (d, 2H), 7.30 (d, 1H), 7.23 (d, 1H), 7.08 (dd, 1H), 6.59 (d, 1H), 4.53 (d, 2H), 4.48 (d, 2H), 2.99 (hept, 1H), 2.48 (t, 1H), 1.31 (d, 6H).
MS: 419 (M+1)⁺

C. Synthesis of 1-[(6-chloro-pyridin-3-ylmethyl)-4-(4-isopropyl-phenyl)-6-propargyloxy-1H-quinazolin-2-one

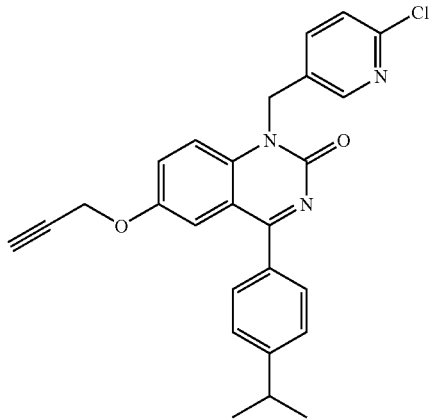

A solution of 320 mg (0.764 mmol) of the starting material (step B) in 4 ml acetic acid is cyclised with 74 mg (1.15 mmol) sodium cyanate. A thick suspension results after 3 h. Distribution between ethyl acetate and aqueous bicarbonate solution, concentration of the organic layer and flash chromatography (hexane/ethyl acetate) of the crude product yields the title quinazolinone in the form of a yellow solid. m.p. 210° C.

$^1$H-NMR (300 MHz, CDCl$_3$): 8.44 (d, 1H), 7.72 (d, 2H), 7.67 (dd, 1H), 7.61 (d, 1H), 7.38 (d, 2H), 7.36 (dd, 1H), 7.27 (d, 1H), 7.21 (d, 1H), 5.51 (broad, 2H), 4.65 (d, 2H), 3.01 (hept, 1H), 2.55 (t, 1H), 1.31 (d, 6H).

MS: 444 (M+1)$^+$

Example 132

(4-Isopropyl-phenyl)-(2-{[6-(2-methoxy-ethoxy)-pyridin-2-ylmethyl]-amino}-5-propargyloxy-phenyl)-methanone

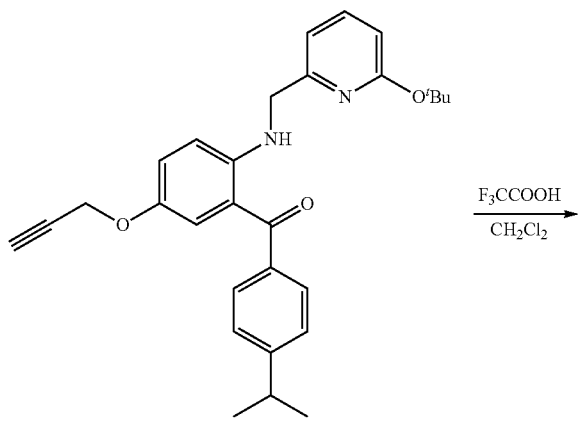

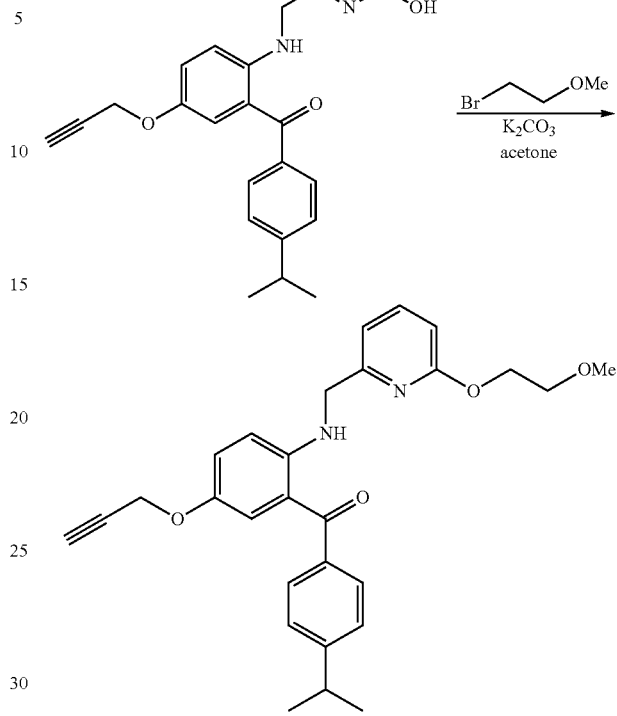

A. Synthesis of {2-[(6-hydroxy-pyridin-3-ylmethyl)-amino]-5-propargyloxy-phenyl}-(4-isopropyl-phenyl)-methanone

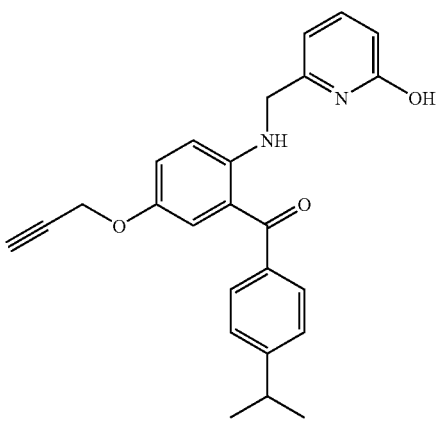 [SMILES: C#CCOc1ccc(NCc2cccc(O)n2)c(C(=O)c2ccc(C(C)C)cc2)c1]

A solution of 120 mg (0.263 mmol) of {2-[(6-tert-butoxy-pyridin-2-ylmethyl)-amino]-5-propargyloxy-phenyl}-(4-isopropyl-phenyl)-methanone (see above) in 3 ml dichloromethane is treated with 30 μl trifluoroacetic acid and stirred overnight.

Workup with ethyl acetate and aqueous bicarbonate solution and flash chromatography of the crude product results in a yellow solid. m.p. 189-193° C.

$^1$H-NMR (300 MHz, CDCl$_3$): 7.65 (d, 2H), 7.40 (dd, 1H), 7.33 (d, 2H), 7.24 (d, 1H), 7.08 (dd, 1H), 6.58 (d, 1H), 6.45 (d, 1H), 6.24 (d, 1H), 4.55 (d, 2H), 4.40 (d, 2H), 3.01 (hept, 1H), 2.49 (t, 1H), 1.32 (d, 6H).

MS: 401 (M+1)$^+$

B. Synthesis of Synthesis of (4-isopropyl-phenyl)-(2-{[6-(2-methoxy-ethoxy)-pyridin-2-ylmethyl]-amino}-5-propargyloxy-phenyl)-methanone

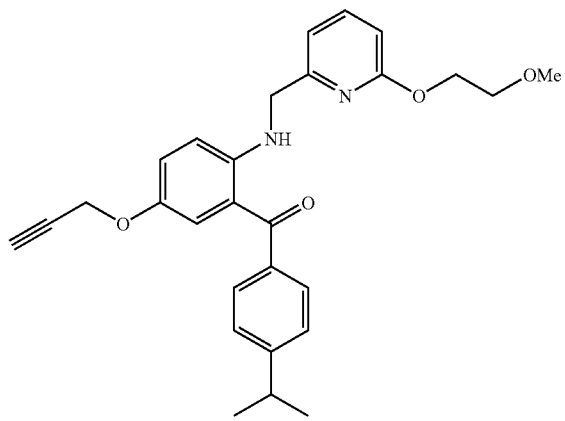 [SMILES: C#CCOc1ccc(NCc2cccc(OCCOC)n2)c(C(=O)c2ccc(C(C)C)cc2)c1]

A suspension of 50 mg (0.125 mmol) of the pyridyl-alcohol obtained in step A, 13 µl (0.137 mmol) 2-bromoethyl methyl ether and 26 mg (0.187 mmol) potassium carbonate in 6 ml acetone is stirred overnight at 70° C. The crude product obtained after extraction with ethyl acetate/water is purified by flash chromatography (hexane/ethyl acetate) to yield a yellow oil.

$^1$H-NMR (300 MHz, CDCl$_3$): 8.83 (t, NH), 7.62 (d, 2H), 7.52 (dd, 1H), 7.30 (d, 2H), 7.21 (d, 1H), 7.10 (dd, 1H), 6.90 (d, 1H), 6.69 (dd, 2H), 4.60 (dd, 2H), 4.53 (d, 2H), 4.48 (d, 2H), 3.78 (dd, 2H), 3.44 (s, 3H), 2.99 (hept, 1H), 2.48 (t, 1H), 1.31 (d, 6H).

MS: 459 (M+1)$^+$

Example 133

1-(2-Hydroxy-pyridin-3-ylmethyl)-4-(4-isopropyl-phenyl)-6-propargyloxy-1H-quinazolin-2-one

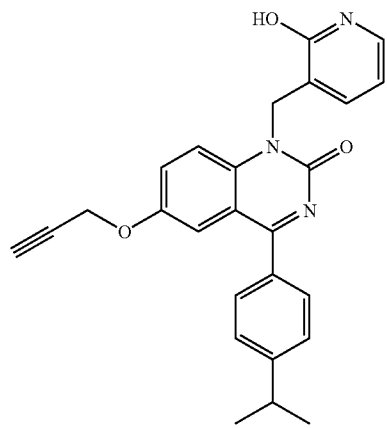

A solution of 290 mg (0.635 mmol) of {2-[(2-tert-butoxy-pyridin-3-ylmethyl)-amino]-5-propargyloxy-phenyl}-(4-isopropyl-phenyl)-methanone and in 7 ml acetic acid is reacted with 50 mg (0.762 mmol) sodium cyanate. After stirring overnight the mixture is distributed between ethyl acetate and aqueous bicarbonate solution. The organic layer is concentrated to yield the title compound in the form of a yellow solid. m.p. 121-123° C.

$^1$H-NMR (300 MHz, CDCl$_3$): 7.74 (d, 2H), 7.48-7.55 (m, 3H), 7.32-7.43 (m, 4H), 6.26 (t, 1H), 5.48 (s, 2H), 4.66 (d, 2H), 3.02 (hept, 1H), 2.66 (t, 1H), 1.33 (d, 6H).

MS: 426 (M+1)$^+$

The compounds of the following examples are prepared by analogy to the example described above:

Example 134

4-(4-Isopropyl-phenyl)-1-(5-methoxy-pyridin-2-ylmethyl)-6-propargyloxy-1H-quinazolin-2-one

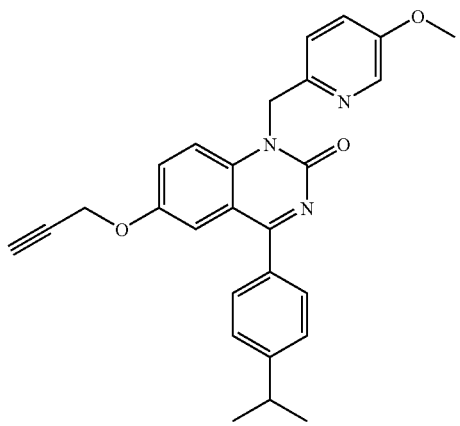 [SMILES: C#CCOc1ccc2c(c1)c(-c1ccc(C(C)C)cc1)nc(=O)n2Cc1ccc(OC)cn1]

m.p. 136-137° C.

$^1$H-NMR (300 MHz, CDCl$_3$): 8.25 (dd, 1H), 7.68-7.74 (m, 3H), 7.42-7.48 (m, 2H), 7.34-7.41 (m, 3H), 7.14 (dd, 1H), 5.60 (broad, 2H), 4.65 (d, 2H), 3.84 (s, 3H), 3.02 (hept, 1H), 2.65 (t, 1H), 1.33 (d, 6H).

MS: 440 (M+1)$^+$

Example 135

4-(4-Isopropyl-phenyl)-1-(6-methyl-pyridin-2-ylmethyl)-6-propargyloxy-1H-quinazolin-2-one

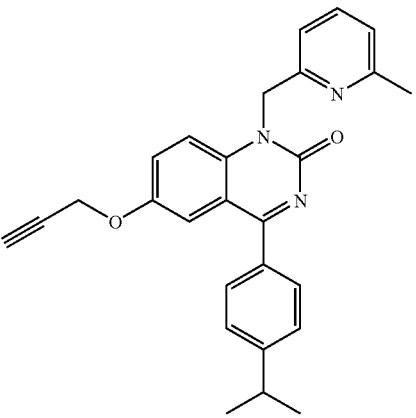 [SMILES: C#CCOc1ccc2c(c1)c(-c1ccc(C(C)C)cc1)nc(=O)n2Cc1cccc(C)n1]

m.p. 165-166° C.

¹H-NMR (300 MHz, CDCl₃): 7.75 (d, 2H), 7.45-7.55 (m, 3H), 7.38 (d, 2H), 7.34 (dd, 1H), 7.10 (d, 1H), 7.05 (d, 1H), 5.62 (broad, 2H), 4.65 (d, 2H), 3.02 (hept, 1H), 2.60 (s, 3H), 2.55 (t, 1H), 1.33 (d, 6H).

MS: 424 (M+1)⁺

Example 136

1-(2-Chloro-pyridin-4-ylmethyl)-4-(4-isopropyl-phenyl)-6-propargyloxy-1H-quinazolin-2-one

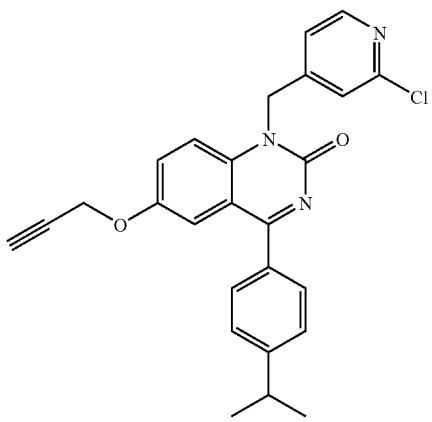 [SMILES: C#CCOc1ccc2c(c1)c(-c1ccc(C(C)C)cc1)nc(=O)n2Cc1ccnc(Cl)c1]

¹H-NMR (300 MHz, CDCl₃): 8.35 (d, 1H), 7.77 (d, 2H), 7.57 (d, 1H), 7.41 (d, 2H), 7.37 (dd, 1H), 7.24 (s, 1H), 7.16 (d, 1H), 7.06 (d, 1H), 5.62 (broad s, 2H), 4.67 (d, 2H), 3.04 (hept, 1H), 2.57 (t, 1H), 1.34 (d, 6H).

MS: 444 (M+1)⁺

Example 137

1-(2-Chloro-pyridin-3-ylmethyl)-4-(4-isopropyl-phenyl)-6-propargyloxy-1H-quinazolin-2-one

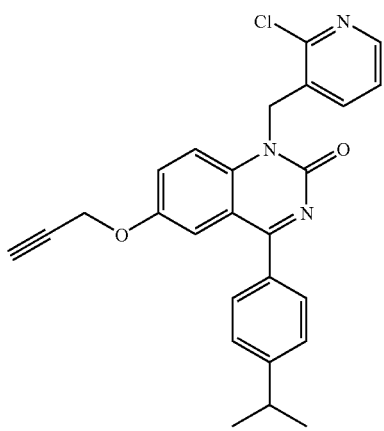

¹H-NMR (300 MHz, CDCl₃): 8.84 (d, 1H), 7.77 (d, 2H), 7.65 (d, 1H), 7.41 (d, 2H) 7.31-7.39 (m, 2H), 7.16 (dd, 1H), 7.07 (d, 1H), 5.61 (s, 2H), 4.67 (d, 2H), 3.91 (broad, 2H), 3.04 (hept, 1H), 2.56 (t, 1H), 1.33 (d, 6H).

MS: 444 (M+1)⁺

Example 138

4-(4-Isopropyl-phenyl)-1-{6-[2-(2-methoxy-ethoxy)-ethoxy]-pyridin-2-ylmethyl)-6-propargyloxy-1H-quinazolin-2-one

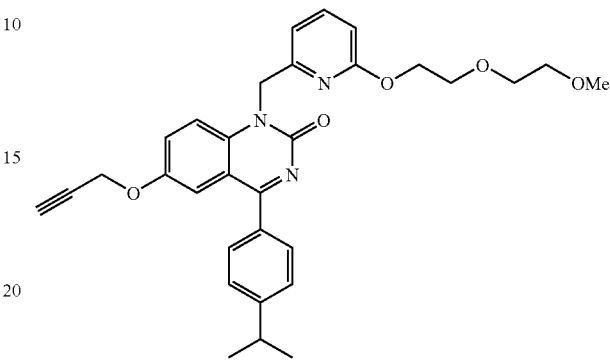

¹H-NMR (300 MHz, CDCl₃): 7.74 (d, 2H), 7.47-7.65 (m, 3H), 7.38 (d, 2H), 7.35 (dd, 1H), 6.93 (d, 1H), 6.66 (d, 1H), 5.52 (broad, 2H), 4.66 (d, 2H), 4.41 (dd, 2H), 3.78 (dd, 2H), 3.79 (dd, 2H), 3.65-3.71 (m, 2H), 3.54-3.60 (m, 2H), 3.39 (s, 3H), 3.02 (hept, 1H), 2.57 (t, 1H), 1.33 (d, 6H).

MS: 528 (M+1)⁺

Example 139

4-(4-Isopropyl-phenyl)-1-[6-(2-methoxy-ethoxy)-ethoxy)-pyridin-2-ylmethyl)-6-propargyloxy-1H-quinazolin-2-one

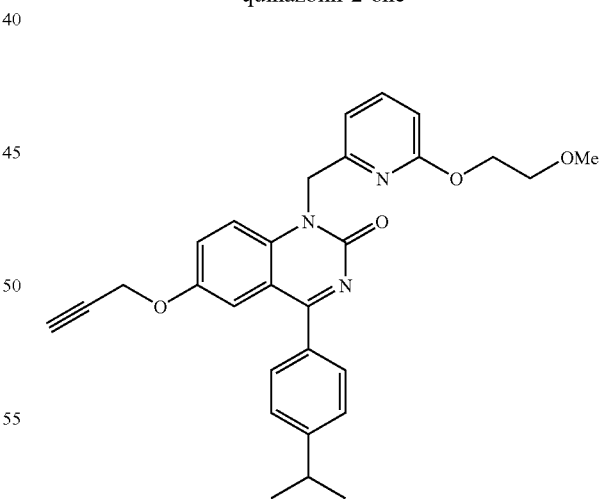

¹H-NMR (300 MHz, CDCl₃): 7.74 (d, 2H), 7.47-7.63 (m, 3H), 7.39 (d, 2H), 7.34 (dd, 1H), 6.92 (d, 1H), 6.69 (d, 1H), 5.53 (broad, 2H), 4.66 (d, 2H), 4.38-4.43 (m, 2H), 3.66-3.71 (m, 2H), 3.42 (s, 3H), 3.02 (hept, 1H), 2.56 (t, 1H), 1.33 (d, 6H).

MS: 484 (M+1)⁺

Example 140
5-Allyl-1-benzyl-6-hydroxy-4-(4-isopropyl-phenyl)-1H-quinazolin-2-one
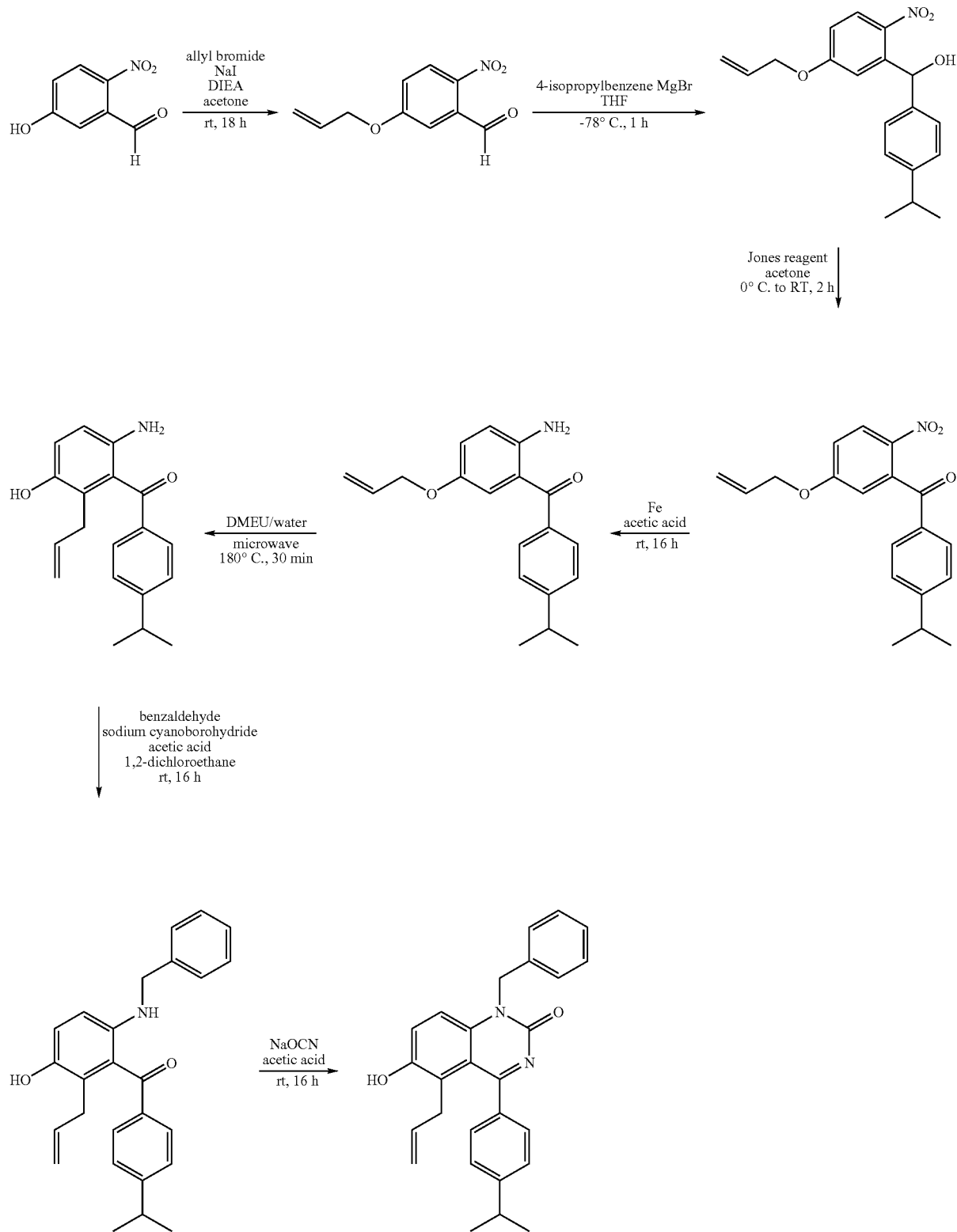

A. Synthesis of 5-allyloxy-2-nitro-benzaldehyde

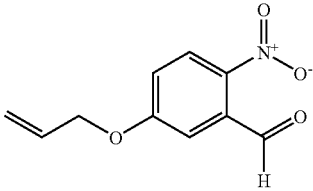

To a solution of 25 g (150 mmol) 5-hydroxy-2-nitro-benzaldehyde and 44.8 g (299 mmol) sodium iodide in 400 ml acetone are added 51.2 ml (299 mmol) N-ethyldiisopropylamine and 25.3 ml (299 mmol) allyl bromide. After stirring for 18 h at r.t. the reaction mixture is filtered and the solvent is evaporated. Extraction of the residue with 1 M aqueous hydrochloric acid/dichloromethane followed by chromatography (hexane/ethyl acetate) yields 5-allyloxy-2-nitro-benzaldehyde.

$^1$H NMR (300 MHz, CDCl$_3$): 10.45 (s, 1H), 8.15 (d, 1H), 7.32 (d, 1H), 7.16 (dd, 1H), 6.03 (ddt, 1H), 5.45 (dq, 1H), 5.37 (dq, 1H), 4.69 (dt, 2H).

B. Synthesis of (5-allyloxy-2-nitro-phenyl)-(4-isopropyl-phenyl)-methanol

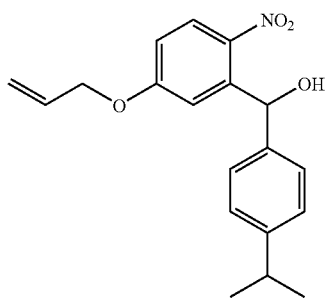 [SMILES: C=CCOc1ccc([N+](=O)[O-])c(C(O)c2ccc(C(C)C)cc2)c1]

A solution of 4-isopropylphenylmagnesium bromide prepared from 2.35 g (96.5 mmol) magnesium and 18.15 g (96.5 mmol) 1-bromo-4-isopropylbenzene in 80 ml THF is added slowly at −78° C. to a solution of 20 g (96.5 mmol) 5-allyloxy-2-nitro-benzaldehyde in 200 ml THF. After allowing the reaction mixture to warm up to r.t. saturated aqueous ammonium chloride solution is added. Extraction with ethyl acetate followed by chromatographic purification on silica (hexane/ethyl acetate) yields (5-allyloxy-2-nitro-phenyl)-(4-isopropyl-phenyl)-methanol.

$^1$H NMR (300 MHz, CDCl$_3$): 8.05 (d, 1H), 7.34 (d, 1H), 7.25 (d, 2H), 7.16 (d, 2H), 6.88 (dd, 1H), 6.50 (s, 1H), 6.01 (ddt, 1H), 5.40 (d, 1H), 5.33 (d, 1H), 4.62 (d, 2H), 2.88 (hept, 1H), 1.22 (d, 6H).

MS: 310 (M-OH)$^+$

C. Synthesis of (5-allyloxy-2-nitro-phenyl)-(4-isopropyl-phenyl)-methanone

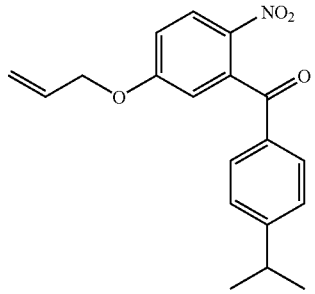 [SMILES: C=CCOc1ccc([N+](=O)[O-])c(C(=O)c2ccc(C(C)C)cc2)c1]

A solution of 16.38 g (50 mmol) (5-allyloxy-2-nitro-phenyl)-(4-isopropyl-phenyl)-methanol in 60 ml acetone is treated at 0° C. with 20 ml (53.4 mmol) Jones reagent. After stirring for 2 h at r.t. isopropanol, an aqueous solution of sodium bisulphite and saturated aqueous ammonium chloride solution are added. Extraction with dichloromethane affords (5-allyloxy-2-nitro-phenyl)-(4-isopropyl-phenyl)-methanone.

$^1$H NMR (300 MHz, CDCl$_3$): 8.24 (d, 1H), 7.69 (d, 2H), 7.30 (d, 2H), 7.09 (dd, 1H), 6.89 (d, 1H), 6.03 (ddt, 1H), 5.43 (dq, 1H), 5.36 (dq, 1H), 4.65 (dt, 2H), 2.97 (hept, 1H), 1.27 (d, 6H).

D. Synthesis of (5-allyloxy-2-amino-phenyl)-(4-isopropyl-phenyl)-methanone

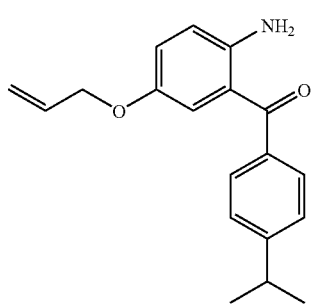 [SMILES: C=CCOc1ccc(N)c(C(=O)c2ccc(C(C)C)cc2)c1]

To an ice chilled solution of 16 g (5-allyloxy-2-nitro-phenyl)-(4-isopropyl-phenyl)-methanone in 65 ml acetic acid are added 21.8 g iron powder. A precipitate that is formed is brought into solution by addition of additional acetic acid. After stirring for 16 h at r.t. the reaction mixture is filtered and basified by addition of aqueous potassium hydroxide solution. Extraction with dichloromethane yields (5-allyloxy-2-amino-phenyl)-(4-isopropyl-phenyl)-methanone.

$^1$H NMR (300 MHz, CDCl$_3$): 7.62 (d, 2H), 7.31 (d, 2H), 7.03-6.98 (m, 2H), 6.71 (d, 1H), 5.98 (ddt, 1H), 5.32 (dd, 1H), 5.25 (dd, 1H), 4.39 (d, 2H), 2.99 (hept, 1H), 1.31 (d, 6H).

MS: 296 (M+1)$^+$

E. Synthesis of (2-allyl-6-amino-3-hydroxy-phenyl)-(4-isopropyl-phenyl)-methanone

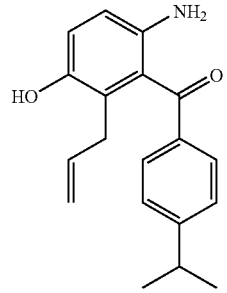 [SMILES: C=CCc1c(O)ccc(N)c1C(=O)c1ccc(C(C)C)cc1]

In a sealed tube a mixture of 50 mg (0.17 mmol) (5-allyloxy-2-nitro-phenyl)-(4-isopropyl-phenyl)-methanone, 1 ml DMEU and 1 ml water is heated by microwave irradiation to 180° C. for 30 min. Water is evaporated and the resulting solution is purified by reversed phase preparative HPLC to yield the rearranged product.

$^1$H NMR (300 MHz, CDCl$_3$): 7.79 (d, 2H), 7.30 (d, 2H), 6.81 (d, 1H), 6.60 (d, 1H), 5.80 (ddt, 1H), 5.03 (dq, 1H), 5.01 (dq, 1H), 3.16 (dt, 2H), 2.97 (hept, 1H), 1.28 (d, 6H).

MS: 296 (M+1)$^+$

F. Synthesis of (2-allyl-6-benzylamino-3-hydroxy-phenyl)-(4-isopropyl-phenyl)-methanone

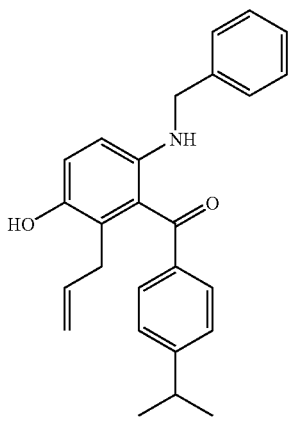 [SMILES: C=CCc1c(O)ccc(NCc2ccccc2)c1C(=O)c1ccc(C(C)C)cc1]

To a solution of 39 mg (0.13 mmol) (2-allyl-6-amino-3-hydroxy-phenyl)-(4-isopropyl-phenyl)-methanone and 13.34 µl (13 mmol) benzaldehyde in 1.3 ml 1,2-dichlorethane and 0.3 g molecular sieves (4 Å pore size) are added after 1 h 13 mg (0.18 mmol) sodium cyanoborohydride and 7.55 µl acetic acid (0.13 mmol). After stirring for 16 h at r.t. 1 M hydrochloric acid is added to destroy the excess of hydride equivalents. By adding 1 M NaOH the mixture is basified. The crude product obtained by extraction with dichloromethane is purified by reversed phase preparative chromatography.

$^1$H NMR (300 MHz, CDCl$_3$): 7.78 (d, 2H), 7.31 (d, 2H), 7.28-7.16 (m, 5H), 6.82 (d, 1H), 6.56 (d, 1H), 5.79 (ddt, 1H), 5.02 (dd, 1H), 5.01 (dd, 1H), 4.22 (s, 2H), 3.17 (d, 2H), 2.99 (hept, 1H), 1.30 (d, 6H).

MS: 386 (M+1)$^+$

G. Synthesis of 5-allyl-1-benzyl-6-hydroxy-4-(4-isopropyl-phenyl)-1H-quinazolin-2-one

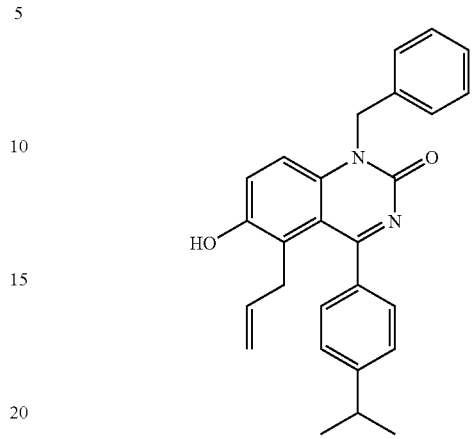

A solution of 15 mg (39 µmol) (2-allyl-6-benzylamino-3-hydroxy-phenyl)-(4-isopropyl-phenyl)-methanone and 2.5 mg sodium cyanate in 0.2 ml acetic acid is stirred at r.t. for 16 h. Aqueous sodium hydroxide solution is added and the product is extracted with dichloromethane.

$^1$H NMR (300 MHz, CDCl$_3$): 7.48 (d, 2H), 7.33-7.24 (m, 8H), 7.14 (d, 1H), 5.65 (ddt, 1H), 5.52 (s, 2H), 5.10 (dd, 1H), 4.95 (dd, 1H), 3.20 (d, 2H), 2.97 (hept, 1H), 1.28 (d, 6H).

MS: 411 (M+1)$^+$

The compounds of the following examples are prepared by analogy to the example described above:

Example 141

5-Allyl-1-[3-(2-chloro-ethoxy)-4-methoxy-benzyl]-6-hydroxy-4-(4-isopropyl-phenyl)-1H-quinazolin-2-one

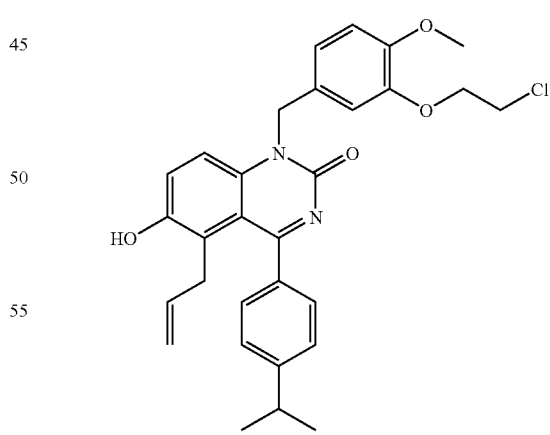

$^1$H NMR (300 MHz, d$_6$DMSO): 9.66 (s, 1H), 7.31 (m, 4H), 7.25 (s, 2H), 6.99 (s, 2H), 6.85 (d, 1H), 6.69 (d, 1H), 5.47-5.32 (m, 1H), 5.29 (s, 2H), 4.64 (d, 1H), 4.30 (d, 1H), 4.14 (t, 2H), 3.86 (t, 2H), 3.67 (s, 3H), 3.03 (d, 2H), 2.94 (hept, 1H), 1.21 (d, 6H).

MS: 519 (M+1)$^+$ (isotop pattern for one chloro atom)

Example 142

5-Allyl-6-hydroxy-4-(4-isopropyl-phenyl)-1-thiophen-2-ylmethyl-1H-quinazolin-2-one

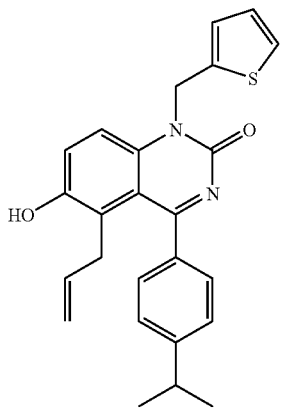 [SMILES: C=CCc1c(O)ccc2c1c(-c1ccc(C(C)C)cc1)nc(=O)n2Cc1cccs1]

$^1$H NMR (300 MHz, CDCl$_3$): 7.45 (d, 2H), 7.39 (d, 1H), 7.31-7.23 (m, 3H), 7.20 (dd, 1H), 7.11 (m, 1H), 6.93 (dd, 1H), 5.69-5.60 (m, 1H), 5.61 (s, 2H), 5.13 (dt, 1H), 5.00 (dt, 1H), 3.17 (d, 2H), 2.95 (hept, 1H), 1.26 (d, 6H).

MS: 417 (M+1)$^+$

Example 143

5-Allyl-6-hydroxy-4-(4-isopropyl-phenyl)-1-(3-methylsulphanyl-butyl)-1H-quinazolin-2-one

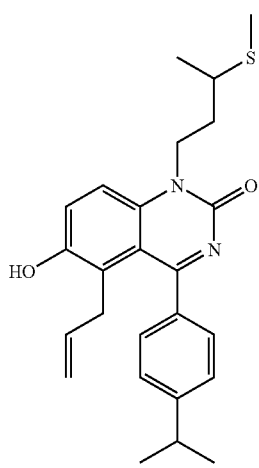 [SMILES: C=CCc1c(O)ccc2c1c(-c1ccc(C(C)C)cc1)nc(=O)n2CCC(C)SC]

$^1$H NMR (300 MHz, CDCl$_3$): 7.47 (d, 2H), 7.38 (d, 2H), 7.25-7.22 (m, 2H), 6.35 (s, broad, 1H), 5.63 (ddt, 1H), 5.05 (d, 1H), 4.90 (d, 1H), 4.40 (t, 2H), 3.20 (dd, 1H), 3.18 (dd, 1H), 2.94 (hept, 1H), 2.88-2.76 (m, 1H), 2.13 (s, 3H), 2.11-1.87 (m, 2H), 1.88 (d, 3H), 1.25 (d, 6H).

MS: 423 (M+1)$^+$

Example 144

5-Allyl-6-hydroxy-4-(4-isopropyl-phenyl)-1-(1-methyl-2-phenyl-ethyl)-1H-quinazolin-2-one

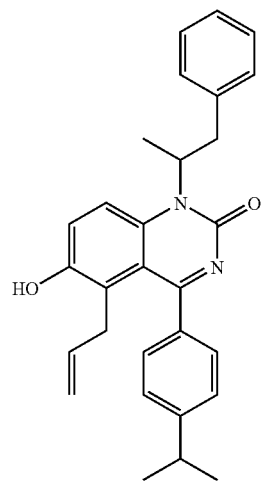 [SMILES: C=CCc1c(O)ccc2c1c(-c1ccc(C(C)C)cc1)nc(=O)n2C(C)Cc1ccccc1]

$^1$H NMR (300 MHz, CDCl$_3$): 7.47-7.43 (m, 3H), 7.32-7.11 (m, 8H), 6.88 (broad, 1H), 5.63 (ddt, 1H), 5.00 (dd, 1H), 4.88 (m, 1H), 4.83 (dd, 1H), 3.52 (dd, 1H), 3.42 (dd, 1H), 3.22 (dd, 1H), 3.18 (dd, 1H), 2.94 (hept, 1H), 1.71 (d, 3H), 1.26 (d, 6H).

MS: 439 (M+1)$^+$

Example 145

5-Allyl-6-hydroxy-4-(4-isopropyl-phenyl)-1-pyridin-3-ylmethyl-1H-quinazolin-2-one

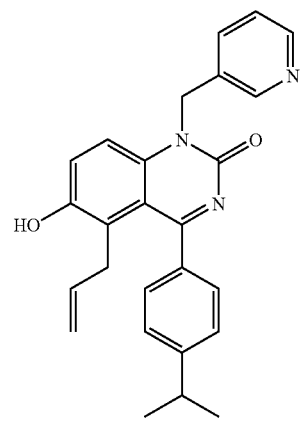 [SMILES: C=CCc1c(O)ccc2c1c(-c1ccc(C(C)C)cc1)nc(=O)n2Cc1cccnc1]

$^1$H NMR (300 MHz, d$_6$DMSO): 9.74 (s, 1H), 8.56 (d, 1H), 8.46 (dd, 1H), 7.61 (dt, 1H), 7.39-7.31 (m, 7H), 5.51-5.41 (m, 3H), 4.70 (dd, 1H), 4.35 (dd, 1H), 3.08 (d, 2H), 2.98 (hept, 1H), 1.25 (d, 6H).

MS: 412 (M+1)$^+$

Example 146

5-Allyl-6-hydroxy-1-(4-hydroxy-3-methoxy-benzyl)-4-(4-isopropyl-phenyl)-1H-quinazolin-2-one

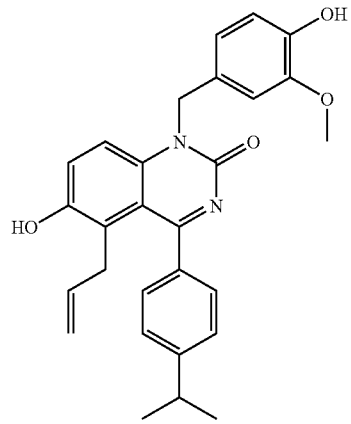 [SMILES: C=CCc1c(O)ccc2c1c(-c1ccc(C(C)C)cc1)nc(=O)n2Cc1ccc(O)c(OC)c1]

$^1$H NMR (300 MHz, d$_6$DMSO): 9.71 (s, 1H), 8.93 (s, 1H), 7.35-7.30 (m, 6H), 6.95 (s, 1H), 6.68-6.57 (m, 2H), 5.44 (m, 1H), 5.30 (s, 2H), 4.68 (d, 1H), 4.33 (d, 1H), 3.70 (s, 3H), 3.06 (m, 2H), 2.97 (m, 1H), 1.25 (d, 6H).

MS: 457 (M+1)$^+$

Example 147

5-Allyl-6-hydroxy-1-[2-(2-hydroxy-ethoxy)-benzyl]-4-(4-isopropyl-phenyl)-1H-quinazolin-2-one

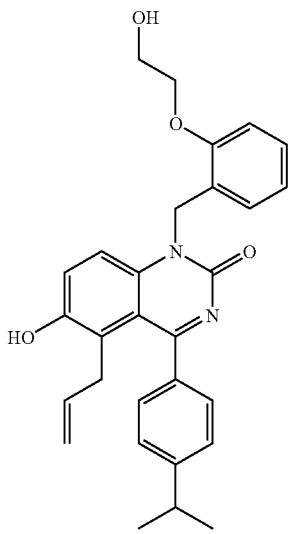 [SMILES: C=CCc1c(O)ccc2c1c(-c1ccc(C(C)C)cc1)nc(=O)n2Cc1ccccc1OCCO]

$^1$H NMR (300 MHz, d$_6$DMSO): 9.70 (s, 1H), 7.38 (d, 2H), 7.35 (d, 2H), 7.30 (d, 1H), 7.22 (td, 1H), 7.17 (d, 1H), 7.05 (d, 1H), 6.80 (t, 1H), 6.74 (dd, 1H), 5.47 (ddt, 1H), 5.38 (s, 2H), 4.96 (t, 1H), 4.70 (dd, 1H), 4.36 (dd, 1H), 4.12 (t, 2H), 3.79 (q, 2H), 3.09 (d, 2H), 2.98 (hept, 1H), 1.25 (d, 6H).

MS: 471 (M+1)$^+$

Example 148

5-Allyl-6-hydroxy-1-[3-(2-hydroxy-ethoxy)-benzyl]-4-(4-isopropyl-phenyl)-1H-quinazolin-2-one

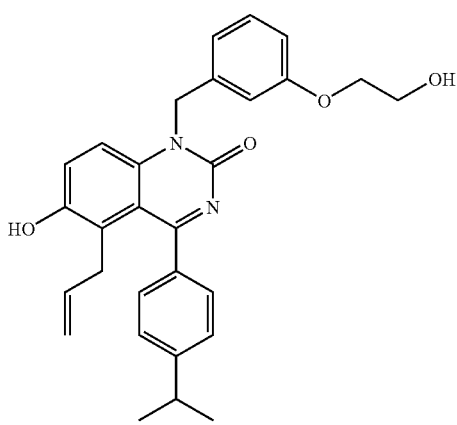 [SMILES: C=CCc1c(O)ccc2c1c(-c1ccc(C(C)C)cc1)nc(=O)n2Cc1cccc(OCCO)c1]

$^1$H NMR (300 MHz, d$_6$DMSO): 9.71 (s, 1H), 7.38 (d, 2H), 7.35 (d, 2H), 7.30 (d, 1H), 7.24-7.18 (m, 2H), 6.82-6.76 (m, 3H), 5.46 (ddt, 1H), 5.39 (s, 2H), 4.83 (t, 1H), 4.70 (dd, 1H), 4.35 (dd, 1H), 3.91 (t, 2H), 3.66 (q, 2H), 3.08 (d, 2H), 2.98 (hept, 1H), 1.25 (d, 6H).

MS: 471 (M+1)$^+$

Example 149

5-Allyl-1-(3,5-dimethoxy-benzyl)-6-hydroxy-4-(4-isopropyl-phenyl)-1H-quinazolin-2-one

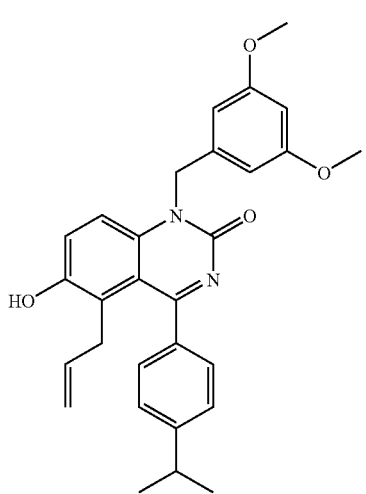 [SMILES: C=CCc1c(O)ccc2c1c(-c1ccc(C(C)C)cc1)nc(=O)n2Cc1cc(OC)cc(OC)c1]

$^1$H NMR (300 MHz, d$_6$DMSO): 9.72 (s, 1H), 7.37 (d, 2H), 7.35 (d, 2H), 7.31 (d, 1H), 7.22 (d, 1H), 6.36 (m, 3H), 5.47 (ddt, 1H), 5.34 (s, 2H), 4.70 (dd, 1H), 4.34 (dd, 1H), 3.67 (s, 6H), 3.08 (d, 2H), 2.98 (hept, 1H), 1.25 (d, 6H).

MS: 471 (M+1)$^+$

Example 150

1-Benzyl-6-hydroxy-4-(4-isopropyl-phenyl)-5-propyl-1H-quinazolin-2-one

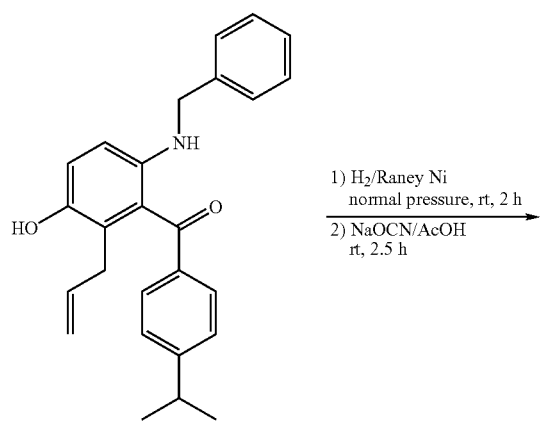

A solution of 200 mg (519 µmol) (2-allyl-6-benzylamino-3-hydroxy-phenyl)-(4-isopropyl-phenyl)-methanone in 6 ml methanol is hydrogenated in the presence of Raney nickel catalyst during 2 h at normal pressure. The catalyst is filtered off and the filtrate is evaporated. A 100 mg portion of the residue is dissolved in 0.6 ml acetic acid and treated with 16.7 mg (258 µmol) sodium cyanate. for 2.5 h at r.t. The crude product obtained after extraction with dichloromethane/aqueous sodium bicarbonate is triturated with ethyl ether and dichloromethane containing a small amount of methanol.

$^1$H NMR (300 MHz, d$_6$DMSO): 9.58 (s, 1H), 7.41-7.16 (m, 11H), 5.43 (s, 2H), 2.99 (hept, 1H), 2.19 (m, 2H), 1.25 (d, 6H), 1.18 (m, 2H), 0.36 (t, 3H).

MS: 413 (M+1)$^+$

The compound of the following example is prepared by analogy to the example described above:

Example 151

6-Hydroxy-1-isobutyl-4-(4-isopropyl-phenyl)-5-propyl-1H-quinazolin-2-one

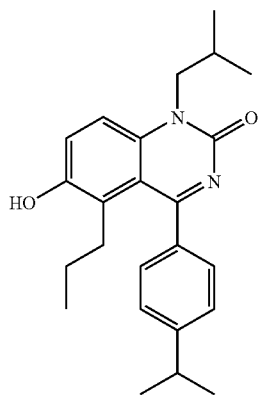 [SMILES: CCCc1c(O)ccc2c1c(-c1ccc(C(C)C)cc1)nc(=O)n2CC(C)C]

$^1$H NMR (300 MHz, CDCl$_3$): 7.44 (d, 2H), 7.36 (d, 1H), 7.27 (d, 2H), 7.11 (d, 1H), 5.7 (broad, 1H), 4.17 (d, 2H), 2.96 (hept, 1H), 2.86 (dd, 2H), 2.26 (hept, 1H), 1.31-1.19 (m, 2H), 1.27 (d, 6H), 1.01 (d, 6H), 0.46 (t, 3H).

MS: 379 (M+1)$^+$

Example 152

5-Cyclopropylmethyl-1-(3,3-dimethyl-butyl)-6-hydroxy-4-(4-isopropyl-phenyl)-1H-quinazolin-2-one

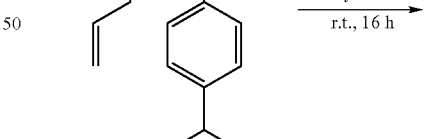

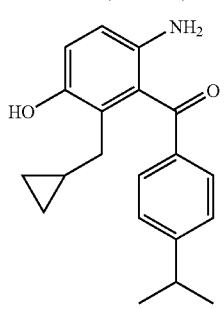

-continued

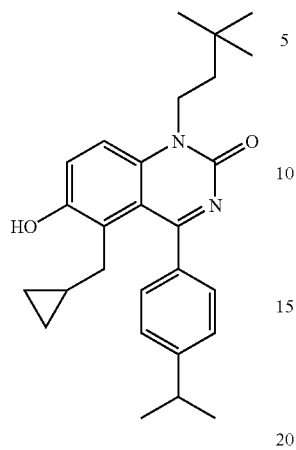

A. Synthesis of (6-amino-2-cyclopropylmethyl-3-hydroxy-phenyl)-(4-isopropyl-phenyl)methanone

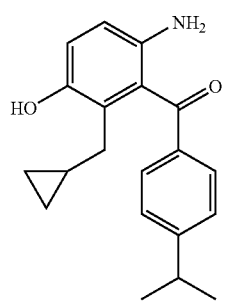 [SMILES: CC(C)c1ccc(C(=O)c2c(N)ccc(O)c2CC2CC2)cc1]

A diazomethane solution is freshly prepared by adding 515 mg (5 mmol) N-nitroso-N-methylurea in small portions to a stirred mixture of 50 ml diethyl ether and 17.5 ml 40% aqueous potassium hydroxide solution at 5° C. Ten minutes after the last addition, the organic layer is separated off and dried over solid potassium hydroxide. This diazomethane solution is added to a concentrated solution of 1.00 g (3.39 mmol) (2-allyl-6-amino-3-hydroxy-phenyl)-(4-isopropyl-phenyl)-methanone in diethyl ether containing 152 mg (0.68 mmol) Pd(OAc)$_2$. After stirring for 16 h at r.t. the reaction mixture is filtered, evaporated to dryness and purified by flash column chromatography.

$^1$H NMR (300 MHz, CDCl$_3$): 7.78 (d, 2H), 7.29 (d, 2H), 6.77 (d, 1H), 6.55 (d, 1H), 4.70 (s, 1H), 3.40 (broad, 2H), 2.96 (hept, 1H), 2.35 (d, 2H), 1.27 (d, 6H), 0.88 (m, 1H), 0.38 (m, 2H), 0.09 (m, 2H).

MS: 310 (M+1)$^+$

B. Synthesis of 5-cyclopropylmethyl-1-(3,3-dimethyl-butyl)-6-hydroxy-4-(4-isopropyl-phenyl)-1H-quinazolin-2-one

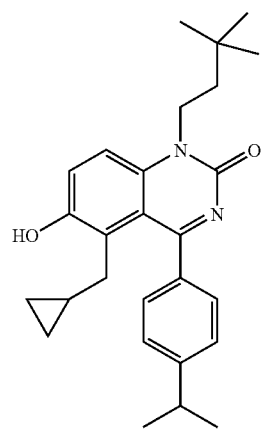 [SMILES: CC(C)c1ccc(-c2nc(=O)n(CCC(C)(C)C)c3ccc(O)c(CC4CC4)c23)cc1]

A mixture of 100 mg (0.32 mmol) (6-amino-2-cyclopropylmethyl-3-hydroxy-phenyl)-(4-isopropyl-phenyl)methanone, 40.5 µl (0.32 mmol) 3,3-dimethylbutyric aldehyde and 28.5 mg (0.45 mmol) NaCNBH$_3$ in 0.5 ml 1,2-dichloroethane containing 18.5 µl (0.32 mmol) acetic acid is stirred for 18 h at r.t. To destroy the excess of hydride 0.1 M hydrochloric acid is added first before by the addition of 0.1 M aqueous sodium hydroxide the mixture is made alkaline. The intermediate is extracted with dichloromethane and purified by preparative reversed phase HPLC.

A 50 mg (0.13 mmol) portion of this intermediate is dissolved in 0.1 ml acetic acid and treated with 8.3 mg (0.13 mmol) sodium cyanate. After stirring for 3 h at r.t. the reaction mixture is extracted with dichloromethane and aqueous bicarbonate solution. The residue obtained after evaporation of the organic phases is triturated with diethyl ether to obtain the pure title compound.

$^1$H NMR (300 MHz, CDCl$_3$): 7.44 (d, 2H), 7.42 (d, 1H), 7.26 (d, 2H), 7.17 (d, 1H), 6.18 (s, 1H), 4.28 (m, 2H), 2.96 (hept, 1H), 2.34 (d, 2H), 1.72 (m, 2H), 1.28 (d, 6H), 1.09 (s, 9H), 0.70 (m, 1H), 0.35 (m, 2H), −0.08 (m, 2H).

MS: 419 (M+1)$^+$

The compounds of the following examples are prepared by analogy to the example described above:

Example 153

1-Benzyl-5-cyclopropylmethyl-6-hydroxy-4-(4-isopropyl-phenyl)-1H-quinazolin-2-one

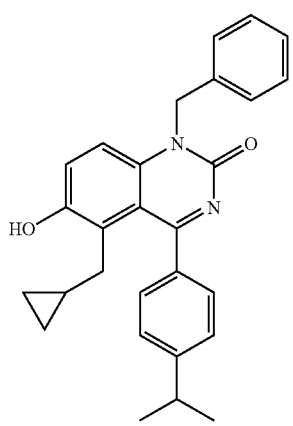 [SMILES: CC(C)c1ccc(-c2nc(=O)n(Cc3ccccc3)c3ccc(O)c(CC4CC4)c23)cc1]

¹H NMR (300 MHz, CDCl₃): 8.0 (broad 1H), 7.47 (d, 2H), 7.29-7.22 (m, 8H), 7.01 (d, 1H), 5.49 (s, 2H), 2.96 (hept, 1H), 2.36 (d, 2H), 1.27 (d, 6H), 0.69 (m, 1H), 0.17 (m, 2H), −0.18 (m, 2H).
MS: 425 (M+1)⁺

Example 154

5-Cyclopropylmethyl-1-(3,4-dimethoxy-benzyl)-6-hydroxy-4-(4-isopropyl-phenyl)-1H-quinazolin-2-one

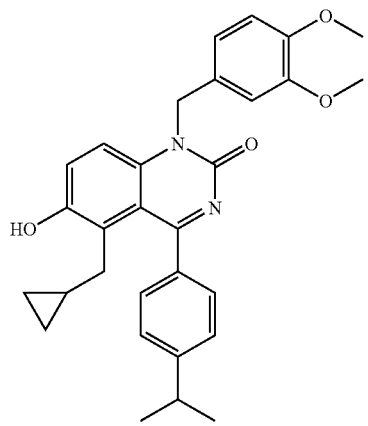 [SMILES: COc1ccc(Cn2c(=O)nc(-c3ccc(C(C)C)cc3)c3c(CC4CC4)c(O)ccc32)cc1OC]

¹H NMR (300 MHz, d₆DMSO): 9.58 (s, 1H), 7.33 (s, 4H), 7.27 (d, 1H), 7.24 (d, 1H), 6.98 (d, 1H), 6.84 (d, 1H), 6.69 (dd, 1H), 5.33 (s, 2H), 3.67 (s, 3H), 3.66 (s, 3H), 2.95 (hept, 1H), 2.20 (d, 2H), 1.22 (d, 6H), 0.60 (m, 1H), 0.05 (m, 2H), −0.36 (m, 2H).
MS: 485 (M+1)⁺

Example 155

5-Cyclopropylmethyl-6-hydroxy-4-(4-isopropyl-phenyl)-1-(3-methoxy-benzyl)-1H-quinazolin-2-one

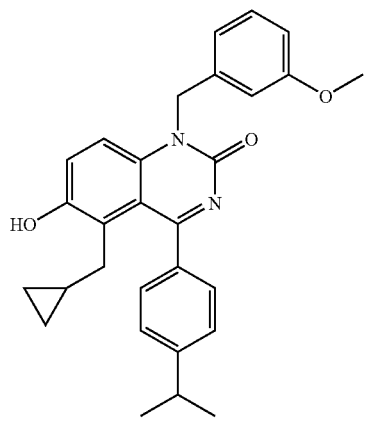 [SMILES: COc1cccc(Cn2c(=O)nc(-c3ccc(C(C)C)cc3)c3c(CC4CC4)c(O)ccc32)c1]

¹H NMR (300 MHz, d₆DMSO): 9.60 (s, 1H), 7.35 (d, 2H), 7.33 (d, 2H), 7.28 (d, 1H), 7.20 (t, 1H), 7.18 (d, 1H), 6.82-6.74 (m, 3H), 5.87 (s, 2H), 3.67 (s, 3H), 2.96 (hept, 1H), 2.21 (d, 2H), 1.22 (d, 6H), 0.61 (m, 1H), 0.05 (m, 2H), −0.35 (m, 2H).
MS: 455 (M+1)⁺

Example 156

5-Cyclopropylmethyl-1-(3,5-dimethoxy-benzyl)-6-hydroxy-4-(4-isopropyl-phenyl)-1H-quinazolin-2-one

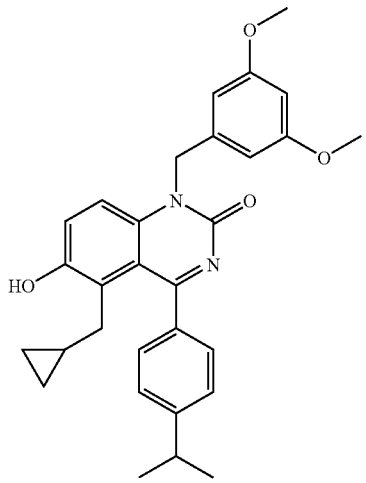 [SMILES: COc1cc(Cn2c(=O)nc(-c3ccc(C(C)C)cc3)c3c(CC4CC4)c(O)ccc32)cc(OC)c1]

¹H NMR (300 MHz, d₆DMSO): 9.60 (s, 1H), 7.34 (s, 4H), 7.28 (d, 1H), 7.17 (d, 1H), 6.35 (s, 3H), 5.32 (s, 2H), 3.65 (s, 6H), 2.95 (hept, 1H), 2.21 (d, 2H), 1.22 (d, 6H), 0.61 (m, 1H), 0.05 (m, 2H), −0.36 (m, 2H).
MS: 485 (M+1)⁺

Example 157

5-Cyclopropylmethyl-6-hydroxy-1-(4-hydroxy-3-methoxy-benzyl)-4-(4-isopropyl-phenyl)-1H-quinazolin-2-one

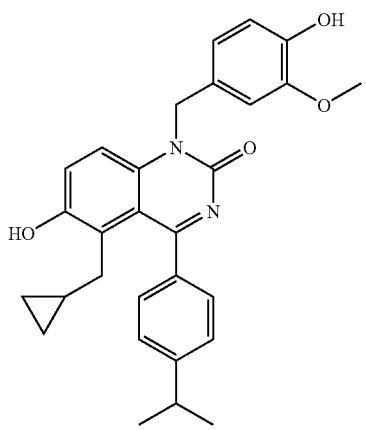 [SMILES: COc1cc(Cn2c(=O)nc(-c3ccc(C(C)C)cc3)c3c(CC4CC4)c(O)ccc32)ccc1O]

¹H NMR (300 MHz, d₆DMSO): 9.59 (s, 1H), 8.91 (s, 1H), 7.33 (s, 4H), 7.28 (d, 1H), 7.27 (d, 1H), 6.94 (d, 1H), 6.65 (d, 1H), 6.60 (dd, 1H), 5.28 (s, 2H), 3.68 (s, 3H), 2.95 (hept, 1H), 2.20 (d, 2H), 1.22 (d, 6H), 0.60 (m, 1H), −0.04 (m, 2H), −0.36 (m, 2H).
MS: 471 (M+1)⁺

Example 158
1-[(3-(3,4-Dimethoxy-phenyl)-propyl)]-4-(4-isopropyl-phenyl)-6-propargyloxy-1H-quinazolin-2-one
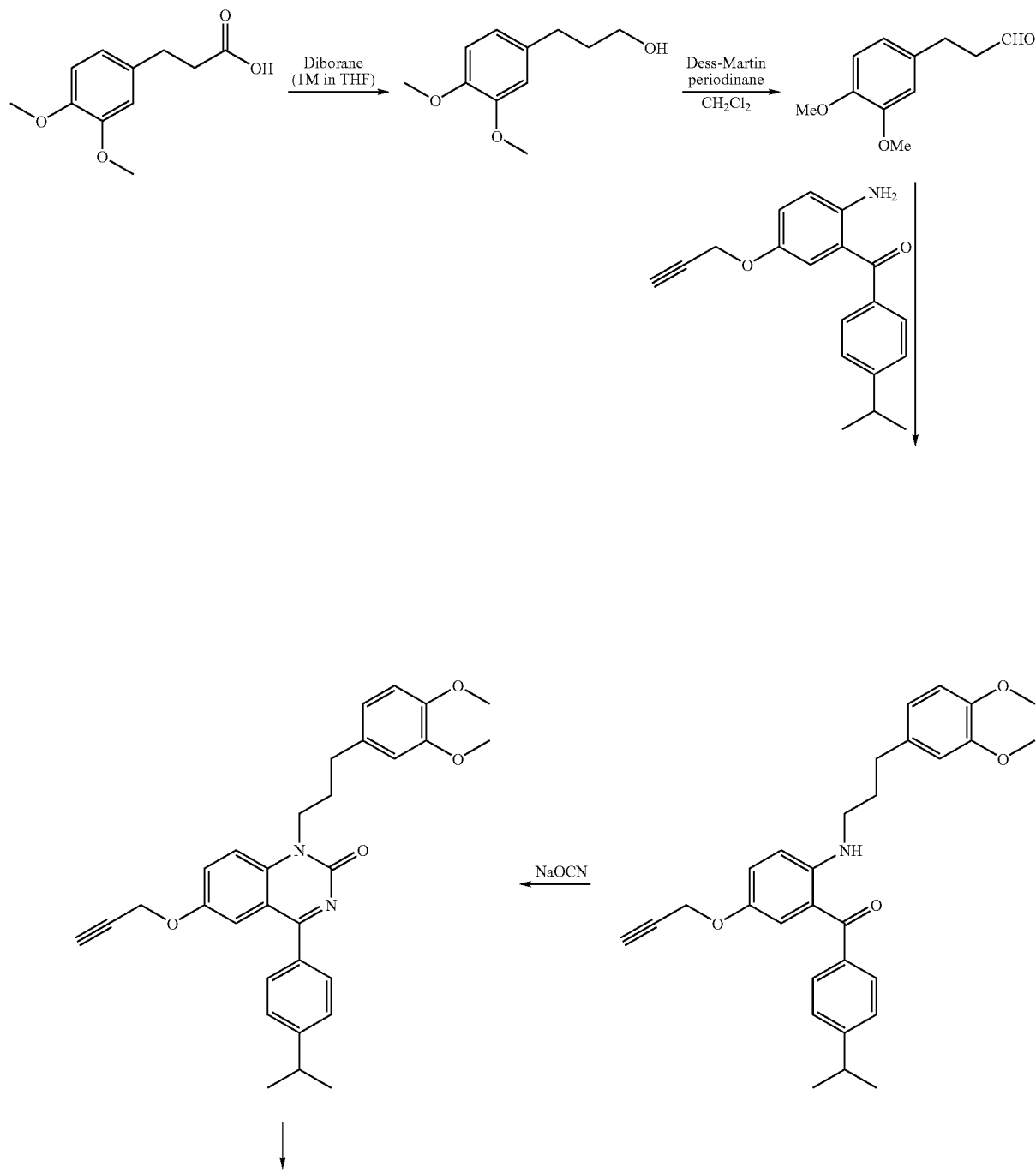

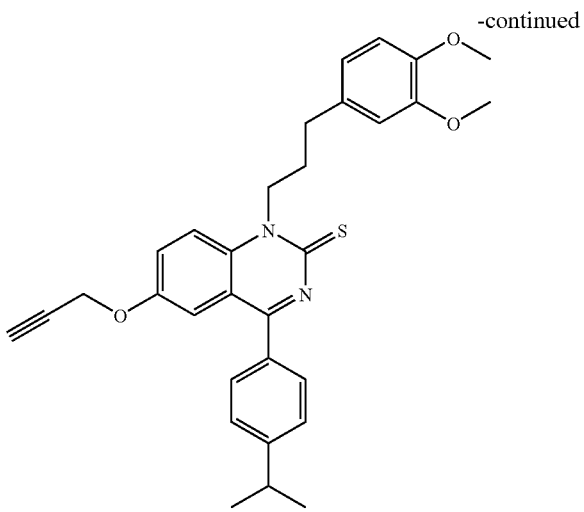

A. Synthesis of 3-(3,4-dimethoxy-phenyl)-propan-1-ol

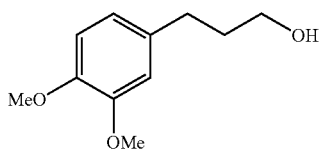

A solution of 6.0 g (28.5 mmol) 3-(3,4-dimethoxyphenyl)-propionic acid in 120 ml anhydrous THF is cooled to 0° C. and treated within 15 minutes with 42.75 ml borane THF complex (1 M solution). Stirring is continued overnight at rt. The resulting clear solution is cooled with an ice/water bath and hydrolyzed by the addition of 100 ml saturated ammonium chloride solution. Extractive work-up with diethyl ether furnishes a colourless oil, which is purified by chromatography (hexane/ethyl acetate) to yield a colourless oil.

$^1$H-NMR (300 MHz, CDCl$_3$): 6.76-6.80 (m, 1H), 6.70-6.74 (m, 2H), 3.86 (s, 3H), 3.85 (s, 3H), 3.67 (t, 2H), 2.62-2.69 (m, 2H), 1.82-1.93 (m, 2H).

MS: 197 (M+1)$^+$

B. Synthesis of 3-(3,4-dimethoxy-phenyl)-propionaldehyde

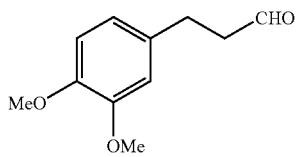 [SMILES: COc1ccc(CCC=O)cc1OC]

A solution of 2.0 g (10.2 mmol) of the aldehyde prepared in step A in 40 ml CH$_2$Cl$_2$ is oxidised in the dark by the addition of 4.32 g (10.2 mmol) Dess-Marin periodinane. The reaction is complete after 30 minutes. The suspension formed is taken up into 50 ml CH$_2$Cl$_2$ and washed twice with sodium bicarbonate and 20% sodium thiosulphate solution. Concentration of the organic layer affords a beige crude product which is purified by chromatography hexane/ethyl acetate) to yield a yellow oil.

$^1$H-NMR (300 MHz, CDCl$_3$): 9.80 (t, 1H), 6.70-6.81 (m, 5H), 3.86 (s, 3H), 3.85 (s, 3H), 3.87-3.94 (m, 2H), 2.72-2.80 (m, 2H).

MS: 193 (M+1)$^+$

C. Synthesis of {2-[3-(3,4-dimethoxy-phenyl)-propylamino]-5-propargyloxy-phenyl}-(4-isopropyl-phenyl)-methanone

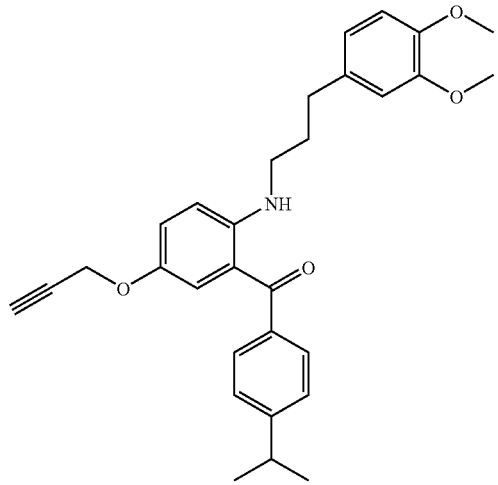 [SMILES: C#CCOc1ccc(NCCCc2ccc(OC)c(OC)c2)c(C(=O)c2ccc(C(C)C)cc2)c1]

To a solution of 298 mg (1.02 mmol) 2-amino-propargyloxy-phenyl)-(4-isopropyl-phenyl)-methanone in 6 ml CH$_2$Cl$_2$ are added 217 mg (1.12 mmol) 3-(3,4-dimethoxy-phenyl)-propionaldehyde and 450 μl (1.52 mmol) tetra-isopropoxy-titanium. The deep red solution is stirred for 7 h at rt. Then 323 mg (1.52 mmol) sodium triacetoxy-borohydride and 300 μl EtOH are added and stirring is continued overnight. The reaction mixture is extracted with water and CH$_2$Cl$_2$ and concentrated i.V. The crude product is purified by chromatography (hexane/ethyl acetate) to yield a yellow oil.

$^1$H-NMR (300 MHz, CDCl$_3$): 8.24 (broad t, NH), 7.67 (d, 2H), 7.28 (d, 2H), 7.17 (d, 1H), 7.11 (dd, 1H), 6.65-6.80 (m, 4H), 4.51 (d, 2H), 3.85 (s, 3H), 3.84 (s, 3H), 3.22 (q, 2H), 2.97 (hept, 1H), 2.72 (t, 2H), 2.46 (t, 1H), 2.00 (quint, 2H), 1.28 (d, 6H).

MS: 472 (M+1)$^+$

D. Synthesis of 1-[3-(3,4-dimethoxy-phenyl)-propyl]-4-(4-isopropyl-phenyl)-6-propargyloxy-1H-quinazolin-2-one

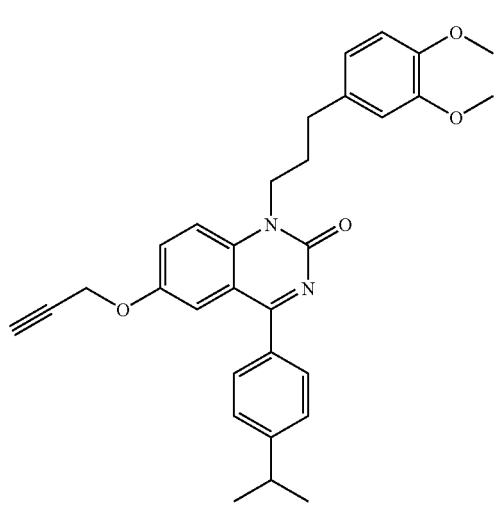 [SMILES: C#CCOc1ccc2c(c1)c(-c1ccc(C(C)C)cc1)nc(=O)n2CCCc1ccc(OC)c(OC)c1]

A solution of 338 mg (0.72 mmol) of the product prepared in step C in 6 ml AcOH is treated with 70 mg (1.1 mmol) sodium cyanate. The mixture is stirred for 1.5 h at rt. A yellow product results after work-up with ethyl acetate/water, which is purified by chromatography (CH$_2$Cl$_2$/MeOH) to afford a yellow foam.

$^1$H-NMR (300 MHz, CDCl$_3$): 7.67 (d, 2H), 7.45 (d, 1H), 7.36 (d, 1H), 7.35 (d, 2H), 7.12 (d, 1H), 6.74-6.80 (m, 3H), 4.64 (d, 2H), 4.25-4.33 (broad m, 2H), 3.86 (s, 3H), 3.85 (s, 3H), 2.99 (hept, 1H), 2.77 (t, 2H), 2.55 (t, 1H), 2.14 (quint, 2H), 1.30 (d, 6H).

MS: 497 (M+1)$^+$

E. Synthesis of 1-[3-(3,4-dimethoxy-phenyl)-propyl]-4-(4-isopropyl-phenyl)-6-propargyloxy-1H-quinazolin-2-thione

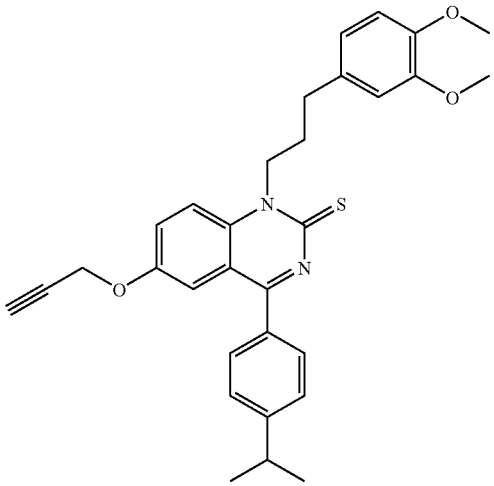

A mixture of 130 mg (0.26 mmol) of the quinazolinone prepared in step D and 122 mg (0.30) mmol Lawesson reagent in 5 ml benzene is stirred for 2 h at 70° C. The solution turns slightly red. Equal amounts of Lawesson reagent are added after a total of 3 and 5 h, but the reaction remained incomplete. After extractive work-up with ethyl acetate and water, followed by chromatography of the crude material (hexane/ethyl acetate) the intermediate is obtained as a yellow oil.

$^1$H-NMR (300 MHz, CDCl$_3$): 7.71 (d, 2H), 7.47 (d, 1H), 7.30-7.40 (m, 4H), 7.16 (d, 1H), 6.82 (s, 2H), 4.67 (d, 2H), 3.89 (s, 3H), 3.87 (s, 3H), 2.99 (hept, 1H), 2.83 (t, 2H), 2.57 (t, 1H), 2.28 (broad, 2H), 1.29 (d, 6H).

MS: 513 (M+1)$^+$

The compound of the following example is prepared by analogy:

Example 159

4-(4-Isopropyl-phenyl)-1-(3-phenyl-propyl)-6-propargyloxy-1H-quinazolin-2-one

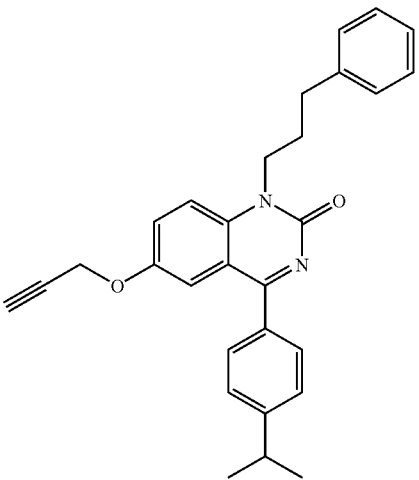 [SMILES: C#CCOc1ccc2c(c1)c(-c1ccc(C(C)C)cc1)nc(=O)n2CCCc1ccccc1]

$^1$H-NMR (300 MHz, CDCl$_3$): 7.69 (d, 2H), 7.46 (d, 1H), 7.28-7.38 (m, 5H), 7.18-7.26 (m, 3H), 7.06 (d, 1H), 4.66 (d, 2H), 4.26-4.34 (m, 2H), 3.00 (hept, 1H), 2.84 (t, 2H), 2.55 (t, 1H), 2.16 (quint, 2H), 1.31 (d, 6H).

MS: 437 (M+1)$^+$

Example 160

{2-[2-(3,4-dimethoxy-phenyl)-2-methyl-propy-lamino]-4,5-dimethoxy-phenyl}-(4-isopropyl-phenyl)-methanone A solution of 2.00 g (8.92 mmol) ethyl-3,4-dimethoxyphenyl acetate, 2.85 ml (17.84 mmol) HMPA and 3.34 ml (53.52 mmol) methyl iodide in 50 ml THF is treated at −75° C. with 51.9 ml (35.7 mmol) of a LDA solution prepared in THF. After 18 h stirring at −75° C. the cold reaction mixture is poured into an aqueous saturated ammonium chloride solution and extracted with ethyl acetate. After evaporation the crude dimethylated compound still containing some HMPA is obtained and is directly further transformed as described below.

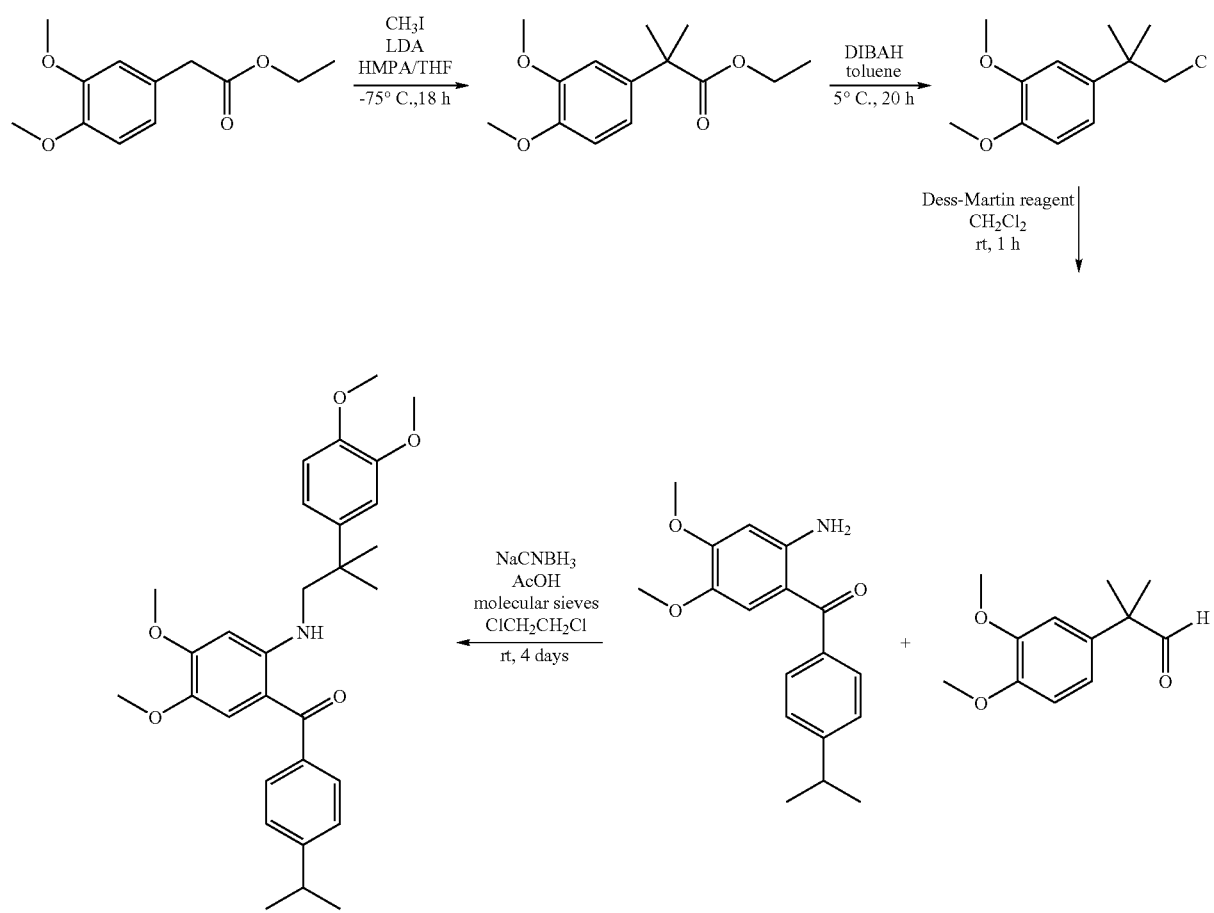

A. Synthesis of 2-3,4-dimethoxy-phenyl)-2-methyl-propionic acid ethyl ester

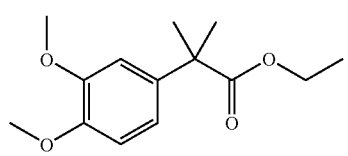 [SMILES: CCOC(=O)C(C)(C)c1ccc(OC)c(OC)c1]

$^1$H NMR (300 MHz, CDCl$_3$): 6.88 (dd, 1H), 6.86 (d, 1H), 6.82 (d, 1H), 4.12 (q, 2H), 3.87 (s, 3H), 3.87 (s, 3H), 1.57 (s, 6H), 1.20 (t, 3H).

B. Synthesis of 2-(3,4-dimethoxy-phenyl)-2-methyl-propan-1-ol

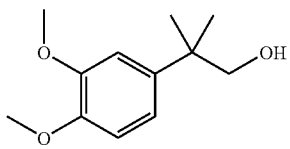

A solution of 909 mg (ca. 2 mmol) of the crude product described directly above in 5 ml toluene is treated twice with 2.69 ml (3.2 mmol) of 1.2 M DIBAH solution in toluene at 5° C. After stirring for 20 h saturated ammonium chloride solution is added. The reaction mixture is filtered and extracted with diethyl ether to obtain after evaporation of the solvent 2-(3,4-dimethoxy-phenyl)-2-methyl-propan-1-ol.

$^1$H NMR (300 MHz, CDCl$_3$): 6.94-6.91 (m, 2H), 6.85 (d, 1H), 3.90 (s, 3H), 3.88 (s, 3H), 3.60 (s, 2H), 1.34 (s, 6H).

C. Synthesis of
2-(3,4-dimethoxy-phenyl)-2-methyl-propionaldehyde

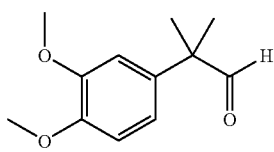

A solution of 100 mg (0.476 mmol) 2-(3,4-dimethoxy-phenyl)-2-methyl-propan-1-ol in 1 ml dichloromethane is treated with 202 mg (0.476 mmol) Dess-Martin reagent at rt. After 1 h aqueous sodium bicarbonate and sodium thiosulphate solutions are added and the product is extracted with dichloromethane. The organic layers are evaporated and the aldehyde is obtained in a sufficient purity to be used in reductive animations.

$^1$H NMR (300 MHz, CDCl$_3$): 9.44 (s, 1H), 6.88 (d, 1H), 6.83 (dd, 1H), 6.74 (d, 1H), 3.88 (s, 6H), 1.46 (s, 6H).

D. Synthesis of {2-[2-(3,4-dimethoxy-phenyl)-2-methyl-propylamino]-4,5-dimethoxy-phenyl}-(4-isopropyl-phenyl)-methanone

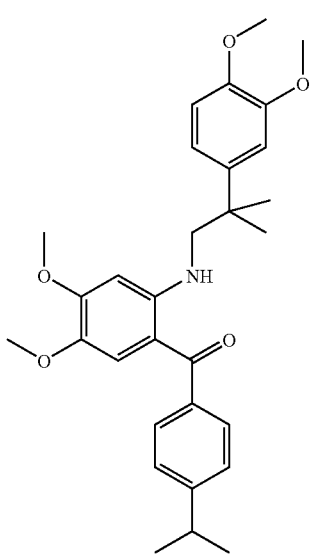

After one hour stirring a mixture of 143 mg (0.476 mmol) (2-amino-4,5-dimethoxy-phenyl)-(4-isopropyl-phenyl)-methanone, 98 mg (0.476 mmol) 2-(3,4-dimethoxy-phenyl)-2-methyl-propionaldehyde, 1.1 g molecular sieves 4 Å pore size, 5 ml 1,2-dichloroethane and 31 µl (0.476 mmol) acetic acid 41 mg (0.666 mmol) NaCNBH$_3$ are added. Over the duration of 4 days three additional portions of 31 µl acetic (0.476 mmol) and 41 mg NaCNBH$_3$ (0.666 mmol) are added. Excess hydride is destroyed by addition of 1 M hydrochloric acid and the reaction mixture is basified by means of 1 M sodium hydroxide. {2-[2-(3,4-Dimethoxy-phenyl)-2-methyl-propylamino]-4,5-dimethoxy-phenyl}-(4-isopropyl-phenyl)-methanone is isolated by filtration followed by extraction with dichloromethane and reversed phase preparative HPLC.

$^1$H NMR (300 Hz, CDCl$_3$): 7.50 (d, 2H), 7.28 (d, 2H), 7.13-7.00 (m, 3H), 6.84 (d, 1H), 6.14 (s, 1H), 3.90 (s, 3H), 3.88 (s, 3H), 3.86 (s, 3H), 3.66 (s, 3H), 3.55 (s, 2H), 2.97 (hept, 1H), 1.52 (s, 6H), 1.29 (d, 6H).

MS: 492 (M+1)$^+$

The compounds of the following examples is prepared by analogy to the example described above.

Example 161

{2-[2-(3,5-Dimethoxy-phenyl)-ethylamino]-4,5-dimethoxy-phenyl}-(4-isopropyl-phenyl)-methanone

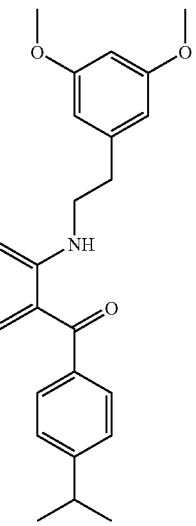

$^1$H NMR (300 MHz, CDCl$_3$): 7.53 (d, H), 7.30 (d, 2H), 7.06 (s, 1H), 6.46 (d, 2H), 6.35 (t, 1H), 6.22 (s, 1H), 3.93 (s, 3H), 3.79 (s, 6H), 3.68 (s, 3H), 3.50 (t, 2H), 3.03-2.94 (m, 3H), 1.31 (d, 6H).

MS: 464 (M+1)$^+$

Example 162

{4,5-Dimethoxy-2-[2-(3-methoxy-phenyl)-2-methyl-propylamino]-phenyl}-(4-isopropyl-phenyl)-methanone

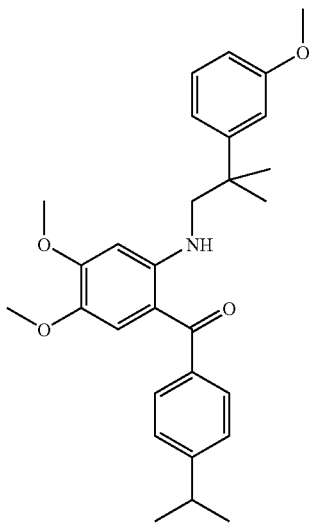

$^1$H NMR (300 MHz, CDCl$_3$): 7.51 (d, 2H), 7.29 (d, 2H), 7.25 (t, 1H), 7.05 (m, 1H), 7.02 (s, 1H), 6.99 (t, 1H), 6.75 (dd, 1H), 6.30 (s, 1H), 3.91 (s, 3H), 3.78 (s, 3H), 3.67 (s, 3H), 3.40 (s, 2H), 1.53 (s, 6H), 1.30 (d, 6H).
MS: 462 (M+1)$^+$

Example 163

{2-[2-(3,5-Dimethoxy-phenyl)-2-methyl-propylamino]-5-prop-2-ynyloxy-phenyl}-(4-isopropyl-phenyl)-methanone

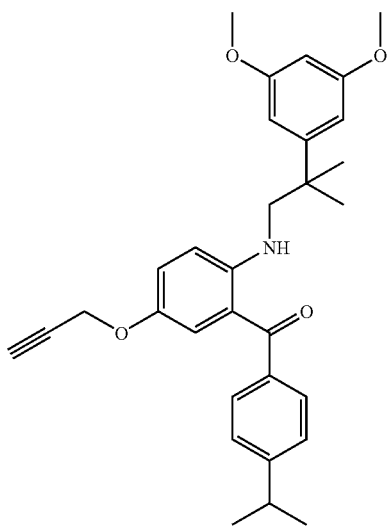 [SMILES: C#CCOc1ccc(NCC(C)(C)c2cc(OC)cc(OC)c2)c(C(=O)c2ccc(C(C)C)cc2)c1]

$^1$H NMR (300 MHz, CDCl$_3$): 7.56 (d, 2H), 7.28 (d, 2H), 7.16 (d, 1H), 7.11 (dd, 1H), 6.87 (d, 1H), 6.68 (d, 2H), 6.30 (s, 1H), 4.54 (d, 2H), 3.77 (s, 6H), 3.36 (s, 2H), 2.98 (hept, 1H), 2.48 (t, 1H), 1.48 (s, 6H), 1.30 (d, 6H).
MS: 486 (M+1)$^+$

Example 164

{2-[2-(3,5-Dimethoxy-phenyl)-ethylamino]-5-prop-2-ynyloxy-phenyl}-(4-isopropyl-phenyl)-methanone

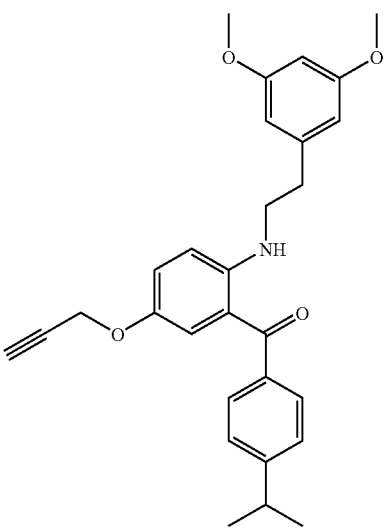 [SMILES: C#CCOc1ccc(NCCc2cc(OC)cc(OC)c2)c(C(=O)c2ccc(C(C)C)cc2)c1]

$^1$H NMR (300 MHz, CDCl$_3$): 7.59 (d, 2H), 7.30 (d, 2H), 7.20 (d, 1H), 7.15 (dd, 1H), 6.82 (d, 1H), 6.44 (d, 2H), 6.84 (t, 1H), 4.55 (d, 2H) 3.79 (s, 6H), 3.48 (t, 2H). 3.03-2.93 (m, 3H), 2.49 (t, 1H), 1.31 (d, H).
MS: 458 (M+1)$^+$

Example 165

{2-[2-(3,4-Dimethoxy-phenyl)-ethylamino]-4,5-dimethoxy-phenyl}-(4-isopropyl-phenyl)-methanone

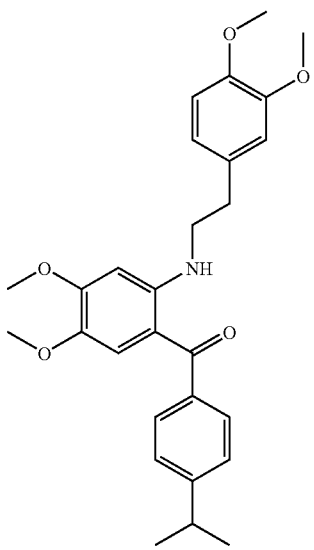

$^1$H NMR (300 MHz, CDCl$_3$): 7.56 (d, 2H), 7.32 (d, 2H), 7.08 (s, 1H), 6.84-6.83 (m, 3H), 6.67 (broad, 1H), 3.97 (s, 3H); 3.87 (s, 3H), 3.87 (s, 3H), (3.72 s, 3H), 3.49 (t, 2H), 3.08 (t, 2H), 2.99 (hept, 1H), 1.31 (d, 6H).

MS: 464 (M+1)+

Example 166

4-Ethyl-4-{[2-(4-isopropyl-benzoyl)-4,5-dimethoxy-phenylamino]-methyl}-hexanenitrile

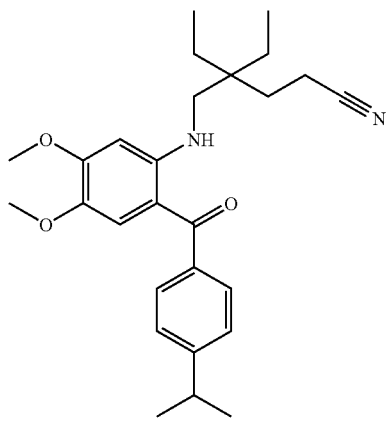 [SMILES: CCC(CC)(CCC#N)CNc1cc(OC)c(OC)cc1C(=O)c1ccc(C(C)C)cc1]

¹H NMR (300 MHz, CDCl₃): 9.18 (m, broad, 1H), 7.55 (d, 2H), 7.30 (d, 2H), 7.09 (s, 1H), 6.19 (s, 1H), 3.98 (s, 3H), 3.69 (s, 3H), 3.01 (d, 2H), 2.97 (hept, 1H), 2.34-2.28 (m, 2H), 1.85-1.80 (m, 2H), 1.49 (q, 4H), 1.29 (d, 6H), 0.88 (t, 6H).

Example 167

1-[2-(3,5-Dimethoxy-phenyl)-ethyl]-4-(4-isopropyl-phenyl)-6-prop-2-ynyloxy-1H-quinazolin-2-one

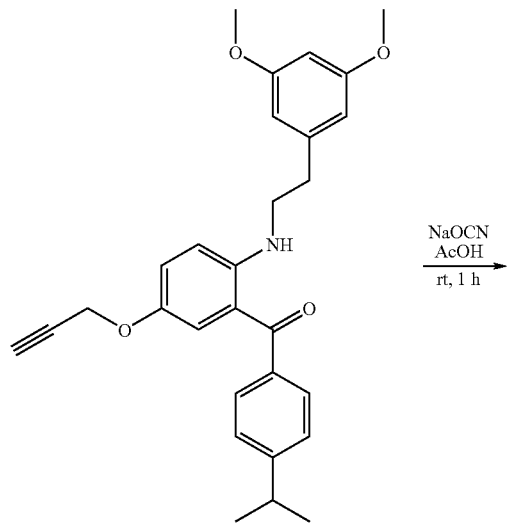

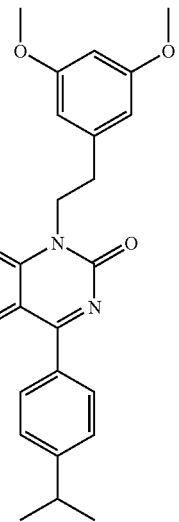

A solution of 15 mg (33 μmol) {2-[2-(3,5-dimethoxy-phenyl)-ethylamino]-5-prop-2-ynyloxy-phenyl}-(4-isopropyl-phenyl)-methanone and 2.1 mg (33 μmol) NaOCN in 300 μl acetic acid is stirred for 1 h at rt. The solvent is evaporated and the product is recrystallised from CH₂Cl₂/diethyl ether.

¹H NMR (300 MHz, CDCl₃): 7.70 (d, 2H), 7.49 (d, 1H), 7.43 (dd, 1H), 7.37 (d, 2H), 7.34 (d, 1H), 6.50 (d, 2H), 6.36 (t, 1H), 4.68 (d, 2H), 4.48 (dd, 2H), 3.80 (s, 6H), 3.09-2.97 (m, 3H), 2.57 (t, 1H), 1.32 (d, 6H).

MS: 483 (M+1)+

Example 168

{2-[2-(3,5-Dimethoxy-phenyl)-2-methyl-propylamino]-4-hydroxy-5-methoxy-phenyl}-(4-isopropyl-phenyl)-methanone

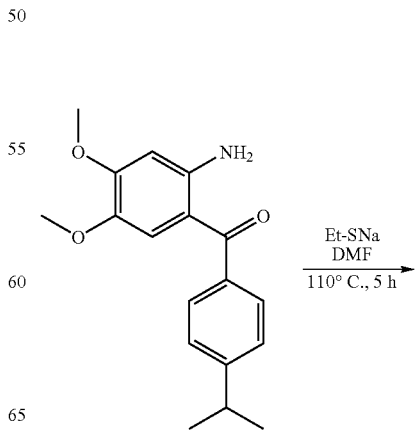

A. Synthesis of (2-amino-4-hydroxy-5-methoxy-phenyl)-(4-isopropyl-phenyl)-methanone

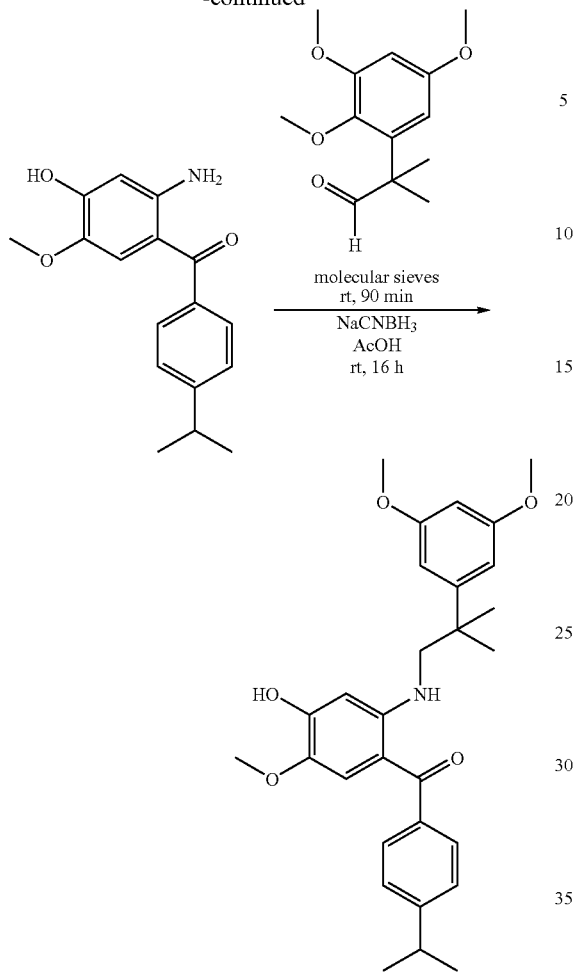

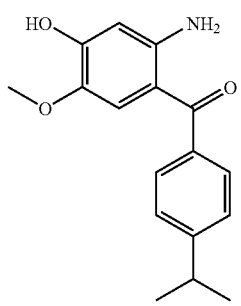 [SMILES: COc1cc(C(=O)c2ccc(C(C)C)cc2)c(N)cc1O]

A mixture of 1.34 g (4.48 mmol) (2-amino-4,5-dimethoxy-phenyl)-(4-isopropyl-phenyl)-methanone, 1.88 g sodium ethanethiolate and 10 ml DMF are heated for 5 h to 110° C. Saturated aqueous bicarbonate solution (10 ml) and 100 ml water are added. The product is extracted with CH$_2$Cl$_2$ and chromatographed on silica (hexane/ethyl acetate).

$^1$H NMR (300 MHz, CDCl$_3$): 7.56 (d, 2H), 7.30 (d, 2H), 6.96 (s, 1H), 6.31 (s, 1H), 3.70 (s, 3H), 1.30 (d, 6H).

MS: 286 (M+1)$^+$

B. Synthesis of {2-[2-(3,5-dimethoxy-phenyl)-2-methyl-propylamino]-4-hydroxy-5-methoxy-phenyl}-(4-isopropyl-phenyl)-methanone

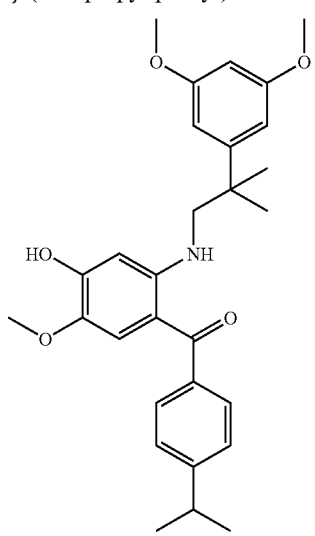

A mixture of 41.1 mg (144 µmol) (2-amino-4-hydroxy-5-methoxy-phenyl)-(4-isopropyl-phenyl)-methanone, 45 mg (216 µmol) 2-(3,5-dimethoxy-phenyl)-2-methyl-propionaldehyde, 180 mg molecular sieves (pore size 4 Å) and 0.50 ml CH$_2$Cl$_2$ is stirred for 90 min before 8.23 µl (144 µmol) and 22 mg NaCNBH$_3$ are added. After 16 h the excess of reducing agent is destroyed by addition of 1 M hydrochloric acid and the mixture is basified with 1 M sodium hydroxide solution. The product is extracted with CH$_2$Cl$_2$ and purified by reversed phase preparative HPLC.

$^1$H NMR (300 MHz, d$_6$DMSO): 10.07 (s, 1H), 8.71 (t, broad, 1H), 7.40 (d, 2H), 7.31 (d, 2H), 6.84 (s, 1H), 6.56 (d, 2H), 6.33 (t, 1H), 6.26 (s, 1H), 3.71 (s, 6H), 3.50 (s, 3H), 3.27 (d, 2H), 2.94 (hept, 1H), 1.35 (s, 6H), 1.23 (d, 6H).

MS: 478 (M+1)$^+$

The compound of the following example is prepared by analogy to the example described above:

Example 169

(2-Benzo[1,3]dioxol-5-yl-ethyl)-[5-hydroxy-2-(4-isopropyl-benzoyl)-4-methoxy-phenyl]-ammonium; chloride

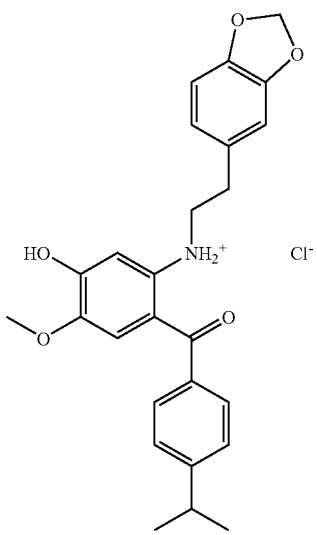 [SMILES: COc1cc(C(=O)c2ccc(C(C)C)cc2)c([NH2+]CCc2ccc3c(c2)OCO3)cc1O ; [Cl-]]

¹H NMR (300 MHz, CD₃OD): 7.71 (d, 2H), 7.44 (d, 2H), 7.19 (s, 1H), 6.98 (m, 1H), 6.79 (s, 1H), 6.75 (s, 2H), 5.90 (s, 2H), 3.79 (s, 3H), 3.63 (t, 2H), 3.08-2.99 (m, 3H), 1.32 (d, 6H).

MS: 434 (M+1)⁺

Example 170

[2-(Cyclopropylmethyl-amino)-4-hydroxy-5-methoxy-phenyl]-(4-isopropyl-phenyl)-methanone

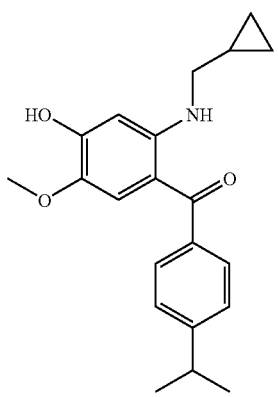 [SMILES: COc1cc(C(=O)c2ccc(C(C)C)cc2)c(NCC2CC2)cc1O]

¹H NMR (300 MHz, CDCl₃): 9.17 (broad 1H), 7.55 (d, 2H), 7.29 (d, 2H), 7.04 (s, 1H), 6.39 (s, 1H), 6.15 (s, 1H), 3.71 (s, 3H), 3.07 (d, 2H), 2.98 (hept, 1H), 1.30 (d, 6H), 1.19 (m, 1H), 0.60 (m, 2H), 0.31 (m, 2H).

Example 171

1-[2-Hydroxy-2-(2,4,6-trimethyl-phenyl)-ethyl]-4-(4-isopropyl-phenyl)-6-prop-2-ynyloxy-1H-quinazolin-2-one

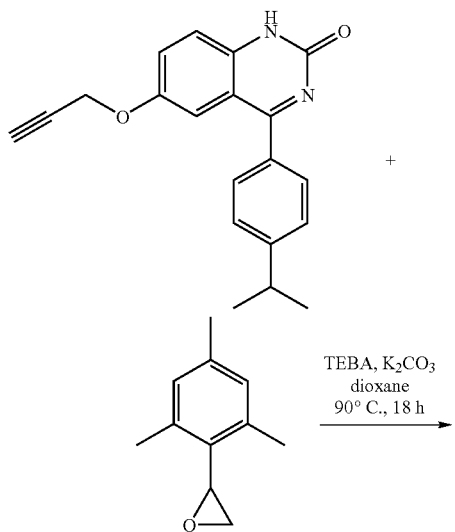

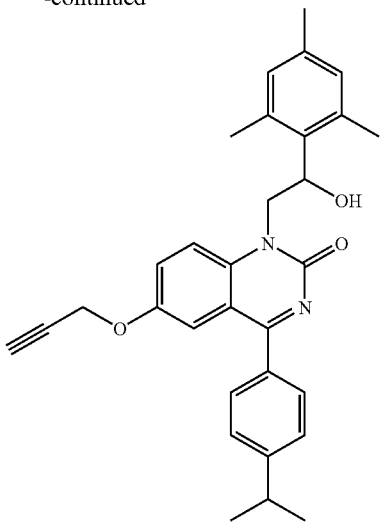

A mixture of 0.5 g (1.57 mmol) 4-(4-isopropyl-phenyl)-6-prop-2-ynyloxy-1H-quinazolin-2-one, 0.254 g (1.57 mmol) mesityl oxirane, 35.7 mg (0.157 mmol) benzyltriethylammonium chloride and 21.7 mg (0.157 mmol) potassium carbonate is stirred in 1 ml dioxane at 90° C. for 6 days. The reaction mixture is extracted with water/dichloromethane and, after evaporation of the organic phases, the residue is purified by preparative reversed phase HPLC.

¹H NMR (300 MHz, CDCl₃): 7.72 (d, 2H), 7.54 (d, 1H), 7.50 (d, 1H), 7.43 (dd, 1H), 7.38 (d, 2H), 6.88 (s, 2H), 5.66 (dd, 1H), 4.93 (d, 1H), 4.68 (d, 2H), 4.37 (dd, 1H), 3.02 (hept, 1H), 2.60 (s, 6H), 2.57 (t, 1H), 2.28 (s, 3H), 1.33 (d, 6H).

MS: 481 (M+1)⁺

The compound of the following example is prepared by analogy to the example described above:

Example 172

1-[2-(3,5-Difluoro-phenyl)-2-hydroxy-ethyl]-4-(4-isopropyl-phenyl)-6-prop-2-ynyloxy-1H-quinazolin-2-one

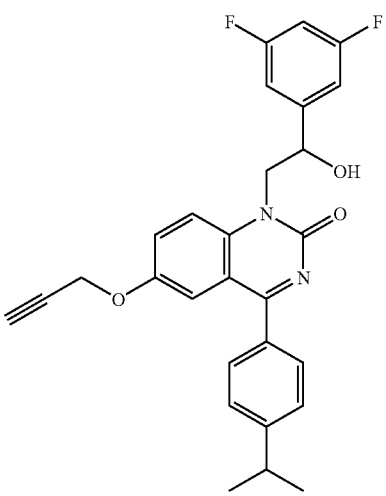 [SMILES: C#CCOc1ccc2c(c1)c(-c1ccc(C(C)C)cc1)nc(=O)n2CC(O)c1cc(F)cc(F)c1]

¹H NMR (300 MHz, CDCl₃): 7.67 (d, 2H), 7.49-7.43 (m, 3H), 7.37 (d, 2H), 7.10 (m, 2H), 6.74 (tt, 1H), 5.81 (dd, 1H), 4.68 (d, 2H), 4.51 (dd, 2H), 4.38 (dd, 2H), 3.01 (hept, 1H), 2.57 (t, 1H), 1.32 (d, 6H).
MS: 475 (M+1)⁺

Example 173

4-(4-Isopropyl-phenyl)-6-prop-2-ynyloxy-1-[(E)-2-(2,4,6-trimethyl-phenyl)-vinyl]-1H-quinazolin-2-one

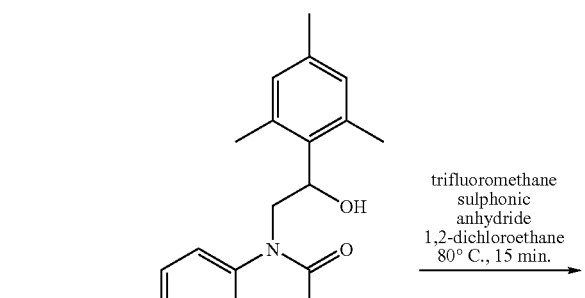

trifluoromethane sulphonic anhydride
1,2-dichloroethane
80° C., 15 min.

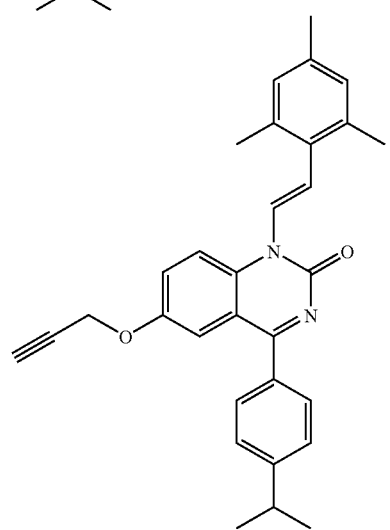

A solution of 50 mg (0.104 mmol) 1-[2-hydroxy-2-(2,4,6-trimethyl-phenyl)-ethyl]-4-(4-isopropyl-phenyl)-6-prop-2-ynyloxy-1H-quinazolin-2-one and 34.3 µl (0.208 mmol) trifluoromethane sulphonic anhydride in 0.5 ml 1,2 dichloroethane is heated to 80° C. for 15 min. Extraction with dichloromethane/aqueous NaHCO₃ followed by preparative reversed phase HPLC yielded the title compound.

¹H NMR (300 MHz, CDCl₃): 7.76 (d, 2H), 7.68 (d, 1H), 7.51 (d, 1H), 7.41 (dd, 1H), 7.40 (d, 2H), 7.03 (d, 1H), 6.94 (s, 2H), 6.71 (d, 1H), 4.69 (d, 2H), 3.03 (hept, 1H), 2.58 (t, 1H), 2.47 (s, 6H), 2.32 (s, 3H), 1.33 (d, 6H).
MS: 463 (M+1)⁺

The compounds of the following examples are prepared by analogy to the example described above:

Example 174

4-(4-Isopropyl-phenyl)-6-prop-2-ynyloxy-1-((E)-styryl)-1H-quinazolin-2-one

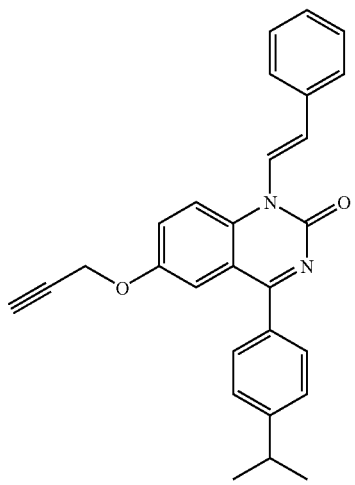 [SMILES: C#CCOc1ccc2c(c1)c(-c1ccc(C(C)C)cc1)nc(=O)n2/C=C/c1ccccc1]

¹H NMR (300 MHz, CDCl₃): 7.78 (d, 2H), 7.64 (d, 1H), 7.56-7.53 (m, 2H), 7.51 (d, 1H), 7.43-7.35 (m, 6H), 7.25 (d, 1H), 7.03 (d, 1H), 4.70 (d, 2H), 3.03 (hept, 1H), 2.58 (t, 1H), 1.34 (d, 6H).
MS: 421 (M+1)⁺

Example 175

1-[(E)-2-(3-Chloro-4-methoxy-phenyl)-vinyl]-4-(4-isopropyl-phenyl)-6-prop-2-ynyloxy-1H-quinazolin-2-one

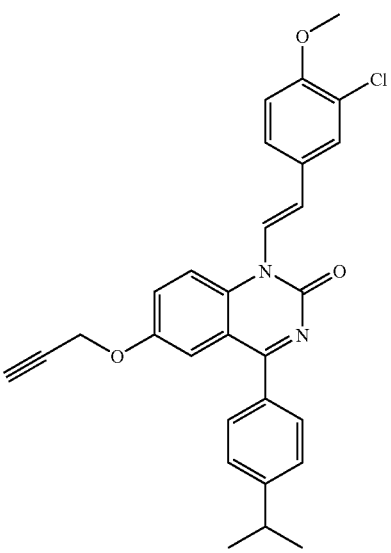 [SMILES: C#CCOc1ccc2c(c1)c(-c1ccc(C(C)C)cc1)nc(=O)n2/C=C/c1ccc(OC)c(Cl)c1]

¹H NMR (300 MHz, CDCl₃): 7.77 (d, 2H), 7.60 (d, 1H), 7.59 (s, 1H), 7.51 (d, 1H), 7.41-7.37 (m, 4H), 7.13 (d, 1H), 6.96 (d, 1H), 6.92 (d, 1H), 4.70 (d, 2H), 3.95 (s, 3H), 3.03 (hept, 1H), 2.58 (t, 1H), 1.33 (d, 6H).
MS: 487 (30), 485 (100) (M+1)⁺ (chlorine isotope pattern)

Example 176

1-[(E)-2-(3,5-Dimethyl-phenyl)-vinyl]-4-(4-isopropyl-phenyl)-6-prop-2-ynyloxy-1H-quinazolin-2-one

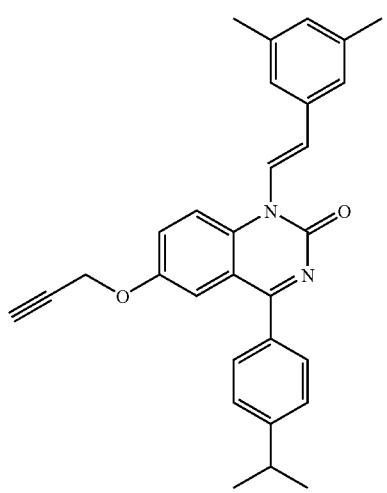 [SMILES: C#CCOc1ccc2c(c1)c(-c1ccc(C(C)C)cc1)nc(=O)n2/C=C/c1cc(C)cc(C)c1]

¹H-NMR (300 MHz, CDCl₃): 7.78 (d, 2H), 7.64 (d, 1H), 7.50 (d, 1H), 7.40 (d, 2H), 7.37 (dd, 1H), 7.23 (d, 1H), 7.17 (s, 2H), 7.00 (s, 1H), 6.93 (d, 1H), 4.69 (d, 2H), 3.03 (hept, 1H), 2.58 (t, 1H), 2.36 (s, 6H), 1.33 (d, 6H).
MS: 449 (M+1)⁺

Example 177

2-Benzylsulphanyl-4-(4-isopropyl-phenyl)-6-prop-2-ynyloxy-quinazoline

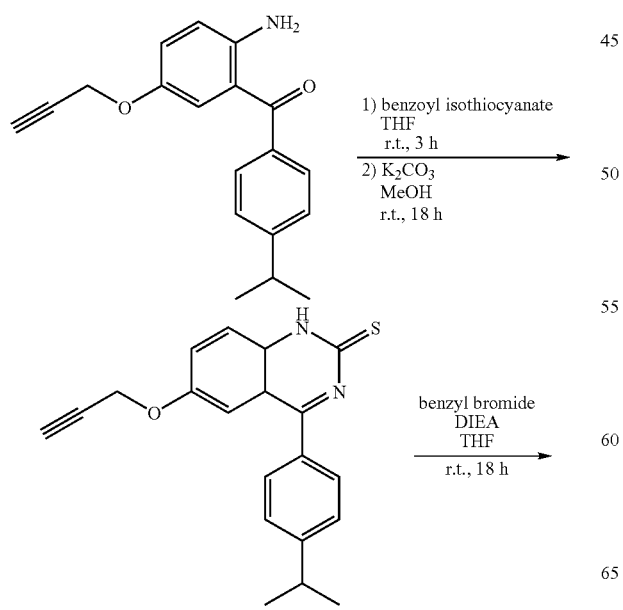

A. Synthesis of 4-(4-isopropyl-phenyl)-6-prop-2-ynyloxy-1H-quinazoline-2-thione

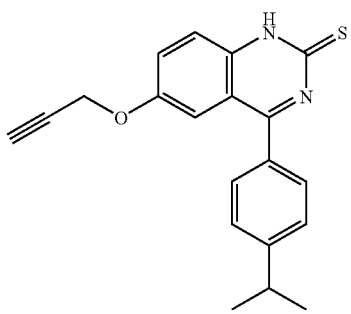 [SMILES: C#CCOc1ccc2[nH]c(=S)nc(-c3ccc(C(C)C)cc3)c2c1]

A solution of 0.5 g (1.71 mmol) (2-amino-5-prop-2-ynyloxy-phenyl)-(4-isopropyl-phenyl)-methanone and 0.23 ml (1.71 mmol) benzoyl isothiocyanate in 5 ml THF is stirred for 3 h at r.t. before 0.235 g potassium carbonate and 5 ml methanol are added. After stirring for 18 h, the reaction mixture is acidified with 0.1 M aqueous hydrochloric acid and extracted with dichloromethane. After evaporation of the organic phases, the residue is triturated with diethyl ether to give the title compound.
¹H NMR (300 MHz, d₆DMSO): 13.79 (s, 1H), 7.70 (d, 2H), 7.54 (s, 2H), 7.44 (d, 2H), 7.32 (s, 1H), 4.80 (s, 2H), 3.69 (s, 1H), 2.99 (hept, 1H), 1.24 (d, 6H).
MS: 335 (M+1)⁺

B. Synthesis of 2-benzylsulphanyl-4-(4-isopropyl-phenyl)-6-prop-2-ynyloxy-quinazoline

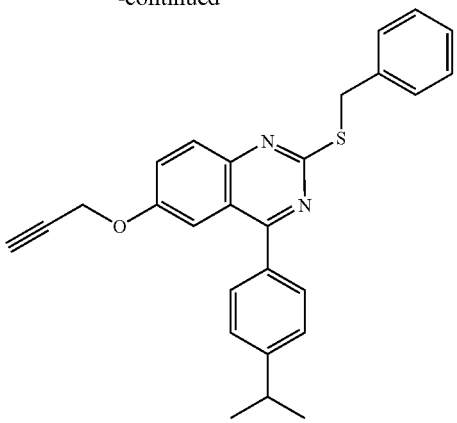

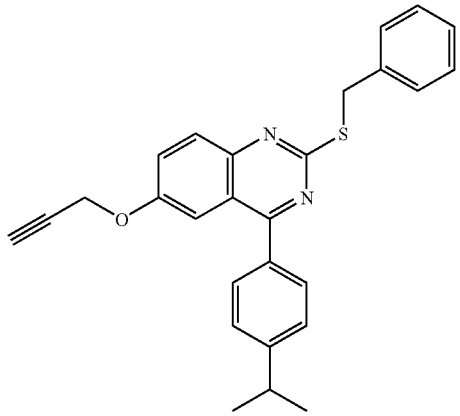 [SMILES: C#CCOc1ccc2nc(SCc3ccccc3)nc(-c3ccc(C(C)C)cc3)c2c1]

To a solution of 100 mg (299 µmol) 4-(4-isopropyl-phenyl)-6-prop-2-ynyloxy-1H-quinazoline-2-thione in 2 ml THF are added 35.5 µl (299 µmol) benzyl bromide and 76 µl (448 µmol) DIEA. After stirring for 18 h at r.t. the reaction mixture is extracted with dichloromethane and water. After evaporation of the organic layers the crude product is purified by flash chromatography using hexanes/ethyl acetate 20:1 as eluent.

$^1$H NMR (300 MHz, CDCl$_3$): 7.88 (d, 1H), 7.72 (d, 2H), 7.53-7.48 (m, 4H), 7.40 (d, 2H), 7.32-7.19 (m, 3H), 4.71 (d, 2H), 4.56 (s, 2H), 3.02 (hept, 1H), 2.58 (t, 1H), 1.33 (d, 6H).

The compounds of the following examples are prepared by analogy to the example described above:

Example 178

4-(4-Isopropyl-phenyl)-2-isopropylsulphanyl-6-prop-2-ynyloxy-quinazoline

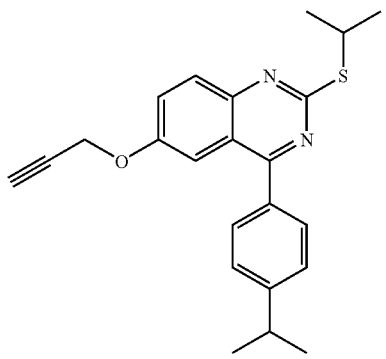 [SMILES: C#CCOc1ccc2nc(SC(C)C)nc(-c3ccc(C(C)C)cc3)c2c1]

$^1$H NMR (300 MHz, CDCl$_3$): 7.83 (dm, 1H), 7.73 (d, 2H), 7.57-7.51 (m, 2H), 7.39 (d, 2H), 4.70 (d, 2H), 4.13 (hept, 1H), 3.01 (hept, 1H), 2.57 (t, 1H), 1.50 (d, 6H), 1.32 (d, 6H).

Example 179

2-Isobutylsulphanyl-4-(4-isopropyl-phenyl)-6-prop-2-ynyloxy-quinazoline

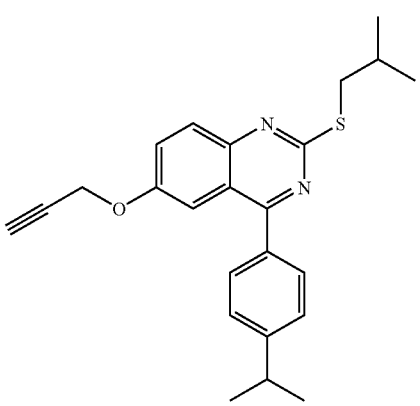 [SMILES: C#CCOc1ccc2nc(SCC(C)C)nc(-c3ccc(C(C)C)cc3)c2c1]

$^1$H NMR (300 MHz, CDCl$_3$): 7.84 (dd, 1H), 7.75 (d, 2H), 7.51 (dd, 1H), 7.49 (s, 1H), 7.40 (d, 2H), 4.72 (d, 2H), 3.22 (d, 2H), 3.03 (hept, 1H), 2.58 (t, 1H), 2.08 (nonet, 1H), 1.34 (d, 6H), 1.10 (d, 6H).

The Agents of the Invention, as defined above, e.g., of formula I or II, particularly as exemplified, in free or pharmaceutically acceptable acid addition salt form, exhibit pharmacological activity and are useful as pharmaceuticals, e.g. for therapy, in the treatment of diseases and conditions as hereinafter set forth.

Inositol Phosphate Formation Assay:

To determine antagonistic activity at the human parathyroid calcium-sensing receptor (PcaR), compounds are tested in functional assays measuring the inhibition of calcium-induced inositol phosphate formation in CCL39 fibroblasts stably transfected with human PcaR.

Cells are seeded into 24 well plates and grown to confluence. Cultures are then labelled with [$^3$H]inositol (74 Mbq/ml) in serum-free medium for 24 h. After labelling, cells are washed once with a modified Hepes-buffered salt solution (mHBS: 130 mM NaCl, 5.4 mM KCl, 0.5 mM CaCl$_2$, 0.9 mM MgSO$_4$, 10 mM glucose, 20 mM HEPES, pH 7.4) and incubated with mHBS at 37° C. in the presence of 20 mM LiCl to block inositol monophosphatase activity. Test compounds are added 3 minutes before stimulating PcaR with 5.5 mM calcium and incubations continued for further 20 min. Thereafter, cells are extracted with 10 mM ice-cold formic acid and inositol phosphates formed are determined using anion exchange chromatography and liquid scintillation counting.

Assay for Intracellular Free Calcium:

An alternative method to determine antagonism at the PcaR consists in measuring the inhibition of intracellular calcium transients stimulated by extracellular calcium. CCL39 fibroblasts stably transfected with human PcaR are seeded at 40,000 cells/well into 96-well Viewplates and incubated for 24 hours. Medium is then removed and replaced with fresh medium containing 2 µM Fluo-3 AM (Molecular Probes, Leiden, The Netherlands), In routine experiments, cells are incubated at 37° C., 5% CO$_2$ for 1 h. Afterwards, plates are washed twice with mHBS and wells are refilled with 100 µl mHBS containing the test compounds. Incubation is continued at room temperature for 15 minutes. To record changes of intracellular free calcium, plates are transferred to fluorescence-imaging plate reader (Molecular Devices, Sunnyvale, Calif., USA). A baseline consisting in 5 measurements of 0.4 seconds each (laser excitation 488 nm) is recorded. Cells are then stimulated with calcium (2.5 mM final), and fluorescence changes recorded over a period of 3 minutes.

When measured in the above assays, Agents of the Invention typically have IC$_{50}$s in the range from about 50 µM down to about 10 nM or less.

It is now well established that controlled treatment of patients with parathyroid hormone (PTH) and analogues and fragments thereof can have a pronounced anabolic effect on bone formation. Thus compounds which promote PTH release, such as the Agents of the Invention may be used for preventing or treating conditions of bone which are associated with increased calcium depletion or resorption or in which stimulation of bone formation and calcium fixation in the bone is desirable.

Thus in a further aspect the invention includes a method for preventing or treating bone conditions which are associated with increased calcium depletion or resorption or in which stimulation of bone formation and calcium fixation in the bone is desirable in which an effective amount of an Agent of the Invention is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising an Agent of the Invention in admixture with a pharmaceutically acceptable excipient, diluent or carrier.

Agents of the Invention are accordingly indicated for preventing or treating all bone conditions which are associated with increased calcium depletion or resorption or in which stimulation of bone formation and calcium fixation in the bone is desirable, e.g. osteoporosis of various genesis (e.g. juvenile, menopausal, post-menopausal, post-traumatic, caused by old age or by corticosteroid therapy or inactivity), fractures, osteopathy, including acute and chronic states associated with skeletal demineralisation, osteo-malacia, periodontal bone loss or bone loss due to arthritis or osteoarthritis or for treating hypoparathyroidism.

Further diseases and disorders which might be prevented or treated include e.g. seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, congestive heart failure; hypertension; gut motility disorders such as diarrhoea, and spastic colon and dermatological disorders, e.g. in tissue healing, for example burns, ulcerations and wounds.

The Agents of the Invention are particularly indicated for preventing or treating osteoporosis of various genesis.

For all the above uses, an indicated daily dosage is in the range from about 0.03 to about 300 mg preferably 0.03 to 30, more preferably 0.1 to 10 mg of a compound of the invention. Agents of the Invention may be administered twice a day or up to twice a week.

The Agents of the Invention may be administered in free form or in pharmaceutically acceptable salt form. Such salts may be prepared in conventional manner and exhibit the same order of activity as the free compounds. The present invention also provides a pharmaceutical composition comprising an Agent of the Invention in free base form or in pharmaceutically acceptable salt form in association with a pharmaceutically acceptable diluent or carrier. Such compositions may be formulated in conventional manner. The Agents of the Invention may be administered by any conventional route, for example parenterally e.g. in form of injectable solutions or suspensions, enterally, e.g. orally, for example in the form of tablets or capsules or in a transdermal, nasal or a suppository form.

In accordance with the foregoing the present invention further provides:
an Agent of the Invention or a pharmaceutically acceptable salt thereof for use as a pharmaceutical;
a method for preventing or treating above mentioned disorders and diseases in a subject in need of such treatment, which method comprises administering to said subject an effective amount of an Agent of the Invention or a pharmaceutically acceptable salt thereof;
c) an Agent of the Invention or a pharmaceutically acceptable salt thereof for use in the preparation of a pharmaceutical composition e.g. for use in the method as in b) above.

According to a further embodiment of the invention, the Agents of the Invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial®), vitamin D or an analogue thereof or PTH, a PTH fragment or a PTH derivative e.g. PTH (1-84), PTH (1-34), PTH (1-36), PTH (1-38), PTH (1-31) $NH_2$ or PTS 893.

When the Agents of the Invention are administered in conjunction with, e.g. as an adjuvant to bone resorption inhibition therapy, dosages for the co-administered inhibitor will of course vary depending on the type of inhibitor drug employed, e.g. whether it is a steroid or a calcitonin, on the condition to be treated, whether it is a curative or preventive therapy, on the regimen and so forth.

The invention claimed is:

1. A compound o formula I

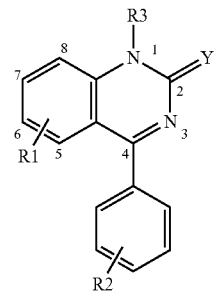

wherein Y is O or S;

R1 represents from 1 to 3 substituents independently selected from OH, SH, halo, $NO_2$, optionally substituted (lower alkyl, lower alkoxy, lower alkenyl, lower alkenyloxy, lower alkynyl, lower alkynyloxy, lower alkanoyl, cycloalkyl, lower alkylsulphone, lower alkylsulphoxide or amino);

R2 represents from 1 to 3 substituents selected from halo, optionally substituted (lower alkyl, lower alkenyl, cycloalkyl or lower alkoxy);

R3 is
a) lower alkyl optionally substituted by 1 to 3 substituents selected from cycloalkyl, lower alkylene, lower alkyl, Br, F, $CF_3$, CN, COOH, lower alkyl-carboxylate, OH, lower alkoxy or —$O_x$—$(CH_2)_y$—$SO_z$-lower alkyl, wherein x is 0 or 1, y is 0, 1 or 2 and z is 0, 1 or 2; or
b) Benzyl which is
  a. mono- or di-substituted by —$O_x$—$(CH_2)_y$—$SO_z$-lower alkyl or —$O_x$—$(CR, R')_y$—COO—R, wherein x, y and z are as defined above and R or R' is H or lower alkyl,
  b. substituted by 1 or 2 substituents selected from morpholino-lower alkoxy, aryl-lower alkoxy, optionally N-lower alkyl substituted arylamino-lower alkoxy,
  c. substituted at the 2-position by lower alkoxy-, hydroxy-lower alkoxy- or lower alkoxy-lower alkoxy,
  d. substituted on the —$CH_2$— group thereof; or
c) optionally substituted (aryl-$C_2$-$C_8$-alkyl, aryl-$C_2$-$C_8$-alkenyl, heteroarylmethyl or 4-heteroarylbenzyl); or when R1 is 2 substituents one of which is OH, and the other of which is optionally substituted (lower alkyl, cycloalkyl-lower-alkyl or lower alkenyl), R3 is H or optionally substituted (lower alkyl, aryl, aryl-lower alkyl, arylcycloalkyl, cycloalkyl-lower alkyl, cycloalkenyl-lower alkyl, hetereoaryl-lower alkyl, hetereoaryl, or carbonyl lower alkyl); or when R1 is 2-propynyloxy and R2 is isopropyl, R3 is also benzyl which is substituted by 1 to 3 substituents selected from lower alkyl, lower alkoxy, halo, halo-lower alkyl, e.g. $CF_3$; or when R1 is 2-propynyloxy and R2 is isopropyl, R3 is also benzyl which is substituted by OH and a second and optionally third substituent selected from lower alkyl, lower alkoxy, halo, —O—CH(H or lower alkyl)-COO(H or lower alkyl); or when R1 is 2-propynyloxy and R2 is cyclopropyl, R3 is also optionally substituted lower alkyl or benzyl; or when Y is S and R1 is as defined above but not methoxy, R3 is also optionally substituted benzyl; or a compound selected from 4-(4-isopropyl-phenyl)-1-(3,4-diamino-benzyl)-6-prop-2-ynyloxy-1H-quinazolin-2-one, 1-(2,6-dichloro-benzyl)-4-(4-isopropyl-phenyl)-6-prop-2-ynyloxy-1H-quinazolin-2-one, 1-benzyl-4-(4-isopropyl-phenyl)-6-prop-2-ynyloxy-1H-quinazoline-2-thione; 1-(3,5di-tert-butyl-4-hydroxy-benzyl)-4-(4-isopropyl-phenyl)-6-prop-2-ynyloxy-1H-quinazolin-2-one, or 1-[3-(2-hydroxy-ethoxy)-benzyl]-4-(4-isopropyl-phenyl)-6-prop-2-ynyloxy-1H-quinazoline-2-thione;

or a pharmaceutically-acceptable and -cleavable ester, or acid addition salt thereof; and provided that when Y is O and R3 is lower alkyl or cycloalkyl, R3 is not isopropyl or cyclopentyl; or provided the compound of formula I is not 4-(4-isopropyl-phenyl)-6-methoxy-1-pyridin-3-ylmethyl-1.H.-quinazolin-2-one, 4-(4-isopropyl-phenyl)-6-methoxy-1-pyridin-2-ylmethyl-1.H.-quinazolin-2-one, 1-(6-chloro-pyridin-3-ylmethyl)-4-(4-isopropyl-phenyl)-6-methoxy-1.H.-quinazolin-2-one, 4-(4-isopropyl-phenyl)-6-methoxy-1-(5-nitro-furan-2-ylmethyl)-1.H.-quinazolin-2-one or 1-[2-(1.H.-indol-2-yl)-ethyl]-4-(4-isopropyl-phenyl)-6-methoxy-1.H.-quinazolin-2-one, 4-(4-isopropyl-phenyl)-6-methoxy-1-phenethyl-1H-quinazolin-2-one, 1-(2-hydroxy-2-phenyl-ethyl)-4-(4-isopropyl-phenyl)-6-prop-2-ynyloxy-1H-quinazolin-2-one, methanesulfonic acid 2-[4-(4-isopropyl-phenyl)-2-oxo-6-prop-2-ynyloxy-2H-quinazolin-1-ylmethyl]-phenyl ester, or acetic acid 2-[4-(4-isopropyl-phenyl)-2-oxo-6-prop-2-ynyloxy-2H-quinazolin-1-yl]-1-phenyl-ethyl ester, 5-allyl-6-hydroxy-1-isopropyl-4-(4-isopropyl-phenyl)-1.H.-quinazolin-2-one, 1-cyclopropylmethyl-4-(o-tolyl)-6-nitro-2(1H)-quinazolinone, 1-ethyl-4-(o-tolyl)-6-chloro-2(1H)-quinazolinone, 1-cyclopropylmethyl-4-(o-tolyl)-6-chloro-2(1H)-quinazolinone, 1-cyclopropylmethyl-4-(o-fluorophenyl)-6-chloro-2(1H)-quinazolinone, 1-cyclopropylmethyl-4-(m-chlorophenyl)-6-chloro-2(1H)-quinazolinone, 1-cyclopropylmethyl-4-(o-chlorophenyl)-6-nitro-2(1H)-quinazolinone.

2. A compound according to claim 1 of formula I'

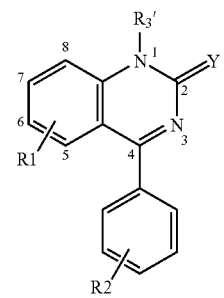

wherein Y is O or S;
R1 and R2 are as defined in claim 1;
R3' is
  a) lower alkyl substituted by 1 to 3 substituents independently selected from —S-lower alkyl, lower alkylene, cycloalkyl, Br, F or $CF_3$; or
  b) benzyl which is
    a. mono- or di-substituted by —$O_x$—$(CH_2)_y$—$SO_z$-lower alkyl, wherein x is 0 or 1, y is 0, 1 or 2 and z is 0, 1 or 2,
    b. substituted by 1 or 2 substituents selected from morpholino-lower alkoxy, aryl-lower alkoxy, optionally N-lower alkyl substituted arylamino-alkoxy,
    c. substituted at the 2-position by lower alkoxy-, hydroxy-lower alkoxy- or lower alkoxy-lower alkoxy; or
  c) optionally substituted (arylvinyl, arylethyl, hetereoarylmethyl or 4-heteroarylbenzyl); or when R1 is 2 substituents one of which is OH and the other of which is optionally substituted (lower alkyl or lower alkenyl), R3 is H or optionally substituted (lower alkyl, aryl, aryl-lower alkyl, arylcycloalkyl, cycloalkyl-lower alkyl, cycloalkenyl-lower alkyl, hetereoaryl-lower alkyl, hetereoaryl, or carbonyl lower alkyl); or when R1 is 2-propynyl and R2 is isopropyl, R3 is also benzyl which is substituted by 1 to 3 substituents selected from lower alkyl, lower alkoxy, halo, halo-lower alkyl, e.g. $CF_3$, —O—CH(H or lower alkyl)-COO(H or lower alkyl); or when R1 is 2-propynyl and R2 is isopropyl, R3 is also benzyl which is substituted by OH and a second and optionally third subtituent selected from lower alkyl, lower alkoxy, halo, —O—CH(H or lower alkyl)-COO(H or lower alkyl); or when R1 is 2-propynyl and R2 is cyclopropyl, R3 is also optionally substituted benzyl; or when X is S and R1 is as defined above but not methoxy, R3 is also optionally substituted benzyl; or a compound selected from 4-(4-isopropyl-phenyl)-1-(3,4-diamino-benzyl)-6-prop-2-ynyloxy-1H-quinazolin-2-one, 1-(2,6-dichloro-benzyl)-4-(4-isopropyl-phenyl)-6-prop-2-ynyloxy-1H-quinazolin-2-one, 1-benzyl-4-(4-isopropyl-phenyl)-6-prop-2-ynyloxy-1H-quinazoline-2-thione;

1-(3di-tert-butyl-4-hydroxy-benzyl)-4-(4-isopropyl-phenyl)-6-prop-2-ynyloxy-1H-quinazolin-2-one, or 1-[3-(2-hydroxy-ethoxy)-benzyl]-4-(4-isopropyl-phenyl)-6-prop-2-ynyloxy-1H-quinazoline-2-thione;

or a pharmaceutically-acceptable and -cleavable ester, or acid addition salt thereof; and provided that when X is O and R3 is lower alkyl or cycloalkyl, R3 is not isopropyl or cyclopentyl; or provided the compound of formula I' is not 4-(4-isopropyl-phenyl)-6-methoxy-1-pyridin-3-ylmethyl-1.H.-quinazolin-2-one, 4-(4-isopropyl-phenyl)-6-methoxy-1-pyridin-2-ylmethyl-1.H.-quinazolin-2-one, 1-(6-chloro-pyridin-3-ylmethyl)-4-(4-isopropyl-phenyl)-6-methoxy-1.H.-quinazolin-2-one, 4-(4-isopropyl-phenyl)-6-methoxy-1-(5-nitro-furan-2-ylmethyl)-1.H.-quinazolin-2-one or 1-[2-(1.H.-indol-2-yl)-ethyl]-4-(4-isopropyl-phenyl)-6-methoxy-1.H.-quinazolin-2-one, 4-(4-isopropyl-phenyl)-6-methoxy-1-phenethyl-1H-quinazolin-2-one, 1-(2hydroxy-2-phenyl-ethyl)-4-(4-isopropyl-phenyl)-6-prop-2-ynyloxy-1H-quinazolin-2-one, methanesulfonic acid 2-[4-(4-isopropyl-phenyl)-2-oxo-6-prop-2-ynyloxy-2H-quinazolin-1-ylmethyl]-phenyl ester, or acetic acid 2-[4-(4-isopropyl-phenyl)-2-oxo-6-prop-2-ynyloxy-2H-quinazolin-1-yl]-1-phenyl-ethyl ester, 5-allyl-6-hydroxy-1-isopropyl-4-(4-isopropyl-phenyl)-1.H.-quinazolin-2-one, 1-cyclopropylmethyl-4-(o-tolyl)-6-nitro-2(1H)-quinazolinone, 1-Ethyl-4-(o-tolyl)-6-chloro-2(1H)-quinazolinone, 1-cyclopropylmethyl-4-(o-tolyl)-6-chloro-2(1H)-quinazolinone, 1-cyclopropylmethyl-4-(o-fluorophenyl)-6-chloro-2(1H)-quinazolinone, 1-cyclopropylmethyl-4-(m-chlorophenyl)-6-chloro-2(1H)-quinazolinone, 1-cyclopropylmethyl-4-(o-chlorophenyl)-6-nitro-2(1H)-quinazolinone.

3. A pharmaceutically acceptable composition comprising a compound of claim 1, or a salt thereof, and a pharmaceutically acceptable excipient.

* * * * *